United States Patent [19]

Biller et al.

[11] Patent Number: 5,212,164
[45] Date of Patent: May 18, 1993

[54] PHOSPHORUS-CONTAINING SQUALENE SYNTHETASE INHIBITORS

[75] Inventors: Scott A. Biller, Ewing, N.J.; Michael J. Sofia, Carmel, Ind.

[73] Assignee: E. R. Squibb & Sons, Inc., Princeton, N.J.

[21] Appl. No.: 501,204

[22] Filed: Mar. 29, 1990

Related U.S. Application Data

[63] Continuation-in-part of Ser. No. 237,940, Aug. 29, 1988, abandoned, and a continuation-in-part of Ser. No. 381,434, Jul. 17, 1989, abandoned.

[51] Int. Cl.$^5$ .................. C07F 9/40; A61K 31/66
[52] U.S. Cl. .................. 514/108; 558/156; 558/157; 558/158; 558/161; 562/9; 562/10; 562/11; 562/13; 562/21
[58] Field of Search ............ 558/156, 161; 514/108; 562/9, 21

[56] References Cited

U.S. PATENT DOCUMENTS 4,871,721 10/1989 Biller .................. 514/102

FOREIGN PATENT DOCUMENTS 0298553 1/1989 European Pat. Off. .
0356866A 3/1990 European Pat. Off. .

OTHER PUBLICATIONS

Schweizer et al. in J. Org. Chemistry, vol. 33, No. 1 pp. 336–339 (1968).
Poulter C. D. et al. J. Org. Chem. 51, 4768 (1986).
Poulter C. D. et al, J.A.C.S 109, 5542 (1987).
Poulter C. D., et al., *Biosynthesis of Isoprenoid Compounds*, "Conversion of Farnesyl Pyrophosphate to Squalene", vol. 1, Chapter 8, pp. 413–441, J. Wiley and Sons, 1981.
Faust, J. R., et al., *Proc. Nat. Acad. Sci., USA*, "Squalene synthetase activity in human fibroblasts: Regulation via the low density lipoprotein receptor", 1979, 76, 5018–5022.
de Montellano, P. Ortiz, et al., *J. Med. Chem.*, "Inhibition of Squalene Synthetase by Farnesyl Pyrophosphate Analogues", 1977 20, 243–249.
Corey and Volante, *J. Am. Chem. Soc.* "Application of Unreactive Analogs of Terpenoid Pyrophosphates to Studies of Multistep Biosynthesis, Demonstration that 'Presqualene Pyrophosphate' is an Essential Intermediate on the Path to Squalene", 1976, 98, 1291–3.
Sandifer, R. M. et al., *J. Am. Chem. Soc.*, 1982, 104, 7376–8, "Squalene Synthetase, Inhibition by an Ammonium Analogue of a Carbocationic Intermediate in the Conversion of Presqualene Pyrophosphate to Squalene".

(List continued on next page.)

Primary Examiner—Thurman K. Page
Assistant Examiner—Jyothsna Venkat
Attorney, Agent, or Firm—Burton Rodney

[57] ABSTRACT

Compounds which are inhibitors of cholesterol biosynthesis (by inhibiting de novo squalene biosynthesis), and thus are useful as hypocholesterolemic agents and antiatherosclerotic agents are provided which have the structure $$R^1-(CH_2)_n-X-(CH_2)_m-\overset{\overset{O}{\|}}{\underset{\underset{OR^2}{|}}{P}}-\overset{\overset{Y^1}{|}}{\underset{\underset{Y^2}{|}}{C}}-\overset{\overset{O}{\|}}{\underset{\underset{OR^4}{|}}{P}}-OR^3$$

wherein
m is 0, 1, 2 or 3; n is 0, 1, 2, 3 or 4;
$Y^1$ and $Y^2$ are H or halogen;
$R^2$, $R^3$ and $R^4$ may be the same or different and are independently H, metal ion, $C_1$ to $C_8$ alkyl or $C_3$ to $C_{12}$ alkenyl;
X is O, S, NH or $NCH_2R^{15}$ wherein $R^{15}$ is H or $C_1$ to $C_5$ alkyl; and
$R^1$ is $R^5$—$Q^1$—$Q^2$—$Q^3$— wherein $R^5$, $Q^1$, $Q^2$ and $Q^3$ are as defined herein;

and when m is o, X is other than S; and if m is o and X is O, then n is 1, 2, 3 or 4; including all stereoisomers thereof.

32 Claims, No Drawings

OTHER PUBLICATIONS

Bertolino, A., et al., *Biochim. Biophys. Acta.*, 1978, 530, 17–23, "Polyisoprenoid Amphiphilic Compounds as Inhibitors of Squalene Synthesis and Other Microsomal Enzymes".

Davisson, V. J. et al., *J. Org. Chem.*, 1986, 51, 4768–4779, "Phosphorylation of Isoprenoid Alcohols".

Stremler, K. E. et al., *J.A.C.S.*, 1987 109, 5542, "Methane and Difluoromethanediphosphonate Analogues of Geranyl Diphosphate: Hydrolysis-Inert Alternate Substrates".

McClard, R. W., et al., *J. Am. Chem. Soc.*, 1987, 109, 5544–5545, "Novel Phosphonylphosphinyl (P-C-P-C) Analogues of Biochemically Interesting Diphosphates, Syntheses and Properties of P-C-P-C Analogues of Isopentenyl Diphosphate and Dimethylallyl Diphosphate".

Capson, T. L., PhD dissertation, Jun. 1987, Dept. of Medicinal Chemistry, the University of Utah, Abstract, Table of Contents, pp. 16, 17, 40–43, 48–51, Summary.

Stowell, M. H. B., et al, "The Phosphonylphosphinyl Dianion: A Convenient Synthon for the Preparation of Biologically Interesting Phoshonylphosphinyl (P-C-P-C) Compounds," Tetrahedron Letters, vol. 30, No. 4, pp. 411–414, 1989.

Biller, S. A. et al, "Isoprenoid (Phosphinylmethyl)phosphonates as Inhibitors of Squalene Synthetase," J. Med. Chem., Oct. 1988, 31, 1869.

PHOSPHORUS-CONTAINING SQUALENE SYNTHETASE INHIBITORS

REFERENCE TO OTHER APPLICATIONS

This application is a continuation-in-part of U.S. patent application Ser. No. 237,940, filed Aug. 29, 1988, now abandoned and U.S. patent application Ser. No. 381,434, filed on Jul. 17, 1989, now abandoned.

FIELD OF THE INVENTION

The present invention relates to new phosphorus-containing compounds which are useful in inhibiting cholesterol biosynthesis by inhibiting de novo squalene production, to hypocholesterolemic and antiatherosclerotic compositions containing such compounds and to a method of using such compounds for inhibiting cholesterol biosynthesis and atherosclerosis.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413–441, J. Wiley and Sons, 1981 and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase, along with HMG-CoA reductase has been shown to be down-regulated by receptor mediated LDL uptake (Faust, J.R.; Goldstein, J.L.; Brown, M.S. *Proc. Nat. Acad. Sci. USA*, 1979, 76, 5018–5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

One approach to inhibitors of squalene synthetase is to design analogs of the substrate FPP. It is clear from the literature that the pyrophosphate moiety is essential for binding to the enzyme. However, such pyrophosphates are unsuitable as components of pharmacological agents due to their chemical and enzymatic lability towards allylic C-O cleavage, as well as their susceptibility to metabolism by phosphatases.

P. Ortiz de Montellano et al in *J. Med. Chem.*, 1977, 20, 243–249 describe the preparation of a series of substituted terpenoid pyrophosphate (Table A), and have shown these to be competitive inhibitors of the squalene synthetase enzyme. These substances retain the unstable allylic pyrophosphate moiety of FPP.

TABLE A

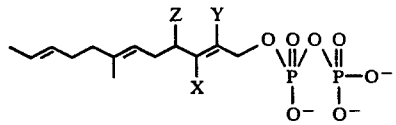

| No. | X | Y | Z |
|-----|-----|-----|-----|
| 1 | CH₃ | CH₃ | H |
| 2 | H | H | H |
| 3 | C₂H₅ | H | H |
| 4 | I | H | H |

TABLE A-continued

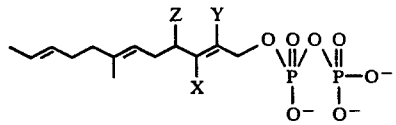

| No. | X | Y | Z |
|-----|-----|-----|-----|
| 5 | H | I | H |
| 6 | CH₃ | H | SCH₃ |

Corey and Volante, *J. Am. Chem. Soc.* 1976, 98, 1291-3, have prepared FPP analog A and presqualene pyrophosphate (PSQ-PP) analog B as inhibitors of squalene biosynthesis. (Presqualene pyrophosphate is an intermediate in the conversion of FPP to squalene). These inhibitors possess methylene groups in place of the allylic oxygen moiety of FPP and PSQ-PP, but still retain the chemically and enzymatically unstable pyrophosphate linkage.

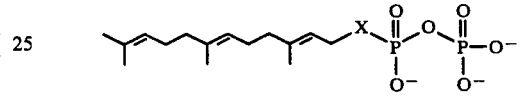

A    X = CH₂
FPP  X = O

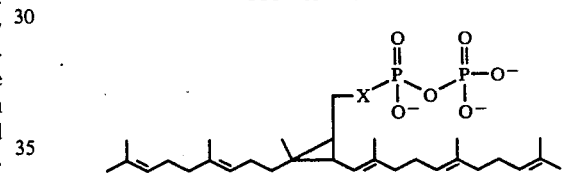

B      X = CH₂
PSQ-PP X = O

Poulter and co-workers have prepared cyclopropane C (Sandifer, R.M., et al., *J. Am. Chem. Soc.* 1982, 104, 7376-8) which in the presence of inorganic pyrophosphate is an intermediate analog inhibitor of the enzyme squalene synthetase.

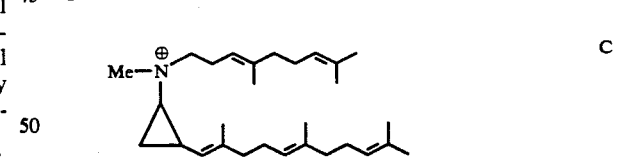

C

Altman and co-workers, Bertolino, A., et al., *Biochem. Biophys. Acta.* 1978, 530, 17–23, reported that farnesyl amine and related derivatives D inhibit squalene synthetase, but provide evidence that this inhibition is non-specific and probably related to membrane disruption.

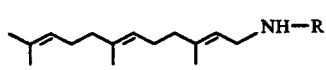

D

R = H, CH₂CH₂OH, CH₂CH₂OCH₃

Poulter, C.D., et al, *J. Org. Chem.*, 1986, 51, 4768, prepared compound E in a demonstration of a synthetic method, but did not report any biological data.

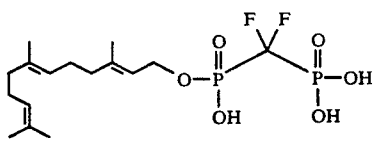

E

Poulter, C.D., Stremler, K.E., *J.A.C.S.*, 7, 109, 5542 describes the synthesis and biological evaluation of compounds having structure F. These compounds were evaluated as alternative substrates for avian liver and lemon peel farnesyl diphosphate cyclase.

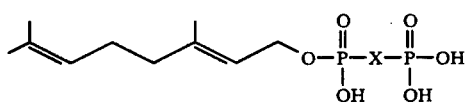

F

X = CH$_2$, CF$_2$

McClard, R. W. and Poulter, C. D., et al., *J.A.C.S* 1987, 109, 5544, reported that phosphinylphosphonates G and H were competitive inhibitors of the 1'-4-condensation between isopentenyl diphosphate and geranyl diphosphate catalyzed by avian liver farnesyl diphosphate synthetase. Phosphinylphosphonates G and H had Ki's of 19 μM and 71 μM, respectively. They also reported the speculative isolation of the farnesyl phosphinylphosphonate I, and the geranyl phosphinylphosphonate J from the enzymatic reaction of G with geranyl pyrophosphate or dimethylallyl pyrophosphate, respectively. The structures of I and J were tentatively assigned based on relative TLC mobilities. They hypothesized that I could be a potential inhibitor of squalene synthetase.

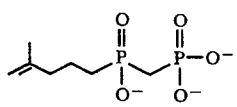

G

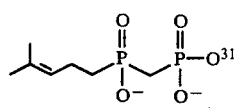

H

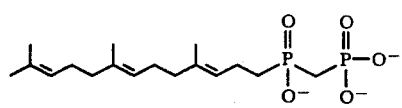

I

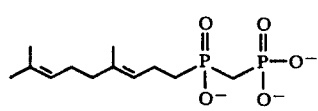

J

Capson, T.L., PhD dissertation, June 1987, Dept. of Medicinal Chemistry, the University of Utah, Abstract, Table of Contents, pp. 16, 17, 40–43, 48–51, Summary, and T.L. Capson, C.D. Poulter et al, *J. Org. Chem.*, 1988, 53, 5903–5908 disclose cyclopropanes of the structure K

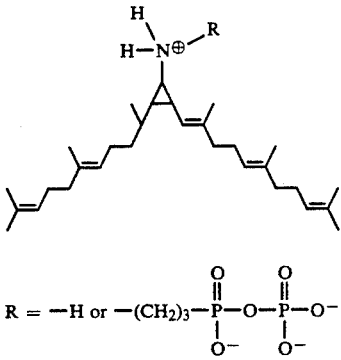

K

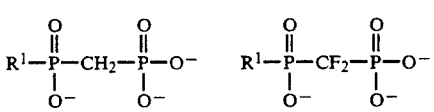

as intermediate analog inhibitors of squalene synthetase.

Biller and coworkers, "Isoprenoid (Phosphinylmethyl)phosphonates as Inhibitors of Squalene Synthetase," J. Med. Chem., 1988, 31, 1869, synthesized analogues of FPP, 2a-d and 3a,b, where the allylic and anhydride oxygen atoms are replaced with carbon. The PMP subunit thereby serves as a stable surrogate for the diphosphate. They demonstrate that isoprenoid (phosphinylmethyl)-phosphonates (PMPs) are effective inhibitors of squalene synthetase, binding to the enzyme with affinity comparable to FPP itself.

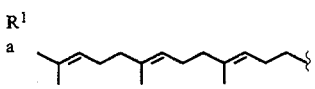

2a-d 3a, b

R$^1$ a 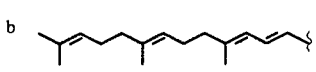

b 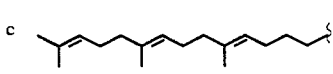

c 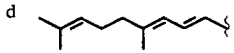

d 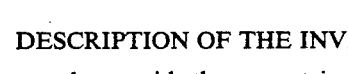

DESCRIPTION OF THE INVENTION

In accordance with the present invention, there is provided phosphorus-containing compounds which inhibit cholesterol biosynthesis, and thus are useful as hypocholesterolemic and antiatherosclerotic agents and have the following structure

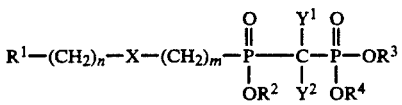

I.

wherein m is 0, 1, 2 or 3; n is 0, 1, 2, 3 or 4; Y$^1$ and Y$^2$ are H or halogen, preferably H or F; R$^2$, R$^3$ and R$^4$ are independently H, metal ion, C$_1$ to C$_8$ alkyl or C$_3$ to C$_{12}$ alkenyl; X is O, NH, $$-\underset{\underset{R^{15}}{|}}{\overset{|}{\underset{CH_2}{N}}}-$$

or S (wherein $R^{15}$ is H or $C_1$ to $C_5$ alkyl); $R^1$ is $R^5-Q^1-Q^2-Q^3-$ wherein $Q^1$, $Q^2$ and $Q^3$ are independently:

$$-\underset{\underset{R^7}{|}}{CH}-\underset{\underset{R^6}{|}}{C}=\underset{\underset{R^8}{|}}{C}-CH_2-, \quad -CH_2-\underset{\underset{R^9}{|}}{CH}-CH_2-CH_2-,$$

$$-CH_2-C\equiv C-CH_2-, \quad -CH_2-\underset{\underset{CH_2}{\|}}{C}-CH_2-CH_2-,$$

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, halo or haloalkyl (e.g. $CH_2F$, $CF_3$); $R^7$ is H, halogen, lower alkyl or alkylthio; $R^8$ is H, halogen, trimethylsilyl or lower alkyl; $R^9$ is H, or lower alkyl;

$R^5$ is $$R^{10}-\underset{\underset{R^{11}}{|}}{C}=\underset{\underset{R^{12}}{|}}{C}-CH_2-, \quad R^{14}-\underset{\underset{R^{13}}{|}}{CH}-CH_2-CH_2-,$$

$R^{16}-C\equiv C-CH_2-$ (wherein $R^{16}$ is lower alkyl or H), $$CH_3-\underset{\underset{CH_2}{\|}}{C}-CH_2-CH_2,$$

$R^{10}$ and $R^{11}$ are independently hydrogen, lower alkyl such as methyl or ethyl, halogen, lower alkenyl or haloalkyl or $R^{10}$ and $R^{11}$ can be taken together to form $(CH_2)_s$, where s is 2 to 7; $R^{12}$ is hydrogen, lower alkyl, halogen or lower alkenyl; $R^{13}$ and $R^{14}$ are independently lower alkyl such as methyl or ethyl; with the provisos that if all of $Q^1$, $Q^2$ and $Q^3$ are bonds, then and $R^{11}$ cannot both be H, and $R^5$ cannot be $CH_3(CH_2)_p-$, with $p<4$; if m is o, X is other than S; and if m is o and X is O, then n is 1, 2, 3 or 4.

The formula I compounds of the invention include all stereoisomers thereof.

Unless otherwise indicated, the term "lower alkyl" or "alkyl" as employed herein alone or as part of another group includes both straight and branched chain hydrocarbons containing 1 to 8 carbons in the normal chain, preferably 1 to 4 carbons, such as methyl, ethyl, propyl, isopropyl, butyl, t-butyl, isobutyl, pentyl, hexyl or isohexyl.

The term "lower alkenyl" or "alkenyl" as used herein by itself or as part of another group refers to straight or branched chain radicals of 2 to 12 carbons, preferably 3 to 6 carbons in the normal chain, which include one double bond in the normal chain, and which may include an aryl or alkyl substituent, such as vinyl, 2-propenyl, 2-butenyl, 3-phenyl-2-propenyl, 2-pentenyl, 2-hexenyl, 2-heptenyl, 2-octenyl, 2-nonenyl, 2-decenyl, 2-undecenyl, 2-dodecenyl and the like.

The term "halogen" or "halo" as used herein refers to chlorine, bromine, fluorine, and iodine with chlorine or fluorine being preferred.

The term "haloalkyl" as used herein refers to any of the lower alkyl groups defined above substituted with a halogen as defined above, for example $CH_2F$, $CF_3$ and the like.

The term "metal ion" refers to alkali metal ions such as sodium, potassium or lithium and alkaline earth metal ions such as magnesium and calcium.

Preferred are those compounds of formula I which have the following formula:

$$R^5-Q^1-Q^2-Q^3-(CH_2)_n-X-(CH_2)_m-\underset{\underset{O-Y^2}{|}}{\overset{\overset{O}{\|}}{P}}-\underset{\underset{|}{|}}{\overset{\overset{Y^1}{|}}{C}}-\underset{\underset{O^-}{|}}{\overset{\overset{O}{\|}}{P}}-O^- \quad \text{IA}$$

wherein $R^5$ is $$CH_3-\underset{\underset{CH_3}{|}}{C}=CH-CH_2-;$$

$Q^3$ is a bond;
$Q^2$ is $$-CH_2-\underset{\underset{CH_3}{|}}{C}=CH-CH_2-; \quad -CH_2-C\equiv C-CH_2-; \text{ or}$$

$$-CH_2-CH=CH-CH_2-;$$

$Q^1=$ $$-CH_2-\underset{\underset{CH_3}{|}}{C}=CH-CH_2-;$$

n is 0 or 1; m is 1 or 2; X is O and $Y^1$ and $Y^2$ are each H or F, in the form of the salts or acid.

In addition, preferred are those compounds of formula I which have the following structure IA-A $$CH_3-\underset{\underset{CH_3}{|}}{C}=CH-CH_2-CH_2-\underset{\underset{CH_3}{|}}{C}=CH-CH_2-Q-(CH_2)_n-X-\underset{\underset{OR^2}{|}}{\overset{\overset{O}{\|}}{P}}-\underset{\underset{Y^2}{|}}{\overset{\overset{Y^1}{|}}{C}}-\underset{\underset{OR^4}{|}}{\overset{\overset{O}{\|}}{P}}-OR^3$$

wherein Q is $$-CH_2-\underset{\underset{CH_3}{|}}{C}=CH-CH_2-$$

or a bond; n is 1 or 2; X is O, $Y^1$ and $Y^2$ are each H or each F; $R^2$, $R^3$ and $R^4$ are alkyl, H or metal ions; or X is NH and n is 0.

The compounds of the invention may be prepared according to the following reaction sequences.

Compounds of formula I of the invention wherein m is 1, 2 or 3, X is O, S, or NH or NCH$_2$R$^{15}$ may be prepared according to the following reaction Sequence I to V:

Scheme I $$R^1-(CH_2)_n-X^1-(CH_2)_m-\underset{\underset{OR^{2a}}{|}}{\overset{\overset{O}{\|}}{P}}-OR^{2a} \quad \xrightarrow[\begin{array}{c}\text{B. NaCN,}\\\text{DMSO or}\\\text{C. NaI, DMF}\end{array}]{\begin{array}{c}\text{A. }^-\text{OH} \quad \text{or}\\\text{(Hydrolysis)} \quad \text{mono-}\\\text{dealkylation}\end{array}}$$

IIA (X$^1$ = O, S or N-Pro)
(R$^{2a}$ is C$_1$-C$_8$ alkyl or C$_3$-C$_{12}$ alkenyl)

$$R^1-(CH_2)_n-X^1-(CH_2)_m-\underset{\underset{OR^{2a}}{|}}{\overset{\overset{O}{\|}}{P}}-OH$$

IIIA (X$^1$ = O, S or N-Pro)

Scheme IA $$\text{IIA (X}^1 = \text{O, S)} \xrightarrow[\begin{array}{c}\text{D. 1. TMSBr}\\\text{2. R}^{2a}\text{OH, DCC,}\\\text{pyridine}\end{array}]{\begin{array}{c}\text{bisdealkylation}\\\text{and reesterification}\end{array}} \text{IIIA}$$

Scheme II $$R^1-(CH_2)_n-X^1-(CH_2)_m-\underset{\underset{OR^{2a}}{|}}{\overset{\overset{O}{\|}}{P}}-OH \xrightarrow[\begin{array}{c}\text{1. (C}_2\text{H}_5)_2\text{NSi(CH}_3)_3\\\text{2. (COCl)}_2\text{, DMF}\end{array}]{} \begin{array}{c}\text{acid}\\\text{chloride}\\\text{formation}\end{array}$$

(m is 1, 2 or 3)
IIIA (X$^1$ = O or S)

$$3. \oplus M^\ominus CY^1Y^2\overset{\overset{O}{\|}}{\underset{\underset{OR^{4a}}{|}}{P}}-OR^{3a} \quad \begin{array}{c}\alpha\text{-phos-}\\\text{phonate}\\\text{anion}\\\text{P-C-P}\\\text{coupling}\end{array}$$

XII $$R^1-(CH_2)_n-X^2-(CH_2)_m-\underset{\underset{OR^{2a}}{|}}{\overset{\overset{O}{\|}}{P}}-\underset{\underset{}{}}{\overset{\overset{Y^1}{}}{C}}\underset{\underset{}{}}{\overset{\overset{Y^2}{}}{}}-\underset{\underset{OR^4}{|}}{\overset{\overset{O}{\|}}{P}}-OR^{3a} \xrightarrow[\begin{array}{c}\text{1. TMSBr or}\\\text{TMSI}\\\text{2,4,6-collidine}\\\text{CH}_2\text{Cl}_2\\\text{2. }^\ominus\text{OH}\end{array}]{}$$

IA (where X$^2$ = O or S)

$$R^1-(CH_2)_n-X^2-(CH_2)_m-\underset{\underset{O^\ominus}{|}}{\overset{\overset{O}{\|}}{P}}-\overset{Y^1 \quad Y^2}{C}-\underset{\underset{O^\ominus}{|}}{\overset{\overset{O}{\|}}{P}}-O^\ominus \xrightarrow{\text{Strong acid}}$$

ID (X$^2$ = O, S)

$$R^1-(CH_2)_n-X^2-(CH_2)_m-\underset{\underset{OH}{|}}{\overset{\overset{O}{\|}}{P}}-\overset{Y^1 \quad Y^2}{C}-\underset{\underset{OH}{|}}{\overset{\overset{O}{\|}}{P}}-OH$$

IE (X$^2$ = O, S)

Scheme III $$R^1-(CH_2)_n-X^1-(CH_2)_m-\underset{\underset{OR^{2a}}{|}}{\overset{\overset{O}{\|}}{P}}-OH \xrightarrow[\begin{array}{c}\text{DCC, DMAP, Pyridine}\\\text{p-NO}_2\text{phenol}\\\text{Esterification}\end{array}]{}$$

(m is 1, 2 or 3)
(X$^1$ = O, S, N-Pro)
IIIA $$R^1-(CH_2)_n-X^1-(CH_2)_m-\underset{\underset{OR^{2a}}{|}}{\overset{\overset{O}{\|}}{P}}-O-\text{C}_6\text{H}_4-NO_2 \xrightarrow{\text{THF}}$$

IV (X$^1$ = O, S, N-Pro)

$$\oplus M^\ominus CY^1Y^2\overset{\overset{O}{\|}}{\underset{\underset{OR^{4a}}{|}}{P}}OR^{3a}$$

(PCP coupling)
VII $$R^1-(CH_2)_n-X^1-(CH_2)_m-\underset{\underset{OR^{2a}}{|}}{\overset{\overset{O}{\|}}{P}}-\overset{Y^1 \quad Y^2}{C}-\underset{\underset{OR^{4a}}{|}}{\overset{\overset{O}{\|}}{P}}-OR^{3a}$$

IB (X$^1$ = O, S or N-Pro)

Scheme IV $$\text{IB (where X}^1 = \text{NPro)} \xrightarrow[\begin{array}{c}\text{1). TMSI, Collidine}\\\text{(Deprotection)}\\\text{2). }^-\text{OH (Hydrolysis)}\end{array}]{}$$

(m is 1, 2 or 3)

$$R^1(CH_2)_n-\underset{\underset{H}{|}}{N}-(CH_2)_m-\underset{\underset{O^\ominus}{|}}{\overset{\overset{O}{\|}}{P}}-\overset{Y^1 \quad Y^2}{C}-\underset{\underset{O^\ominus}{|}}{\overset{\overset{O}{\|}}{P}}-O^\ominus$$

IC

Scheme V $$\text{IC} \xrightarrow[\begin{array}{c}R^{15}CHO\\\text{alcoholic solvent}\\\text{or acetonitrile}\\\text{NaBH}_3\text{CN, pH 3 to 8}\end{array}]{}$$

(m is 1 2 or 3)

$$R^1-(CH_2)_n-\underset{\underset{\underset{\underset{R^{15}}{|}}{CH_2}}{|}}{N}-(CH_2)_m-\underset{\underset{O^\ominus}{|}}{\overset{\overset{O}{\|}}{P}}-\overset{Y^1 \quad Y^2}{C}-\underset{\underset{O^\ominus}{|}}{\overset{\overset{O}{\|}}{P}}-O^\ominus$$

IC$^1$

Scheme V'

IIIA + [2-fluoro-N-methylpyridinium tosylate] $\xrightarrow{\text{Organic base}}$ $$R^1-(CH_2)_n-X^1-(CH_2)_m-\underset{\underset{OR^{2a}}{|}}{\overset{\overset{O}{\|}}{P}}-F \xrightarrow[\begin{array}{c}\text{VII}\\\text{PCP}\\\text{coupling}\\\text{THF}\end{array}]{} \text{IB}$$

IVA

Scheme VI. Compounds of formula I of the invention wherein m is O, X is —O— and n is 2, 3 or 4, may be prepared using the methylene bisphosphonate synthesis methodology developed by Poulter, C.D. et al., *J. Org. Chem.*, 1986, 51, 4768, as outlined below:

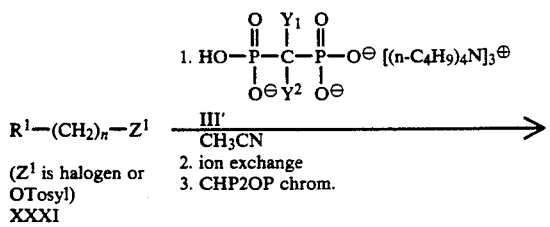

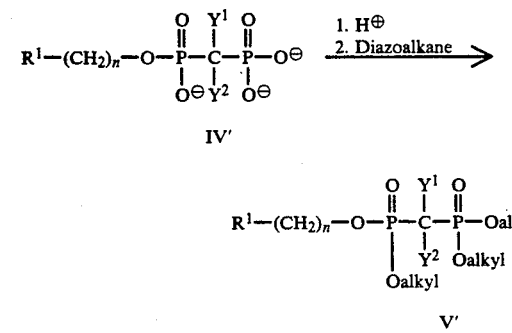

Scheme VII. Compounds of formula I wherein m is 0, X is 0, and R is lower alkyl may be prepared according to the following reactions:

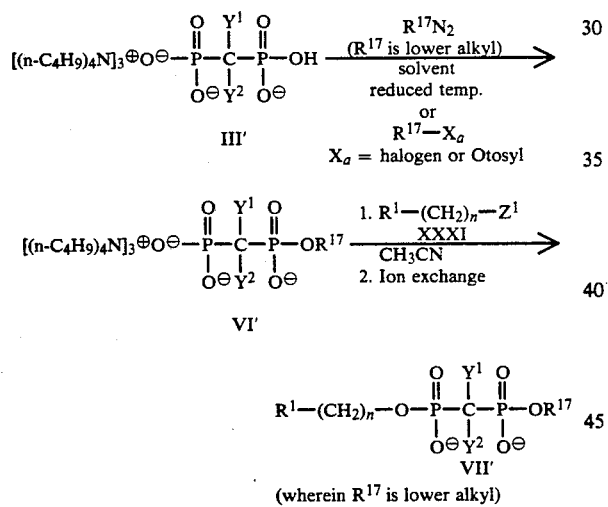

Scheme VII'. In an alternative method, compounds of formula I where m is o, X is O and R is lower alkyl may be prepared according to the following reaction:

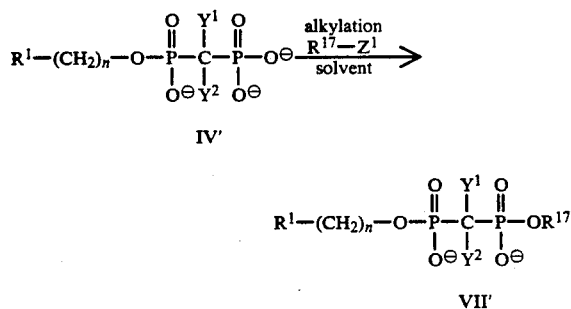

Scheme VIII. Triester compounds of formula I wherein m is o and X is —NH— or —N(CH$_2$R$^{15}$)— may be prepared according to the following reaction sequence:

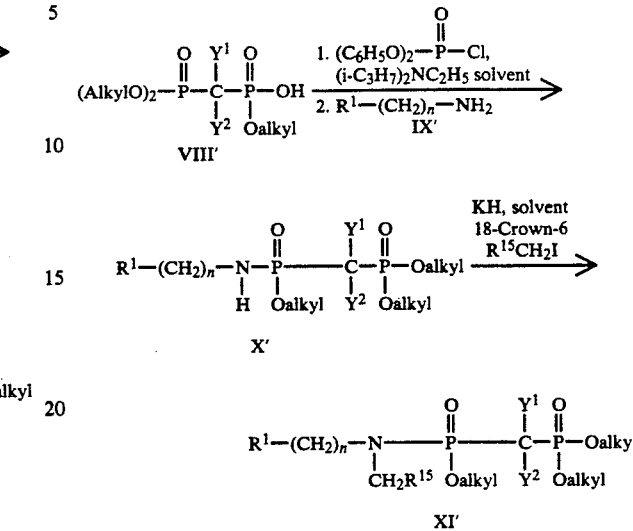

Scheme IX. Di- and tri-acid salts of formula I where m is o and X=—NH— and —N(CH$_2$R$^{15}$)— may be prepared according to the following scheme:

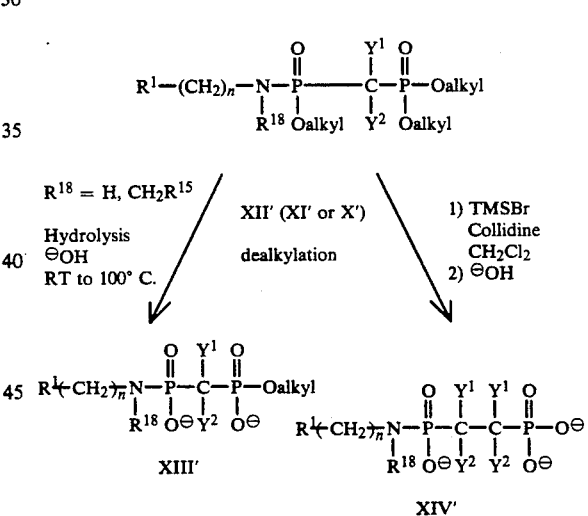

As seen in Reaction Scheme I, compounds of formula I where X is O, S or NH may be prepared in accordance with the following method of the invention starting with diester IIA (which is a new intermediate).

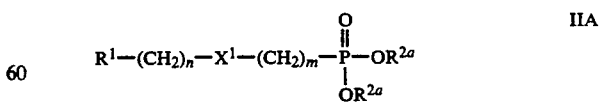

wherein X$^1$ is O, S or N-Pro and Pro is a nitrogen protecting group such as t-butyloxycarbonyl (t-BOC) or benzyloxycarbonyl (CBZ).

The diester IIA may be converted to the corresponding monoester IIIA (which is a new intermediate)

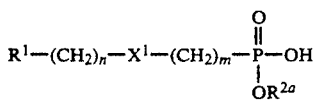   IIIA by any of four methods (A, B, C or D) as discussed below.

In Method A, diester IIA is treated with a strong aqueous base such as NaOH, KOH or LiOH, typically in the presence of a solvent such as dioxane, isopropanol, methanol or ethanol at a temperature within the range of from about 25° to about 125° C. to form monoester IIIA.

In Methods B and C of the invention, diester IIA is subjected to a monodealkylation by treatment with sodium cyanide, potassium cyanide or lithium cyanide and a solvent such as dimetyl sulfoxide or dimethylformamide (Method B) or with sodium iodide, lithium iodide or lithium chloride in the presence of a solvent such as dimethylformamide, dimethyl sulfoxide or acetone, the above reactions being carried out at a temperature of within the range of from about 40° to about 160° C., to form monoester IIIA.

In Method D of the invention (Reaction Scheme IA), diester IIA is subjected to a bisdealkylation by treating IIA with bromotrimethylsilane under an inert atmosphere such as argon in the presence of 2,4,6-collidine or triethylamine in dichloromethane and then reesterifying by reacting with an alcohol (R$^{2a}$OH) in the presence of dicyclohexylcarbodiimide (DCC) and an organic base such as pyridine, or 4-dimethylaminopyridine (DMAP) to form monoester IIIA.

As seen in Reaction Scheme II, compounds of formula I where X is O or S may be prepared in accordance with the following method of the invention starting with monoester IIIA where X$^1$ is O or S which is dissolved in an inert organic solvent such as dichloromethane and treated, under an inert atmosphere such as argon, with diethyl(trimethylsilyl)amine. After evaporation of solvent, the residue is dissolved in dichloromethane or an aromatic solvent such as benzene or toluene, or other appropriate inert organic solvent, preferably containing dimethylformamide as a catalyst, under an inert atmosphere such as argon, and oxalyl chloride is added thereto. The reaction mixture is evaporated t give acid chloride V (which is a new intermediate)

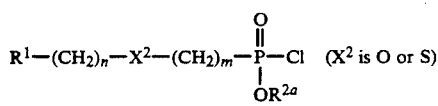   V where R$^{2a}$ is C$_1$–C$_8$ alkyl or C$_3$–C$_{12}$ alkenyl.

An α-phosphonate anion P—C—P coupling is carried out on the acid chloride V as follows.

To a stirred solution of an optionally substituted dialkyl methyl phosphonate

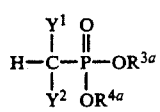   VI wherein Y$^1$, and Y$^2$ are as defined hereinbefore and R$^{3a}$ and R$^4a$ are independently C$_1$–C$_8$ alkyl or C$_3$–C$_{12}$ alkenyl, in an inert organic solvent such as tetrahydrofuran cooled to a temperature within the range of from about −90° C. to about 0° C. is added a strong base, such as n-butyl lithium or lithium diisopropylamide, in hexane, tetrahydrofuran or other inert organic solvent under an inert atmosphere such as argon, followed in some instances by transmetallation by the addition of a metal halide, such as CeCl$_3$, ZnCl$_2$, MgBr$_2$, CuI, to form the metal salt VII

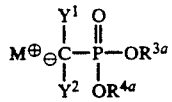   VII wherein M is Li+, Na+, K+, +MgHal, +ZnHal, +Ce(-Hal)$_2$ or +Cu wherein Hal is a halogen ion such as Cl−, Br− or I−.

The metal salt VII is maintained at a reduced temperature as described above and acid chloride V in an inert organic solvent such as tetrahydrofuran or diethyl ether is added to form the phosphinyl-phosphonate IA.

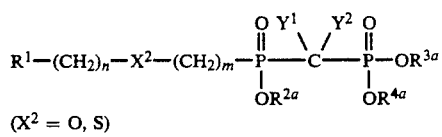   IA (X$^2$ = O, S)

The metal salt VII will be employed in a molar ratio to acid chloride V of within the range of from about 1.0:1 to about 2.5:1 and preferably from about 1.8:1 to about 2.4:1. Triester IA, in an inert organic solvent such as methylene chloride, may then be subjected to dealkylation by treating with excess bromotrimethylsilane or iodotrimethylsilane in the presence of 2,4,6-collidine or bis(trimethylsilyl)trifluoroacetamide and then treating with a strong inorganic base such as aqueous NaOH, KOH, LiOH or Mg(OH)$_2$, optionally in the presence of an alcohol such as methyl alcohol, to form the salt ID which may be separated out by chromatography. Salt ID may be treated with a strong acid such as HCl to form acid IE.

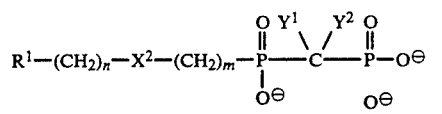   ID

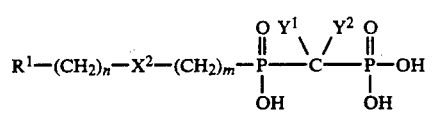   IE

As seen in Reaction Scheme III, compounds of formula I where X is O, S or NH may be prepared according to the following method of the invention starting with monoester IIIA (X$^1$=O,S,N-Pro) which is dissolved in pyridine, and treated with p-nitrophenol and 4-dimethylaminopyridine and dicyclohexylcarbodiimide under an inert atmosphere such as argon at 25°–60° C. (employing a molar ratio of phenol:IIIA of within the range of from about 0.8:1 to about 1.2:1) to form the p-nitrophenyl ester IV (which is a new intermediate)

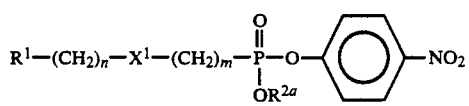

(where $X^1$ is O, S or N-Pro)

An -phosphonate anion P—C—P coupling is carried out on nitrophenyl ester IV by reacting nitrophenyl ester IV with metal salt VII in a manner similar to that described above for IA to form the phosphinyl-phosphonate IB

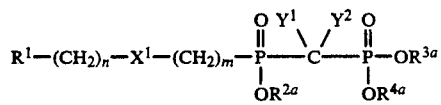

($X^1$ is O, S or N-Pro)

The metal salt VII will be employed in a molar ratio to p-nitrophenyl ester IV of within the range of from about 1.0:1 to about 2.5:1 and preferably from about 1.8:1 to about 2.4:1. Triester IB, ($X^1$=O,S) is identical to IA above, and may be subjected to dealkylation as described for IA to form ID and IE.

As seen in Reaction Scheme V', phosphonic acid IIIa could be converted to acid fluoride IVA by treatment with 2-fluoro-1-methylpyridinium toluene-4-sulfonate and an organic base such as an amine base ($(CH_3CH_2)_3N, ((CH_3)_2NCH_2CH_3)$), followed by reaction with anion VII to provide IB.

As seen in Reaction Scheme IV, compounds of formula IC wherein X is

may be prepared according to the following method of the invention by treating compound IB where $X^1$ is N-Pro with a solution of iodotrimethylsilane, and 2,4,6-collidine or bis(trimethylsilyl)trifluoroacetamide followed by treating with strong alkali metal base, such as NaOH, KOH or LiOH to form the corresponding salt IC.

In Reaction Scheme V, compounds of formula I wherein X is

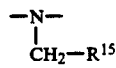

may be prepared by treating compound IC with aldehyde wherein $R^{15}$ is H or $C_1$ to $C_5$ alkyl) in the presence of an alcoholic solvent such as ethanol or acetonitrile at a pH of 3 to 8 to form $IC^1$.

The triesters IA or IB (X=O,S) may be hydrolyzed to the corresponding monoester IJ as follows.

Triester IA or IB where $X^1$ and $X^2$ are O or S may be treated with strong inorganic bases such as KOH, NaOH or LiOH in $H_2O$ or $H_2O$/alcohol mixtures, or with nucleophiles such as, NaCN, KCN, NaI, LiCl, or LiBr in dimethylformamide or dimethylsulfoxide, under an inert atmosphere such as argon, employing a molar ratio of base or nucleophile to triester of within the range of from about 2:1 to about 10:1, and at a temperature within the range of from about 25° to about 160° C. to form the monoester IJ

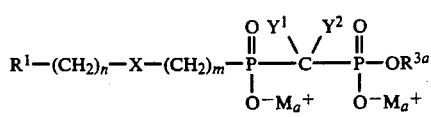

where $M_a$ is an alkali metal.

Triester IB where $X^1$ is N-Pro may be hydrolyzed to the monoester IK by treating IB ($X^1$=N-Pro) with p-toluenesulfonic acid in refluxing benzene or trifluoroacetic acid at −20° C. to 25° C. to remove the N-protecting group and then hydrolyzing as described above with respect to triester IA and IB to form monoester IK

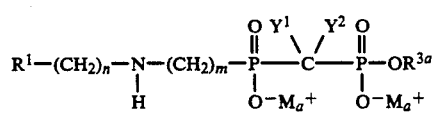

In preparing compounds wherein X is NH, the nitrogen atom in the starting material may be protected by treating a solution of amine IIC (which is a new intermediate)

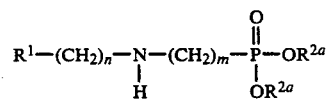

with an inert organic solvent such as methylene chloride, under an inert atmosphere, with a protecting reagent such as di-t-butyl dicarbonate, or benzyl chloroformate, optionally in the presence of an amine base such as triethylamine or pyridine, to form the protected starting material IID (which is a new intermediate)

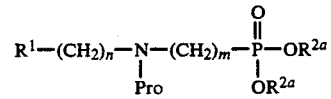

where Pro can be

As seen in the above reaction sequence VI compounds of formula V' of the invention may be prepared by treating compound XXXI XXXI 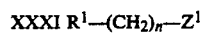

(where $Z^1$ is halogen or Otosyl) with dry tris(tetra-n-butyl)ammonium hydrogen diphosphonate III'

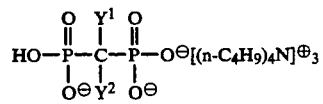

in an inert organic solvent such as dry acetonitrile ($CH_3CN$), nitromethane ($CH_3NO_2$) or methylene chloride ($CH_2Cl_2$) under an inert atmosphere such as argon, employing a molar ratio of III':XXXI of within the range of from about 1:1 to about 5:1 and preferably about 3:1. The solvent is removed and the residue is run through an ion exchange column to form compound IV' as an alkali metal or ammonium salt.

Compound IV' is converted to the free acid by typical acid-base extraction, and the free triacid may be treated with a diazoalkane to form the ester V. The latter reaction is carried out employing a molar ratio of diazoalkane:IV' of within the range of from about 3:1 to about >10:1 and preferably from about 3:1 to about 4:1.

In reaction sequence VII, compounds of formula I wherein m is o, X is O and R is lower alkyl may be prepared by treating III' with a diazoalkane ($R^{17}N_2$) in the presence of a suitable solvent such as ethyl ether or benzene, at a reduced temperature of within the range of from about 25° C. to about −10° C. employing a molar ratio of diazoalkane:III of within the range of from about 1:1 to about 1.5:1.

Alternatively, as seen in Scheme VII, III' can be reacted with an alkylating agent $R^{17}$-Xa (in a molar of 2:1 to 1:2) in an inert solvent such as THF or acetonitrile, at temperatures ranging from about 25° to about 65° C., to provide VI'.

The resulting reaction product VI' is reacted with tosyl compound XXXI in the presence of an organic solvent such as acetonitrile, $CH_3NO_2$ or $CH_2Cl_2$ employing a molar ratio of VI':XXXI of within the range of from about 1:1 to about 5:1 and preferably from about 1:1 to about 3:1, to form the monoester of the invention VII'.

In carrying out the alternative method for preparing compounds of formula I where X is O and R is lower alkyl, the alkylation reaction VII' is carried out employing a molar ratio of $R^{17}$-$Z^1$:IV' of within the range of from about 1:1 to about 1.5:1. The reaction is carried out in the presence of an inert organic solvent such as acetonitrile or dimethylformamide at a reduced temperature of from about 0° to about 100° C.

Referring to reaction sequence VIII, wherein compounds of formula I and intermediates where X is —NH— and —$NR^{18}$— are prepared, a solution of trialkylmethylene diphosphonate VIII' and diisopropylethylamine in an organic solvent such as methylene chloride, under an inert atmosphere such as argon, is treated with diphenylchlorophosphate. The resulting solution is reacted with amine IX' employing a molar ratio of VIII':IX' of within the range of from about 1:1.2 to about 1.2:1 to form the trialkyl compound of the invention X'.

Compounds of formula I where X is —$N(CH_2R^{15})$ may be prepared by treating X' with KH, 18-crown-6 and $R^{18}I$ at a temperature of about 0° C. to about 65° C. employing a molar ratio of $R^{15}CH_2I$ to X' of within the range of from about 2:1 to about 3:1.

Referring now to reaction sequence IX, compounds XII', where $R^{18}$=H or $CH_2R^{15}$, can be converted to the corresponding monoester XIII' by treatment with excess hydroxide between room temperature and about 100° C. Compounds XII' can be dealkylated to triacid salts XIV' by reaction with bromotrimethyl silane (TMSBr) (from about 3 to about 6 equiv.) and 2,4,6-collidine (from about 1 to about 4 equiv) in dichloromethane between about 0° C. and room temperature, followed by hydrolysis with hydroxide.

The starting material IIA may be prepared in accordance with the following method of the invention starting with compound X X  $R^1$—$(CH_2)_n$—$X^1H$ where $X^1$ is O, S or N-Pro which is made to undergo carbene insertion by treating a solution of X in dry deoxygenated solvent such as deoxygenated benzene under an inert atmosphere such as argon with

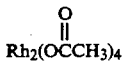

and then with phosphonate XI

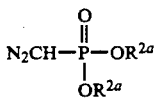

(prepared as described by Seyferth, D. et al, J.O.C. 1971, 36, 1379) in dry deoxygenated solvent as described above to form compound IIA.

In carrying out the above carbene insertion compound X is employed in a molar ratio to phosphonate XI of within the range of from about 1:1 to about 1:3 and preferably about 1:2.

In a preferred method, the starting material IIA wherein $R^{2a}$ is alkyl, m is 1, n is 0 and $X^1$ is O may be prepared by reacting farnesyl chloride with phosphonate alkoxide XIa

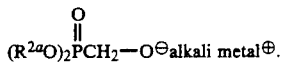

In another preferred method, in accordance with the following method of the invention, starting material IIA where $X^1$ is O or S and IIC where X is NH, may be prepared by alkylating XA XA  $R^1(CH_2)_n$—XH where X is O, S or NH, by treating XA in an inert organic solvent such as tetrahydrofuran, diethyl ether or benzene with a base such as n-butyllithium, NaH or $((CH_3)_3$—$Si)_2NLi$ when X is O or S or a trialkylamine base such as triethylamine or diisopropylethylamine when X is NH followed by treatment with XII

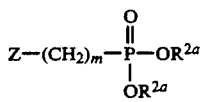

where Z=p—CH or $CF_3C_6H_5SO_3$—. The reaction is carried out under argon within the range of from about −78° C. to about 25° C. where X is O or S to form IIA ($X^1$=O,S) and from about −20° C. to about 80° C. where X is NH, to form IIC (X=NH).

In carrying out the above alkylation XA will be employed in a molar ratio to phosphonate XII of within the range of from about 2:1 to about 0.5:1 and preferably from about 0.9:1 to about 1.1:1.

The phosphonate XII where m is 1 may be prepared by treating phosphite XIII

XIII (R$^{2a}$O)$_2$—P—OH with paraformaldehyde and organic base such as triethylamine at a temperature within the range of from about 70° to about 120° C. under an inert atmosphere such as nitrogen to form compound XIV

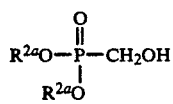    XIV

Compound XIV is dissolved in a suitable dry organic solvent such as diethyl ether, tetrahydrofuran or toluene and cooled to a temperature within the range of from about 25° C. to about −80° C. and then is treated with organic base such as diisopropylethyl amine, triethylamine and pyridine, optionally containing 4-dimethylaminopyridine, and then trifluoromethanesulfonic anhydride or p-toluenesulfonyl chloride in a suitable organic solvent such as diethyl ether, dichloromethane or pyridine to form phosphonate XII where m is 1.

The above reaction is carried out employing a molar ratio of XIII: paraformaldehyde of within the range of from about 0.8:1 to about 1.2:1 and a molar ratio of XV to trifluoromethanesulfonic anhydride or tosyl chloride of within the range of from about 0.8:1 to about 1.2:1.

Phosphonate XII where m is 2 or 3 may be prepared by treating alcohol XV

XV  Hal—(CH$_2$)$_t$CH$_2$OH where Hal is Cl, Br, or I and t is 1 or 2, with dihydropyran, employing a molar ratio of dihydropyran:XV of from about 2:1 to about 1:1, in the presence of an inert organic solvent such as methylene chloride, chloroform or toluene and catalytic amounts of p-toluenesulfonic acid or pyridinium p-toluenesulfonate at temperatures of from about 0° to about 25° C. to form tetrahydropyranyl ether XVI

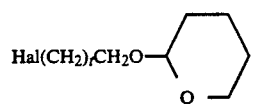    XVI

Tetrahydropyran XVI is treated with phosphite XVII

XVII  P(OR$^{2a}$)$_3$ (in a molar ratio of XVII:XVI of from about 20:1 to about 3:1) at 70–160° C. to form phosphonate XVIII

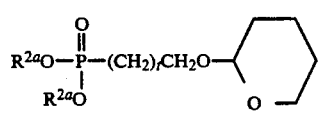    XVIII which is treated with acid such as pyridinium p-toluenesulfonate or p-toluenesulfonic acid in an alcohol solvent such as ethanol to form the phosphonate XIX

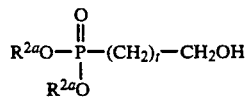    XIX

Phosphonate XIX is then treated with organic base and trifluoromethanesulfonic anhydride or p-toluene-sulfonyl chloride (as described above in forming phosphonate XII where m is 1) to form phosphonate XII where m is 2 or 3.

Compound IIA (X=O,S) where m is 2 may be prepared by a Michael addition to a vinyl phosphonate by treating a solution of compound XA (where X is O,S) and tetra-n-butyl-ammonium fluoride catalyst in tetrahydrofuran or other solvent such as benzene under an inert atmosphere such as argon with a vinyl phosphonate XX (employing a molar ratio of XA:XX of from about 0.8:1 to about 1.2:1)

    XX to form compound IIA where m is 2.

Compound IIC where m=2 is prepared by treating XA (X=NH) with XX (0.9–1.2 equiv) in alcohol solvent (for example, CH$_3$OH) at from 25° C.–80° C.

Compound IIA where X is S and where m is 1 may be prepared starting with compound XXI

    XXI (prepared as described by Farrington, G.F. et al, J. Med. Chem. 1988, 28, 1968) which is reacted with sodium ethoxide in ethanol followed by halide XXII XXII  R$^1$—(CH$_2$)$_n$—Hal (employing a molar ratio of XXI:XXII of from about 2:1 to about 1:1).

Compound IIA where X is S and m is 2 or 3 may be prepared starting with phosphonate XXIII

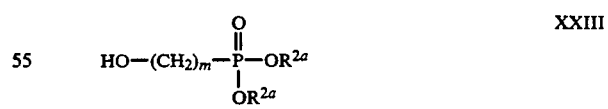    XXIII (where m is 2 or 3) which is subjected to a Mitsunobu coupling by treating XXIII with diisopropyl- or diethyl azodicarboxylate (DIAD, DEAD, resp.) and triphenyl phosphine in the presence of

to form XXIV

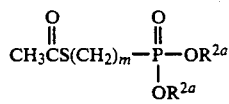

XXIV which is treated with sodium ethoxide in ethanol and then halide XXII (as described above) to form IIA where X is S and m is 2 or 3.

Compounds of formula IIA where m is 3 and X is O or S may be prepared starting with halide XXV XXV  $R^1$—$(CH_2)_n$—X—$CH_2CH_2$—Hal where X is O or S, and Hal is preferably Br or I, which is subjected to an α-phosphonate anion alkylation by treating XXV with phosphonate anion XXVI

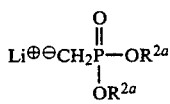

XXVI (molar ratio of XXV:XXVI of from about 1:2 to about 1:1) in an inert organic solvent such as tetrahydrofuran or diethyl ether to form compound IIA where m is 3 and X is O or S.

Halide XXV where X is O or S may be prepared by treating alcohol or thioalcohol XG XG  $R^1$—$(CH_2)_n$—$X^2$—H where $X^2$ is O or S with sodium hydride in the presence of an inert organic solvent such as tetrahydrofuran, and the alkylating agent $ClCH_2CH_2 \ominus \oplus Na$ in the presence of $(C_4H_9)_4NI$ followed by $(CH_3O)_2SO_2$ and the addition of a cosolvent such as dimethylformamide at from 0° C. to 60° C. to form ester XXVII XXVII  $R^1$—$(CH_2)_n$—$X^1$—$CH_2CO_2CH_3$ Ester XXVII is then reduced by treating with lithium aluminum hydride, lithium triethylborohydride or lithium borohydride in the presence of diethyl ether, or tetrahydrofuran to form alcohol XXVIII XXVIII  $R^1$—$(CH_2)_n$—$X^1$—$CH_2CH_2OH$ which is then converted to the corresponding mesylate by treating XXVIII with mesyl chloride, organic base such as triethylamine in an organic solvent such as methylene chloride. The resulitng mesylate is treated with a sodium halide such as sodium iodide in acetone while heating to a temperature within the range of from about 45° to about 65° C. to form the halide XXV.

Halide XXVA may be converted to phosphonate IIA or IIC via an Arbuzov reaction wherein XXVA is treated with phosphite XVII XXVA  $R^1$—$(CH_2)_n$—$X^1$—$(CH_2)_m$—Hal (where $X^1$ is O, S or N-Pro and m=2,3)

XVII  $P(OR^{2a})_3$ in a molar ratio of XVII:XXVA=20:1 to 3:1 while heating at a temperature within the range of from about 60° C. to about 160° C.

Halide XXVA where m=2 and $X^1$=O,S is identical to XXV. Other examples of XXVA are made by treating X with a base, such as NaH in tetrahydrofuran at 0° C. to 25° C., followed by reaction with dihalide Hal$^1$—$(CH_2)_m$—Hal$^2$, n=2,3, where Hal is Cl, Br or I.

The alcohol starting material X where n is 1 and $X^1$ is O that is XB

XB  $R^1$—$CH_2$—OH may be prepared according to the following reaction sequence (following the procedure of E.J. Leopold, *Organic Synthesis* 1985, 64, pp 164–173)

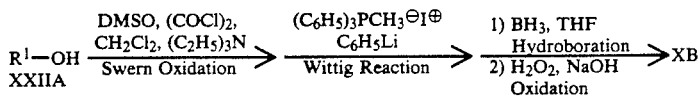

The alcohol starting material X where n is 2 and $X^1$ is O that is XC

XC  $R^1$—$CH_2CH_2$—OH may be prepared according to the following reaction sequence:

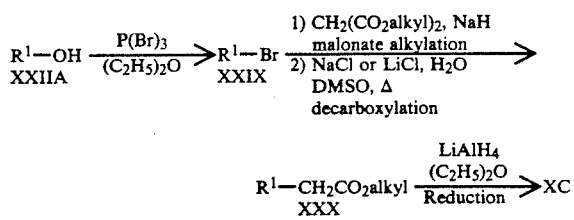

The alcohol starting material X where n is 3 and $X^1$ is O, that is XD

XD  $R^1$—$CH_2CH_2CH_2$—OH may be prepared according to the following reaction sequence

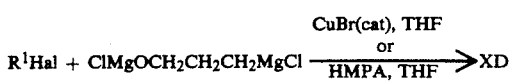

The amine starting material (X) where X is NH, namely

XE  $R^1$—$(CH_2)_n$—$NH_2$ may be prepared according to the following reaction sequence:

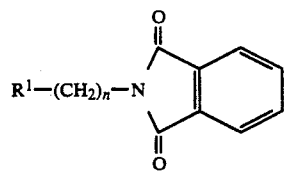

($Z^1$ is OTosyl or Hal)
when n is 1, 2 or 3
or $Z^1$ is Hal when n is 0)
XXXI

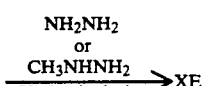

XXXII

The thiol starting material X where $X^1$ is S, that is XF

XF  $R^1-(CH_2)_nSH$ may be prepared according to the following reaction sequence:

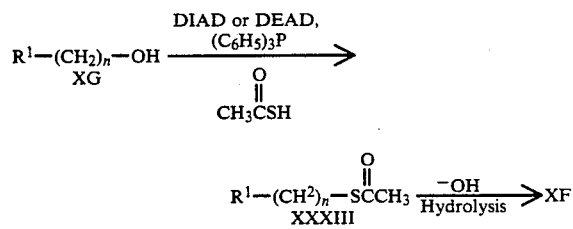

Examples of starting material X that is $R^1-(CH_2)_n-X^1H$ wherein $X^1$ is O, S, NH or N-Pro and n is 0, 1, 2, 3 or 4 suitable for use herein include the following which are either known in the literature or are simple derivatives of known compounds prepared by employing conventional procedures.

It will be appreciated that the compounds listed in the following table represent all possible stereoisomers.

$R^1-(CH_2)_n-X^1H$ (where $X^1$ is O, S, NH, NPro, n is 0, 1, 2 or 3) where
$R^1$ is $R^5-Q^1-Q^2-Q^3-$ as follows in A. through F.

A. 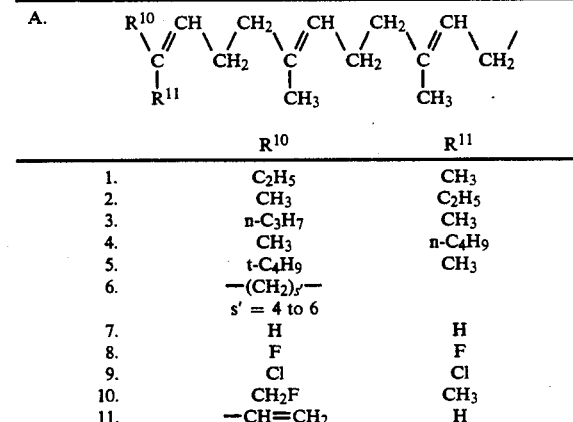

| | $R^{10}$ | $R^{11}$ |
|---|---|---|
| 1. | $C_2H_5$ | $CH_3$ |
| 2. | $CH_3$ | $C_2H_5$ |
| 3. | n-$C_3H_7$ | $CH_3$ |
| 4. | $CH_3$ | n-$C_4H_9$ |
| 5. | t-$C_4H_9$ | $CH_3$ |
| 6. | $-(CH_2)_{s'}-$ s' = 4 to 6 | |
| 7. | H | H |
| 8. | F | F |
| 9. | Cl | Cl |
| 10. | $CH_2F$ | $CH_3$ |
| 11. | $-CH=CH_2$ | H |

B. 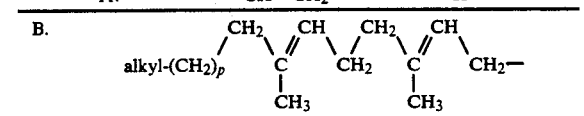

$R^1-(CH_2)_n-X^1H$ (where $X^1$ is O, S, NH, NPro, n is 0, 1, 2 or 3) where
$R^1$ is $R^5-Q^1-Q^2-Q^3-$ as follows in A. through F.

1. alkyl$(CH_2)_pCH_3(CH_2)_p$ where p is 3 to 7

2. 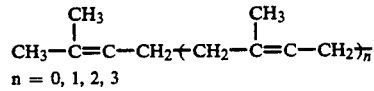 where p is 2 to 4

C. 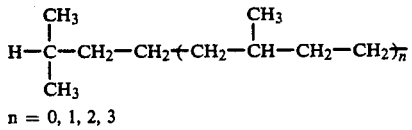
n = 0, 1, 2, 3

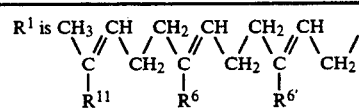
n = 0, 1, 2, 3

D. 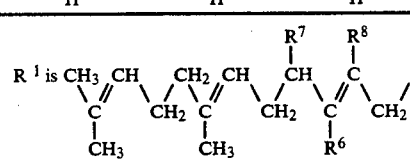

| | $R^{11}$ | $R^6$ | $R^{6'}$ |
|---|---|---|---|
| 1. | $C_2H_5$ | $C_2H_5$ | $CH_3$ |
| 2. | $CH_3$ | $CH_3$ | $C_2H_5$ |
| 3. | $CH_3$ | $C_2H_5$ | $C_2H_5$ |
| 4. | $C_2H_5$ | $C_2H_5$ | $C_2H_5$ |
| 5. | $CH_3$ | $C_2H_5$ | $CH_3$ |
| 6. | $CH_3$ | H | $CH_3$ |
| 7. | $CH_3$ | $CH_3$ | H |
| 8. | H | H | H |

E. 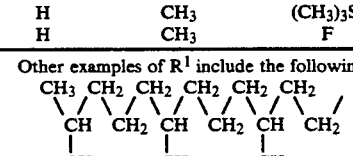

| | $R^7$ | $R^6$ | $R^8$ |
|---|---|---|---|
| 1. | H | I | H |
| 2. | H | H | I |
| 3. | H | $CH_3$ | $CH_3$ |
| 4. | $CH_3S$ | $CH_3$ | H |
| 5. | F | $CH_3$ | H |
| 6. | $CH_3$ | $CH_3$ | H |
| 7. | H | $CH_3$ | $CH_3$ |
| 8. | H | $CH_3$ | Cl |
| 9. | H | $CF_3$ | H |
| 10. | H | Cl | H |
| 11. | H | $CH_3$ | $(CH_3)_3Si$ |
| 12. | H | $CH_3$ | F |

F. Other examples of $R^1$ include the following

1. 

2. 

3. 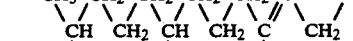

| -continued |
|---|
| R¹—(CH₂)ₙ—X¹H (where X¹ is O, S, NH, NPro, n is 0, 1, 2 or 3) where R¹ is R⁵—Q¹—Q²—Q³— as follows in A. through F. |

4. 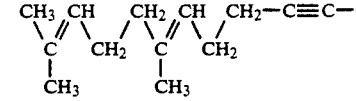

5. 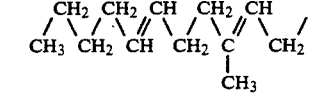

6. 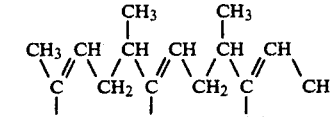

7. 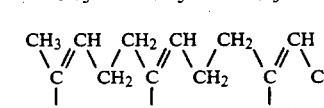

8. 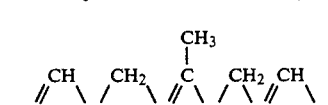

9. 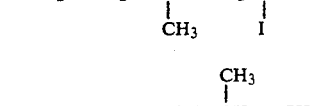

10. 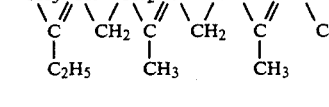

11. 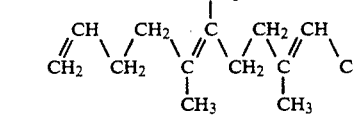

12. 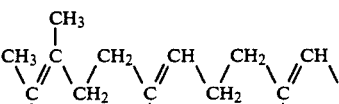

13. 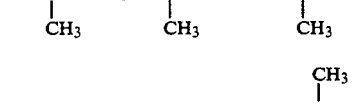

14. 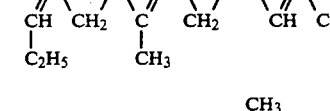

| -continued |
|---|
| R¹—(CH₂)ₙ—X¹H (where X¹ is O, S, NH, NPro, n is 0, 1, 2 or 3) where R¹ is R⁵—Q¹—Q²—Q³— as follows in A. through F. |

15.

16.

The compounds of Formula I of the invention inhibit cholesterol biosynthesis by inhibition of de novo squalene production. These compounds inhibit the squalene synthetase enzyme and, in addition, some of the compounds of Formula I of the invention inhibit other enzymes in the pathway from isopentenyl diphosphate to squalene, that is, farnesyl diphosphate synthetase and isopentenyl diphosphate-dimethylallyl diphosphate isomerase.

Thus, the compounds of the invention are useful in treating atherosclerosis to inhibit progression of disease and in treating hyperlipidemia to inhibit development of atherosclerosis. In addition, the compounds of the invention may increase plasma high density lipoprotein cholesterol levels.

As squalene synthetase inhibitors, the compounds of the invention may also be useful in inhibiting formation of gallstones and in treating tumors.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin.

The above compounds to be employed in combination with the squalene synthetase inhibitor of the invention will be used in amounts as indicated in the Physicians' Desk Reference (PDR).

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

Preparation of Rat Liver Microsomes

Livers are dissected from 2 or 3 decapitated Sprague Dawley rats and are quickly transferred to ice cold buffer (potassium phosphate, 0.05 M, (pH 7.4); MgC1₂, 0.004 M; EDTA, 0.001 M; and 2-mercaptoethanol 0.01 M) and rinsed thoroughly. The livers are minced in cold buffer (2.0 ml/g) and homogenized using a Potter-Elvejhem homogenizer. The homogenate is centrifuged at 5,000 x g, 10 minutes (4° C.), and the supernatant poured through 2 layers of cheese cloth. The supernatant is then centrifuged at 15,000 x g for 15 minutes (4°). Again the supernatant is filtered through 2 layers of cheese cloth, and centrifuged a third time at 100,000×g for 1.0 hour at 4° C. Following centrifugation the microsomal pellet is resuspended in a volume of buffer equivalent to 1/5 the volume of the original homogenate, and homogenized in a ground glass homogenizer. Aliquotted microsomes are frozen at −80° C., and retain activity for at least two months.

Enzyme Assay

Reaction, Mixtures are prepared in 50 ml round bottom pyrex glass tubes with tight-fitting, teflon-lined, screw caps. Tubes are cooled to 4° C., and the following components are added in sequence:

| | | |
|---|---|---|
| 1. | Potassium phosphate buffer 0.275M, pH 7.4) | 0.36 ml |
| 2. | KF (55 mM) | 0.36 ml |
| 3. | NADPH (5.0 mM, freshly prepared) | 0.36 ml |
| 4. | $H_2O$ (or $H_2O$ + test compound) | 0.16 ml |
| 5. | $MgCl_2$ (27.5 mM) | 0.36 ml |
| 6. | Microsomal Enzyme (0.48 mg microsomal protein in homogenization buffer) (15 μl prep. 4/23/86 | 0.20 ml |
| | | 1.8 ml |

This mixture is equilibrated under $N_2$ at 4° C. for 5–15 minutes. Reaction mixtures are then warmed to 30° C., and the enzyme reaction initiated by adding 0.2 ml of farnesyl pyrophosphate (219 μM) prepared in $H_2O$. Each tube is again overlayered with $N_2$, and incubated at 30° C. for 60 minutes. The reaction is stopped by the addition of 1.0 ml KOH (40%). Ethanol (95%) (spectral grade) (1.0 ml) is added to each tube. Docosane (5 nmoles in hexane) is added to each tube as an internal standard. The mixture is saponified at 65° C. for 30 minutes. The tubes are cooled to room temperature and extracted twice with 10.0 ml spectral grade hexane.

The upper organic phase fractions are pooled in glass 20.0 ml scintillation vials and reduced in volume to ~1.0 ml under a stream of $N_2$. The sample is then transferred to acid-washed, conical bottom, glass (1.0 ml) microvials, and brought to dryness under $N_2$. The residue is resuspended in 50 μl hexane (spectral grade), and these samples are spun at 1000 rpm at room temperature for 10 minutes. Following centrifugation approximately 40 μl of supernatant is transferred to 100 μl acid-washed microvials with septa/crimp-top caps (compatible with the Hewlett-Packard GC auto injector).

GAS CHROMATOGRAPHY

Two μL of each sample is injected onto a fused silica megabore DB-17 column (15 M×0.525 mm) (J&W Scientific) using a splitless mode of injection. Gas flow rates are listed below:

| | |
|---|---|
| Make up gas (helium) | 20 ml/min. |
| Air | 400 ml/min. |
| Hydrogen | 30 ml/min. |
| Carrier (helium) | 15 ml/min. |
| Septum purge vent | 5 ml/min. |
| | (Septum purge off 0.00 min., on at 0.5 min.) |

The injector temperature is 200° C., and the FID detector temperature is set at 270° C. Oven temperature is programmed through a two ramp sequence as follows:

OVEN

Initial temperature 180° C., initial time 10 minutes
Ramp one: 20° C./minute
Second temperature 250° C., second time 10 minutes
Ramp two: 20° C./minute
Third temperature 260° C., third time 10 minutes
(Equilibration time 1.0 minute)

Using this gas chromatographic system, docosane (internal standard) has a retention time of 3.6–3.7 minutes, and squalene has a retention time of 14.7–14.9 minutes. The amount of squalene in each reaction mixture is determined by obtaining the areas under the squalene and docosane peaks and using the following formula to calculate the amount of squalene (nmoles) in the total reaction mixture.

$$\text{Squalene (nmoles/reaction mixture)} = \frac{5.0 \text{ (nmoles docasane} \times \text{internal standard)}}{} $$

$$\frac{\text{Squalene Peak Area}}{\text{Docasane Peak Area}} \times RR^*$$

*$RR$ = Response Ratio [Docasane/Squalene]
*$RR$ = 0.56

COMPOUNDS TESTING

Compounds are dissolved in $H_2O$ and added to reaction mixtures prior to addition of farnesyl pyrophosphate substrate. All reaction mixtures are run in duplicate, at several concentrations. Additionally, all compound $I_{50}$ values are derived from composite dose response data.

A further aspect of the present invention is a pharmaceutical composition consisting of at least one of the compounds of Formula I in association with a pharmaceutical vehicle or diluent. The pharmaceutical compostion can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectible preparation is produced by asceptically placing 250 mg of sterile active ingredient into a vial, aseptically freeze-drying and sealing. For use, the contents of the vial are mixed with 2 ml of physiological saline, to produce an injectible preparation.

The following Examples represent preferred embodiments of the present invention.

INTRODUCTION TO EXPERIMENTAL

All temperatures are reported in degrees Centigrade. $^1H$ and $^{13}C$ chemical shifts are reported as δ-values with respect to $Me_4Si$ (δ=0). $^{31}P$ spectra were measured on a JEOL FX90Q FT-NMR spectrometer, at 36.2 MHz, utilizing the $^1H$ decoupled mode. The $^{31}P$ data were obtained using 85% $H_3PO_4$ as an external reference ($\delta=0$). Coupling constants J are reported in Hz. Chemical ionization mass spectra (CI-MS) were determined with a Finnigan TSQ-4600 instrument equipped with a direct exposure probe using the indicated reagent gases. Fast atom bombardment mass spectra (FAB-MS) were recorded on a VG Analytical ZAB-2F spectrometer. Ions were sputtered (8keV Xe) from a matrix containing dithiothreitol, dithioerythritol, DMSO, glycerol and water.

All reactions were carried out under an atmosphere of dry argon or nitrogen. The following reagents and solvents were distilled prior to use from the indicated drying agents, where applicable: $CH_2Cl_2$, 2,4,6-collidine, and diisopropylamine ($CaH_2$); THF and diethyl ether (K, benzophenone); N,N-diethyltrimethylsilylamine and oxalyl chloride. Benzene was passed through neutral alumina (activity I) and stored over 4A-molecular sieves. Lithium bromide was dried at 100° C. over $P_2O_5$.(E,E)-Farnesol was purchased from Aldrich Chemical Company.

TLC was performed on E. Merck Silica Gel 60 F-254 plates (0.25 mm) or E. Merck Cellulose F plates (0.1 mm). Flash chromatography was carried out using E. Merck Kieselgel 60 (230–400 mesh).

Reverse-phase chromatographic purification of PMP salts was carried on CHP20P gel (75–150 $\mu$), a highly porous, polystyrene-divinyl benzene copolymer available from Mitsubishi Chemical Industries. The indicated general procedure was followed: An FMI Model RP-SY pump was utilized for solvent delivery. A column of CHP20P (2.5 cm diameter, 12–22 cm height) was slurry packed and washed with water (500–1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300–500 mL of the organic solvent, or an aqueous-organic mixture, just beneath the surface of a reservoir containing 300–500 mL of pure water. To start the gradient, the stopcock of the separatory funnel was opened, so that as the solvent was withdrawn by the pump from the reservoir, it was replaced with the solvent from the separatory funnel. HPLC-grade solvents and Lectrostill steam distilled water were employed. Fractions were collected (10–15 mL each) at a flow rate of 5–10 mL per minute. Those fractions that contained pure product as judged by TLC were pooled, the organic solvents were evaporated and the aqueous residue was lyophilized to dryness.

EXAMPLE 1

(E,E)-[[(1-Methylethoxy)[[(3,7,11-trimethyl-2,6,10-dodecatrienyl)oxymethyl]phosphinyl]methyl]phosphonic acid, dimethyl ester A. (Hydroxymethyl)phosphonic acid, bis(1-methylethyl) ester A mixture of 33.2 g (0.20 mol) of diisopropyl phosphite, 2.8 ml (0.02 mol) of triethylamine, and 6.0 g (0.20 mol) of paraformaldehyde, was immersed in a 100° C. oil bath and then heated between 100°–120° C. for 45 minutes under nitrogen. An exotherm occurred within 10 minutes and all of the paraformaldehyde dissolved rapidly. The triethylamine was removed at reduced pressure, and the residue was bulb-to-bulb distilled in four portions to provide a total of 35.17 g (91%) of title compound as a colorless oil. TLC Silica gel (5:95 $CH_3OH:CH_2Cl_2$) $R_f=0.17$ $^1H$ NMR ($CDCl_3$, 270 MHz) $\delta 4.73$ (sextet, 3H, J=6 Hz) 3.84 (d, 2H, J=6 Hz) 1.34 (d, 12H, J=6 Hz) ppm.

$^{13}C$ NMR ($CDCl_3$, 67.8 MHz) $\delta 70.9$ (d, J=6 Hz) 57.5 (d, J=162 Hz) 23.8 (d, J=6 Hz) ppm.

B. [[[(Trifluoromethyl)sulfonyl]oxy]methyl]phosphonic acid, bis(1-methylethyl) ester To a stirred solution of 6.0 g (30.6 mmol) of Part A phosphonate in 100 ml of dry diethyl ether (also referred to as ether) at −78° C. was added 5.90 ml (33.9 mmol) of diisopropylethylamine followed by the addition of 5.20 ml (31.0 mmol) of trifluoromethanesulfonic anhydride in 10 ml of ether over 30 minutes. An additional 40 ml of ethyl ether was added to aid stirring through the thick precipitate. After 45 minutes at −78° C., the reaction was allowed to warm to 0° C. for 45 minutes, and the solids were filtered and washed with ether. The filtrate was evaporated to afford 9.4 g of a colorless liquid. The crude product was flash chromatographed on 150 g of silica gel eluted with 40:60 ethyl acetate:hexane to provide 5.7 g (57%) of pure title triflate as a colorless liquid.

GTLC Silica gel (50:50 Ethyl Acetate:Hexane) $R_f=0.34$. $^1H$ NMR ($CDCl_3$, 270 MHz) $\delta 4.79$ (m, 2H) 4.55 (d, 2H, J=8.8 Hz) 1.37, 1.39 (two d, J=6 Hz) ppm.

$^{13}C$ NMR ($CDC1_3$, 67.8 MHz) $\delta 18.5$ (q, J=319 Hz) 73.0 (d, J=7.8, Hz) 67.1 (d, J=170 Hz) 23.8, 23.7 (two d, J=10 Hz) ppm.

C. (E,E)-[[(3,7,11-Trimethyl-2,6,10-dodecatrienyl)oxy]methyl]phosphonic acid, bis(1-methylethyl) ester 1) Preferred Method A solution of potassium hexamethyldisilazide (1.4 M in tetrahydrofuran (THF), 14.3 mL, 20 mmol) was added dropwise over 5 minutes to a solution of (hydroxymethyl)phosphonic acid, bis(1-methylethyl) ester (3.92 g, 20 mmol) in THF (40 mL) at ice bath temperature under argon. A precipitate formed in 3 minutes. After 10 minutes a solution of (E,E)-farnesyl chloride (4.82 g, 20 mmol) in dry THF (10 mL) was added dropwise over 4 minutes and the mixture was stirred for 2.5 hours at 0° and for 3 hours at room temperature. The reaction was quenched with acetic acid (1.2 g, 20 mmol); the color changed from orange to pale yellow. The mixture was poured into ethyl acetate (EtOAc) (50 mL) and washed twice with 30 mL 50% brine and 30 mL brine. The organic layer was dried ($MgSO_4$) and solvent was evaporated to give 8.1 g (100%) of crude title product. The product was purified by flash column chromatography over silica gel (200 g). The column was prepared in hexane, the material was charged neat and eluted successively with 100 mL hexane, 4 L 25% EtOAc/hexane and 1 L 50% EtOAc/hexane. Fractions 53 to 108 (45 mL each) were combined and evaporated to give 5.6 g (yield 70%) of title product.

TLC Silica gel (50:50 Ethyl Acetate:Hexane) $R_f=0.26$. IR ($CCl_4$) 2978, 2929, 1450, 1384, 1374, 1256, 1240, 1107, 990 $cm^{-1}$.

$^1H$ NMR ($CDC1_3$, 270 MHz) $\delta 5.32$ (t, $^1H$, J=7 Hz) 5.09 (m, 2H) 4.76 (m, 2H) 4.12 (d, 2H, J=7 Hz) 3.68 (d, 2H, J=8.8 Hz) 2.06 (m, 8H) 1.68 (s, 6H) 1.60 (s, 6H) 1.34, 1.33 (two d, 12 H, J=6 Hz) ppm.

Mass Spec (Cl-$CH_4$, +ions) m/e 401 (M+H), 197.

Anal. Calcd. for $C_{22}H_{41}O_4P$: C, 65.97; H, 10.32; P, 7.73 Found: C, 66.03; H, 10.32; P, 7.67

2) Alternate Preferred Method (E,E)-Farnesol was purified further by flash chromatography on silica gel eluted with 5:95 ethyl acetate:-hexane.

To a stirred solution of 2.0 g (9.0 mmol) of purified (E,E)-farnesol in 22 ml of tetrahydrofuran (THF) under argon at −78° C. was added 5.4 ml (8.61 mmol) of 1.6 M n-butyllithium in hexanes over 15 minutes. The reaction was allowed to stir for 40 minutes at −78° C., when 2.69 g (8.19 mmol) of the Part B triflate in 7 ml of THF was added via cannula. After 30 minutes at −78° C., the reaction was allowed to warm to 0° C. for two hours. The reaction was quenched with saturated ammonium chloride and partitioned between ethyl ether and water. The ether layer was washed with brine, dried (MgSO$_4$) and evaporated to provide 3.5 g of a pale yellow oil. The crude product was purified by flash chromatography on 350 g of silica gel packed in 20:80 and eluted with 30:70 ethyl acetate:hexane to provide 3.04 g (92%) of title ether as a colorless liquid.

D. (E,E)-[3,7,11-Trimethyl-2,6,10-dodecatrienyl)oxy]-methyl]phosphonic acid, mono(1-methylethyl) ester To a solution of 1.57 g (3.91 mmol) of Part C ether in 20 ml of 2-propanol under argon was added ml of 1 N KOH, and the reaction was heated to ° C. for 48 hours. After cooling to room temperature, the 2-propanol was evaporated and the aqueous residue was stirred with dichloromethane and acidified with 10% HCl. The organic layer was washed with water and brine, dried (MgSO$_4$), and evaporated to provide 1.39 g (96%, corrected for 0.37 mol equiv of dichloromethane) of title compound as a colorless oil.

TLC Silica gel (8:1:1 1-propanol:con NH$_3$:H$_2$O) R$_f$=0.55.

$^1$H NMR (CDC$_{13}$, 270 MHz) δ5.28 (t, $^1$H, J=7 Hz) 5.09 (m, 2H) 4.72 (m, 2H) 4.12 (d, 2H, J=7 Hz) 3.70 (d, 2H, J=7 Hz) 2.06 (m, 8H) 1.67 (s, 6H) 1.60 (s, 6H) 1.33 (d, 6H, J=6 Hz) ppm.

E. (E,E)-[[(1-Methylethoxy)[[(3,7,11-trimethyl-2,6,10-dodecatrienyl)oxy]-methyl]phosphinyl]methyl]phosphonic acid, dimethyl ester To a stirred solution of 1.395 g (3.89 mmol) of Part D compound in 8 ml of dichloromethane under argon was added 1.5 ml (7.51 mmol) of distilled N,N-diethyl(trimethylsilyl)amine. The reaction was allowed to stir for 1.5 hours at room temperature, the solvent was evaporated and the residue was dissolved in benzene, evaporated and then pumped at high vacuum. The remainder was dissolved in 8 ml of dichloromethane containing three drops of dimethylformamide (DMF) under argon at 0° C., and 0.68 ml (7.8 mmol) of distilled oxalyl chloride was added dropwise over 10 minutes, with much gas evolution. After 45 minutes at 0° C., the reaction was allowed to warm to room temperature for 45 minutes. The solution was evaporated and the residue was twice dissolved in benzene and evaporated, followed by pumping at high vacuum.

To a solution of 0.93 ml (8.58 mmol) of dimethyl methylphosphonate in 22 ml of THF at −78° C. under argon was added 5.2 ml (8.36 mmol) of n-butyllithium in hexane over 5 minutes to give a white suspension. After 40 minutes, the acid chloride prepared above was added in 8 ml of THF over 10 minutes. The reaction was allowed to stir for one hour at −78° C., when it was quenched with saturated ammonium chloride and diluted with ethyl ether. The aqueous layer was made acidic with 10% HCl and the organic layer was separated and washed with brine. The aqueous layer was re-extracted with dichloromethane, and the dichloromethane layer was washed with brine. The combined organic layers were dried (MgSO$_4$) and evaporated to provide 1.84 g of a crude yellow oil. Flash chromatography on 200 g of silica gel eluted with 98 methanol:dichloromethane gave 1.49 g (82%) of pure title triester as a colorless oil.

TLC Silica gel (5:95 CH$_3$OH:CH$_2$Cl$_2$) R$_f$=0.21 IR (CCl$_4$) 2977, 2954, 2926, 2853, 1449, 1385, 1375, 1256, 1229, 1063, 1036, 992, 841 cm$^{-1}$.

$^1$H NMR (CDC$_{13}$, 270 MHz) δ5.32 (t, 2H, J=7 Hz) 5.09 (m, 2H) 4.78 (m, 2H) 4.10 (d, 2H, J=7 Hz) 3.79, 3.83 (two d, 6H, J=6 Hz) 3.6–3.9 (m, 2H) 2.50 (m, 2H) 2.07 (m, 8H) 1.68 (s, 6H) 1.60 (s, 6H) 1.34, 1.37 (two d, 6H, J=7 Hz) ppm.

Mass Spec (CI—CH$_4$, +ions) m/e 505 (M+C$_3$H$_5$), 493 (M+C$_2$H$_5$), 465 (M+H).

EXAMPLE 2

(E,E)-[[Hydroxy[[(3,7,11-trimethyl-2,6,10-dodecatrienyl)oxy]methyl]phosphinyl]methyl]phosphonic acid, tripotassium salt To a stirred solution of 654 mg (1.42 mmol) of Example 1 triester in 7 ml of dry dichloromethane at room temperature was added 0.47 ml (3.54 mmol) of 2,4,6-collidine followed by 0.94 ml (7.09 mmol) of bromotrimethylsilane. The reaction was allowed to stir for 23 hours at room temperature, the solution was evaporated, the residue was dissolved in benzene, evaporated, and pumped at high vacuum. The remainder was dissolved in 8 ml of 1 M KOH, stirred for 30 minutes, diluted with water and lyophilized. The crude material was purified by MPLC on a column of CHP20P (2.5 cm diameter×20 cm height) eluted with water (fractions 1–12), followed by a gradient created by the gradual addition of acetonitrile (500 ml) to a reservoir of 400 ml of water. Approximately 15 ml fractions were collected. Fractions 27–33 were combined, the acetonitrile was evaporated at reduced pressure, and the aqueous solution was lyophilized to provide 680 mg (93%) of title product in the form of a dense, amorphous white lyophilate. Further drying under vacuum led to an insignificant loss of mass. The pH of a 1% w/v solution was 8.9.

TLC Silica gel (5:4:1 1-propanol:con NH$_3$:H$_2$O) R$_f$=0 44.

IR (KBr) 3400 (broad), 2967, 2921, 2860, 1662, 1445, 1381, 1180, 1146, 1085, 1054, 967, 867, 789, 466 cm$^{-1}$.

$^1$H NMR (D$_2$O, 270 MHz) δ5.34 (t, $^1$H, J=7 Hz) 5.07, 5.08 (two t, 2H, J=7 Hz) 4.07 (d, 2H, J=7 Hz) 3.57 (d, 2H, J=6.4 Hz) 1.8–2.2 (m, 10H) 1.64 (s, 3H) 1.60 (s, 3H) 1.54 (s, 6H) ppm.

$^{13}$C NMR (67.8 MHz, D$_2$O) δ144.35, 137.63, 134.48, 125.46, 125.30, 120.50, 70.17 (d, J=11.36 Hz), 69.30 (d, J=113.55 Hz), 39.9, 39.8, 30.45 (dd, J=119.23 Hz, 79.48 Hz) 26.78, 26.64, 25.89, 17.99, 16.74, 16.29 ppm.

$^{31}$P NMR (D$_2$O, 36.2 MHz) δ632.1 (d, J=9.6 Hz) 12.7 (d, J=9.6 Hz) ppm.

Mass Spec (FAB, +ions) m/e 509 (M+H).

Analysis Calcd for C$_{17}$H$_{29}$K$_3$P$_2$O$_6$+0.37 mol H$_2$O (Effective MW=515.3): C, 39.61; H, 5.83; P, 12.02 Found: C, 39.98; H, 5.99; P, 12.29

EXAMPLE 3

(E,E)-[[Methoxy[[(3,7,11-trimethyl-2,6,10-dodecatrienyl)oxy]methylphosphinyl]methyl]phosphonic acid, dimethyl ester A. (E,E)-[[(3,7,11-Trimethyl-2,6,10-dodecatrienyl)oxymethyl]phosphonic acid, dimethyl ester (E,E)-Farnesol, (5.0 mmol, 1.11 g, 1.26 ml) was stirred under argon in 10 ml of dry deoxygenated benzene (10 ml) and treated in one portion with

(1.0 mmol, 0.442 g). The dark blue/green solution was stirred at room temperature and a solution of (1.5 g, 10.0 mmol) of dimethyl diazomethylphosphonate (prepared according to D. Seyferth et al, *J. Org. Chem.*, 1971, vol. 36, No. 10, pages 1379 to 1386) in 20 ml of dry, deoxygenated benzene was added dropwise over 4 hours via syringe pump. After addition, the reaction mixture was stirred an additional 45 minutes. The reaction mixture was stripped of solvent and applied as a 75% ethyl acetate/Hexane solution to a flash chromatography column (50 mm diameter, 6" of silica gel) eluted with 75% ethyl acetate/hexane to afford 0.627 g, yield), of the ether as a dark blue/green oil.

TLC: Silica gel (EtOAc) $R_f$=0.32

IR (film) 2960, 2920, 2855, 1720, 1665, 1595, 1445, 1380, 1260, 1185, 1110, 1070–1025 (br), 890, 835 805, cm$^{-1}$.

Mass Spec (CI, +ions) m/e 345 (M+H)

$^1$H NMR (270 MHz, CDCl$_3$) δ5.32 (t, $^1$H, J=7 Hz) 5.09 (m, 2H) 4.13 (d, 2H, J=7 Hz) 3.83 (d, 6H, J=11 Hz) 3.79 (d, 2H, J=11 Hz) 2.13–1.93 (m, 8H) 1.71 (s, 6H) 1.62 (s, 6H) ppm.

$^{13}$C NMR (67.8 MHz, CDCl$_3$) δ142.03, 135.28, 131.13, 124.18, 123.54, 119.52, 69.26, (d, J=13.24 Hz), 62.44 (d, J=166.53 Hz), 52.82 (d, J=7.57 Hz), 39.53 (d, J=3.78 Hz), 26.61, 26.17, 25.53, 17.52, 16.37, 15.87 ppm.

B. (E,E)-[[(3,7,11-Trimethyl-2,6,10-dodecatrienyl)oxy]methyl]phosphonic acid, monomethyl ester The Part A dimethylphosphonate (1.73 mmol, 0.595 g) was stirred under argon in 8.65 ml of methanol and treated with a solution of KOH (34.55 mmol, 1.93 g) in 8.65 ml of H$_2$O. The pale yellow reaction mixture was heated to reflux for 8 hours, cooled to room temperature, and the methanol removed in vacuo. The resulting residue was diluted with 30 ml H$_2$O and treated portionwise with 5% HCl (aqueous) until the pH=1. This aqueous phase was extracted with ethyl acetate. The organic extracts were combined, dried over MgSO$_4$, azeotroped with benzene, and stripped in vacuo to afford (0.483 g, 84% yield) of the title phosphonate monoester as a brown oil. TLC Silica gel (20:1:1 CH$_2$Cl$_2$:CH$_3$OH:CH$_3$COOH) $R_f$=0.05 IR (film) 2960, 2920, 2860, 1730, 1710, 1705, 1695, 1680, 1665, 1445, 1380, 1245–1175 (broad), 1110, 1050, 995, 880, 830, 740, 680, cm$^{-1}$.

Mass Spec (CI, -ions) m/e 329 (M-H)

$^1$H NMR (270 MHz, CDCl$_3$) δ5.32 (t, $^1$H, J=6.9 Hz) 5.08 (m, 2H) 4.13 (d, 2H, J=6.9 Hz) 3.81 (d, 3H, J=10.2 Hz) 3.76 (d, 2H, J=10.2 Hz) 2.21–1.92 (m, 8H) 1.71 (s, 6H) 1.61 (s, 6H) ppm.

$^{13}$C NMR (67 8 MHz, CDCl$_3$) δ41.98, 135.39, 131.24, 124.29, 123.68, 119.69, 69.37, (d, J=13.24 Hz), 63.22 (d, J=170.32 Hz) 52.58 (d, J=7.57 Hz), 39.64, 26.70, 26.31, 25.64, 17.63, 16.49, 15.98 ppm.

C. (E,E)-[Methoxy[[(3,7,11-trimethyl-2,6,10-dodecatrienyl)oxy]methyl]phosphinyl]methyl]phosphonic acid, dimethyl ester The Part B phosphonate monoester (1.39 mmol, 0.460 g) was stirred under argon in 12.5 ml of dry CH$_2$Cl$_2$ and treated dropwise with diethyl trimethylsilylamine (2.78 mmol, 0.405 g, 0.528 ml, freshly distilled). This reaction mixture was stirred at room temperature for 2 hours. Then, the solvent was evaporated and the resulting residue azeotroped two times with 40 ml of benzene and pumped under high vacuum for 30 minutes. The residue was then stirred under argon in 12.5 ml of dry CH$_2$Cl$_2$, cooled to 0° C. and treated with 2 drops of dry dimethylformamide (DMF), followed by dropwise addition of oxalyl chloride (2.50 mmol, 0.318 g, 0.218 ml). This reaction was stirred at 0° C. for 1 hour and then warmed to room temperature and stirred for 45 minutes. Then, the solvent was removed and the residue azeotroped and pumped under high vacuum as above. Finally, the phosphonochloridate was stirred under argon in 2 ml of dry THF and cooled to −78° C. and added dropwise (10 minutes) to a −78° C. solution of the lithium anion of dimethylmethylphosphonate.

The anion of dimethylmethylphosphonate was formed by stirring dimethylmethylphosphonate (3.18 mmol, 0.395 g, 0.345 ml) under argon in 8 ml of dry THF cooling to −78° C., treating this solution dropwise with n-butyllithium (3.05 mmol, 1.22 ml of a 2.5 M solution in hexane) and then stirring at −78° C. for 30 minutes. The cooled solution of the phosphonochloridate (see above) was added dropwise to the −78° C. solution of the dimethylmethylphosphonate anion and then the reaction was stirred at −78° C. for 1 hour, warmed to 0° C. and stirred an additional 45 minutes. The reaction mixture was quenched with 20 ml saturated aqueous NH$_4$Cl warmed to room temperature, diluted with 20 ml H$_2$O, and the aqueous layer extracted 2 times with ethyl acetate and 2 times with ethyl ether. The organic extracts were combined, dried over MgSO$_4$, filtered and the solvent removed in vacuo. The product was isolated via flash chromatography (50 mm diameter column, 6" of silica gel, 4% CH$_3$OH/CH$_2$Cl$_2$ eluent) to afford 0.273 g, (45% yield) of the title triester as an orange oil.

TLC Silica gel (5% CH$_3$OH/CH $R_f$=0.29

IR (film) 2960, 2920, 2858, 1710, 1663, 1448, 1380, 1310, 1250, 1185, 1070–1020, 920, 888, 842, 820 cm$^{-1}$.

Mass Spec (CI, +ions) m/e 437 (M+H).

$^1$H NMR (270 MHz, CDCl$_3$) δ5.32 (t, $^1$H) 5.09 (m, 2H) 4.12 (d, 2H, J=6.9 Hz) 3.83 (d, 3H, J=11 Hz) 3.83 (d, 2H, J=7.9 Hz) 3.81 (d, 6H, J=11 Hz) 2.66–2.44 (m, 2H) 2.16–1.96 (m, 8H) 1.69 (s, 6H) 1.60 (s, 6H) ppm.

$^{13}$C NMR (67.8 MHz, CDCl$_3$) δ142.03, 135.25, 131.07, 124.12, 123.48, 119.41, 69.45, (d, J=13.25 Hz), 64.77 (d, J=119.23 Hz), 52.96 (d, J=5.68 Hz), 52.77 (d, J=5.68 Hz), 51.74 (d, J=5.68 Hz), 39.47, 26.56, 26.17, 24.02 (dd, J=136.25 Hz, 83.27 Hz), 25.50, 17.49, 16.37, 15.82 ppm.

EXAMPLE 4

(E,E)-[[Hydroxy[[(3,7,11-trimethyl-2,6,10-dodecatrienyl)oxy]methyl]phosphinyl]methyl]phosphonic acid, tripotassium salt The Example 3 triester (0.459 mmol, 0.20 g) was stirred under argon in 3.0 ml of dry CH$_2$Cl$_2$. This solution was cooled to 0° C. and treated with dry 2,4,6-collidine (0.918 mmol, 0.111 g, 0.121 ml) followed by dropwise addition of bromotrimethylsilane (1.84 mmol, 0.281 g, 0.242 ml). The reaction mixture was stirred at 0° C. for 1 hour, warmed to room temperature, and stirred an additional 2 hours. The solvent was evaporated in vacuo and the residue dried under high vacuum for 40 minutes. The resulting yellow solid was dissolved in 1.8 ml of methanol. This solution was cooled to 0° C. and treated with 1.8 ml of 1N KOH. The solution was stirred at room temperature for 30 minutes. The solvents were removed in vacuo and the residue pumped under high vacuum for 3 hours. The product was purified via CHP20P chromatography. The reaction product in 3 ml of distilled $H_2O$ was applied to a CHP20P column (2.5 cm diameter, 17 cm height). The column was eluted with 250 mL $H_2O$, followed by an acetonitrile/water gradient. Fractions were collected every 1.4 minutes (~10 ml). Product fractions were combined, evaporated, lyophilized (16 hours), and dried under high vacuum over $P_2O_5$ for 8 hours to afford 0.113 g (48% yield) of title salt as a slightly off-white, hygroscopic lyophilate.

For spectroscopic characterization, see Example 2.

Anal. Calcd. for C .0.5 moles $H_2O$ C, 42.57; H, 6.30 Found: C, 42.70; H, 6.64

EXAMPLE 5

(E)-[[[[(3,7-Dimethyl-2,6-octadienyl)oxy]methyl]-ethoxyphosphinyl]methyl]phosphonic acid, dimethyl ester A. (Hydroxymethyl)phosphonic acid, diethyl ester The procedure of Kluge was followed (Org Syn 1986, Vol. 64, 80-84). The following ingredients were combined: 69 g (0.50 mol) of diethyl phosphite, g (0.50 mol) of paraformaldehyde, and 5.1 g (0.05 mol) of triethylamine. The stirred mixture was immersed in a preheated oil bath at 120° C. and heated for one hour. Upon cooling, the triethylamine was removed on the rotary evaporator at 80° C., and the residue was then Kugelrohr distilled (150°-160° C., 0.10 mm) to provide 57.5 g (68%) of title compound as a colorless liquid.

TLC: Silica gel (5:95 $CH_3OH:CH_2Cl_2$) $R_f$=0.19

$^1H$ NMR ($CDCl_3$) (270 MHz) δ4.95 (br, $^1H$) 4.09 (quint, 4H, J=7 Hz Hz) 3.83 (d, 2H, J=5.8, Hz) 1.27 (t, 6H, J=7 Hz) ppm.

$^{13}C$ NMR ($CDCl_3$) (67.8 MHz) δ62.2 (d, J=7.6 Hz) 56.5 (d, J=162.8 Hz) 16.1 (d, J=5.7 Hz) ppm.

B. [[[(Trifluoromethyl)sulfonyl]oxy]methyl]phosphonic acid, diethyl ester

A modification of the literature procedure was developed (Phillipon, D.P.; Andrew, S.S. Tetrahedron Letters 1986, 27, 1477-80). To a solution of 5.00 g (30.0 mmol) of Part A phosphonate and 5.2 ml (30.0 mmol) of diisopropylethylamine in 100 ml of dry ethyl ether at −78° C. under nitrogen was added a solution of 5.05 ml (30.0 mmol) of trifluoromethanesulfonic anhydride in 10 ml of ether over 15 minutes. After one hour at −78° C., the reaction was allowed to warm gradually to 10° C. over 75 minutes. The precipitated amine salt was removed by filtration and the filtrate was concentrated to provide 5.94 g of crude triflate as a yellow oil. Flash chromatography on 100 g of silica gel eluted with 50:50 ethyl acetate:petroleum ether provided 4.31 g (48%) of title triflate as a clear, colorless liquid.

TLC Silica gel (50:50 ethyl acetate:hexane) $R_f$=0.30.

$^1H$ NMR ($CDCl_3$) (270 MHz) δ4.63 (d, 2H, J=9 Hz) 4.25 (quint, 4H, J=7 Hz) 1.39 (t, 6H, J=7 Hz) ppm.

$^{13}C$ NMR ($CDCl_3$) (67.B MHz) δ118.4 (q, J=319.B Hz) 66.3 (d, J=16B.5 Hz) 63.B (d, J=7.6 Hz) 16.1 (d, J=5.7 Hz) ppm.

C. (E)-[[(3,7-Dimethyl-2,6-octadienyl)oxy]-methyl]-phosphonic acid, diethyl ester To a stirred solution of 830 mg (5.38 mmol) of (E)-geraniol (Aldrich Chemical) in 12 ml of tetrahydrofuran at −78° C. under argon was added 3.5 ml (5.65 mmol) of 1.6 M n-butyllithium in hexane over five minutes. After 30 minutes, 1.78 g (5.92 mmol) of Part B triflate in 6 ml of tetrahydrofuran was added over five minutes. After 30 minutes at −78° C., the solution was allowed to warm to −20° C. for one hour. The reaction was diluted with ethyl ether, washed with saturated $NH_4Cl$, water and brine, dried ($MgSO_4$), and evaporated to provide 1.65 g of a colorless oil. Flash chromatography on 200 g of silica gel eluted with 43:57 ethyl acetate:hexane gave 1.21 g (74%) of title diester containing a trace impurity. An additional chromatography on 150 g of silica eluted with 30:70 ethyl acetate: hexane gave pure title diester as a colorless oil.

TLC Silica gel (75.25 acetate:hexane) $R_f$=0.29.

IR ($CCl_4$) 2981, 2929, 2912, 1443, 1391, 1259, 1098, 1055, 1031, 967 $cm^{-1}$.

$^1H$ NMR ($CDCl_3$) (270 MHz) δ5.32 (t, $^1H$, J=7 Hz) 5.08 (br, $^1H$) 4.18 (m, 6H) 3.74 (d, 2H) 2.08 (m, 4H) 1.68 (s, 6H) 1.60 (s, 3H) 1.35 (t, 3H, J=7 Hz) ppm.

Mass Spec (CI-CH, +ions) m/e 609 (2M+H), 473, 345 (M+$C_3H_5$), 333 (M+$C_2H_5$), 305 (M+H).

D. (E)-[[(3,7-Dimethyl-2,6-octadienyl)-oxy]methyl]-phosphonic acid, monoethyl ester A solution of 1.00 g (3.28 mmol) of Part C diester in 25 ml of ethanol was treated with 17 ml of 1M KOH under nitrogen and the solution was heated to 75° C. for 2.75 hours. The pH was adjusted to 7 with 10% HCl, and the ethanol was evaporated. The aqueous residue was stirred with ml of dichloromethane and acidified with 10% HCl. The aqueous layer was extracted with an additional 50 ml of dichloromethane and the combined organic layers were washed with 20 ml of 1:1 brine:water, dried ($MgSO_4$) and evaporated to provide 911 mg (100%) of title compound as a pale yellow oil.

TLC Silica gel (7:2:1 n-$C_3H_7OH$:con $NH_3:H_2O$) $R_f$=0.59

$^1H$ NMR ($CDCl_3$) (270 MHz) δ5.32 (t, $^1H$, J=7 Hz) 5.08 (br t, $^1H$) 4.15 (m, 4H) 3.74 (d, 2H, J=9 Hz) 2.06 (m, 4H) 1.67 (s, 6H) 1.60 (s, 3H) 1.35 (t, 3H, J=7 Hz) ppm.

E. [[[[(3,7-Dimethyl-2,6-octadienyl)oxy]methyl]ethoxyphosphinyl]methyl]phosphonic acid, dimethyl ester A solution of 903 mg (3.27 mmol) of Part D compound in 8 ml of dichloromethane under argon was treated with 1.25 ml (6.54 mmol) of diethyl(trimethylsilyl)amine. After 100 minutes, the solution was evaporated, and the residue was evaporated with benzene and pumped at high vacuum. To the silyl ester in 8 ml of dichloromethane containing two drops of dimethylformamide at 0° C. under nitrogen was added 0.57 ml (6.54 mmol) of oxalyl chloride, dropwise over 15 minutes. After 20 minutes, the reaction was allowed to warm to room temperature for one hour. The volatiles were evaporated and the acid chloride residue was evaporated with benzene and pumped at high vacuum.

To a solution of 0.78 ml (7.19 mmol) of dimethyl methylphosphonate in 15 ml of -: tetrahydrofuran at −78° C. under argon was added 4.4 ml (7.03 mmol) of 1.6 M n-butyllithium over 10 minutes, resulting in a white precipitate. After 30 minutes, a solution of the acid chloride described above in 5 ml of tetrahydrofuran was added dropwise over 5 minutes. After 70 minutes at −78° C., the reaction was quenched with saturated $NH_4Cl$, diluted with dichloromethane (100 ml) and the aqueous layer acidified with 1M HCl. The aqueous layer was separated and re-extracted with 100 ml of dichloromethane. The combined organic layers were dried (MgSO$_4$) and evaporated to provide 1.65 g of crude product. After pumping under high vacuum overnight to remove excess dimethyl methylphosphonate, the crude product was chromatographed to provide 1.04 g (80%, corrected for 0.2 equiv of CH$_2$Cl$_2$ observed by $^1$H NMR) of pure title compound as a colorless oil.

TLC Silica gel (5:95 CH$_3$OH:CH$_2$Cl$_2$) R$_f$=0.19

IR(CCl$_4$) 2955, 2928, 2855, 1455, 1257, 1230, 1063, 1037, 841 cm$^{-1}$.

$^1$H NMR (CDCl$_3$), (270 MHz) δ5.32 (td, $^1$H, J=7, $^1$Hz) 5.09 (br t, $^1$H) 4.19 (m, 2H) 4.14 (d, 2H, J=6.8 Hz) 3.83 (d, 3H, J=11.6 Hz) 3.80 (d, 3H, J=11 Hz) 2.52 (m, 2H) 2.07 (m, 4H) 1.68 (s, 6H) 1.60 (s, 3H) 1.36 (t, 3H, J=7 Hz) ppm.

Mass Spec (C , +ions) m/e 383 (M+H), 351 (M+H−CH$_3$OH), 247.

EXAMPLE 6

(E)-[[[[(3,7-Dimethyl-2,6-octadienyl)oxy]methyl]hydroxyphosphinyl]methyl]phosphonic acid, trisodium salt To a solution of 536.3 mg (1.40 mmol) of Example 5 triester in 6 ml of dichloromethane under argon was added 0.42 ml (3.16 mmol) of 2,4,6-collidine followed by 0.83 ml (6.30 mmol) of bromotrimethylsilane. The reaction was allowed to stir for 3.5 hours at room temperature, and was then evaporated and pumped at high vacuum. The residue was dissolved in 4.5 ml (4.5 mmol) of 1 M NaOH and then adjusted to pH 12 with several additional drops of 1 M NaOH. This solution was lyophilized and the residue was purified by MPLC on a 2.5 cm diameter, 22 cm height column of CHP20P packed and eluted with water to provide, after freeze-drying and further drying at high vacuum, 496 mg (90%) of title compound as a white lyophilate.

TLC Silica gel (4:4:1 n-C$_3$H$_7$OH:con NH$_3$:H$_2$O) R$_f$=0.46

IR (KBr) 3435, 2967, 2923, 2857, 1636, 1175, 1153, 1088, 1056, 974, 797 cm$^{-1}$.

$^1$H NMR (D 0 (400 MHz) δ5.35 (t, $^1$H, J=7 Hz) 5.14 (t, $^1$H, J=7 Hz) 4.08 (d, 2H, J=7 Hz) 3.60 (d, 2H, J=6.2 Hz) 2.0-2.1 (m, 4H) 1.92 (t, 2H, J=18 Hz) 1.62; 1.64 (two S, 6H) 1.56 (s, 3H) ppm.

$^{31}$P NMR (D $_2$O) (36.2 MHz) δ35.3 (d, J=8.8 Hz) 15.1 (d, J=8.8 Hz) ppm.

Mass Spec (FAB, +ions) m/e 415 (M+Na), 393 (M+H)

Anal Calcd for C$_{12}$H$_{21}$P$_2$O$_6$Na$_3$.1.03 H$_2$O: C, 35.09; H, 5.66; P, 15.08 Found: C, 35.49; H, 5.97, P, 14.74

EXAMPLE 7

(E,E)-[[Ethoxy[[(4,8,12-trimethyl-3,7,11-tridecatrienyl)oxymethyl]phosphinyl]methyl]phosphonic acid, dimethyl ester A. (E,E)-4,8,12-Trimethyl-3,7,11-tridecatrien-1-ol (1) (E,E)-3,7,11-Trimethyl-2,6,10-dodecatrienaldehyde [(E,E)-Farnesal]

A solution of oxalyl chloride (4.68 g, 0.037 mol) in dry CH$_2$Cl$_2$ under argon atmosphere was cooled to −65° C. A solution of dimethyl sulfoxide (DMSO) (5.33 ml) in CH$_2$Cl$_2$ (17 ml) was added rapidly, dropwise, to the cooled oxalyl chloride solution. After stirring for 7 minutes at −65° C., a 10 ml CH$_2$Cl$_2$ solution of (E,E)-farnesol (7.0 g, 0.032 mol) was added over 10 minutes to the reaction solution at −65° C.: a precipitate formed upon the addition of approximately half of the farnesol solution. After the addition of the farnesol solution was completed, the reaction was stirred at −65° C. for 25 minutes, and then 22.4 ml (0.16 mol) of triethylamine was added over 10 minutes. After stirring for an additional 15 minutes at −65° C., the reaction was warmed to room temperature, and then diluted with water (∼200 ml). The resulting aqueous layer was extracted several times with CH$_2$Cl$_2$. The combined organic layers were washed once with saturated aqueous NaCl solution once with 1% HCl, once with 5% Na$_2$CO$_3$ solution and once with saturated aqueous NaCl solution. The resulting organic layer was dried over MgSO$_4$ to give 7.05 g (100%) of a clear oil after filtration and solvent removal.

TLC Silica gel (20% ethyl acetate/hexane) R$_f$=0.34.

$^1$H NMR (CDCl$_3$) (270 MHz) δ9.98 (d, $^1$H, J=7 Hz) 5.88 (broad d, $^1$H, J=7 Hz) 5.08 (m, 2H) 2.22 (m, 4H) 2.17 (s, 3H) 2.02 (m, 4H) 1.66 (s, 3H) 1.60 (s, 6H) ppm.

$^{13}$C-NMR (CDCl$_3$) (67.8 MHz) δ191.0, 163.6, 136.5, 131.3, 127.4, 124.0, 122.4, 40.5, 39.6, 26.6, 25.6, 17.6, 17.5, 15.9 ppm.

(2) 4,8,12-Trimethyl-1,3,7,11-tridecatetraene

A suspension of methyltriphenylphosphonium iodide (8.07 g, 0.02 mole) in 61 ml of dry tetrahydrofuran (THF), under argon atmosphere was cooled to 0° C. To this suspension at 0° C. was added 9 mL (18 mmol) of phenyllithium (2.0 M in diethyl ether/hexane 30:70) over 10 minutes. After the addition was complete, the reaction mixture containing excess phosphonium salt was warmed to room temperature and stirred for 40 minutes. The reaction mixture was then recooled to 0° C., and a 10 ml THF solution of the Part (1) aldehyde (4.0 g, 0.018 mol) was added over 12 minutes. After stirring for 10 minutes at 0° C., the reaction was warmed to room temperature. The reaction was quenched with CH$_3$OH after 2 hours at room temperature. The THF was removed from the reaction mixture to give a slurry which was triturated with petroleum ether, and subsequently, filtered through a Celite pad in a sintered glass funnel. The solids were then boiled in petroleum ether and refiltered as above. The resulting yellow oil was passed through 50 g of Florisil (100-200 mesh) eluted with ∼400 ml of petroleum ether providing the title tetraene (3.36 g, 86%) as a clear oil after solvent removal. TLC Silica gel (20% ethyl acetate/hexane) R$_f$=0.68

$^1$H NMR (CDCl$_3$) (270 MHz) δ6.56 (ddd, $^1$H, J=17, 12, 6 Hz) 5.85 (d, $^1$H, J=12 Hz) 5.10 (m, 2H) 5.02 (m, 2H) 2.05 (m, 8H) 1.75 (s, 3H) 1.67 (s, 3H) 1.60 (s, 6H) ppm.

$^{13}$C-NMR (CDCl$_3$) (67.8 MHz) δ139.3, 135.3, 133.4, 131.2, 125.5, 124.3, 123.9, 114.5, 39.9, 39.7, 26.8, 26.4, 25.6, 17.7, 16.6, 15.9 ppm.

(3) (E,E)-4,8,12-Trimethyl-3,7,11-tridecatrien-1-ol

Neat 2-methyl-2-butene (2.25 g, 0.032 mol) was added to a 1.0 M BH$_3$-THF solution (16.9 ml) at −50° C. and under argon. After the addition was complete, the reaction was stirred for 2 hours at 0° C. The resulting disiamylborane solution was transferred via cannula over 1 hour to a flask containing a 17 ml THF solution of Part A(2) tetraene (3.36 g, 0.015 mol) under argon atmosphere and cooled to 0° C. After the transfer was complete, the reaction was allowed to gradually warm to room temperature, and then it was stirred overnight at room temperature. The reaction mixture was cooled to 0° C., and 5.1 ml of 3N NaOH was added rapidly. After stirring for 10 minutes, the reaction mixture was cooled in an ice-salt bath and 5.1 ml of 30% H$_2$O$_2$ was added dropwise. Subsequently, the reaction was warmed to room temperature and stirred for 4 hours after which it was diluted with H$_2$O, and the resulting aqueous layer was extracted several times with ethyl ether. The combined organic layers were dried over MgSO$_4$. Purification by flash chromatography eluting with 20% ethyl acetate/hexane provided the title alcohol (2.62 g, 74%) as a clear oil.

TLC Silica gel (20% ethyl acetate/hexane) R$_f$=0.23

IR (Film) 3340 (br), 2965, 2920, 1665, 1440, 1380, 1100, 1050 cm$^{-1}$.

$^1$H NMR (CDCl$_3$) (270 MHz) δ5.10 (m, 3H) 3.61 (t, 2H, J=6 Hz) 2.29 (q, 2H, J=6 Hz) 2.03 (m, 8H) 1.67 (s, 3H) 1.65 (s, 3H) 1.60 (s, 6H) ppm.

$^{13}$C NMR (CDCl$_3$) (67.8 MHz) δ138.8, 135.2, 131.2, 124.3, 123.9, 119.9, 62.4, 39.8, 39.7, 31.5, 26.7, 26.5, 25.6, 17.6, 16.1, 5.9 ppm.

B. (E,E)-[[(4,8,12-Trimethyl-3,7,11-tridecatrienyl)oxy]methyl]phosphonic acid, diethyl ester To a solution of 1.204 g (5.09 mmol) of Part A homofarnesol in 12 ml of tetrahydrofuran (THF) at −78° C. under argon was added over 15 minutes a solution of 3.35 ml (5.34 mmol, 1.05 eq.) of 1.6 M n-butyllithium in hexanes. The resulting solution was stirred at −78° C. for 0.5 hour, then treated with a solution of 1.68 g (5.60 mmol, 1.1 eq.) of triflate prepared as described in Example 5 Part B, in 8 ml of THF. The reaction mixture was allowed to stir for 0.5 hour at −78° C. and 1.5 hours at −20° C. (salt-ice bath). The mixture was diluted with ethyl ether, quenched with NH$_4$Cl and separated. The organic phase was washed with water and brine, dried over MgSO$_4$ and evaporated to yield 1.972 g of a clear, colorless oil. Purification by flash chromatography on 200 g of silica, eluted with a 3:7 acetone:petroleum ether provided two portions of product, each coeluting with a different impurity. Portion A (556.7 mg) was passed through a second flash chromatographic column of 65 g silica gel eluted with 2:8 acetone:petroleum ether to provide 443.7 mg of impure material. This was further purified by medium pressure chromatography on a Merck Lobar silica gel column (size B), which was eluted with 4:6 ethyl acetate:hexane to obtain 259.8 mg (13%) of desired product. Portion B (864.1 mg) from the first column was rechromatographed on 40 g of silica, eluted with a 4:6 ethyl acetate:petroleum ether to provide 788.1 mg (40%) of desired product. Title compound was thus obtained as 1.048 g of a clear oil in 53% yield.

TLC silica gel (1:1 ethyl acetate:hexanes) R$_f$=0.18.

IR(CCl$_4$) 2980, 2928, 2914, 2868, 2858, 1443, 1391, 1259, 1245, 1119, 1099, 1056, 1032, 968 cm$^{-1}$.

$^1$H NMR (CDCl$_3$) (270 MHz) δ5.10 (m, 3H) 4.17 (quint, 4H, J=7.1 Hz) 3.78 (d, 2H, J=8.4 Hz) 3.54 (t, 2H, J=7.1 Hz) 2.31 (q, 2H, J=7.1 Hz) 1.9-2.2 (m, 8H) 1.67 (s, 3H) 1.62 (s, 3H) 1.60 (s, 6H) 1.35 (t, 6H, J=7.1 Hz) ppm.

Mass Spec (FAB, +ions) m/e 387 (M+H), 169, 141.

C. (E,E)-[[(4,8,12-Trimethyl-3,7,11-tridecatrienyl)oxy]methyl]phosphonic acid, monoethyl ester A mixture of 1.001 g (2.59 mmol) of Part B compound, 26 ml of ethanol and 25.9 ml (25.9 mmol, eq.) of 1 M KOH was stirred at 60-70° C. under nitrogen for six hours, then cooled and stirred at room temperature for 20 hours. After adjusting to ~pH 6 with 10% HCl, the ethanol was evaporated. The remaining aqueous phase was acidified with 10% HCl and extracted with four 50 ml portions of ethyl acetate. The combined organic layers were washed with 25 ml of 1:1 H$_2$O:brine and 25 ml of brine, dried over MgSO$_4$ and evaporated to yield title phosphonic acid 938.3 mg (100%) in the form of a pale yellow oil.

TLC Silica gel (6:3:1 n-C$_3$H$_7$0H:concentrated NH:H$_2$O) R$_f$=0.63.

$^1$H NMR(CDCl$_3$) (270 MHz) δ10.9-11.1 (br, $^1$H) 5.10 (m, 3H) 4.18 (quint, 2H, J=7.0 Hz) 3.80 (d, 2H, J=8.4 Hz) 3.54 (t, 2H, J=7.0 Hz) 2.31 (q, 2H, J=7.0 Hz) 1.9-2.1 (m, 8H) 1.68 (s, 3H) 1.61 (s, 3H) 1.60 (s, 6H) 1.35 (t, 3H, J=7.0 Hz) ppm.

D. (E,E)-[[Ethoxy[[4,8,12-trimethyl3,7,11-tridecatrienyl]oxy]methyl]phosphinyl]methyl]phosphonic acid, dimethyl ester A solution of 936.1 mg (2.59 mmol) of Part C monoethyl, dimethyl triester phosphonic acid in ml of dry CH$_2$Cl$_2$ at room temperature under argon was treated with 980 μl (5.18 mmol, 2 eq.) of diethyl(trimethylsilyl)amine. After 1.5 hours, the solvent was evaporated and the residue was twice evaporated from benzene, then dried at high vacuum for 0.5 hour.

The residue was dissolved in 8 ml of CH$_2$Cl$_2$ and two drops of dimethyl formamide (DMF) at 0° C. under nitrogen and treated with 410 1 (4.66 mmol, 1.8 eq) of oxalyl chloride. The mixture was allowed to warm to room temperature and stirred for two hours. The solvent was evaporated and the residue was twice evaporated from benzene, then dried at high vacuum for 0.5 hour.

The anion solution was prepared by adding over five minutes a solution of 3.50 ml (5.57 mmole, 2.15 eq.) of 1.6 M n-butyllithium in hexanes to a solution of 620 μl (5.70 mmole, 2.2 eq.) of dimethyl methylphosphonate in 15 ml of tetrahydrofuran (THF) at −78° C. under argon, followed by stirring for 0.5 hour.

A solution of the phosphonic acid chloride prepared above in 6 ml of THF at −78° C. under argon was added quickly via cannula to the anion solution. The resulting mixture was stirred at −78° C. for 1.5 hours, then quenched with 300 μl (5.2 mmol, 2 eq.) of glacial acetic acid and allowed to stir for ten minutes. Approximately 3 ml of saturated NH$_4$Cl was added and the cold bath was removed. Once at room temperature, 10 ml of H$_2$O was added and the mixture was extracted with five 40 ml portions of CH$_2$Cl$_2$. The combined organic phases were washed with 30 ml of 1:1 H$_2$O:brine and 30 ml of brine, dried over MgSO$_4$ and evaporated to obtain 1.241 g of crude coupling product. Purification by flash chromatography on 120 g of silica gel eluted with 2:98 CH$_3$OH:CH$_2$Cl$_2$ provided 501.7 mg (42%) of title product.

TLC Silica gel (5:95 CH$_3$OH:C ) R$_f$=0.17

IR(CCl$_4$) 2956, 2917, 2856, 1447, 1257, 1231, 1166, 1111, 1063, 1037, 960, 842 cm$^{-1}$.

$^1$H NMR(CDCl$_3$) (270 MHz) δ5.10 (m, 3H) 4.19 (d quint, 2H, J=2.6, 7.4 Hz) 3.82 (d, 3H, J=10.6 Hz) 3.80 (d, 3H, J=11.6 Hz) 3.7-3.9 (m, 2H) 3.55 (dt, 2H, J=1.3, 6.9 Hz) 2.4-2.7 (m, 2H) 2.30 (quint, 2H, J=6.9 Hz) 1.9-2.1 (m, 8H) 1.68 (s, 3H) 1.62 (s, 3H) 1.60 (s, 6H) 1.36 (t, 3H, J=7.4 Hz) ppm.

Mass Spec (CI-CH +ions) m/e 505 (M+C$_3$H$_5$), 493 (M+C , 465 (M+H).

EXAMPLE 8

(E,E)-[[Hydroxy[[4,8,12-trimethyl-3,7,11-tridecatrienyl]oxy]methyl]phosphinyl]methyl]phosphonic acid, trisodium salt To a solution of 485.9 mg (1.05 mmol) of Example 7 triester and 310 1 (2.35 mmol, 2.25 eq.) of 2,4,6-collidine in 5 ml of dry $CH_2Cl_2$ at room temperature under nitrogen in the dark was added dropwise 620 µl (4.71 mmol, 4.5 eq.) of bromotrimethylsilane. This solution was allowed to stir for seven hours, then evaporated twice with benzene and dried at high vacuum for 0.5 hour. The residue was treated with 8.40 mL (8.40 mmol, 8 eq.) of 1 M NaOH and the aqueous solution was lyophilized overnight. Purification was by chromatography on a 12 cm height×2.5 cm diameter column of CHP20P packed with water and eluted with 100 ml of $H_2O$ followed by a gradient created by the gradual addition of 400 ml of $CH_3CN$ into 400 ml of $H_2O$. Approximately 8-10 ml fractions were collected every 1.2 minutes. Fractions 52-55 and 58-59 were combined, filtered, evaporated, lyophilized overnight and pump-dried for eight hours to provide 294.0 mg (59%) of title salt as a fluffy white lyophilate. (In addition, fractions and 57 were combined, filtered and lyophilized to obtain 159.8 mg (32%) of title salt containing a trace impurity by TLC).

TLC Silica gel (5:4:1 n-$C_3H_7OH$:con. $NH_3$:$H_2O$) $R_f$=0.28

IR(KBr) 3000-3500(br), 2966, 2916, 2856, 1442, 1381, 1178, 1148, 1093, 976, 873, 812, 798, 783, 761, 741, 490, 478 cm$^{-1}$.

$^1$H NMR($D_2O$) (400 MHz) δ5.13 (m, 3H) 3.63 (d, 2H, J=6.5 Hz) 3.54 (t, 2H, J=7.3 Hz) 2.32 (q, 2H, J=6.5 Hz) i 1.9-2.1 (m, 10H) 1.65 (s, 3H) 1.63 s, 3H) 1.58 (s, 3H) ppm.

$^{31}$P-NMR ($D_2O$) δ34.7 (d, J=10.3 Hz) 15.7 (d, J=10.3 Hz) ppm.

Mass Spec (FAB, +ions) m/e 497 (M+Na), 475 (M+H), 453 (M+2H-Na).

Anal Calcd for C .0.86 H 0 (MW 489.76): C, 44.14; H, 6.73; P, 12.65 Found: C, 44.04, H, 6.85; P, 12.90.

EXAMPLE 9

(E,E)-[[Hydroxy[[(3,7,11-trimethyl-2,6,10-dodecatrienyl)oxy]methyl]phosphinylmethyl]phosphonic acid, monomethyl ester, dipotassium salt The Example 3 triester (0.321 mmol, 0.140 g) was stirred under argon in 1.6 mL of 1 N KOH. The reaction mixture was heated in a 55° C. oil bath for 24 hours. The reaction mixture was cooled to room temperature and applied directly to a chromatography column containing CHP20P resin (12 cm×2.5 cm/equilibrated with 1000 ml distilled $H_2O$). The column was eluted with 100 ml of $H_2O$, followed by a gradient created by gradual addition of 400 ml of $CH_3CN$ to 400 ml of $H_2O$. Fractions were collected every 1.7 minutes (~10 ml). Fractions 54-63 were combined, evaporated in vacuo, lyophilized, and pumped under high vacuum over $P_2O_5$ for 16 hours to afford 0.115 g (0.237 mmol, 74% yield) of the title dipotassium salt as a white lyophilate.

TLC:Silica gel, (7:2:1 n-$C_3H_7OH$/con. $NH_3$/$H_2O$) $R_f$=0.45

$^1$H NMR (400 MHz, $D_2O$) δ5.36 (t, $^1$H, J=6.96 Hz) 5.14 (m, 2H) 4.08 (d, 2H, J=6.96 Hz) 3.57 (d, 2H, J=6.96 Hz) 3.51 (d, 3H, J=11 Hz) 2.12-1.95 (m, 10H) 1.66 (s, 3H) 1.63 (s, 3H) 1.57 (s, 6H) ppm.

$^{13}$C NMR (67.8 MHz, $D_2O$) δ144.16, 137.60, 134.45, 125.46, 125.30, 120.61, 70.14 (d, J=11.35 Hz), 69.39 (d, J=113.54 Hz), 52.35 (d, J=5.6 Hz), 39.9, 39.8, 28.34 (dd, J=79.48 Hz, 124.9 Hz), 26.81, 26.67, 25.89, 18.02, 16.74, 16.32 ppm.

Mass Spec (FAB, +ions) m/e 485 (M+H)

IR(KBr) 2966, 2924, 2855, 1446, 1222, 1191, 1151, 1107, 1065, 1053, 787, 741 cm$^{-1}$.

Anal Calcd for C 0.14 moles $H_2O$: C, 44.39; H, 6.68; P, 12.72 Found: C, 44.38; H, 6.74; P, 12.74

EXAMPLE 10

(E-E)-[[Hydroxy[[(3,7,11-trimethyl-2,6,10-dodecatrienyl)oxy]methyl]phosphinyl]methyl]phosphonic acid, trisodium salt A sample of 660 mg (1.42 mmol) of Example 1 triester was treated with 0.47 ml (3.54 mmol) of 2,4,6-collidine and 0.94 ml (7.09 mmol) of bromotrimethylsilane in precisely the same manner on identical scale as in the preparation of the Example 2 tripotassium salt. For the salt formation, 8 ml of IM NaOH was substituted for KOH, and similarly, CHP20P chromatography gave 630 mg (94%) of title salt as a fluffy white lyophilate. TLC, $^1$H NMR, $^{31}$P NMR, $^{13}$C NMR, IR and Mass Spec is essentially identical to the Example 2 tripotassium salt.

Anal Calcd for $C_{17}H_{29}Na_3P_2O_6$+0.46 mol $H_2O$: C, 43.57; H, 6.44; P, 13.22 Found: C, 43.71; H, 6.46; P, 13.40

EXAMPLE 11

(E,E)-[[Ethoxy[[(5,9,13-trimethyl-4,8,12-tetradecatrienyl)oxymethyl]phosphinyl]methylphosphonic acid, dimethyl ester A. Bishomofarnesol (1) (E,E)-3,7,11-Trimethyl-2,6,10-dodecatrineyl bromide A solution of 1.00 g (4.5 mmol) of (E,E)-farnesol (Aldrich, further purified by flash chromatography) in 10 ml of distilled ether at 0° C. under argon in the dark was treated dropwise with a solution of 195 µL (2.05 mmol, 0.45 eq.) of $PBr_3$ in 2 ml of ether. The resultant mixture was stirred at 0° C. for one hour, then quenched with water and separated. The organic phase was washed with 5 ml of $H_2O$, 5 ml of saturated $NaHCO_3$, and 5 ml of brine, dried over $Na_2SO_4$ and evaporated to give 1.26 g (98%) of crude bromide as a clear oil.

TLC Silica (2:8 ethyl acetate:Hexane) $R_f$=0.69.

$^1$H NMR (CDCl$_3$, 270 MHz) δ5.52 (t, $^1$H, J=8.5 Hz) 5.08 (m, 2H) 4.01 (d, 2H, J=8.5 Hz) 1.9-2.2 (m, 8H) 1.73 (s, 3H) 1.68 (s, 3H) 1.60 (s, 6H) ppm.

(2) (E,E)-5,9,13-Trimethyl-4,8,12-tetradecatrienoic acid, 1,1-dimethylethyl ester To a solution of 9.60 ml (68.5 mmol, 1.5 eq.) of diisopropylamine in 100 ml of THF at −78° C. under argon was added 28.2 ml (45.0 mmol, 1.0 eq.) of 1.6 M n-butyllithium in hexanes over 20 minutes. After warming to 0° C. for 15 minutes, the solution was recooled to −78° C. and 6.05 ml (45 mmol, 1.0 eq) of t-butyl acetate was added over 20 minutes. After an additional 15 minutes, 16.0 ml (92 mmol, 2.05 eq.) of hexamethylphosphoramide (HMPA) was added, followed by a solution of 12.53 g (45.0 mmol) of Part A(1) farnesyl bromide in 100 ml of THF over 20 minutes. The reaction was stirred at −78° C. for 2.5 hours, quenched with saturated $NH_4Cl$ and allowed to warm to room temperature. After diluting with 400 ml of ethyl acetate, the mixture was washed with four 100 ml portions of water, and 200 ml of brine, dried over MgSO$_4$ and evaporated to provide 12.96 g of crude product as a yellow oil. Purification by flash chromatography on 1 kg of silica gel, eluted with 1:9 ethyl acetate:petroleum ether afforded 9.39 g (65%) of title compound as a pale yellow oil.

TLC Silica gel (2:98 ethyl acetate:hexane) $R_f$=0.16.

IR(neat) 2977, 2925, 2857, 1733, 1452, 1368, 1258, 1149 cm$^{-1}$.

$^1$H NMR(CDCl$_3$) (270 MHz) δ5.10 (m, 3H) 2.25 (m, 4H) 1.9–2 1 (m, 8H) 1.68 (s, 3H) 1.62 (s, 3H) 1.59 (s, 6H) 1.44 (s, 9H) ppm.

Mass Spec (CI-CH$_4$/N$_2$O) (+ions) m/e 165 (M+H-C$_4$H$_8$), 247, 183, 137, 68, 57. (−ions) m/e 319 (M-H), 279, 251, 100.

(3) Bishomofarnesol

To a stirred solution of 5.00 g (15.6 mmol) of Part (2) compound in 45 ml of dry diethyl ether at 0° C. under argon was added 592 mg (15.6 mmol, 1 mol - eq.) of lithium aluminum hydride, and the resulting suspension was stirred at room temperature for 20 hours. After cooling to 0° C., the reaction was quenched by treating with 5 ml of H$_2$O, 5 ml of 15% NaOH, and 15 ml of H$_2$O and stirring the suspension for ½ hour. After adding Na$_2$SO$_4$, the slurry was filtered through Celite, washing well with diethyl ether and evaporated to obtain 3.62 g of crude product. Purification by flash chromatography on 300 g of silica gel, eluted with 1:9 ethyl acetate:petroleum ether provided 3.516 g (90%) of bishomofarnesol as a colorless liquid.

TLC Silica gel (2:8 ethyl acetate:hexane) $R_f$=0.19

IR(neat) 3330, 2964, 2926, 2873, 2958, 1448, 1384, 1107, 1059, 401 cm$^{-1}$.

$^1$H NMR(CDCl$_3$) (270 MHz) δ5.10 (m, 3H) 3.63 (t, 2H, J=6.5 Hz) 1.9–2.2 (m, 10H) 1.68 (s, 3H) 1.62 (2, 3H) 1.60 (s, 7H) ppm.

Mass Spec (CI-C +ions) m/e 251 (M+H), 249 (M+H-31 H$_2$), 137, 123, 109, 69.

B. (E,E)-[[(5,9,13-Trimethyl-4,8,12-tetradecatrien-1-yl)oxy]methyl]phosphonic acid, diethyl ester To a solution of 1.198 g (4.80 mmol) of Part A bishomofarnesol in 25 ml of tetrahydrofuran at −78° C. under argon was dropwise added 3.00 ml (4.80 mmol) of 1.6 M n-butyllithium in hexanes over ten minutes. After 0.5 hours at −78° C., a solution of 1.299 g (4.32 mmol, 0.9 equiv.) of Example 5 Part B triflate in 20 ml of tetrahydrofuran was added. The reaction mixture was warmed to 0° C. and stirred for two hours. After diluting with 40 ml of diethyl ether and quenching with 25 ml of saturated NH$_4$Cl, the layers were separated and the aqueous phase extracted with 180 ml of diethyl ether. The organic layers were combined, washed with 20 ml of brine, dried over MgSO$_4$, and evaporated to yield 1.814 g of crude product. Purification by flash chromatography on 180 g of silica gel, eluted with 2:8 acetone:hexane provided 721.2 mg (42%) of pure title diester as a colorless oil.

TLC silica gel (1:1 ethyl acetate:hexane) $R_f$=0.27.

IR(CCl$_4$) 2980, 2929, 2914, 2866, 2859, 1443, 1392, 1384, 1378, 1260, 1243, 1165, 1120, 1099, 1057, 1031, 968, 812, 798, 795, 773 cm$^{-1}$.

$^1$H NMR (CDCl$_3$) (270 MHz) δ5.11 (br s, 3H) 4.17 (quint, 4H, J=7.1 Hz) 3.76 (d, 2H, J=8.8 Hz, H$_{18}$) 3.55 (t, 2H, J=6.3 Hz) 1.9–2.1 (m, 10H) 1.68 (s, 3H) 1.60 (m, 11H) 1.35 (t, 6H, J=7.1 Hz) ppm.

Mass Spec (CI-CH$_4$/N$_2$O, + ions) m/e 401 (M+H), 281, 253.

C. (E,E)-[(5,9,13-Trimethyl-4,8,12-tetradecatrien-1-yl)oxy]methyl]phosphonic acid, monoethyl ester A solution of 711.1 mg (1.75 mmol) of Part B diester in a mixture of 17.5 ml (17.5 mmol, 10 eq) of 1 M NaOH and 17.5 ml of ethanol was heated at 65°–70° C. for 2.5 hours, then cooled to room temperature. The mixture was adjusted to ~pH 7 with 1 M HCl and the ethanol was evaporated. The aqueous solution was further acidified and extracted with four 30 ml portions of ethyl acetate. The combined organic phases were washed with 20 ml of 50% brine and 20 ml of brine, dried over MgSO$_4$ and evaporated to obtain 652.4 mg (100%) of crude title phosphonic acid mono ester.

TLC Silica gel (8:1:1 n-C$_3$H$_{70}$H:con.NH$_3$:H$_2$O) $R_f$=0.43

$^1$H-NMR(CDCl$_3$) (270 MHz) δ5.10 (br s, 3H) 4.17 (t, 2H, J=7.1 Hz) 3.76 (d, 2H, J=8.8 Hz) 3.55 (t, 2H, J=6.6 Hz) 1.9–2.1 (m, 10H) 1.68 (s, 3H) 1.60 (m, 1$^1$H) 1.34 (t, 3H, J=7.1 Hz) ppm.

D. (E,E)-[[Ethoxy[[(5,9,13-trimethyl-4,8,12-tetradecatrienyl)oxy]methyl]phosphinyl]methyl]phosphonic acid, dimethyl ester A solution of 652 mg (1.75 mmol) of Part C phosphonic monoester in 5 ml of CH$_2$Cl$_2$ at room temperature under argon was treated with 665 μl (3.50 mmol, 2 equiv.) of N,N-diethyl(trimethylsilyl)-amine and stirred for two hours. The solvent was evaporated, and the residue was twice evaporated from benzene, then dried at high vacuum for 0.5 hours.

The residue was dissolved in 5 ml of CH$_2$Cl$_2$ and one drop of dimethylformamide at 0° C. under nitrogen and was treated dropwise with 275 μl (3.15 mmol, 1.8 eq) of oxalyl chloride over five minutes. The solution was allowed to warm to room temperature and stirred for two hours. The solvent was evaporated, and the residue was twice evaporated from benzene, then dried at high vacuum for 0.5 hours.

The anion solution was prepared by treating a solution of 420 μl (3.85 mmol, 2.2 equiv.) of dimethyl methylphosphonate in 5 ml of tetrahydrofuran at −78° C. under argon with a solution of 2.35 ml (3.76 mmol, 2.15 equiv.) of 1.6 M n-butyllithium in hexanes over ten minutes. The solution was allowed to stir for 0.5 hours, then a solution of the acid chloride prepared above in 3 ml of tetrahydrofuran was rapidly added. The resulting orange solution was stirred at −78 C for 1.5 hours, then quenched with a solution of 200 μl (3.50 mmol, 2 equiv.) of acetic acid in 1 ml of tetrahydrofuran. After stirring for ten minutes, 1 ml of saturated NH$_4$Cl was added and the cold batch was removed. Water was added (~5 ml) and the mixture was extracted with five 20 ml portions of CH$_2$Cl$_2$. The combined organic phases were washed with 20 ml of 50% brine and 20 ml of brine, dried over MgSO$_4$ and evaporated to give 781.1 mg of a yellow oil. Purification required two chromatographies, the first on 75 g of silica, eluted with 3:97 CH$_3$OH:CH$_2$Cl$_2$; the second on 60 g of silica, eluted with 1.5:98.5 CH$_3$OH:CH$_2$Cl$_2$, affording 335.4 mg (40%) of title compound as a clear, colorless oil.

TLC:Silica gel (5:95 CH$_3$OH:CH$_2$Cl$_2$) $R_f$=0.14

IR(CCl$_4$) 2954, 2927, 2917, 2855, 1447, 1391, 1383, 1377, 1365, 1258, 1231, 1184, 1165, 1113, 1063, 1036, 960, 842, 801, 790, 770, 759, 752, 737 cm$^{-1}$.

$^1$H NMR(CDCl$_3$) (270 MHz) δ5.10 (br s, 3H) 4.18 (m, 2H) 3.82 (d, 3H, J=11.0 Hz) 3.80 (d, 3H, J=11.0 Hz) 3.7–3.95 (m, 2H) 3.56 (t, 2H, J=6.3 Hz) 2.51 (m, 2H) 1.9–2.1 (m, 10H) 1.68 (s, 3H) 1.60 (s, 1$^1$H) 1.36 (t, 3H, J=7.1 Hz) ppm.

Mass Spec (CI-CH$_4$/N$_2$O, + ions) m/e 479 (M+H).

EXAMPLE 12

(E,E)-[[Hydroxy[[(5,9,13-trimethyl-4,8,12-tetradeca-trienyl)oxy]methyl]phosphinyl]methyl]phosphonic acid, trisodium salt A solution of 318.6 mg (0.67 mmol) of Example 11 triester in 3.5 ml of CH$_2$Cl$_2$ at room temperature under argon was treated with 220 μl (1.68 mmol, 2.5 equiv.) of 2,4,6-collidine and 445 μl (3.35 mmol, 5 equiv.) of bromotrimethylsilane and stirred for six hours. The solvent was evaporated, and the residue was treated with 6.7 ml (6.70 mmol, 10 equiv.) of 1 M NaOH and lyophilized. The crude product was purified by chromatography on a 12 cm height×2.5 cm diameter column of CHP20P resin loaded in water and eluted with 100 ml of water, followed by a gradient created by the gradual addition of 400 ml of 7:3 CH$_3$CN:water into 400 ml of water, collection of approximately 10 ml fractions every 1.5 minutes. Fractions 43–54 were combined, evaporated, lyophilized and pump-dried for six hours to afford 240.1 mg (73%) of title product as a white lyophilate.

TLC Silica gel (4:4:1 n-C$_3$H$_7$OH:con. NH :H$_2$O) R$_f$=0.33

IR(KBr) 3000–3700 (br), 2964, 2925, 2859, 1661, 1638, 1177, 1148, 1096, 975, 793 cm$^{-1}$.

$^1$HNMR (D$_2$O) (400 MHz) δ5.17 (t, $^1$H, J=6.4 Hz) 5.10 (m, 2H) 3.57 (m, 4H) 1.9–2.1 (m, 12H) 1.64 (s, 3H) 1.59 (s, 3H) 1.57 (s, 6H) 1.5–1.7 (m, 2H) ppm.

$^{31}$P-NMR (D$_2$O) (36.2 MHz) δ32.1 (d, J=11.5 Hz) 13.1 (d, J=11.5 Hz) ppm.

Mass Spec (FAB, +ions) m/e 489 (M+H), 467 (M+2H-Na), 445 (M+3H-2Na)

Anal calcd for C .0.73 H$_2$O: C, 45.51; H, 6.92; P, 12.35 Found: C, 45.29; H, 7.06; P, 12.59

EXAMPLE 13

(E,E)-[[Hydroxy[(3,7,11-trimethyl-2,6,10-dodeca-trienyl)amino]methylphosphinyl]methyl]phosphonic acid, disodium salt A. (E,E)-3,7,11-Trimethyl-2,6,10-dodecatrien-1-amine, monohydrochloride 1) 2-(3,7,11-Trimethyl-2,6,10-dodecatrienyl)-1H-isoindole-1,3(2H)-dione A solution of 2.00 g (9.0 mmol) of (E,E)-farnesol in 20 ml of dry diethyl ether at 0° C. under argon in the dark was treated dropwise with a solution of 735 1 (4.0 mmol, 0.45 eq.) of PBr$_3$ in 4 ml of dry diethyl ether. The resultant mixture was stirred at 0° C. for one hour, then quenched with H$_2$O and separated. The organic phase was washed with 15 ml of NaHC0$_3$, 15 ml of H$_2$O, and 15 ml of brine, dried over MgSO$_4$ and evaporated to provide 2.47 g of crude farnesyl bromide as a clear oil.

A solution of 2.47 g of the above farnesyl bromide in 20 ml of dry dimethylformamide (DMF) at room temperature under argon was treated with 1.83 g (9.9 mmol, 1.1 eq.) of potassium phthalimide and stirred for 3 hours at room temperature. The solvent was removed under reduced pressure, the residue was triturated with 150 ml of ethyl ether, and the precipitate was filtered off. The ethereal solution was washed with 50 ml of H 0 and 50 ml of brine, dried over MgSO$_4$ and evaporated to yield 2.96 g of crude title compound as a milky oil. Purification by flash chromatography on 300 g of Merck 9385 silica, eluted with 7:93 ethyl acetate:petroleum ether afforded 2.56 g (81%) of the desired product as a colorless oil.

TLC Silica gel (2:8 ethyl acetate:hexane) R$_f$=0.37

IR(neat) 2967, 2920, 2856, 1772, 1716, 1468, 1432, 1394, 1366, 1325, 1112, 1088, 1073, 947, 721, 531

$^1$H NMR (CDCl$_3$) (270 MHz) δ7.82 (dd, 2H, J=3.0, 5.5 Hz) 7.68 (dd, 2H, J=3.0, 5.5 Hz) 5.27 (t, $^1$H, J=7.0 Hz) 5.05 (d, 2H, J=7.0 Hz) 4.27 (d, 2H, J=7.0 Hz) 1.9–2.1 (m, 8H) 1.83 (s, 3H) 1.66 (s, 3H) 1.56 (s, 6H) ppm.

Mass Spec (CI-CH$_4$/N$_2$O, + ions) m/e 392 (M+C$_3$H$_5$), 380 (M+C$_2$H$_5$), 352 (M+H), 296, 284, 270, 228, 216.

(2) Farnesyl amine

A solution 2.50 g (7.1 mmol) of Part (1) compound in 15 ml of absolute ethanol at room temperature under argon was treated with 1.9 ml (35.57 mmol, 5.0 eq.) of methyl hydrazine and stirred for 2 hours at room temperature and 4 hours at reflux. After cooling and the addition of 7.1 ml (7.1 mmol, 1.0 eq.) of 1M NaOH, the ethanol was removed under reduced pressure. The residue was extracted with 350 ml of ethyl ether and the ether layer washed with 100 ml of 1M NaOH, 50 ml of H$_2$O and 50 ml of brine, dried (MgSO$_4$) and evaporated to obtain 1.45 g of crude product. Purification by bulb-to-bulb distillation at 120° C./0.005 mm provided 1.405 g (89%) of title compound as a colorless oil.

TLC:Silica gel (8:1:1 n-propanol:con.NH :H$_2$O) R$_f$=0.64

IR(neat) 3291, 2967, 2923, 2856, 1574, 1483, 1453, 1383, 1378, 1347, 1288, 819, 777 cm$^{-1}$.

$^1$H NMR (CDCl$_3$) (270 MHz) δ5.26 (t, $^1$H, J=7.0 Hz) 5.10 (br, 2H) 3.27 (d, 2H, J=7.0 Hz) 1.9–2.1 (m, 8H) 1.68 (s, 3H) 1.63 (s, 3H) 1.60 (s, 6H) 1.20 (br s, 2H) ppm.

Mass Spec (CI-CH$_4$/N$_2$O, + ions) m/e 443 (2M+H), 222 (M+H), 205, 137.

(3) (E,E)-3,7,11-Trimethyl-2,6,10-dodecatrien-1-amine, monohydrochloride

A solution of 254.5 mg (1.15 mmol) of Part (2) farnesyl amine in diethyl ether was treated with HCl-saturated diethyl ether and the resulting precipitate was filtered off and dried for 20 hours under vacuum to obtain 197.3 mg (67%) of a white solid, m.p. 121°–122° C.

TLC Silica gel (8:1:1 n-C$_3$H$_7$OH:con.NH$_3$:H$_2$O) R$_f$=0.56

IR(KBr) 2983, 2929, 1600, 1464, 1384, 1106, 890, $^1$H NMR (CD$_3$OD) (400 MHz) δ5.31 (t, $^1$H, J=7.5 Hz) 5.13 (t, $^1$H, J=7.5 Hz) 5.09 (t, $^1$H, J=7.5 Hz) 3.56 (d, 2H, J=7.5 Hz) 2.0–2.2 (m, 6H) 1.98 (t, 2H, J=7.5 Hz) 1.76 (s, 3H) 1.66 (s, 3H) 1.61 (s, 3H) 1.60 (s, 3H) ppm.

$^{13}$C-NMR (CD$_3$OD) (67.8 MHz) 145.8, 136.7, 132.1, 125.3, 124.7, 116.6, 40.8, 40.6, 38.3, 27.8, 27.2, 25.9, 17.8, 16.6, 16.1 ppm.

Mass Spec (CI-CH$_4$/N$_2$O, + ions) m/e 222 (M+H-HCl), 205, 137, 81.

Anal Calcd for HCl (MW 257.849): C, 69.87; H, 10.95; N, 5.43; Cl, 13.75 Found: C, 69.96; H, 10.87; N, 5.39; Cl, 13.78

B. (E,E)-[[(3,7,11-Trimethyl-2,6,10-dodecatrienyl)amino]methyl]phosphonic acid, diethyl ester To a stirred solution of 1.88 g (7.29 mmol) of Part A hydrochloride salt and 2.9 ml (16.6 mmol) of diisopropylethylamine in 30 ml of CH$_2$Cl$_2$ under argon at 0° C. was added 2.46 g (6.63 mmol) of Example 5 Part B trifluoromethylsulfonate in 5 ml of CH$_2$Cl$_2$ over 45 minutes. After 1.5 hours at 0° C., the reaction was diluted with 100 ml of CH$_2$Cl$_2$, washed with 20 ml of 2 M Na$_2$CO$_3$, and the aqueous layer was back-extracted with 20 ml of CH$_2$Cl$_2$. The combined organic layers were dried (MgSO$_4$) and evaporated to provide 2.87 g of a yellow oil. The crude product was flash chromatographed on 200 g of silica gel packed in 12.5:87.5 and eluted with 25:75 acetone:hexane to provide 2.18 g (89%) of pure title amine as a pale yellow liquid.

TLC silica gel (50:50 acetone:hexane) R$_f$=0.33

IR (CCl$_4$) 2980, 2928, 2913, 2856, 1444, 1241, 1098, 1058, 1031, 964 cm$^{-1}$.

$^1$H NMR (CDCl$_3$) δ5.22 (t, 1H, J=7 Hz) 5.08 (m, 2H) 4.15 (quint, 4H, J=7 Hz) 3.29 (d, 2H, J=6.8 Hz) 2.96 (d, 2H, J=12.6 Hz) 2.05 (m, 8H) 1.68 (s, 3H) 1.64 (s, 3H) 1.60 (s, 6H) 1.43 (t, 6H, J=7 Hz) ppm.

Mass Spec (CI-CH$_4$/N$_2$O, + ions) m/e 372 (M+H), 168.

C. (E,E)-[[[(1,1-Dimethylethoxy)carbonyl]-(3,7,11-trimethyl-2,6,10-dodecatrienyl)-amino]methyl]phosphonic acid, diethyl ester To a solution of 1.045 g (2.81 mmol) of Part B amine in 9 ml of CH$_2$Cl$_2$ under argon was added 860 mg (3.94 mmol) of di-tert-butyl dicarbonate. The solution was allowed to stir for hours at room temperature and evaporated, and the residue was flash chromatographed on 70 g of silica gel eluted with 50:50 ethyl acetate:hexane to provide 1.28 g (96%) of title compound as a thick, colorless oil.

TLC Silica gel (50:50 ethyl acetate:hexane) R$_f$=0.24.

IR(CCl$_4$) 2979, 2929, 2915, 2856, 1698, 1477, 1452, 1421, 1367, 1240, 1161, 1055, 1030, 968 cm$^{-1}$.

$^1$H NMR (CDCl$_3$) δ5.09 (m, 3H) 4.13 (quint, 4H, J=7 Hz) 4.02 (br d, 2H, J=5.8 Hz) 3.63 (br d, 2H, J=8.4 Hz) 2.10 (m, 8H) 1.69, 1.68 (two s, 3H each) 1.60 (s, 6H) 1.47 (s, 9H) 1.33 (t, 6H, J=7 Hz) ppm.

Mass Spec (CI - CH$_4$/N$_2$O, + ions) m/e 512 (M+C$_3$H$_5$), 500 (M+C$_2$H$_5$), 472 (M+H), 372, 212, 168.

D. (E,E)-[[(1,1-Dimethylethoxy)carbonyl]-(3,7,11-trimethyl-2,6,10-dodecatrienyl)-amino]methyl]phosphonic acid, monoethyl ester A solution of 595 mg (1.26 mmol) of Part C compound in 7 ml of ethanol was treated with 7 ml of 1 M KOH and heated to reflux for 6 hours. The ethanol was evaporated; the residue was stirred with C$_2$Cl$_2$, and was acidified with 10% HCl. The organic layer was washed with brine, dried (MgSO$_4$) and evaporated to provide 564.9 mg (100%) of title acid as a colorless oil.

TLC Silica gel (7:2:1 n-C$_3$H$_7$OH:con NH$_3$:H$_2$O) R$_f$=0.62.

$^1$H NMR (CDCl$_3$) δ65.10 (m, 3H) 4.13 (quint, 2H, J=7 Hz) 4.02 (br, 2H) 3.60 (br, 2H) 2.08 (m, 8H) 1.68 (s, 6H) 1.60 (s, 6H) 1.46 (s, 9H) 1.33 (t, 3H, J=7 Hz) ppm.

E. (E,E)-[[(1,1-Dimethylethoxy)carbonyl]-(3,7,11-trimethyl-2,6,10-dodecatrienyl)-amino]methyl]phosphonic acid, ethyl 4-nitrophenyl ester To a solution of 327.4 mg (0.75 mmol) of Part D acid in 4 ml of dry pyridine at room temperature under argon was added 106 mg (0.76 mmol) of p-nitrophenol and 9 mg (0.074 mmol) of 4-dimethylaminopyridine followed by 198 mg (0.959 mmol) of dicyclohexyl carbodiimide (DCC) in 3 ml of pyridine. The reaction was allowed to stir for 24 hours at room temperature, when another 91 mg (0.44 mmol) of DCC was added, and the reaction was heated at 45°-50° C. for 5 hours. The reaction was allowed to cool to room temperature, filtered to remove the precipitate and the pyridine was evaporated. The residue was taken up in ethyl acetate, stirred with 10% HCl, and the two-phase mixture was filtered to remove additional precipitate. The organic layer was separated, washed with 10% HCl, water and brine, dried (MgSO$_4$), and evaporated to provide an oil containing some suspended solid. The mixture was triturated with diethyl ether, filtered once more, and evaporated to provide 409 mg of a colorless oil. Rapid flash chromatography on 40 g of pH 4 buffered silica gel packed in 10:90 and eluted with 20:80 ethyl acetate:hexane gave 357.1 mg of a colorless oil. $^1$H NMR indicated that this was a 5:1 mixture of desired title p-nitrophenyl ester and p-nitrophenol, for a corrected yield of 80%.

TLC Silica gel (40:60 ethyl acetate:hexane) R$_f$=0.38 for title p-nitrophenyl ester; 0.28 for p-nitrophenol.

IR (CCl$_4$) 2979, 2928, 1699, 1593, 1527, 1492, 1417, 1391, 1368, 1345, 1286, 1245, 1223, 1161, 1037, 921 cm$^{-1}$.

$^1$H NMR (CDCl$_3$) δ8.22 (d, 2H, J=10 Hz) 7 40 (d, 2H, J=10 Hz) 5.09 (m, 3H) 4.27 (m, 2H) 4.06 (br, 2H) 3.86 (br d, 2H, J=B.4 Hz) 2.07 (m, 8H) 1.69, 1,6B (two s, 3H eaoh) 1.60 (s, 6H) 1.44 (s, 9H) 1.35 (t, 6H, J=7 Hz) ppm.

Mass Spec (Cl-CH$_4$, + ions) m/e 565 (M+H), 375, 261, 205.

F. (E,E)-[[[[(1,1-Dimethylethoxy)-carbonyl](3,7,11-trimethyl-2,6,10-dodecatrienyl)amino]methyl]ethoxyphosphinyl]methyl]phosphonic acid, dimethyl ester To a stirred solution of 51 1 (0.468 mmol) of dimethyl methylphosphonate in 2 ml of tetrahydrofuran (THF) at −78° C. under argon was added 0.28 ml (0.449 mmol) of 1.6 M n-butyllithium in hexane over 5 minutes. After 20 minutes, the 105 mg (0.185 mmol) of Part E p-nitrophenyl ester in 2 ml of THF was added over 5 minutes to give a yellow solution. The reaction was allowed to stir for 30 minutes at −78° C. followed by warming to 0° C. for 30 minutes. The reaction was quenched with 50 μl (0.874 mmol) of acetic acid in 1 ml of diethyl ether. The mixture was partitioned between ethyl acetate and saturated NH$_4$Cl, the organic layer was washed with saturated NaHC$_{03}$ and brine, dried (MgSO$_4$) and evaporated to provide 125.3 mg of a pale yellow oil. The crude product was chromatographed on 10 g of silica gel, eluted with 3:97 CH$_3$OH:CH$_2$Cl$_2$, and the impure fractions were repurified, eluting 2:98 CH$_3$OH:CH$_2$Cl$_2$. The pure fractions were combined to provide 85.5 mg (84%) of a pure title compound as a colorless oil.

TLC Silica gel (5:95 CH$_3$OH:CH ) R$_f$=0.26

IR (CCl$_4$) 2978, 2928, 1695, 1453, 1420, 1391, 1367, 1256, 1230, 1160, 1063, 1036 cm$^{-1}$.

$^1$H NMR (CDCl$_3$) δ5.10 (m, 3H) 4.24 (quint, 2H, J=7 Hz) 4.03 (br d, 2H, J=5.5 Hz) 3.82, 3.80 (two d, 3H each, J=11 Hz) 3.72 (br m, 2H) 2.53 (br t, 2H, J=17.5 Hz) 2.06 (m, 8H) 1.70, 1.68 (two s, 3H each) 1.60 (s, 6H) 1.47 (s, 9H) 1.35 (t, 3H, J=7 Hz) ppm.

$^{31}$P NMR (CDCl$_3$) δ40.6 (br) 22.9 (d, J=11.7 Hz) ppm.

Mass Spec (CI-CH$_4$/N$_2$O, + ions) 590 (M+C$_3$H$_5$), 578 (M+C$_2$H$_5$), 550 (M+H).

G. (E,E)-[[Hydroxy[[(3,7,11-trimethyl-2,6,10-dodecatrienyl)amino]methyl]-phosphinyl]methyl]phosphonic acid, disodium salt To a stirred solution of 581 mg (1.06 mmol) of Part F compound in 5 ml of dry CH$_2$Cl$_2$ at 0° C. under argon was added 0.42 ml (3.18 mmol) of 2,4,6-collidine followed by 0.90 ml (6.34 mmol) of iodotrimethylsilane (TMSI). After 2.5 hours at ° C., the reaction was allowed to warm to room temperature and stirred for 4.5 hours. Additional portions of 2,4,6-collidine (0.14 ml, 1.06 mmol) and TMSI (0.30 ml, 2.12 mmol) were added at this point, and again after another 16 hours at room temperature. Seven hours after the final addition of reagents, 5 ml of dry $CH_2Cl_2$ was added, and the reaction was allowed to stir for 18 hours. The solvent was evaporated, the dark residue was dissolved in 10 ml of $CH_3OH$, and after 15 minutes, was treated with 10 ml of 1 M NaOH and 20 ml of water. A precipitate formed, and the reaction was stirred for four hours, at which the mixture was homogeneous. The $CH_3OH$ was evaporated and the aqueous solution was allowed to stir for an additional three hours and then lyophilized to provide a green residue. The crude product was chromatographed on CHP20P, eluting with water (fractions 1–15) followed by a gradient created by the gradual addition of 3:1 acetonitrile:water to a 500 ml reservoir of water, collecting 8–10ml fractions. Fractions 48–53 (Cut A, 150 mg) contained relatively pure material, whereas fractions 54–58 (Cut B, 273 mg) were contaminated with a UV absorbing material tentatively assigned to be the 1-methyl-2,4,6-collidinium cation. Cut B was dissolved in water, adjusted to pH 2, and passed through a column of AG 50W-X8 resin (Na+form, 30 ml resin bed), eluting with water, to remove the contaminating cation. Fractions containing the desired product were lyophilized and combined with Cut A from above. An aqueous solution of this material was made basic with 1 M NaOH and was purified by MPLC on a 20 cm height, 2.5 cm diameter column of CHP20P, eluted with water (fractions 1–7) followed by gradient created by the gradual addition of 7:3 acetonitrile:water to a 500 ml reservoir of water, collecting 6–8 ml fractions. Fractions 46–58 gave 331.2 mg (71%) of title product as a pale yellow-white lyophilate. TLC Silica gel (6:3:1 n-$C_3H_7OH$:con $NH_3$:$H_2O$) $R_f$=0.4 IR(KBr) 3446, 2967, 2924, 2860, 1629, 1175, 1072, 967 cm$^{-1}$.

$^1$H NMR ($D_2O$) (400 MHz) δ5.29 (t, $^1$H, J=7.3 Hz) 5.15 (m, 2H) 3.66 (d, 2H, J=7.7 Hz) 3.03 (d, 2H, J=11, Hz) 1.9–2.2 (m, 10H) 1.72 (s, 3H) 1.66 (s, 3H) 1.59, 1.60 (two s, 3H each) ppm.

$^{31}$P NMR ($D_2O$, NaOD) δ35.1 (d, J=11 Hz) 12.9 (d, J=11 Hz) ppm.

Mass Spec (FAB, + ions) m/e 460 (M+Na), 438 (M+H), 234, 187.

Anal Calcd for $C_{17}H_{31}NO_5P_2Na_2 \times 0.32$ mol $H_2O$: C, 46.08; H, 7.20; N, 3.16; P, 13.98 Found: C, 46.27; H, 7.53; N, 3.35; P, 13.58

EXAMPLE 14

(E,E)-[[Ethoxy[2-[(3,7,11-trimethyl-2,6,10-dodecatrienyl)oxyethyl]phosphinyl]methyl]phosphonic acid, dimethyl ester A. (E,E)-[2-(3,7,11-Trimethyl-2,6,10-dodecatrienyl)oxy]ethyl]phosphonic acid, diethyl ester (E,E)-Farnesol was purchased from Aldrich Chemical and further purified by preparative scale chromatography prior to use.

A solution of 3.00 g (13.5 mmol) of said farnesol and 2.70 ml (2.7 mmol, 0.2 eq.) of a 1M solution of tetra-n-butylammonium fluoride in THF in 25 ml of THF at room temperature under argon 5 was stirred for four hours over 4% molecular sieves. Then, 6.25 ml (40.5 mmol, 3 eq.) of diethyl vinylphosphonate was added and the reaction was allowed to stir for 70 minutes. After diluting with 75 ml of diethyl ether, the mixture was filtered through Celite, washed with three 20 ml portions of water and 20 ml of brine, dried over $MgSO_4$ and evaporated to leave 5.62 g of crude mixture. Purification by flash chromatography on 500 g of silica gel, eluted with 4:6 ethyl acetate:petroleum ether provided 2.483 g (48%) of title compound as a clear colorless oil.

TLC Silica gel (1:1 ethyl acetate:hexane) $R_f$=0.16

IR($CCl_4$) 2979, 2927, 2915, 2862, 1444, 1389, 1249, 1096, 1056, 1032, 990, 960 cm$^{-1}$.

$^1$H NMR ($CDCl_3$) (270 MHz) δ5.33 (t, $^1$H, J=6.9 Hz) 5.08 (m, 2H) 4.10 (m, 4H) 3.99 (d, 2H, J=6.9 Hz) 3.67 (dt, 2H, J=11.1, 6.9 Hz) 1.9–2.2 (m, 10H) 1.67 (s, 6H) 1.59 (s, 6H) 1.32 (dt, 6H, J=1.1, 6.9 Hz) ppm.

Mass Spec (CI-$CH_4$/$N_2O$, + ions) m/e 427 (M+$C_3H_5$), 415 (M+$C_2H_5$), 387 (M+H), 183.

B. (E,E)-[2-[(3,7,11-Trimethyl-2,6,10-dodecatrienyl)oxy]ethyl]phosphonic acid, monoethyl ester A solution of 2.481 g (6.42 mmol) of Part A phosphonate in 64 ml of ethanol and 64.2 ml (64.2 mmol, 10 eq.) of 1M NaOH at 60°–70° C. under nitrogen was stirred for 18 hours. The mixture was cooled and adjusted to ~pH 7 with 10% HCl. The ethanol was evaporated and the residue was acidified. The aqueous mixture was extracted with four 150 ml portions of ethyl acetate. The combined organic phases were washed with 100 ml each of 50% brine and saturated brine, dried over $MgSO_4$ and evaporated to yield 2.345 g (100%) of title compound as a pale yellow oil.

TLC Silica gel (6:3:1 n-$C_3H_7OH$:con. NH :$H_2O$) $R_f$=0.68.

IR($CCl_4$) 2978, 2972, 2926, 2916, 2870, 2859, 2450, 1669, 1445, 1379, 1237, 1202, 1090, 1049, 1001, 965, 802, 780, 771, 751, 740 cm$^{-1}$.

$^1$H NMR ($CDCl_3$) (270 MHz) δ5.34 (t, $^1$H, J=6.9 Hz) 5.10 (m, 2H) 4.09 (quint, 2H, J=6.9 Hz) 3.99 (d, 2H, J=6.9 Hz) 3.68 (dt, 2H, J=9.5, 7.9 Hz) 1.9–2.2 (m, 10H) 1.67 (s, 6H) 1.60 (s, 6H) 1.33 (t, 3H, J=6.9 Hz) ppm.

Mass Spec (FAB, + ions) m/e 397 (M+K), 381 (M+Na), 359 (M+H), 331, 313, 155.

C. (E,E)-[[Ethoxy[2-[(3,7,11-trimethyl-2,6,10-dodecatrienyl)oxy]ethyl]phosphinyl]methyl]phosphonic acid, dimethyl ester A solution of 2.123 g (6.54 mmol) of crude Part B phosphonic acid in 20 ml of dry $CH_2Cl_2$ at room temperature under argon was treated with 2.50 ml (13.1 mmol, 2 eq.) of diethyl(trimethylsilyl)-amine. After two hours, the solvent was evaporated and the residue was twice evaporated from benzene, then dried at high vacuum for 0.5 hours.

The residue was dissolved in 20 ml of dry $CH_2Cl_2$ and two drops of dimethylformamide (DMF) at 0° C. under nitrogen and treated with 1.00 ml (11.8 mmol, 1.8 eq.) of oxalyl chloride. The mixture was allowed to warm to room temperature and stirred for 3 hours. The solvent was evaporated and the residue was twice evaporated from benzene, then dried at high vacuum for 0.5 hour.

The anion solution was prepared by adding over five minutes a solution of 8.75 ml (14.1 mmol, 2.15 eq.) of 1.6M n-butyllithium in hexanes to a solution of 1.55 ml (14.4 mmol, 2.2 eq.) of dimethyl methylphosphonate in 15 ml of THF at −78° C. under argon, followed by stirring for 0.5 hour.

A solution of the phosphonic acid chloride prepared above in 15 ml of THF at −78° C. under argon was added as quickly as possible via cannula to the anion solution. The resulting mixture was stirred at −78° C. for 1.5 hours, then quenched with 0.75 ml (13.1 mmol, 2 eq.) of glacial acetic acid, and allowed to stir for ten minutes. Approximately 3 ml of saturated ammonium chloride was added, and the cold bath was removed. Once at room temperature, 20 ml of H₂O was added and the mixture was extracted with five 80 ml portions of CH₂Cl₂. The combined organic phases were washed with 100 ml each of 1:1 brine:water and then brine, dried over MgSO₄ and evaporated to yield 2.773 g of crude product. Gross impurities were removed by flash chromatography on 300 g of Merck 9385 silica, eluted with 2:98 CH₃OH:CH₂Cl₂ to provide 913 mg (33%) of nearly pure material. A second flash chromatography on 100 g of Merck 9385 silica, eluted with 2:8 ethyl acetate:acetone afforded 414.2 mg (15%) of title compound as a clear, colorless oil.

TLC Silica gel (5:95 CH₃OH:CH₂Cl₂) $R_f=0.17$

IR(CCl₄) 2955, 2918, 2856, 1448, 1377, 1369, 1257, 1240, 1185, 1167, 1064, 1037, 995, 957, 844 cm$^{-1}$.

¹H NMR (CDCl₃) (270 MHz) δ5.33 (t, ¹H, J=6.9 Hz) 5.10 (m, 2H) 4.16 (quint, 2H, J=7.2 Hz) 4.01 (d, 2H, J=6.9 Hz) 3.80 (d, 6H, J=11.1 Hz) 3.6–3.8 (m, 2H) 2.53 (dd, 2H, J=20.6, 16.9 Hz) 2.26 (m, 2H) 1.9–2.2 (m, 8H) 1.67 (s, 6H) 1.60 (s, 6H) 1.34 (t, 3H, J=7.2 Hz) ppm.

Mass Spec (CI-CH₄/N₂O, + ions) m/e 493 (M+C₂H₅), 465 (M+H), 261.

EXAMPLE 15

(E,E)-[[Hydroxy[2-[(3,7,11-trimethyl-2,6,10-dodecatrienyl)oxy]ethyl]phosphinyl]methyl]phosphonic acid, trisodium salt To a solution of 343.3 mg (0.79 mmol) of Example 14 triester and 315 μl (2.37 mmol, 3 eq.) of 2,4,6-collidine in 5 ml of dry CH₂Cl₂ at room temperature under nitrogen in the dark was added 630 μl (4.75 mmol, 6 eq.) of bromotrimethyl-silane. After 6 hours, additional 105 μl (0.79 mmol, 1 eq.) of 2,4,6-collidine and 210 μl (1.58 mmol, 2 eq.) of bromotrimethylsilane were added and the reaction was allowed to stir overnight. The solvent was evaporated and the residue was twice evaporated from benzene and dried at high vacuum for 0.5 hour. Then 6.35 ml (6.35 mmol, 8 eq.) of 1M NaOH was added and the solution was lyophilized. Preliminary purification was by HP-20 chromatography on a 16cm height x 2.5cm diameter column packed with water and eluted with 200 ml of water followed by a gradient created by the gradual addition of 400 ml acetonitrile to 400 ml of H₂O. Approximately 8–10 ml fractions were collected every 1.5 minutes. Fractions 24–53 were combined, evaporated and lyophilized to afford 220.2 mg (54%) of a fluffy white lyophilate, which however, showed impurities on NMR analysis. The lyophilate was dissolved in water, adjusted to pH 12 with 1M NaOH, and was chromatographed on a 12 cm height×2.5 cm diameter column of CHP20P resin packed in water. The column was eluted with a gradient created by the gradual addition of 300 mL of acetonitrile into 300 mL of 2:98 acetonitrile: water. Approximately 8–10 mL fractions were collected every 1.5 minutes. Fractions 22–26 were combined, evaporated, lyophilized and pump-dried for 6 hours to provide 145.7 mg (42%) of title product as a flocculent white lyophilate.

TLC Silica gel (5:4:1 n-C₃H₇OH con. NH₃ H₂O) $R_f=0.36$.

IR(KBr) 3400 (br), 2967, 2923, 2859, 1663, 1640, 1631, 1448, 1381, 1167, 1128, 1099, 1083, 978, cm$^{-1}$.

¹H NMR (D₂O) (400 MHz) δ5.33 (t, ¹H, J=7.1 Hz) 5.14 (t, ¹H, J=7.1 Hz) 5.12 (t, ¹H, J=7.1 Hz) 4.01 (d, 2H, J=7.1 Hz) 3.70 (m, 2H) 2.0–2.1 (m, 8H) 1.96 (t, 2H, J=7.1 Hz) 1.87 (t, 2H, J=18.3 Hz) 1.64 (s, 3H) 1.62 (s, 3H) 1.56 (s, 3H) ppm.

³¹P-NMR (D₂O) δ38.7 (d, J=5.86 Hz) 14.6 (d, J=5.86 Hz) ppm.

Mass Spec (FAB, + ions) m/e 497 (M+Na, 475 (M+H), 453 (M+2H-Na).

Anal Calcd for C₁₈H₃₁O₆P₂Na₃.1.05 H₂O (MW 493.33): C, 43.82; H, 6.76; P, 12.56 Found: C, 43.59; H, 6.72; P, 12.52

EXAMPLE 16

(E)-[[[[(7,11-Dimethyl-6,10-dodecadien-2-ynyl)oxy]methyl](1-methylethoxy)phosphinyl]methyl]phosphonic acid, dimethyl ester A. (E)-2,6-Dimethyl-2,6-undecadien-10-yne A solution of 4.60 ml (27.0 mmol, 1.05 equiv.) of 2,2,6,6-tetramethylpiperidine in 55 ml of tetrahydrofuran at 0° C. under argon was treated with 17.0 ml (27.0 mmol, 1.05 equiv.) of 1.6 M n-butyllithium in hexanes and the mixture was stirred at 0° C. for 0.5 hours. After cooling to −78° C. a solution of 5.75 ml (25.7 mmol) of (E)-geranyl acetone (obtained from FLUKA) and used in 15 ml of tetrahydrofuran was added over 15 minutes. The reaction was stirred for one hour, then 4.10 ml (28.3 mmol, 1.1 equiv.) of diethyl chlorophosphate was added. The mixture was allowed to warm to room temperature over two hours to provide a solution of the enol phosphate.

A second solution of the lithium piperidide was prepared by treating a solution of 9.8 ml (57.8 mmol, 2.25 equiv.) of 2,2,6,6-tetramethylpiperidine in 120 ml of tetrahydrofuran at 0° C. under argon with 36.2 ml (157.8 mmol, 2.25 eq.) of 1.6M n-butyllithium in hexanes, stirring at 0° C. for 0.5 hour, then cooling to −78° C. The enol phosphate solution was added to the anion solution dropwise over 65 minutes and the resulting mixture was allowed to warm to room temperature over two hours. After quenching the reaction with H₂O, the acetylene was extracted with three 250 ml portions of hexane. The combined organic phase was washed with 100 ml of 1 M HCl, 100 ml of H₂O, 100 ml of saturated NaHCO₃, and 100 ml of brine, dried over MgSO₄ and evaporated to obtain 6.123 g of crude product as a dark orange oil. Purification by flash chromatography on 600 g Merck 9385 silica eluted with hexane provided 2.201 g (49%) of title acetylene as a clear, colorless oil.

TLC Silica gel (hexane) $R_f=0.23$

IR(CCl₄) 3314, 2968, 2915, 2856, 2119, 1448, 1433, 1383, 1377, 805, 797, 789, 779, 754, 634 cm$^{-1}$.

¹H-NMR (CDCl₃) (270 MHz) δ5.18 (t, ¹H, J=5.6 Hz) 5.10 (t, ¹H, J=6.1 Hz) 2.20 (m, 4H) 2.0–2.1 (m, 4H) 1.92 (t, ¹H, J=2.3 Hz) 1.68 (s, 3H) 1.62 (s, 3H) 1.61 (s, 3H) ppm.

Mass Spec (CI-NH₃, + ions) m/e 353 (2M+H), 283, 177 (M+H).

B. (E)-7,11-Dimethyl-6,10-dodecadien-2-yn-1-ol

A solution of 2.162 g (12.3 mmol) of Part A terminal acetylene in 40 ml of tetrahydrofuran at −78° C. under argon was treated with 8.45 ml (13.5 mmol, 1.1 equiv.) of 1.6 M n-butyllithium in hexanes. After one hour, 554 mg (18.5 mmol, 1.5 equiv.) of dry paraformaldehyde was gradually added, and the reaction was allowed to warm slowly to room temperature and was stirred for four hours. Saturated NH₄Cl was added and the mixture was extracted with 200 ml of diethyl ether. The organic phase was washed with 20 ml of H₂O, and 20 ml of brine, dried over MgSO₄ and evaporated to give 2.561 g of a pale yellow oil. Purification by flash chromatography on 200 g of silica gel eluted with 1:9 ethyl acetate:hexane yielded 2.172 g (86%) of title alcohol as a clear, colorless oil.

TLC Silica gel (2:8 ethyl acetate:hexane) $R_f$=0.36.

IR(CCl₄) 3622, 3520, 2967, 2917, 2873, 2857, 2284, 2221, 1660, 1447, 1381, 1134, 1009, 805, 794, 777, 756, 738 cm⁻¹.

¹H NMR (CDCl₃) (270 MHz) δ5.16 (m, ¹H) 5.10 (m, ¹H) 4.24 (br s, 2H) 2.30 (br t, ¹H) 2.22 (m, 4H) 1.9–2.1 (m, 4H) 1.68 (s, 3H) 1.62 (s, 3H) 1.60 (s, 3H) ppm.

Mass Spec. (CI-NH₃, + ions) m/e 224 (M+NH₄).

C. (E)-[[(7,11-Dimethyl-6,10-dodecadien-2-ynyl)oxy]methyl]phosphonic acid, bis(1-methylethyl) ester A solution of 603 mg (2.91 mmol) of Part B propargylic alcohol in 10 ml of tetrahydrofuran at −78° C. under argon was treated with 1.90 ml (3.06 mmol, 1.05 equiv.) of 1.6 M n-butyllithium in hexanes. The reaction was stirred 15 minutes at −78° C., 15 minutes at 0° C., then recooled to −78° C. A solution of 1.004 g (3.06 mmol, 1.05 equiv.) of Example 1 Part B triflate in 3 ml of tetrahydrofuran was added in rapid drops. The solution was stirred 1.5 hours at −78° C. and 4.5 hours at 0° C. The reaction was quenched with saturated NH₄Cl and extracted with 100 ml of diethyl ether. The organic phase was washed with three 20 ml portions of H₂O, and 20 ml brine, dried over MgSO₄ and evaporated to yield 1.087 g of crude product. Purification by flash chromatography on 70 g of silica gel, eluted with 3:7 ethyl acetate:hexane provided 964 mg (87%) of title phosphonate as a clear, pale yellow oil.

TLC Silica gel (2:8 ethyl acetate:hexane) $R_f$=0.07

IR(CCl₄) 2979, 2928, 2854, 1465, 1450, 1385, 1375, 1357, 1256, 1242, 1178, 1136, 1105, 991, 937, 901, 889, 795, 788, 777, 772, 754 cm⁻¹.

¹H NMR (CDCl₃) (270 MHz) δ5.17 (br t, ¹H, J=6.2 Hz) 5.09 (br t, ¹H J=6.2 Hz) 4.76 (m, 2H) 4.25 (s, 2H) 3.80 (d, 2H, J=8.8 Hz) 2.22 (m, 4H) 1.9–2.1 (m, 4H) 1.68 (d, 3H, J=1.2 Hz) 1.62 (d, 3H, J=1.2 Hz) 1.60 (s, 3H) 1.34 (d, 12H, J=6.5 Hz) ppm.

Mass Spec (CI-NH₃, + ions) m/e 402 (M+NH₄), 385 (M+H).

D. (E)-[[(7,11-Dimethyl-6,10-dodecadien-2-ynyl)oxy]methyl]phosphonic acid, mono(1-methylethyl) ester A mixture of 951.3 mg of Part C diester, 25 ml of isopropanol and 25 ml (25 mmol, 10.1 equiv.) of 1 M KOH under nitrogen was stirred three days at 85°–90° C., then cooled. The solution was neutralized to ~pH7 with 10% HCl and the isopropanol was evaporated. The remaining aqueous solution was diluted with ethyl acetate, acidified to pH 1 and separated. The aqueous phase was extracted with three 50 ml portions of ethyl acetate. The organic layers were combined and washed with 30 ml of brine, dried over MgSO₄ and evaporated to obtain 827.0 mg ("98%") of title phosphonic acid.

TLC Silica gel (8:1:1 n-C₃H₇OH:con. NH₃:H₂O) $R_f$=0.57

IR(CCl₄) 2979, 2922, 2918, 2853, 1385, 1237, 1221, 1202, 1179, 1135, 1100, 1013 cm⁻¹.

¹H NMR (CDCl₃) (270 MHz) δ10.9–11.1 (br, ¹H) 5.15 (br, ¹H) 5.09 (br t, ¹H) 4.76 (m, ¹H) 4.26 (s, 2H) 3.83 (d, 2H, J=8.8 Hz) 2.23 (m, 4H) 1.9–2.1 (m, 4H) 1.68 (s, 3H) 1.61 (s, 3H) 1.60 (s, 3H) 1.35 (d, 6H, J=6.45 Hz) ppm.

Mass Spec (FAB,-ions) m/e 341 (M-H), 299

E. (E)- [[[(7,11-dimethyl-6,10-dodecadien-2-ynyl)oxy]methyl](1-methylethoxy)phosphinyl]methylphosphonic acid, dimethyl ester A solution of 798.3 mg (2.34 mmol) of Part D phosphonic acid in 12 ml of CH₂Cl₂ at room temperature under argon was treated with 890 μl (4.68 mmol, 2 equiv.) of N,N-diethyl(trimethylsilyl)-amine, stirred 1.5 hours and evaporated. The residue was twice evaporated from benzene and pump-dried for 30 minutes.

The residue was dissolved in 12 ml of CH₂Cl₂ and one drop of dimethylformamide at 0° C. under nitrogen, treated with 370 μl (4.21 mmol, 1.8 equiv.) of oxalyl chloride, and stirred at room temperature for 2.5 hours. The solvent was evaporated, and the residue was twice evaporated from benzene and pump-dried for 30 minutes.

The anion solution was prepared by treating 560 μl (5.15 mmol, 2.2 equiv.) of dimethyl methylphosphonate in 12 ml of tetrahydrofuran at −78° C. under argon with 3.5 ml (5.03 mmol, 2.15 equiv.) of 1.6 M n-butyllithium in hexanes. After 0.5 hours a solution of the phosphonic acid chloride prepared above in 2 ml of tetrahydrofuran was added. The mixture was stirred for 1.5 hours, then quenched with 300 μl (5.15 mmol, 2 equiv.) of acetic acid in tetrahydrofuran and stirred for ten minutes. Then, 5 ml of NH₄Cl was added and the product was extracted with four 30 ml portions of CH₂Cl₂. The combined organic phases were washed with brine, dried over MgSO₄ and evaporated to obtain 1.193 g of crude product. Purification required two chromatographies. The first was run on 70 g of silica gel, eluted with 2.5:97.5 CH₃OH:CH₂Cl₂ to provide 140.6 mg of pure title compound and 509.3 mg of impure fractions. The impure fractions were rechromatographed on 50 g of silica gel, eluted with 1.8:98.2 CH₃OH:CH₂Cl₂ to provide 466.1 mg of pure title compound. The combined yield of 606.7 mg (58%) of title compound was obtained as a yellow oil.

TLC Silica gel (2:98 CH₃OH:CH₂Cl₂) $R_f$=0.09

IR(CCl₄) 2977, 2954, 2923, 2853, 1257, 1230, 1179, 166, 1094, 1063, 1036, 993, 841, 818 cm⁻¹.

¹H NMR (CDCl₃) (270 MHz) δ5.08 (br t, ¹H, J=5.9 Hz) 5.02 (br t, ¹H, J=6.5 Hz) 4.74 (m, ¹H) 4.21 (d, ¹H, J=15.5 Hz) 4.14 (d, ¹H, J=15.5 Hz) 3.85 (d, 2H, J=7.6 Hz) 3.75 (d, 3H, J=12 Hz) 3.72 (d, 3H, J=11 Hz) 2.43 (m, 2H) 2.16 (m, 4H) 1.9–2.0 (m, 4H) 1.60 (s, 3H) 1.55 (s, 3H) 1.52 (s, 3H) 1.30 (d, 3H, J=5.9 Hz) 1.28 (d, 3H, J=5.9 Hz) ppm.

Mass Spec (CI-CH₄/N₂O, + ions) m/e 489 (M+C₃H₅), 477 (M+C₂H₅), 449 (M+H), 435, 407, 219.

EXAMPLE 17

(E)-[[[[(7,11-dimethyl-6,10-dodecadien-2-ynyl)oxy]methyl]hydroxyphosphinyl]methyl]phosphonic acid, tripotassium salt A solution of 598 mg (1.33 mg (1.33 mmol) of Example 16 triester in 8 ml of CH₂Cl₂ at room temperature under argon was treated with 530 μl (3.99 mmol, 3 equiv.) of 2,4,6-collidine and 1.05 ml (7.98 mmol, 6 equiv.) of bromotrimethylsilane and stirred for 24 hours. Additional 90 μl (67 mmol, 0.5 equiv.) of 2,4,6-collidine and 175 μl (1.33 mmol, 1 equiv.) of bromotrimethylsilane were added. The reaction was stirred for three hours and evaporated. The residue was dissolved in 18.6 ml (18.6 mmol, 14 equiv.) of 1 M KOH and 10 ml of H₂O, and lyophilized. The lyophilate was dissolved in 5 ml of H₂O and purified on a 2.5 cm diameter×16 cm height column of HP-20 resin packed in water. The column was eluted with 100 ml of H₂O followed by a gradient created by the gradual addition of 300 ml CH₃CN into 300 ml of H₂O. Approximately 10 ml fractions were collected every 1.8 minutes. Fractions 20–27 were combined, evaporated and lyophilized and dried under vacuum to obtain 472.4 mg (72%) title salt as a white lyophilate.

TLC Silica gel (5:4:1 n-C₃H₇OH:con. NH₃:H₂O) $R_f$=0.63.

IR (KBr) 3424, 2966, 2924, 2858, 1634, 1175, 1130, 1066, 970 cm⁻¹.

¹H NMR (D₂O) (400 MHz) δ5.20 (t, ¹H, J=6.8 Hz) 5.14 (t, ¹H, J=6.2 Hz) 4.19 (s, 2H) 3.67 (d, 2H, J=6.2 Hz) 2.15–2.25 (m, 4H) 2.06 (m, 2H) 1.99 (m, 2H) 1.91 (t, 2H, J=18.1 Hz) 1.63 (s, 3H) 1.58 (s, 3H) 1.56 (s, 3H) ppm.

³¹P NMR (D₂O) δ32.47 (d, J=8.06 Hz) 11.72 (d, J=8.06 Hz) ppm.

Mass Spec (FAB, + ions) m/e 531 (M+K), 493 (M+H), (M+2H-K), 437 (M+2H-K-H₂O)

Anal Calcd for C₁₆H₂₅O₆P₂.K₃.1.55 mol H₂O: C, 36.92; H, 5.44; P, 11.90 Found: C, 36.58; H, 5.16; P, 12.22

EXAMPLE 18

(E,E)-[[[[(3,7-Dimethyl-2,6-dodecadienyl)oxy]methyl](1-methylethoxy)phosphinyl]methyl]phosphonic acid, dimethyl ester A. 2,2-Dimethylpropanoic acid, (E,E)-3,7,11-trimethyl-2,6,10-dodecatrienyl ester To a stirred solution of 4.08 g (18.3 mmol) of (E,E)-farnesol in 50 ml of CH₂Cl₂ at 0° C. under argon was added 206 mg (1.69 mmol) of 4-dimethylaminopyridine and 3.8 ml (27.4 mmol) of triethylamine, followed by the dropwise addition of 2.7 ml (22.0 mmol) of trimethylacetyl chloride over 15 minutes. The suspension was stirred for 1 hour at 0° C. followed by 45 minutes at room temperature, and partitioned between CH₂Cl₂ and water. The organic layer was washed with 10% HCl, saturated NaHCO₃, and brine, dried (MgSO₄), and evaporated to provide 5.9 g of a crude liquid. Flash chromatography on 200 g of silica gel, packed and eluted with 1.5:98.5 ethyl acetate:hexane gave 5.53 g (98%) of pure title pivalate as a colorless liquid.

TLC Silica gel (5:95 ethyl acetate:hexane) $R_f$=0.39.

IR (CCl₄) 2970, 2930, 2875, 2857, 1727, 1480, 1456, 1281, 1152 cm⁻¹.

¹H NMR (CDCl₃) δ5.35 (td, ¹H, J=7, 1 Hz) 5.11 (m, 2H) 4.59 (d, 2H, J=7 Hz) 2.10 (m, 8H) 1.73 (s, 3H) 1.70 (s, 3H) 1.62 (s, 6H) 1.22 (s, 9H) ppm.

Mass Spec (EI) m/e 306 (M), 204, 136, 69.

B. 2,2-Dimethylpropanoic acid, (E,E)-10-bromo-11-hydroxy-3,7,11-trimethyl-2,6-dodecadienyl ester To a solution of 8.18 g (26.7 mmol) of Part A pivalate in 100 ml of 7:3 t-butanol:water at 0° C. was added 4.74 g (26.7 mmol) of recrystallized N-bromosuccinimide, portionwise over 30 minutes. After 135 minutes at 0° C., the reaction mixture was diluted with 400 ml of diethyl ether and washed with water, 2 M K₂CO₃ (two portions), water and brine. The organic layer was dried (MgSO₄) and evaporated to provide 10.9 g of a pale yellow liquid. Flash chromatography on 400 g of silica gel eluted with 10:90 ethyl acetate:hexane gave 6.76 g 63%) of pure title compound as a colorless liquid.

TLC Silica gel (20:80 ethyl acetate:hexane) $R_f$=0.31

¹H NMR (CDCl₃) δ5.32 (td, ¹H, J=7, 1 Hz) 5.20 (t, 2H, J=7 Hz) 4.57 (d, 2H, J=7 Hz) 3.95 (dd, ¹H, J=11.2, 1.7 Hz) 2.30 (m, 2H) 1.90–2.20 (m, 6H) 1.80 (m, ¹H) 1.70 (s, 6H) 1.60 (s, 6H) 1.339, 1.343 (two s, 6H total) 1.19 (s, 9H) ppm.

IR (CCl₄) 3610, 3580, 2978, 2958, 2874, 1726, 1282, 1152 cm⁻¹.

Mass Spec (CI-NH₃, + ions) m/e 420, 422 (M+NH₄), 403, 405 (M+H), 318, 320, 301, 303, 283, 285.

C. 2,2-Dimethylpropanoic acid, (E,E)-10,11-epoxy-3,7,11-trimethyl-2,6-dodecadienyl ester To a stirred solution of 6.65 g (16.5 mmol) of Part B compound in 50 ml of tetrahydrofuran under argon at −78° C. was added 17 ml (17 mmol) of M sodium bis(-trimethylsilylamide) in tetrahydrofuran over 20 minutes. After 30 minutes, the reaction was allowed to warm to 0° C. for 40 minutes, when it was diluted with CH₂Cl₂ and quenched with water. The organic layer was washed with water and brine, dried (MgSO₄) and evaporated to provide 5.30 g (99%) of the title epoxide as a colorless liquid.

TLC Silica gel (20:80 ethyl acetate:hexane) $R_f$=0.48.

IR (CCl₄) 2963, 2929, 2874, 1727, 1479, 1281, 1151 cm⁻¹.

¹H NMR (CDCl₃) δ5.33 (td, ¹H, J=7,1 Hz) 5.11 (td, ¹H, J=7,1 Hz) 4.57 (d, 2H, J=7 Hz) 2.69 (t, ¹H, J=6 Hz) 2.10 (m, 6H) 1.70 (s, 3H) 1.62 (s, 3H) 1.50–1.70 (m, 2H) 1.26, 1.30 (two s, 6H) 1.20 (s, 9H) ppm.

Mass Spec (CI-NH₃, + ions) m/e 340 (M+NH₄), 323 (M+H), 221.

D. 2,2-Dimethylpropanoic acid, (E,E)-3,7-dimethyl-10-oxo-2,6-decadienyl ester

To a stirred solution of 4.22 g (13.1 mmol) of the Part C epoxide in 50 ml of tetrahydrofuran at 0° C. was added 3.1 g (13.6 mmol) of periodic acid, portionwise over 10 minutes. After 40 minutes, the reaction was diluted with diethyl ether, washed with water, saturated NaHCO₃, and brine, dried (MgSO₄) and evaporated to provide 3.88 g of crude aldehyde. The crude product was purified by flash chromatography on 300 g of silica gel, packed in 3:97 and eluted with 5:95 ethyl acetate: hexane to afford 2.59 g (70%) of pure title aldehyde as a colorless oil.

TLC Silica gel (10:90 ethyl acetate:hexane) $R_f$=0.26.

IR (CCl₄) 2972, 2931, 2917, 1728, 1479, 1291, 1151 cm⁻¹.

¹H NMR (CDCl₃) δ9.74 (t, ¹H, J=1.7 Hz) 5.33 (td, ¹H, J=7,1 Hz) 5.13 (td, ¹H, J=7,1 Hz) 4.56 (d, 2H, J=6.5 Hz) 2.50 (td, 2H, J=7,1.7 Hz) 2.31 (t, 2H, J=7 Hz) 2.07 (m, 4H) 1.69 (s, 3H) 1.62 (s, 3H) 1.19 (s, 9H) ppm.

Mass Spec (CI-NH₃, + ions) m/e 298 (M+NH₄) dimethyl-10-[[(4-methylphenyl)sulfonyl]oxy]−2,6-dodecadienyl ester To a solution of 1.01 g (3.59 mmol) of Part D aldehyde in 12 ml of tetrahydrofuran at −78° C. was added 1.8 ml (3.60 mmol) of 2 M ethylmagnesium bromide in diethyl ether. After 30 minutes, the reaction was allowed to warm to 0° C. for 40 minutes. A solution of 753 mg (3.95 mmol) of p-toluenesulphonyl chloride in 5 ml of tetrahydrofuran was added rapidly via cannula, and the reaction was allowed to stir for 210 minutes at 0° C. The mixture was diluted with diethyl ether, washed successively with 1 M HCl, water, saturated NaHCO₃ and brine, dried (MgSO₄) and evaporated to provide 1.72 g of crude tosylate. Flash chromatography on 180 g of silica gel, eluted with 5:95 ethyl acetate:hexane gave 1.29 g (78%) of pure title tosylate as a colorless oil.

TLC Silica gel (20:80 ethyl acetate:hexane) $R_f=0.19$
IR (CCl$_4$) 2972, 2958, 2935, 1726, 1370, 1344, 1281, 1188, 1177, 1151, 915 cm$^{-1}$.

$^1$H NMR (CDCl$_3$) δ7.79 (d, 2H, J=8 Hz) 7.32 (d, 2H, J=8 Hz) 5.32 (t, $^1$H, J=7 Hz) 5.02 (t, $^1$H, J=7 Hz) 4.57 (d, 2H, J=7 Hz) 4.50 (quint, $^1$H, J=6 Hz) 2.44 (s, 3H) 2.04 (m, 4H) 1.91 (m, 2H) 1.69 (s, 3H) 1.52 (s, 3H) 1.50–1.80 (m, 4H) 1.19 (s, 9H) 0.83 (t, 3H, J=7 Hz) ppm.

Mass Spec (CI-NH$_3$, + ions) m/e 482 (m+NH$_4$)

F. (E,E)-3,7-Dimethyl-2,6-dodecadien-1-ol

To a stirred solution of 1.27 g 2.75 mmol) of Part E tosylate in 15 ml of tetrahydrofuran at ° C. under argon was added 17 ml (17 mmol) of 1 M LiB(C$_2$H$_5$)$_3$H in tetrahydrofuran over 30 minutes. The mixture was allowed to warm to room temperature for 3 hours, then cooled to −15° C. and the excess hydride was slowly quenched with water. The mixture was treated with 8.5 ml of 10% NaOH, followed by the cautious, dropwise addition of 7 ml of 30% hydrogen peroxide. After 1 hour, the reaction was allowed to warm to room temperature for 2 hours and then diluted with 300 ml of 1:1 diethyl ether:hexane. The organic layer was washed with water (four-100 ml portions) and brine, dried (MgSO$_4$), and evaporated to provide mg of crude alcohol. Flash chromatography on g of silica gel eluted with 10:90 ethyl acetate:hexane gave 553 mg (95%) of pure title alcohol as a colorless oil.

TLC Silica gel (20:80 ethyl acetate:hexane) $R_f=0.24$.
IR (CCl$_4$) 3622, 3400 (br), 2959, 2929, 2858, 1666, 1456, 1382, 1175, 999 cm$^{-1}$.

$^1$H NMR (CDCl$_3$) δ5.41 (td, $^1$H, J=7, 1 Hz) 5.09 (td, $^1$H, J=7, 1 Hz) 4.13 (d, 2H, J=7 Hz) 2.07 (m, 4H) 1.95 (t, 2H, J=7 Hz) 1.76 (br s, $^1$H) 1.67 (s, 3H) 1.58 (s, 3H) 1.10–1.50 (m, 6H) 0.88 (t, 3H, J=7 Hz) ppm.

Mass Spec (EI) m/e 210 (M), 192 (M-H$_2$O).

G. (E,E)-[[(3,7-Dimethyl-2,6-dodecadienyl)oxy]methyl]phosphonic acid, bis(1-methylethyl) ester To a stirred solution of 776.8 mg 3.69 mmol) of Part F alcohol in 8 ml of THF at −78° C. under argon was added 2.3 ml (3.69 mmol) of 1.6 M n-butyllithium in hexane over 10 minutes. After 1 hour at −78° C., a solution of 1.21 g (3.69 mmol) of Example 1 Part B triflate in 6 ml of THF was added via cannula. The reaction was maintained at −78° C. for 30 minutes, and then allowed to warm to 0° C. for 2 hours. After quenching with saturated NH$_4$Cl, the mixture was extracted with diethyl ether and the organic layer was washed with water and brine, dried (MgSO$_4$) and evaporated to provide 1.41 g of a crude yellow liquid. Flash chromatography on 70 g of silica gel packed in 80 and eluted with 30:70 ethyl acetate:hexane provided 1.24 g (86%) of pure title ether as a colorless oil.

TLC Silica gel (50:50 ethyl acetate:hexane) $R_f=0.30$.
IR(CCl$_4$) 2978, 2958, 2929, 2867, 1456, 1380, 1257, 1107, 990 cm$^{-1}$.

$^1$H NMR (CDCl$_3$) δ5.32 (td, $^1$H, J=7, 1 Hz) 5.09 (t, $^1$H, J=6.5 Hz) 4.77 (m, 2H) 4.12 (d, 2H, J=7 Hz) 3.68 (d, 2H, J=8.2 Hz) 2.07 (m, 4H) 1.95 (t, 2H, J=7 Hz) 1.68 (s, 3H) 1.58 (s, 3H) 1.35, 1.36 (two d, 12H total, J=6 Hz) 1.10–1.50 (m, 6H) 0.88 (t, 3H, J=7 Hz) ppm.

Mass Spec (CI-CH$_4$/N$_2$O, + ions) m/e 429 (M+C$_3$H$_5$), 417 (M+C$_2$H$_5$), 389 (M+H), 197.

H. (E,E)-[[(3,7-Dimethyl-2,6-dodecadienyl)oxy]methyl]phosphonic acid, mono(1-methylethyl) ester A solution of 749.2 mg (1.93 mmol) of Part G ether in 12 ml of 2-propanol was treated with 12 ml of 1 M KOH and was heated to reflux under nitrogen for 48 hours. The 2-propanol was evaporated and the aqueous solution was stirred with dichloromethane and acidified with 10% HCl. The organic layer was washed with water and brine, dried (MgSO$_4$) and evaporated to provide 660 mg (99%) of a colorless oil.

TLC Silica gel (8:1:1 n-C$_3$H$_7$OH:con. NH$_3$:H$_2$O) $R_f=0.48$.

$^1$H NMR (CDCl$_3$) δ5.31 (t, $^1$H, J=7 Hz) 5.09 (t, $^1$H, J=6.5 Hz) 4.77 (m, $^1$H) 4.12 (d, 2H, J=7 Hz) 3.71 (d, 2H, J=8.2 Hz) 2.07 (m, 4H) 1.95 (t, 2H, J=7 Hz) 1.67 (s, 3H) 1.58 (s, 3H) 1.33 (d, 6H, J=6 Hz) 1.10–1.50 (m, 6H) 0.88 (t, 3H, J=7 Hz) ppm.

I. (E,E)-[[[(3,7-Dimethyl-2,6-dodecadienyl)oxy]methyl](1-methylethoxy)phosphinyl]methyl]phosphonic acid, dimethyl ester To a stirred solution of 643.8 mg (1.85 mmol) of Part G ether in 7 ml of CH$_2$Cl$_2$ under argon was added 0.72 ml (3.80 mmol) of diethyl(trimethylsilyl)amine and the reaction was allowed to stir for 1.5 hours at room temperature. The solvent was evaporated, the remainder was dissolved in benzene, the solution was concentrated and the residual oil was pumped at high vacuum. To the residue in 7 ml of CH$_2$Cl$_2$ containing a drop of dimethyl formamide at 0° C. under nitrogen was added 0.33 ml (3.80 mmol) of oxalyl chloride over 10 minutes. After 30 minutes at 0° C., the mixture was allowed to warm to room temperature for 45 minutes. The solvent was evaporated, and the remainder was dissolved in benzene, the solution was evaporated and the residual orange oil was pumped at high vacuum.

In a separate flask, to 0.44 ml (4.07 mmol) of dimethyl methylphosphonate in 15 ml of THF at −78° C. under argon was added 2.5 ml (4.00 mmol) of 1.6 M n-butyllithium in hexane over 10 minutes. After 30 minutes, a solution of the above acid chloride in 6 ml of THF was added over 15 minutes. The reaction was allowed to stir for 1.5 hours at −78° C. and was quenched with saturated NH$_4$Cl. The mixture was diluted with CH$_2$Cl$_2$ and water, and the aqueous layer was acidified with 10% HCl. The organic layer was separated, the aqueous layer was re-extracted with CH$_2$Cl$_2$, and the combined organic layers were washed with brine, dried (MgSO$_4$), and evaporated to provide 821 mg of a yellow oil. The crude product was purified by flash chromatography on 70 g of silica gel eluted with 2:98 CH$_3$OH:CH$_2$Cl$_2$ to provide 693.6 mg (83%) of pure title compund as a colorless oil.

TLC Silica gel (5:95 CH$_3$OH:CH$_2$Cl $R_f=0.23$.
IR (CCl$_4$) 2956, 2928, 2872, 1451, 1385, 1256, 1229, 1063, 1036, 992, 841 cm$^{-1}$.

$^1$H NMR (CDCl$_3$) δ5.32 (td, $^1$H, J=7,1 Hz) 5.08 (td, $^1$H, J=7,1 Hz) 4.80 (m, $^1$H) 4.12 (d, 2H, J=7 Hz) 3.80, 3.82 (two d, 6H total, J=11 Hz) 3.70–3.90 (m, 2H) 2.40 (m, 2H) 2.07 (m, 4H) 1.95 (t, 2H, J=7 Hz) 1.68 (s, 3H) 1.58 (s, 3H) 1.34, 1.37 (two d, 6H total, J=6.5 Hz) 1.10–1.50 (m, 6H) 0.88 (t, 3H, J=7 Hz) ppm.

Mass Spec (CI-NH$_3$, + ions) m/e 470 (M+NH$_4$), 453 (M+H), 261.

EXAMPLE 19

(E,E)-[[[[(3,7-Dimethyl-2,6-dodeoadienyl)oxy]methyl]hydroxyphosphinyl]methyl]phosphonic acid, trisodium salt A solution of Example 18 triester (653.3 mg, 1.44 mmol) in 7 ml of CH$_2$Cl$_2$ at room temperature under argon was treated with 0.60 ml (4.54 mmol) of 2,4,6-collidine followed by 1.2 ml (9.09 mmol) of bromotrimethylsilane. After 23 hours, the solution was concentrated, the residue was dissolved in benzene, the solvent was evaporated and the remainder was dried under vacuum. After dissolution in 8 ml of 1 M NaOH, the aqueous mixture was lyophilized. The crude product was purified by MPLC on a 22 cm tall, 2.5 cm diameter column of CHP20P gel, eluted with water (fractions 1-12), followed by a gradient created by the gradual addition on 500 ml of 80:20 acetonitrile:water to 500 ml of water, collecting approximately 8 ml fractions. Fractions 37-47 were combined, the acetonitrile was evaporated, the aqueous solution was lyophilized and the resulting powder dried under vacuum to provide 605.7 mg (92%) of title salt as a white, amorphous solid.

TLC Silica gel (5:4:1 n-$C_3H_7OH$:con NH ) $R_f$=0.4.

IR (KBr) 3500 (br), 2957, 2872, 2858, 1664, 1456, 1381, 1192, 1149, 1135, 1104, 1081, 1051, 976, 800, 765 $cm^{-1}$.

$^1$H NMR ($D_2O$) δ5.35 (t, $^1$H, J=7 Hz) 5.12 (t, $^1$H, J=7 Hz) 4.07 (d, 2H, J=7 Hz) 3.58 (d, 2H, J=6.6 Hz) 1.80-2.20 (m, 8H) 1.65 (s, 3H) 1.54 (s, 3H) 1.33 (quint, 2H, J=7 Hz) 1.20 (m, 4H) 0.80 (t, 3H, J=7 Hz) ppm.

$^{31}$P NMR ($D_2O$) δ32.3 (d, J=10.3 Hz) 12.8 (d, J=10.3 Hz) ppm.

Mass Spec (FAB, + ions) m/e 449 (M+H), 427 (M+2H-Na), 405 (M+3H-2Na)

Anal Calcd for C×0.55 mol (2.16%) $H_2O$: C, 41.94; H, 6.62; P, 13.52 Found: C, 42.27; H. 7.02; P, 13.87

EXAMPLE 20

(E,E)-[[(1-Methylethoxy)[(3,7,11-trimethyl-2,6-dodecadienyl)oxy]methyl]phosphinyl]methyl]phosphonic acid, dimethyl ester A. 2,2-Dimethylpropanoic acid, (E,E)-3,7,11-trimethyl-10-[[(4-methylphenyl)-sulfonyl]oxy]−2,6-dodecadienyl ester A solution of 1.56 g (5.55 mmol) of Example 18 Part D aldehyde in 15 ml of tetrahydrofuran at −78° C. was added 2.9 ml (5.80 mmol) of 2 M 2-propyl-magnesium chloride, in diethyl ether over 10 minutes. After 30 minutes, the reaction was allowed to warm to 0° C. for 1 hour. A solution of 1.11 mg (5.82 mmol) of p-toluenesulphonyl chloride in 6 ml of tetrahydrofuran was added rapidly via cannula, and the reaction was allowed to stir for 4.5 hours at 0° C. The mixture was diluted with diethyl ether, washed successively with 1 M HCl, water, saturated $NaHCO_3$ and brine, dried ($MgSO_4$) and evaporated to provide 2.53 g of crude tosylate. Flash chromatography on 200 g of silica gel, eluted with 4:96 ethyl acetate:hexane gave 1.98 g (75%) of pure title tosylate as a thick, colorless oil.

TLC Silica gel (10:90 ethyl acetate:hexane) $R_f$=0.24.

IR ($CCl_4$) 2969, 2931, 1726, 1479, 1457, 1367, 1345, 1281, 1176, 1152, 905 $cm^{-1}$.

$^1$H NMR ($CDCl_3$) δ7.79 (d, 2H, J=8 Hz) 7.32 (d, 2H, J=8 Hz) 5.32 (td, $^1$H, J=7,1 Hz) 5.02 (td, $^1$H, J=7,1 Hz) 4.57 (d, 2H, J=7 Hz) 4.50 (q, $^1$H, J=5 Hz) 2.44 (s, 3H) 1.80-2.20 (m, 7H) 1.69 (s, 3H) 1.68 (m, 2H) 1.52 (s, 3H) 1.19 (s, 9H) 0.84, 0.85 (two d, 6H total, J=7 Hz) ppm.

Mass Spec (CI-$CH_4/N_2O$, + ions) m/e 496 (M+$NH_4$), 377, 205.

B. (E,E)-3,7,11-Trimethyl-2,6-dodecadien-1-ol

To a stirred solution of 1.98 g (4.16 mmol) Part A tosylate in 25 ml of tetrahydrofuran at 0° C. under argon was added 25 ml (25 mmol) of 1 M LiB($C_2H_5$)$_3$H in tetrahydrofuran over 30 minutes. The solution was maintained at 0° C. for 24 hours, then cooled to −20° C. and the excess hydride was slowly quenched with water. The mixture was treated with 12.5 ml of 10% NaOH, followed by the cautious, dropwise addition of 11 ml of 30% hydrogen peroxide. After 30 minutes, the reaction was allowed to warm to room temperature for 1 hour and then diluted with 300 ml of 1:1 diethyl ether:hexane. The organic layer was washed with water (three-100 ml portions) and brine, dried ($MgSO_4$), and evaporated to provide 951 mg of crude alcohol. This material contained about 8% of farnesol, which was separated by chromatography on g of 20% $AgNO_3$ on silica gel, packed in 10:90 and eluted with 20:80 ethyl acetate:hexane. The appropriate fractions were combined and further purified by flash chromatography on 70 g of silica gel, eluted with 13:87 ethyl acetate:hexane to provide 732.5 mg (78%) of pure title alcohol as a colorless oil.

TLC Silica gel (20:80 ethyl acetate:hexane) $R_f$=0.29.

IR ($CCl_4$) 3622, 2955, 2930, 2870, 1665, 1467, 383, 1366, 994 $cm^{-1}$.

$^1$H NMR ($CDCl_3$) δ5.41 (td, $^1$H, J=7,1 Hz) 5.09 (td, $^1$H, J=7,1 Hz) 4.14 (d, 2H, J=7 Hz) 2.07 (m, 4H) 1.94 (t, 2H, J=7 Hz) 1.68 (s, 3H) 1.58 (s, 3H) 1.56 (nonet, $^1$H, J=7 Hz) 1.37 (m, 2H) 1.12 (m, 2H) 0.87 (d, 6H, J=7 Hz) ppm.

Mass Spec CI-$NH_3$, + ions) m/e 242 (M+$NH_4$), 224 (M+H), 207 (M+H-$H_2O$), 193.

C. (E,E)-[[(3,7,11-Trimethyl-2,6-dodecadienyl)oxy]methyl]phosphonic acid, bis(1-methylethyl) ester To a stirred solution of 490.7 mg (2.19 mmol) of Part B alcohol in 6 ml of THF at −78° C. under argon was added 1.4 ml (2.24 mmol) of 1.6 M n-butyllithium in hexane over 15 minutes. After 40 minutes at −78° C., a solution of 735 mg (2.24 mmol) of Example 1 Part B triflate in 6 ml of THF was added via cannula. The reaction was maintained at −78° C. for 1 hour, and then allowed to warm to 0° C. for 3 hours. After quenching with saturated $NH_4Cl$, the mixture was extracted with diethyl ether and the organic layer was washed with water and brine, dried ($MgSO_4$) and evaporated to provide 0.88 g of a crude yellow liquid. Flash chromatography on 70 g of silica gel packed in 87 and eluted with 27:73 ethyl acetate:hexane provided 786.7 mg (89%) of pure title ether as a colorless oil.

TLC Silica gel (50:50 ethyl acetate:hexane) $R_f$=0.25.

IR ($CCl_4$) 2978, 2955, 2931, 1466, 1385, 1256, 1107, 990 $cm^{-1}$.

$^1$H NMR ($CDCl_3$) δ5.33 (t, $^1$H, J=6.5 Hz) 5.09 (t, $^1$H, J=7 Hz) 4.77 (m, 2H) 4.12 (d, 2H, J=6.5 Hz) 3.68 (d, 2H, J=8.8 Hz) 2.07 (m, 4H) 1.95 (t, 2H, J=7 Hz) 1.68 (s, 3H) 1.58 (s, 3H) 1.53 (m, $^1$H) 1.33, 1.35 (two d, 12H total, J=6.5 Hz) 1.20-1 40 (m, 2H) 1.13 (m, 2H) 0.87 (d, J=7 Hz) ppm.

Mass Spec (CI-$NH_3$, + ions) m/e 420 (M+$NH_4$), 403 (M+H), 223, 197.

D. (E,E)-[[(3,7,11-Trimethyl-2,6-dodecadienyl)oxy]methyl]phosphonic acid, mono(1-methylethyl) ester A solution of 565.6 mg (1.41 mmol) of Part C ether in 8 ml of 2-propanol was treated with 8 ml of 1 M KOH and was heated to reflux under nitrogen for 48 hours. The 2-propanol was evaporated and the aqueous solution was stirred with dichloromethane and acidified with 10% HCl. The organic layer was washed with water and brine, dried ($MgSO_4$) and evaporated to provide 479.9 mg (95%) of title compound as a colorless oil.

TLC Silica gel (8:1:1 n-C$_3$H$_7$OH:con NH$_3$:H$_2$O) R$_f$=0.56.

$^1$H NMR (CDCl$_3$) δ5.33 (t, $^1$H, J=7 Hz) 5.09 (t, $^1$H, J=6.5 Hz) 4.77 (m, $^1$H) 4.13 (d, 2H, J=7 Hz) 3.72 (d, 2H, J=8.8 Hz) 2.07 (m, 4H) 1.95 (t, 2H, J=7.5 Hz) 1.67 (s, 3H) 1.58 (s, 3H) 1.53 (m, $^1$H) 1.34 (d, 6H, J=6 Hz) 1.20–1.40 (m, 2H) 1.13 (m, 2H) 0.86 (d, 6H, J=6.5 Hz) ppm.

E. (E,E)-[[(1-Methylethoxy)[[(3,7,11-trimethyl-2,6-dodecadienyl)oxy]methyl]phosphinyl]methyl]phosphonic acid, dimethyl ester To a stirred solution of 479.9 mg (1.33 mmol) of Part D compound in 5 ml of CH$_2$Cl$_2$ under argon was added 0.50 ml (2.66 mmol) of diethyl(trimethylsilyl)amine and the reaction was allowed to stir for 1.5 hours at room temperature. The solvent was evaporated, the remainder was dissolved in benzene, the solution was concentrated and the residual oil was pumped at high vacuum. To the residue in 5 ml of CH$_2$Cl$_2$ containing a drop of DMF at 0° C. under nitrogen was added 0.24 ml (2.75 mmol) of oxalyl chloride over 15 minutes. After 45 minutes at 0° C., the mixture was allowed to warm to room temperature for 30 minutes. The solvent was evaporated, and the remainder was dissolved in benzene, the solvent was evaporated and the residual orange oil was pumped at high vacuum.

In a separate flask, to 0.32 ml (2.93 mmol) of dimethyl methylphosphonate in 7 ml of THF at −78° C. under argon was added 1.8 ml (2.86 mmol) of 1.6 M n-butyllithium in hexane over 10 minutes. After 30 minutes, a solution of the above acid chloride in 5 ml of THF was added over 15 minutes. The reaction was allowed to stir for 1.5 hours at −78° C. and was quenched with saturated NH$_4$Cl. The mixture was diluted with CH$_2$Cl$_2$ and water, and the aqueous layer was acidified with 10% HCl. The organic layer was separated, the aqueous layer was re-extracted with CH$_2$Cl$_2$, and the combined organic layers were washed with brine, dried (MgSO$_4$), and evaporated to provide 605 mg of a colorless oil. The crude product was purified by flash chromatography on 70 g of silica gel eluted with 2:98 CH$_3$OH:CH$_2$Cl$_2$ to provide 513 mg (83%) of pure title ester as a colorless oil.

TLC Silica gel (5:95 CH$_3$OH:CH )R$_f$=0.27.

IR(CCl$_4$) 2954, 2930, 2869, 1465, 1385, 1256, 1229, 1063, 1036, 992, 841 cm$^{-1}$.

$^1$H NMR (CDCl$_3$) δ5.32 (td, $^1$H, J=7,1 Hz) 5.08 (td, $^1$H, J=6.5,1 Hz) 4.80 (m, $^1$H) 4.12 (d, 2H, J=7 Hz) 3.79, 3.83 (two d, 6H total, J=6 Hz) 3.70–3.90 (m, 2H) 2.48 (m, 2H) 2.08 (m, 4H) 1.94 (t, 2H, J=7.5 Hz) 1.67 (s, 3H) 1.58 (s, 3H) 1.53 (m, $^1$H) 1.37 (d, 3H, J=6.5 Hz) 1.34 (d, 3H, J=7 Hz) 1.20–1.40 (m, 2H) 1.12 (m, 2H) 0.86 (d, J=7 Hz) ppm.

Mass Spec CI-NH$_3$, + ions) m/e 484 (M+NH$_4$), 467 (M+H), 261.

EXAMPLE 21

(E,E)-[[Hydroxy[[(3,7,11-Trimethyl-2,6-dodecadienyl)oxy]methyl]phosphinyl]methyl]phosphonic acid, trisodium salt A solution of Example 20 triester (503.3 mg, 1.08 mmol) in 7 ml of CH$_2$Cl$_2$ at room temperature under argon was treated with 0.43 ml (3.25 mmol) of 2,4,6-collidine followed by 0.86 ml (6.48 mmol) of bromotrimethylsilane. After 24 hours, the solution was concentrated, the residue was dissolved in benzene, the solvent was evaporated and the remainder was dried under vacuum. After dissolution in 6 ml of 1 M NaOH, the aqueous mixture was lyophilized. The crude product was purified by MPLC on a 20 cm tall, 2.5 cm diameter column of CHP20P gel, eluted with water (fractions 1–15), followed by a gradient created by the gradual addition on 500 ml of acetonitrile to 500 ml of water, collecting approximately 8 ml fractions. Fractions 37–47 were combined, the acetonitrile was evaporated, the aqueous solution was lyophilized and the resulting powder dried under vacuum to provide 487.3 mg (93%) of title salt as a white, amorphous solid.

TLC Silica gel (5:4:1 n-C$_3$H$_7$OH con NH$_3$ H$_2$O) R$_f$=0.42.

IR (KBr) 3500 (br), 2953, 2927, 2869, 1635, 1456, 1382, 1191, 1135, 1105, 1076, 1050, 972 cm$^{-1}$.

$^1$H NMR {D$_2$O} δ5.36 t, $^1$H, J=7 Hz) 5.15 (t, $^1$H, J=7 Hz) 4.09 (d, 2H, J=7 Hz) 3.62 (d, 2H, J=6.3 Hz) 2.08 (m, 4H) 1.92 (m, 4H) 1.65 (s, 3H) 1.55 (s, 3H) 1.47 (nonet, 2H, J=7 Hz) 1.34 (quintet, 2H, J=7 Hz) 1.06 (q, 2H, J=7 Hz) 0.79 (d, 3H, J=7 Hz) ppm.

$^{31}$P NMR (D$_2$O) δ32.4 (d, J=10.3 Hz) 12.8 (d, J=10.3 Hz) ppm.

Mass Spec (FAB, + ions) m/e 463 (M+H), 441 (M+2H-Na).

Anal Calcd for C×0.90 mol (3.39%) H$_2$O: C, 42.67; H, 6.91; P, 12.94 Found: C, 42.98; H, 7.31; P, 13.26

EXAMPLE 22A (E,E)-[[Methoxy[[(3,7,11-trimethyl-2,6,10-dodecatrienyl)oxy]methyl]phosphinyl]difluoromethyl]phosphonic acid, diethyl ester A solution of the Example 3, Part B phosphonate monoester (585 mg, 1.77 mmol) in 16 mL of dry CH$_2$Cl$_2$ under argon atmosphere and at room temperature was treated with N,N-diethyl(trimethylsilyl)amine (0.671 mL, 3.54 mmol). The resulting pale yellow solution was stirred at room temperature for 2 hours. The CH$_2$Cl$_2$ was removed from the reaction mixture and the resulting residue was evaporated one time with benzene and then placed under high vacuum for 40 minutes. The resulting residue was stirred under argon in 16 mL of dry CH$_2$Cl$_2$. Two drops of DMF were added, and this solution was cooled to 0° C. and treated dropwise with oxalyl chloride (0.278 mL, 3.19 mmol). The reaction mixture was stirred at 0° C. for 20 minutes and then warmed to room temperature. After 2.5 hours at room temperature, the CH$_2$Cl$_2$ was removed on the rotavap, and the dark residue was azeotroped with benzene. The residue was pumped under high vacuum to give the desired phosphonochloridate.

A solution of lithium diisopropylamide (LDA) was prepared by the dropwise addition of n-butyllithium (0.920 mL of a 2.5 M solution in hexane, 2.29 mmol) to a 3.8 mL THF solution of diisopropyl-amine (0.353 mL, 2.52 mmol) which had been cooled to −78° C. under argon atmosphere. After the addition of the n-butyllithium was complete, the reaction was warmed to 0° C., stirred for 15 minutes, and then recooled to −78° C.. A solution of diethyl difluoro-methylphosphonate (0.450 g. 2.39 mmol) in 2.7 mL of THF was then added to the LDA solution at −78° C.. After stirring for 1 hour at −78° C., the reaction mixture was treated quickly with a solution of the phosphonochloridate prepared above. The amber reaction mixture was stirred for 2.5 hours at −78° C., and then quenched with NH$_4$Cl solution. After warming to room temperature, the reaction mixture was diluted with 12 mL of water and 15 mL of ethyl acetate. The aqueous layer was extracted several times with ethyl acetate. The organic extracts were combined, washed with brine and dried over MgSO$_4$. The desired title product (211 mg) was purified by flash chromatography on silica gel eluting with 75% ethyl acetate/hexane.

TLC Silica gel (75% ethyl acetate/hexane) R$_f$=0.42

$^1$H NMR (CDCl$_3$) δ 5.28 (m, $^1$H), 5.05 (m, 2H), 4.3 (m, 4H), 4.13 (d, 2H, J=7 Hz), 4.00 (d, 2H, J=5.0 Hz), 3.95 (d, 3H, J=12 Hz), 2.15 to 1.80 (m, 8), 1.65 (s, 6), 1.55 (s, 6H), 1.35 (t, 6H, J=7.0 Hz) ppm.

$^{13}$C NMR (CDCl$_3$) δ 142.08, 135.34, 131.18, 124.23, 123.62, 119.27, 69.75 (d, J=9.46 Hz), 65.42 (t, J=9.46 Hz), 63.43 (d, J=115.44), 54.01 (d, J=7.57), 39.61, 26.67, 26.25, 25.58, 17.60, 16.46, 16.35, 16.26, 15.93 ppm.

Mass Spec (CI, + ions) m/e 297 (M+-C H$_{25}$), 205 (M$^+$-C$_7$H$_{15}$O$_6$F$_2$P$_2$)

EXAMPLE 22B (E,E)-[[Hydroxy[[(3,7,11-trimethyl-2,6,10-dodecatrienyl)oxy]methyl]phosphinyl]difluoromethyl]phosphonic acid monoethyl ester, disodium salt The Example 22A triester (6.5 mg, 0.013 mmol) was stirred under argon atmosphere in dry DMSO in the presence of dry NaCN (2.5 mg, 0.052 mmol). The reaction mixture was then heated in a 145° C. oil bath for 20 hours. The reaction mixture was cooled to room temperature, and the solvent was removed in vacuo to provide title compound as a tan solid.

TLC Silica gel (7:2:1 n-C$_3$H$_7$OH:con. NH$_4$:H$_2$O) R$_f$=0.29

Mass Spec (FAB, + ions) m/e 525 (M+Na), 479 (M+2H-Na)

EXAMPLE 22C (E,E)-[[Hydroxy[[(3,7,11-trimethyl-2,6,10-dodecatrienyl)oxy]methyl]phosphinyl]difluoromethyl]phosphonic acid, trisodium salt A solution of Example 22A triester in dry CH$_2$Cl$_2$ and containing 2,4,6-collidine (3eq) is stirred at 0° C. under argon atmosphere. To this solution is added trimethyl silyl iodide (4eq), and the reaction is stirred at 0° C.. The solvent is removed from the reaction mixture and the resulting solid is treated with 1N NaOH solution. The solvents are removed in vacuo. Purification on CHP20P chromatography gives the title triacid as its trisodium salt.

EXAMPLE 23

(E,E)-[[[[(7,11-Dimethyl-2,6,10-dodecatrienyl)oxy]methyl](1-methylethoxy)phosphinyl]methyl]phosphonic acid, dimethyl ester A. (E,E)-7,11-Dimethyl-2,6,10-dodecatrien-1-ol A solution of 798 mg (3.88 mmol) of Example 16 Part B propargylic alcohol in 20 mL of tetrahydro-furan at room temperature under argon was treated dropwise with a solution of 3.45 mL (11.6 mmol, 3 equiv) of 3.4 M sodium bis(2-methoxyethoxy) aluminum) hydride (Red-Al trademark) in 5 mL of tetrahydrofuran. The mixture was refluxed for two hours, then cooled to 0° C. and quenched with 1 M H$_2$SO$_4$. The mixture was filtered through Celite, washing copiously with water and diethyl ether. The filtrate was diluted with diethyl ether, separated, and washed with H$_2$O and brine, dried over MgSO$_4$ and evaporated. Purification by flash chromatography on 70 g of silica gel, eluted with 1:9 ethyl acetate: hexane provided 730 mg (90%) of title allylic alcohol as a clear, colorless oil.

TLC Silica gel (2:8 ethyl acetate: hexane) Rf 0.36

IR (CCl$_4$) 3619, 2967, 2917, 2855, 1448, 1441, 1380, 1377, 1088, 996, 970, 803, 795 cm$^{-1}$.

$^1$H-NMR (CDCl$_3$, 270 MHz) δ 5.66 (m, 2H), 5.10 (m 2H), 4.06 (d, 2H, J=4.7 Hz , 1.9-2.2 (m, 9H), 1.68 (s, 3H), 1.60 (s, 6H) ppm.

Mass Spec (CI-CH$_4$/N$_2$O, − ions) m/e 415 (2M-H), 207 (M-H), 189 (M-H-H$_2$O).

B. (E,E)-[7,11-Dimethyl-2,6,10-dodecatrienyl)oxy]methyl]phosphonic acid, bis(1-methylethyl) ester A solution of 721 mg (3.46 mmol) of Part A allylic alcohol in 12 mL of tetrahydrofuran at −78° C. under argon was treated with 2.25 mL (3.63 mmol, 1.05 equiv) of a 1.6 M solution of n-butyllithium in hexanes over ten minutes and allowed to stir for 15 minutes at −78° C. and 15 minutes at 0° C.. After cooling to −78° C., a solution of 1.193 g (3.63 mmol, 1.05 equiv) of Example 1, Part B triflate in 5 mL of tetrahydrofuran was added over three minutes. The mixture was stirred for 1.5 hours at −78° C. and 3 hours at 0° C., then quenched with saturated NH$_4$Cl and diluted with 150 mL of diethyl ether. The organic phase was washed with two 30 mL portions of water and 30 mL of brine, dried over MgSO$_4$ and evaporated to give 1.215 g of crude product. Purification by flash chromatography on 70 g of silica gel, eluted with 3:7 ethyl acetate: hexane yielded 1.189 g (89%) of title phosphonate.

TLC Silica gel (3:7 ethyl acetate: hexane) Rf 0.17

IR (CCl$_4$) 2979, 2932, 2916, 1385, 1375, 1257, 1241, 1107, 1008, 990 cm$^{-1}$.

$^1$H-NMR (CDCl$_3$, 270 MHz) δ 5.73 (br dt, $^1$H, J=15.2, 6.1 Hz), 5.52 (dt, $^1$H, J=15.2, 6.5 Hz), 5.10 (m, 2H), 4.77 (m, 2H), 4.04 (d, 2H, J=6.5 Hz), 3.67 (d, 2H, J=8.8 Hz), 1.9-2.1 (m, 8H), 1.68 (s, 3H), 1.60 (s, 6H), 1.34 (dd, 12H, J=5.9, 1.8 Hz), ppm.

Mass Spec (CI-NH$_3$, + ions) m/e 404 (M+NH$_4$), 387 (M+H), 197.

C. (E,E)-[[(7,11-Dimethyl-2,6,10-dodecamethylethyl) ester

A mixture of 1.094 g (2.83 mmol) of Part B phosphonate, 28 mL of 2-propanol, and 28 mL (28 mmol, 10 equiv) of 1 M KOH was stirred at 85-90° C. under argon for three days and at room temperature for three days. The solution was neutralized to pH 6 with 10% HCl and the 2-propanol was evaporated. The aqueous residue was diluted with CH$_2$Cl$_2$, acidified to pH 1 and separated. Three additional CH$_2$Cl$_2$ extractions were combined with the first, washed with brine, dried over MgSO$_4$ and evaporated to obtain 968.4 mg 99%) of title phosphonic acid.

TLC Silica gel (8:1:1 n-C$_3$H$_7$OH: con. NH$_3$:H$_2$O) Rf 0.55

IR (CCl$_4$) 2978, 2926, 2853, 1450, 1385, 1375, 1220, 1200, 1179, 1107, 1012, 780, 752 cm$^{-1}$.

$^1$H-NMR (CDCl$_3$) δ 10.75 (br, $^1$H), 5.73 (br dt, $^1$H, J=15.3, 6.2 Hz), 5.52 (dt, $^1$H, J=15.3, 6.5 Hz), 5.10 (m, 2H), 4.75 (m, $^1$H), 4.05 (d, 2H, J=6.5 Hz), 3.71 (d, 2H, J=8.8 Hz), 1.9-2.1 (m, 8H), 1.68 (s, 3H), 1.59 (s, 6H), 1.35 (d, 6H, J=6.5 Hz) ppm.

Mass Spec (FAB, -ions) m/e 343 (M-H), 301

D. (E,E)-[[[[(7,11-Dimethyl-2,6,10-dodecatrienyl)oxy]-methyl](1-methylethyloxy)phosphinyl]methyl]phosphonic acid, dimethyl ester A solution of 965.3 mg (2.80 mmol) of Part C phosphonic acid in 15 mL of CH$_2$Cl$_2$ at room temperature under argon was treated with 1.05 mL (5.6 mmol, 2 equiv) of N,N-diethyl(trimethylsilyl)amine and stirred for 1.5 hours. The solvent was evaporated and residue was twice evaporated from benzene, then dried at high vacuum for ½ hour. The residue was dissolved in 15 mL of $CH_2Cl_2$ and one drop of dimethylformamide and treated at 0° C. under nitrogen with 440 %L (5.04 mmol, 1.8 equiv) of oxalyl chloride. After 2.5 hours at room temperature the solvent was evaporated, and the residue was twice evaporated from benzene, then dried at high vacuum for ½ hour.

The anion solution was prepared by treating a solution of 670 μL (6.16 mmol, 2.2 equiv) of dimethyl methylphosphonate in 15 mL of tetrahydrofuran at −78° C. under argon with 3.75 mL (6.02 mmol, 2.15 equiv) of 1.6 M n-butyllithium in hexanes and stirring for ½ hour. The phosphonic acid chloride prepared above in 3 mL of tetrahydrofuran was added over ten minutes, and the mixture was stirred for 1.5 hours at −78° C. The reaction was quenched by adding a solution of 320 μL (5.6 mmol, 2 equiv) of glacial acetic acid in 1 mL of tetrahydrofuran, warming to 0° C., and adding saturated $NH_4Cl$. After dilution with 30 mL of $CH_2Cl_2$ and 2 mL of $H_2O$, the layers were separated and the aqueous phase was re-extracted with three 30 mL portions of $CH_2Cl_2$. The combined organic layers were washed with brine, dried over $MgSO_4$ and evaporated to give 1.253 g of an orange oil. Purification by flash chromatography on 70 g of silica gel, eluted with 2:98 $CH_3OH$: $CH_2Cl_2$ provided 567.4 mg (45%) of pure title triester.

TLC Silica gel (5:95 $CH_3OH$: CH Rf 0.39

$^1$H-NMR ($CDCl_3$, 270 MHz) δ5.74 (br dt, $^1$H, J=15.9, 6.0 Hz), 5.52 (dt, $^1$H, J=15.9, 6.0 Hz), 5.10 (m, 2H), 4.79 (m, $^1$H), 4.04 (ABX, 2H, $J_{AB}$=11.7, $J_{AX}$=$J_{BX}$=6.0 Hz), 3.81 (m, 2H), 3.82 (d, 3H, J=11.1 Hz), 3.80 (d, 3H, J=12.3 Hz), 2.50 (m, 2H), 1.9–2.1 (m, 8H), 1.68 (s, 3H), 1.60 (s, 6H), 1.37 (d, 3H, J=7.0 Hz), 1.34 (d, 3H, J=7.0 Hz) ppm.

Mass Spec (CI-$CH_4$/$N_2O$+ ions) m/e 451 (M+H), 261, 219, 69.

EXAMPLE 24

(E,E)-[[[(7,11-Dimethyl-2,6,10-dodecatrienyl)oxy]methyl]hydroxyphosphinyl]methyl]phosphonic acid, trisodium salt A solution of 558.7 mg (1.24 mmol) of Example 23 triester in 7 mL of $CH_2Cl_2$ at room temperature under nitrogen was treated with 495 μL (3.72 mmol 3 equiv) of 2,4,6-collidine and 990 μL (7.44 mmol, 6 equiv) of bromotrimethylsilane and stirred for 18 hours. The solvent was evaporated and the residue was dissolved in 14.9 mL (14.9 mmol, 12 equiv) of 1 M NaOH and lyophilized overnight. Purification was by chromatography on a 2.5 cm diameter × 18 cm height column of CHP20P resin packed in water and eluted with 100 mL of $H_2O$ followed by a gradient created by the gradual addition of 300 mL of $CH_3CN$ into 300 mL of $H_2O$. Two fractions of product were collected, identical by 270 MHz $^1$H-NMR, one of which was contaminated with base. A second chromatography of the combined material was carried out on a 2.5 cm diameter × 18 cm height column of CHP20P resin loaded in $H_2O$ and eluted with 100 mL of $H_2O$ followed by a gradient created by the gradual addition of 350 mL of $CH_3CN$ into 350 mL of $H_2O$. Approximately 10 mL fractions were collected every 1.8 minutes. Fractions 30–38 were combined, evaporated, lyophilized, and pump-dried overnight to obtain 365.9 mg (66%) of title salt as a white lyophilate.

TLC Silica gel (5:4:1 n-$C_3H_7OH$: con. $NH_3$ H 0) $R_f$=0.33

IR (KBr) 3420 (br), 2969, 2924, 1648, 1639, 1164, 1106, 1073, 1051, 971 $cm^{-1}$.

$^1$H-NMR (D20, 400 MHz) δ5.79 (br dt, $^1$H, $J_d$=15.4 Hz), 5.59 (dt, $^1$H, J=15.4, 6.6 Hz), 5.18 (br, $^1$H), 5.13 (t, $^1$H, J=6.8 Hz), 4.00 (d, 2H, J=6.6 Hz), 3.63 (d, 2H, J=6.2 Hz), 2.05 (m, 6H), 1.97 (m, 2H), 1.92 (t, 2H, J=18.1 Hz), 1.63 (s, 3H), 1.56 (s, 6H) ppm $^{13}$P-NMR (D20, 36.2 MHz) δ 32.8 (d, J=8.06 Hz), 12.3 (d, J=8.06 Hz) ppm Mass Spec (FAB, + ions) m/e 469 (M+Na), 447 (M+H), 425 (M+2H-Na), 255, 226, 140, 125

Anal. calc'd for Na 0.72 $H_2O$: C, 41.84, H, 6.24; P, 13.49 Found: C, 41.84; H, 6.48; P, 13.22

EXAMPLE 25

(E,E)-[[[[(3-Chloro-7,11-dimethyl-2,6,10-dodecatrienyl)oxy]methylethoxyphosphinylmethyl]phosphonic acid, dimethyl ester A. (E,E)-3-Chloro-7,11-dimethyl-2,6,10-dodecatrien-1-ol A solution of 3.191 g (15.5 mmol) of Example 16, Part B propargylic alcohol in 75 mL of tetrahydrofuran at room temperature under argon was treated dropwise over 15 minutes with 7.3 mL (24.8 mmol, 1.6 equiv) of a 3.4 M solution of sodium bis(2-methoxyethoxy)aluminum hydride (Red-Al) in toluene and stirred for six hours. After cooling to −78° C. a solution of 4.55 g (34.1 mmol, 2.2 equiv) of N-chlorosuccinimide in 10 mL of $CH_2Cl_2$ was added dropwise over ten minutes. The resulting mixture was stirred for one hour at −78° C. and one hour at −20° C., then quenched with 8 mL of saturated aqueous $Na_2S_2O_3$ and 8 mL of saturated aqueous sodium potassium tartrate. After partitioning between 300 mL of diethyl ether and 40 mL of $H_2O$ the layers were separated. The organic phase was washed with 30 mL of saturated Na 30 mL of 1 M K , 30 mL of $H_2O$ and 30 mL of brine, dried over $MgSO_4$ and evaporated to yield 4.522 g of an orange oil. Purification by flash chromatography on 400 g of Merck 9385 silica eluted with 1:200:200 (CH )20: $CH_2Cl_2$ hexane provided 1.620 g (43%) of title alcohol as a colorless oil.

TLC Silica gel (2.5: 47.5: 50 %)20 $CH_2Cl_2$: hexane) $R_f$0.24

IR ($CCl_4$) 3618, 3400 (br), 2968, 2926, 2916, 2856, 1684, 1446, 1380, 1377, 1158, 1106, 1084, 1012 $cm^{-1}$ $^1$H-NMR ($CDCl_3$ 270 MHz) δ 5.71 t, $^1$H, J=6.8 Hz), 5.09 (m, 2H), 4.28 (d, 2H, J=6.8 Hz), 2.2–2.4 (m, 4H), 1.9–2.1 (m, 4H), 1.73 (br, $^1$H), 1.68 (s, 3H), 1.61 (s, 3H), 1.60 (s, 3H) ppm Mass Spec (CI-$NH_3$, + ions) m/e 260 (M + $NH_4$, 242 (M), 224 (M-$H_2O$)

B. (E,E)-[[(3-Chloro-7,11-dimethyl-2,6,10-dodecatrienyl)oxy]methyl]phosphonic acid, diethyl ester A solution of 1.523 g (6.26 mmol, 1.05 equiv) of Part A alcohol in 25 mL of tetrahydrofuran at −78° C. under argon was treated with 3.9 mL (6.26 mmol, 1.05 equiv) of 1.6 M -butyllithium in hexanes and stirred for 0.5 hours. A solution of 1.790 g (5.96 mmol) of Example 5, Part B triflate in 10 mL of tetrahydrofuran was added over ten minutes. The mixture was allowed to warm to 0° C. over 75 minutes and was stirred at 0° C. for two hours. The reaction was diluted with 125 mL of diethyl ether and quenched with 5 mL of $NH_4Cl$. After separation, the organic phase was washed with 25 mL of H$_2$O and 25 mL of brine, dried over MgSO$_4$ and evaporated to obtain 2.145 g of crude title product. Purification required two chromatographies. The first was run on a column of 200 g of silica gel eluted with 3:7 ethyl acetate:hexane to give 1.133 g of title compound and a coeluting impurity. A second flash column of 125 g of silica gel eluted with 15:85 acetone: hexane provided 796.8 mg (34%) of pure title phosphonate.

TLC Silica gel (2:8 acetone: hexane) R$_f$=0.23

IR (CCl$_4$) 2981, 2929, 2913, 2871, 2857, 1660, 1443, 1390, 1260, 1164, 1098, 1055, 1031, 969 cm$^{-1}$.

$^1$H-NMR (CDCl$_3$, 270 MHz) δ 5.63 (t, $^1$H, J=6.45 Hz), 5.08 (m, 2H), 4.26 (d, 2H, J=6.45 Hz), 4.18 (quint, 4H, J=7.0 Hz), 3.76 (d, 2H, J=10.0 Hz), 2.37 (t, 2H, J=6.8 Hz), 2.25 (q, 2H, J=6.8 Hz), 1.9–2.1 (m, 4H), 1.68 (s, 3H), 1.61 (s, 3H), 1.60 (s, 3H), 1.35 (t, 6H, J=7.0 Hz) ppm.

Mass Spec (CI-CH$_4$/N$_2$O, + ions) m/e 421 (M+C$_2$H$_5$), 393 (M+H), 357 (M+H-HCl), 169.

C. (E,E)-[[(3-Chloro-7,11-dimethyl-2,6,10-dodecatrienyl)oxymethyl]phosphonic acid, monoethyl ester A mixture of 518.9 mg (1.32 mmol) of Part B phosphonate, 6.6 mL of ethanol, and 6.6 mL (6.6 mmol, 1.5 equiv) of 1 M KOH was stirred at room temperature under nitrogen for 40 hours. The mixture was neutralized to pH 6 with 10% HCl, and the ethanol was evaporated. The aqueous residue was diluted with 20 mL of CH$_2$Cl$_2$ and H$_2$O, acidified to pH 1 and separated. The aqueous phase was extracted with three 25 mL portions of CH$_2$Cl$_2$. The organic layers were combined, washed with brine, dried over MgSO$_4$, and evaporated to yield 477.5 mg (99%) of crude title phosphonic acid.

TLC Silica gel (8:1:1 n-C$_3$H$_7$OH: con NH$_3$ H$_2$O) R$_f$=0.47

$^1$H-NMR (CDCl$_3$, 270 MHz) δ 9.6 (br, $^1$H), 5.63 (t, $^1$H, J=5.9 Hz), 5.08 (t, $^1$H, J=5.9 Hz), 5.07 (t, $^1$H, J=5.9 Hz), 4.25 (d, 2H, J=5.9 Hz), 4.18 (quint, 2H, J=7.0 Hz), 3.77 (d, 2H, J=9.4 Hz), 2.36 (t, 2H, J=7.0 Hz), 2.25 (q, 2H, J=7.0 Hz), 1.9–2.1 (m, 4H), 1.68 (s, 3H), 1.61 (s, 3H), 1.59 (s, 3H), 1.35 (t, 3H, J=7.0 Hz) ppm.

D. (E,E)-[[[[(3-Chloro-7,11-dimethyl-2,6,10-dodecatrienyl)oxy]methyl]ethoxyphosphinyl]methyl]phosphonic acid, dimethyl ester A solution of 476.2 mg (1.31 mmol) of Part C phosphonic acid in 8 mL of CH$_2$Cl$_2$ at room temperature under argon was treated with 500 μL (2.62 mmol, 2 equiv) of N,N-diethyl(trimethylsilyl)amine and stirred for 1.5 hours. The solvent was evaporated, the residue was twice evaporated from benzene and the residue was dried at high vacuum for ½ hour. The residue, dissolved in 8 mL of CH$_2$Cl$_2$ and one drop of dimethyl formamide at 0° C. under nitrogen, was treated with 1.2 mL (2.35 mmol, 1.8 equiv) of a 2.0M solution of oxalyl chloride in CH$_2$Cl$_2$. The reaction was stirred for 2.5 hours at room temperature. The solvent was evaporated, the residue was twice evaporated from benzene and the residue was dried at high vacuum for ½ hour.

The anion solution was prepared by treating a solution of 310 μL (2.86 mmol, 2.2 equiv) of dimethyl methylphosphonate in 8 mL of tetrahydrofuran at −78° C. under argon with 1.75 mL (2.8 mmol, 2.15 equiv) of a 1.6M solution of n-butyllithium in hexanes over ten minutes, and stirring for ½ hour. The phosphonic acid chloride prepared above, in 2 mL of tetrahydrofuran was added dropwise over ten minutes. After 1.5 hours the reaction was quenched with 150 μL (2.62 mmol, 2 equiv) of glacial acetic acid in 1 mL of tetrahydrofuran, allowed to warm to 0° C. and quenched with saturated NH$_4$Cl. The mixture was partitioned between 30 mL of CH$_2$Cl$_2$ and 10 mL of H$_2$O. The aqueous phase was re-extracted with two 30 mL portions of CH$_2$Cl$_2$. The combined organic layers were washed with brine, dried over MgSO$_4$ and evaporated to obtain 524.9 mg of crude product as a dark orange oil. Purification required two chromatographies. The first column was loaded with 50 g of silica gel and eluted with 2:98 CH$_3$OH: CH$_2$Cl$_2$ to yield 343.5 mg of product plus an impurity. The second column was run on 40 g of silica gel, eluted with 2:98 CH$_3$OH: CH$_2$Cl$_2$ and provided 257.9 mg (42%) of pure title diester as a pale yellow oil.

TLC Silica gel (5:95 CH$_3$OH: CH$_2$Cl$_2$) R$_f$ 0.36

IR (CCl$_4$) 2955, 2928, 2915, 2854, 1660, 1447, 1258, 1232, 1184, 1165, 1106, 1063, 1036, 961, 842, 816, 801, 785, 779 cm$^{-1}$.

$^1$H-NMR (CDCl$_3$) δ 5.64, (t, 1H, J=5.9 Hz), 5.08 (br t, 2H, J=5.8 Hz), 4.25 (d, 2H, J=5.9 Hz), 4.19 (m, 2H), 3.86 (m, 2H), 3.82 (d, 3H, J=11.5 Hz), 3.80 (d, 3H, J=11.5 Hz), 2.50 (m, 2H), 2.37 (br t, 2H, J=7.5 Hz), 2.25 (br q, 2H, J=7.5 Hz), 1.9–2.1 (m, 4H), 1.67 (s, 3H), 1.61 (s, 3H), 1.60 (s, 3H), 1.36 (t, 3H, J=7.0 Hz) ppm.

Mass Spec CI-NH$_3$, +ions) m/e 488 (M+NH$_4$), 471 (M+H), 247, 264

EXAMPLE 26

(E,E)-[[[[(3-Chloro-7,11-dimethyl-2,6,10-dodecatrienyl)oxy]methyl]hydroxyphosphinyl]methyl]phosphonic acid, trisodium salt A solution of 253.0 mg (0.54 mmol) of Example 25 triester in 4 mL of CH$_2$Cl$_2$ was treated with 215 μL (1.62 mmol, 3 equiv) of 2,4,6-collidine and 430 μL (3.24 mmol, 6 equiv) of bromotrimethylsilane and stirred at room temperature under nitrogen for 24 hours. The solvent was evaporated, and the residue was treated with 1.65 mL (1.65 mmol, 3.0 equiv) of 1M NaOH. The aqueous solution was then adjusted to pH 14 with 1M NaOH and lyophilized overnight. The crude lyophilate was purified by chromatography on a 2.5 cm diameter×20 cm height column of HP-20 resin loaded in water. The column was eluted with 100 mL of H$_2$O followed by a gradient created by the gradual addition of 400 mL of CH$_3$CN into 400 mL of H$_2$O. Approximately 10 mL fractions were collected every 1.3 minutes. Fractions 25–32 were combined, evaporated, lyophilized and dried at high vacuum overnight to obtain 245.3 mg (94%) of title salt as a white lyophilate. A 1.0% aqueous solution of title salt has pH 9.15.

TLC Silica gel (4:4:1 n-C$_3$H$_7$OH: con NH$_3$: H$_2$O) R$_f$=0.31

IR (KBr) 3427 (br), 2969, 2921, 2859, 1661, 1445, 1380, 1178, 1153, 1093, 1056, 977, 873, 796, 709 cm$^{-1}$.

$^1$H-NMR (D$_2$O, 400 MHz) δ 5.76 (t, 1H, J=6.2 Hz), 5.13 (br, 2H), 4.22 (d, 2H, J=6.2 Hz), 3.64 (d, 2H, J=6.2 Hz), 2.38 (t, 2H, J=7.1 Hz), 2.23 (q, 2H, J=7.1 Hz), 2.06 (q, 2H, J=6.9 Hz), 1.98 (t, 2H, J=6.9 Hz), 1.93 (t, 2H, J=17.9 Hz), 1.63 (s, 3H), 1.58 (s, 3H), 1.56 (s, 3H) ppm.

$^{31}$P-NMR (D$_2$O, 36.2 MHz) δ 32.34 (d, J=8.8 Hz), 12.42 (d, J=8.8 Hz) ppm.

Mass Spec (FAB +ions) m/e 503 (M+Na, 481 (M+H), 459 (M+2H-Na).

Anal Calcd for C$_{16}$H$_{26}$ClO$_6$P$_2$.1.05 H$_2$O (3.79% H$_2$O): C 38.46 H 5.67 Cl 7.10 P 12.38 Found: C 38.83 H 5.93 Cl 7.48 P 12.02

EXAMPLE 27

(E,E)-[[Ethoxy[[(3,7,11-trimethyl-2,6,10-dodecatrienyl)thio]methyl]phosphinyl]methyl]phosphonic acid, dimethyl ester A. Ethanethioic acid, S-(hydroxymethyl) ester Thiolacetic acid, obtained from Evans Chemetics, Inc., was purified prior to use by distillation from $P_2O_5$.

The procedure of Boehme, H., et al, (Ann., (1959), 623, p. 92) was followed. A mixture of 10.7 mL (0.15 mol) of thiolacetic acid and 4.5 g (0.15 mol) of paraformaldehyde was stirred at 100° C. for 1.5 hours. The yellow liquid was fractionally distilled to obtain 12.50 g (79%) of title compound as a yellow liquid, bp. 68°–71° C./25 mm (lit. bp 68°–70° C./20 mm).

TLC Silica gel (3:7 ethyl acetate: hexane) $R_f = 0.23$.

$^1$H-NMR (CDCL$_3$, 270 MHz) δ 5.06 (s, 2H), 2.40 (s, 3H) ppm.

B. Ethanethioic acid, S-(bromomethyl) ester

A mixture of 12.35 g (0.117 mol) of Part A compound and 3.67 mL (38.7 mmol, 0.33 equiv) of phosphorus tribromide was heated at 100° C. for ½ hour. After cooling, 40 mL of 0° C. water was added, and the layers were separated. The organic phase was washed with $H_2O$, dried over MgSO$_4$, filtered and evaporated. Fractional distillation provided 10.79 g (55%) of title compound as a pale yellow liquid with bp 38°–40° C./0.8 mm.

TLC Silica gel (hexane) $R_f = 0.26$.

$^1$H-NMR (CDCl$_3$, 270 MHz) δ 4.74, (d, 2H, J=2.11 Hz), 2.42 (d, 2H, J=2.11 Hz) ppm.

C. [(Acetylthio)methyl]phosphonic acid, diethyl ester

The procedure of Farrington, G. K., et al, (J. Med. Chem., (1985), 28, 1668) was followed.

A mixture of 10.51 g (62.1 mmol) of Part B compound and 11.7 mL (68.3 mmol, 1.05 equiv) of triethylphosphite was stirred at 130° C. for 2.5 hours. The product was isolated by fractional distillation, which yielded 10.10 g (72%) of title compound as a colorless oil with bp 82°–84° C./0.005 mm (lit. b.p. 105°–106° C./0.03 mm).

TLC Silica gel (7:3 Ethyl acetate: hexane) $R_f = 0.17$.

$^1$H-NMR (CDCl$_3$, 270 MHz) δ 4.14 (quint, 4H, J=7.7 Hz), 3.23 (d, 2H, J=14.2 Hz), 2.40 (s, 3H), 1.33 (t, 6H, J=7.7 Hz) ppm.

D. (E,E)-3,7,11-Trimethyl-2,6,10-dodecatrienyl bromide

A solution of 1.00 g (4.5 mmol) of (E,E)-farnesol in 10 mL of distilled diethyl ether at 0° C. under argon in the dark was treated dropwise with a solution of 195 μL (2.05 mmol, 0.45 eq.) of PBr$_3$ in 2 mL of ether. The resultant mixture was stirred at 0° C. for one hour, then quenched with water and separated. The organic phase was washed with 5 mL of $H_2O$, 5 mL of saturated NaHCO$_3$, and 5 mL of brine, dried over Na$_2$SO$_4$ and evaporated to give 1.26 (98%) of crude bromide as a clear oil.

TLC Silica gel (2:8 ethyl acetate:hexane) $R_f = 0.69$ (decomposes).

$^1$H NMR (CDCl$_3$) δ 5.52 (t, 1H, J=8.5 Hz), 5.08 (m, 2H), 4.01 (d, 2H), 1.9–2.2 (m, 8H), 1.73 (s, 3H), 1.68 (s, 3H), 1.60 (s, 6H) ppm.

E. (E,E)-[[(3,7,11-Trimethyl-2,6,10-dodecatrienyl)thio]methyl]phosphonic acid, diethyl ester To a solution of 3.661 g (16.2 mmol, 1.2 equiv) of Part C thioacetate in 35 mL of freshly distilled ethanol was added 10 mL (15 mmol, 1.1 equiv) of a freshly prepared 1.5M solution of sodium ethoxide. After two hours, a solution of 3.85 g (13.5 mmol) of Part D farnesyl bromide in 30 mL of benzene was added over ½ hour. The reaction was allowed to stir for 1.5 hours, then quenched with saturated NH$_4$Cl and evaporated. The residue was dissolved in water and 200 mL of diethyl ether and the layers were separated. The organic phase was washed with brine, dried over MgSO$_4$ and evaporated to give 5.107 g of a crude oil. Purification by flash chromatography on 500 g silica gel, eluted with 3:7 ethyl acetate:hexane provided 3.813 g (73%) of title compound as a clear, colorless oil.

TLC Silica gel (4:6 ethyl acetate: hexane) $R_f 0.27$

IR (CCl$_4$) 2980, 2926, 2915, 1444, 1375, 1218, 1046, 991, 962 cm$^{-1}$.

$^1$H-NMR (CDCl$_3$, 270 MHz) δ 5.22 (t, 1H, J=7.9 Hz), 5.09 (m, 2H), 4.17 (quint, 4H, J=7.0 Hz), 3.34 (d, 2H, J=7.9 Hz), 2.65 (d, 2H, J=12.3 Hz), 1.9–2.2 (m, 8H), 1.69 (s, 3H), 1.68 (s, 3H), 1.60 (s, 6H), 1.35 (t, 6H, J=7.0 Hz) ppm.

Mass Spec (CI-CH$_4$/N$_2$O, +ions) m/e 429 (M+C$_3$H$_5$), 417 (M+C$_2$H$_5$), 389 (M+H), 185.

F. (E,E)-[[(3,7,11-Trimethyl-2,6,10-dodecatrienyl)thio]methyl]phosphonic acid, monoethyl ester A mixture of 798 mg (2.06 mmol) of Part E compound, 20 mL of ethanol and 20 mL (20.0 mmol, 9.7 equiv) of 1M KOH under argon was heated at 65°–70° C. for 16 hours. After cooling, the mixture was neutralized to pH 6 with 10% HCl and the ethanol was evaporated. The aqueous residue was diluted with 25 mL of CH$_2$Cl$_2$, acidified to pH 1 and separated. The aqueous phase was extracted with four 20 mL portions of CH$_2$Cl$_2$. The combined organic layers were washed with 20 mL of brine, dried over MgSO$_4$, and evaporated to yield 777 mg (100%) of title phosphonic acid.

TLC Silica gel (8:1:1 n-C$_3$H$_7$OH: con NH$_3$:H$_2$O) $R_f = 0.60$ $^1$H-NMR (CDCl$_3$, 270 MHz) δ 10.5 (br, 1H), 5.21 (t, 1H, J=7.9 Hz), 5.09 (m, 2H), 4.17 (quint, 2H, J=7.0 Hz), 3.33 (d, 2H, J=7.9 Hz), 2.66 (d, 2H, J=12.9 Hz), 1.9–2.2 (m, 8H), 1.68 (s, 6H), 1.60 (s, 6H), 1.35 (t, 3H, J=7.0 Hz) ppm.

G. (E,E)-[[Ethoxy[[(3,7,11-trimethyl-2,6,10-dodecatrienyl)thio]methyl]phosphinyl]methyl]phosphonic acid, dimethyl ester A solution of 460 mg (1.28 mmol) of Part F phosphonic acid in 7 mL of CH$_2$Cl$_2$ at room temperature under argon was treated with 490 μL (2.58 mmol, 2 equiv) of N,N-diethyl(trimethylsilyl)amine and was allowed to stir for 1.5 hours. The solvent was evaporated, the residue was twice evaporated from benzene and dried at high vacuum. The residue was dissolved in 3 mL of CH$_2$Cl$_2$ at 0° C. under nitrogen and was treated with 1 drop of dimethyl formamide and dropwise with 200 μL (2.30 mmol, 1.8 equiv) of oxalyl chloride, then stirred at room temperature for 2.5 hours. The solvent was evaporated, the residue was twice evaporated from benzene and dried at high vacuum for ½ hour. The residue was dissolved in 2.0 mL of tetrahydrofuran.

The anion solution was prepared by treating a solution of 160 μL (1.47 mmol, 2.3 equiv) of dimethyl methylphosphonate in 3 mL of tetrahydrofuran at −78° C. under argon with 880 μL (1.41 mmol, 2.2 equiv) of a 1.6M solution of n-butyllithium in hexanes over five minutes. After ½ hour, 525.4 mg (1.41 mmol, 2.2 equiv) of CeCl$_3$.7 H$_2$O (dried for 2 hours at 140° C. at high vacuum) was added and the resulting suspension was stirred for one hour. One half (1.0 mL) of the solution of phosphonic acid chloride prepared above was added over five minutes. The reaction was stirred two hours at −78° C. then quenched with a solution of 75 μL (1.31 mmol, 2 equiv) of glacial acetic acid in 0.5 mL of THF. After warming to 0° C. the reaction was quenched with saturated NH₄Cl. The mixture was diluted with ethyl acetate and H₂O and separated. The aqueous phase was extracted with three 20 mL portions of ethyl acetate, and the organic layers were combined, washed with water and brine and dried over MgSO₄ to yield 168.2 mg of crude product mixture. Flash chromatography on 15 g of silica gel, eluted with 2:98 CH₃OH: CH₂Cl₂ provided 51.8 mg (17%) of pure title compound as a clear, colorless oil.

TLC Silica gel (3:7 acetone: ethyl acetate) $R_f$=0.24
IR (CCl₄) 3468 (br), 2961, 2917, 2854, 1448, 1384, 1376, 1246, 1184, 1033, 960, 846, 819 cm⁻¹.

¹H-NMR (CDCl₃, 270 MHz) δ 5.23 (td, 1H, J=8.2, 1.2 Hz), 5.09 (m, 2H), 4.20 (quint, 2H, J=7.0 Hz), 3.81 (d, 3H, J=12.3 Hz), 3.80 (d, 3H, J=11.1 Hz), 3.37 (ABX, 2H, $J_{AB}$13.5 Hz, $J_{AX}=J_{BX}$=8 Hz), 2.85 (ABX, 2H, $J_{AB}$=12 Hz, $J_{AX}=J_{BX}$=11 Hz), 2.62 (dd, 2H, J=17.0, 21.1 Hz), 1.9–2.1 (m, 8H), 1.70 (s, 3H), 1.68 (s, 3H), 1.60 (s, 6H), 1.36 (t, 3H, J=7.0 Hz) ppm Mass Spec. (CI-CH₄/N₂O, +ions) m/e 507 (M+C₃H₅), 495 (M+C₂H₅), 467 (M+H), 263

EXAMPLE 28

(E,E)-[[Hydroxy[[(3,7,11-trimethyl-2,6,10-dodecatrienyl)thio]methyl]phosphinyl]methyl]phosphonic acid, trisodium salt A solution of 56.3 mg (0.12 mmol) of Example 27 triester in 2 mL of CH₂Cl₂ at room temperature under nitrogen was treated with 49 μL (0.36 mmol, 3 equiv) of 2,4,6-collidine and 100 μL (0.72 mmol, 6 equiv) of bromotrimethylsilane and stirred for 24 hours. The solvent was evaporated and pumped under vacuum. The residue was dissolved in 1.5 mL of H₂O, treated with 400 μL (0.40 mmol, 3.3 equiv) of 1M NaOH and lyophilized. The brown lyophilate was dissolved in 3 mL of H₂O and purified by chromatography on a 1.5 cm diameter×24 cm height column of CHP20P resin loaded in water. The column was eluted with 50 mL of H₂O followed by a gradient created by the gradual addition of 150 mL of CH₃CN into 150 mL of H₂O. Approximately 5 mL fractions were collected every minute. Fractions 33–38 were combined, evaporated, lyophilized and dried at high vacuum to obtain 53.4 mg (92%) of title product as a white lyophilate.

TLC Silica gel (4:4:1 n-C₃H₇OH: con NH₃:H₂O) $R_f$=0.62

IR (KBr) 3428 (br), 2965, 2920, 2854, 1658, 1652, 1635, 1446, 1380, 1171, 1096, 1055, 897, 796 cm⁻¹.

¹H-NMR (D₂O, 400 MHz) δ 5.27 (t, 1H, J=8.0 Hz), 5.13 (m, 2H), 3.28 (d, 2H, J=8.0 Hz), 2.72 (d, 2H, J=11.0 Hz), 1.9–2.1 (m, 10H), 1.64 (s, 3H), 1.63 (s, 3H), 1.56 (s, 6H) ppm.

³¹P-NMR (D₂O, 36.2 MHz) δ 33.0 (d, J=6.6 Hz), 14.0 (d, J=6.6 Hz) ppm.

Mass Spec (FAB, +ions) m/e 499 (M+Na), 477 (M+H), 455 (M+2H-Na)

Anal Calcd for C₁₇H₂₉O₅P₂S.3Na.0.31 mole H₂O: C, 42.37; H, 6.19; P, 12.85 Found: C, 42.37; H, 6.26; P, 12.71

EXAMPLE 29

(E,E)-[[[[(3-Ethyl-7,11-dimethyl-2,6,10-dodecatrienyl)oxy]methyl](1-methylethoxy)phosphinyl]methyl]phosphonic acid, dimethyl ester A. (E)-5,9-Dimethyl-2-(1-oxopropyl)-4,8-decadienoic acid, ethyl ester To a suspension of 3.92 g (97.5 mmol, 3 equiv) of 60% NaH in mineral oil (washed three times with pentane) in 200 mL of tetrahydrofuran at 0° C. under argon was added dropwise a solution of 15.3 mL (107 mmol, 3.3 equiv) of ethyl propionylacetate. After 0.5 hour, a solution of 7.04 g (32.4 mmol) of (E)-geranyl bromide in 20 mL of tetrahydrofuran was added dropwise over 45 minutes. The mixture was stirred one hour at 0° C. and one hour at room temperture, quenched with NH₄Cl and diluted with 500 mL of diethyl ether. The organic layer was washed with water and brine, and dried over MgSO₄ to obtain 20.157 g of crude product as a yellow oil. Purification by flash chromatography on 800 g of silica gel, eluted with 3:97 ethyl acetate:hexanes provided 7.024 g (77%) of pure product as a clear, colorless oil.

TLC Silica gel (5:95 ethyl acetate:hexane) $R_f$=0.31
IR (CCL4) 2980, 2929, 2915, 2856, 1743, 1717, 1475, 1458, 1446, 1411, 1377, 1368, 1347, 1331, 1300, 1264, 1231, 1193, 1152, 1108, 1080, 1034, 798, 790, 775, 760, 748, 737 cm⁻¹.

¹H-NMR (CDCl₃, 270 MHz) δ 5.05 (m, 2H), 4.17 (q, 2H, J=7.04 Hz), 3.46 (t, 1H, J=7.62 Hz), 2.4–2.7 (m, 4H), 1.9–2.1 (m, 4H), 1.67 (s, 3H), 1.62 (s, 3H), 1.59 (s, 3H), 1.25 (t, 3H, J=7.04 Hz), 1.06 (t, 3H, J=7.04 Hz) ppm.

Mass Spec (CI-CH₄/N₂O, +ions) m/e 281 (M+H), 263.

B. (E)-7,11-Dimethyl-6,10-dodecadien-3-one

A mixture of 7.776 g (27.7 mmol) of Part A keto-ester in 80 mL of 15% NaOH at 60°–63° C. under argon was stirred for 75 minutes, then allowed to cool to room temperature. The mixture was diluted with 200 mL of diethyl ether and separated. The aqueous phase was re-extracted with 200 mL of diethyl ether. The combined organic layers were washed with 8 mL of water and 80 mL of brine, dried over MgSO₄ and evaporated to give 5.496 g of crude product as a clear, colorless oil. Purification by bulb-to-bulb distillation at 120° C./0.05 mm provided 4.823 g (83%) of pure title ketone.

TLC Silica gel (5:95 ethyl acetate:hexane) $R_f$=0.44
IR (CCl₄) 2971, 2915, 2855, 1718, 1529, 1510, 1500, 1450, 1413, 1377, 1353, 1261, 1238, 1196, 1157, 1111, 1064, 974, 946, 836, 794, 773, 758, 753, 748, 736, cm⁻¹.

¹H-NMR (CDCl₃, 270 MHz) δ 5.08 (m, 2H), 2.43 (t, 2H, J=7 Hz), 2.41 (q, 2H, J=7 Hz), 2.26 (q, 2H, J=7 Hz), 2.00 (m, 4H), 1.67 (s, 3H), 1.61 (s, 3H), 1.59 (s, 3H), 1.05 (t, 3H, J=7 Hz) ppm.

Mass Spec (CI-NH₃, +ions) m/e 226 (M+NH₄), 209 (M+H), 191, 165

C. (E,E)-3-Ethyl-7,11-dimethyl-2,6,10-dodecatrien-1-ol (2E, 6E-isomer)

D. (Z,E)-3-Ethyl-7,11-dimethyl-2,6,10-dodecatrien-1-ol (2Z, 6E-isomer)

A solution of 2.30 mL (11.5 mmol, 1.2 equiv) of triethyl phosphonoacetate in 40 mL of tetrahydrofuran at 0° C. under argon was treated dropwise over 20 minutes with 11.5 mL (11.5 mmol, 1.2 equiv) of 1M sodium bis(trimethylsilyl)amide in tetrahydrofuran. After warming to room temperature, a solution of 2.008 g (9.60 mmol) of Part B ketone in 5 mL of tetrahydrofuran was added over 15 minutes and the mixture was refluxed for 24 hours. After cooling, the solvent was evaporated and the gummy orange residue was dissolved in 40 mL of hexane and 15 mL of water. The aqueous layer was extracted with two additional portions of 35 mL of hexane. The combined organic layers were washed with brine, dried over MgSO$_4$, and evaporated to give 2.465 g of crude title product as an isomer ratio of approximately 1.5:1 2E:2Z isomers. Purification by flash chromatography on 200 g silica gel, eluted with 2:8 toluene:hexane provided 256 mg (15%) of 3-ethyl-7,11-dimethyl-2,6,10-dodecatrienoic acid, ethyl ester as a 1:10 2E:2Z mixture, and 1.60 g (62%) as a 2:1 2E:2Z mixture.

A solution of 1.327 g (4.77 mmol) of the above ester isomers (2:1 2E:2Z) in 25 mL of dry toluene at 0° C. was treated over 30 minutes with 9.5 mL (14.3 mmol, 3 equiv) of a 1.5M solution of diisobutylaluminum hydride in toluene. After two hours, the reaction was quenched with 250 μL (6.2 mmol, 1.3 equiv) of methanol, then with 250 μL of water, 250 μL of 15% NaOH, and 750 μL of water. After stirring for 0.5 hour, Na$_2$SO$_4$ was added and the reaction stirred an additional one hour before filtering through a pad of Celite, washing copiously with diethyl ether. Evaporation provided 1.014 g of crude product. Purification was accomplished by a series of flash chromatographies run on 20% silver nitrate on silica gel eluted with 3:7 ethyl acetate:toluene, followed by flash chromatography on normal silica gel, eluted with 7:93 ethyl acetate:hexane. In this manner was obtained 195 mg (17%) of pure title 2Z, 6E-isomer and 433 mg (39%) of pure title 2E, 6E-isomer.

2E, 6E-Isomer Data

TLC Silica gel (2:8 ethyl acetate:hexane) R$_f$=0.34
IR (CCl$_4$) 3620, 2967, 2928, 2877, 2857, 1661, 1451, 1381, 1376, 1327, 1308, 1267, 1255, 1222, 1214, 1182, 1178, 1153, 1106, 11082, 1066, 1048, 1003, 974, 939, 838 cm$^{-1}$.
$^1$H-NMR (CDCl$_3$, 400 MHz) δ 5.38 (t, 1H, J=6.8 Hz), 5.11 (m, 2H), 4.16 (d, 2H, J=5.5 Hz), 2.0-2.1 (m, 8H), 1.98 (t, 2H, J=7.3 Hz), 1.68 (s, 3H), 1.60 (s, 6H), 1.12 (br s, 1H), 0.99 (t, 3H, J=7.3 Hz) ppm.
Mass Spec (CI-NH$_3$, +ions) m/e 236 (M), 219 (M+H-H$_2$O), 149, 135, 123, 69

2Z, 6E-Isomer Data

TLC Silica gel (2:8 ethyl acetate:hexane) R$_f$=0.37
IR (CCl$_4$) 3621, 2966, 2929, 2879, 2858, 1662, 1451, 1381, 1376, 1226, 1107, 1058, 994, 940, 839 cm$^{-1}$.
$^1$H-HMR (CDCl$_3$, 400 MHz) δ 5.41 (t, 1H, J=6.96 Hz), 5.09 (m, 2H), 4.14 (d, 2H, J=6.96 Hz), 1.9-2.1 (m, 10H), 1.68 (s, 3H), 1.60 (s, 6H), 1.16 (br s, 1H), 1.03 (t, 3H, J=7.5 Hz) ppm.
Mass Spec (CI-NH$_3$, +ions) m/e 236 (M+H), 219 (M+H-H$_2$O), 149, 135, 123, 69.

E. (E,E)-[[(3-Ethyl-7,11-dimethyl-2,6,10-dodecatrienyl)oxy]methyl]phosphonic acid, bis(1-methylethyl) ester A solution of 392 mg (1.66 mmol) of Part C alcohol (2E, 6E-isomer), in 5 mL of tetrahydrofuran at −78° C. under argon was treated with 1.05 mL (1.66 mmol, 1.0 equiv) of a solution of 1.6M n-butyllithium in hexanes and stirred for 0.5 hours. A solution of 601 mg (1.82 mmol, 1.1 equiv) of Example 1, Part B triflate in 3 mL of tetrahydrofuran was added rapidly via cannula. The reaction was stirred 0.5 hour at −78° C. and two hours at 0° C., then quenched with NH$_4$Cl and diluted with 80 mL of diethyl ether and 20 mL of water. The organic phase was washed with 20 mL of water and 20 mL of brine, dried over MgSO$_4$ and evaporated to give 892 mg of crude product. Chromatography on 70 g of silica gel, eluted with 1:1 diethyl ether:hexane provided 552 mg (83%) of title phosphonate as clear, colorless oil.

TLC Silica gel (1:1 ethyl acetate:hexane) R$_f$=0.32
IR (CCl$_4$) 2978, 2933, 2877, 1385, 1375, 1257, 1241, 1107, 1006, 990, 773, 750, 738 cm$^{-1}$.
$^1$H-NMR (CDCl$_3$, 270 MHz) δ 5.28 (t, 1H, J=7.04 Hz), 5.10 (m, 2H), 4.77 (m, 2H), 4.14 (d, 2H, J=7.04 Hz), 3.69 (dd, 2H, J=8.80, 1.76 Hz), 1.9-2.1 (m, 10H), 1.68 (s, 3H), 1.60 (s, 6H), 1.34 (d, 12H, J=5.67 Hz), 0.98 (dd, 3H, J=7.63, 1.76 Hz) ppm
Mass Spec (CI-CH$_4$/N$_2$O, +ions) m/e 455 (M+C$_3$H$_5$), 443 (M+C$_2$H$_5$), 415 (M+H), 197

F. (E,E)-[[(3-Ethyl-7,11-dimethyl-2,6,10-dodecatrienyl)oxy]methyl]phosphonic acid, mono(1-methylethyl) ester A mixture of 536 mg (1.28 mmol) of Part E phosphonate, 6.40 mL (6.4 mmol, 5 equiv) of 1M KOH, and 6.40 mL of isopropanol was stirred at 85°-90° C. under nitrogen for 24 hours. After cooling to room temperature, the isopropanol was evaporated and the residue was diluted with 50 mL of CH$_2$Cl$_2$, acidified with 10% HCl, and separated. The aqueous phase was re-extracted with 50 mL of CH$_2$Cl$_2$. The combined organic layers were washed with brine, dried over MgSO$_4$, and evaporated to obtain 493 mg (100%) of crude title monophosphonic acid.

TLC Silica gel (8:1:1 n-C$_3$H$_7$OH:con NH$_3$:H$_2$O) R$_f$=0.59
$^1$H-NMR (CDCl$_3$, 270 MHz) δ 5.29 (t, 1H, J=7.04 Hz), 5.10 (m, 2H), 4.76 (m, 1H), 4.15 (d, 2H, J=7.04 Hz), 3.72 (d, 2H, J=8.79 Hz), 1.9-2.1 (m, 10H), 1.68 (s, 3H), 1.60 (s, 6H), 1.35 (d, 6H, J=5.86 Hz), 0.98 (t, 3H, J=7.63 Hz) ppm.

G. (E,E)-[[[[(3-Ethyl-7,11-dimethyl-2,6,10-dodecatrienyl)oxy]methyl](1-methylethoxy)phosphinyl]methyl]phosphonic acid, dimethyl ester A solution of 481 mg (1.29 mmol) of Part F phosphonic acid in 7 mL of dry CH$_2$Cl$_2$ at room temperature under argon was treated with 490 μL (2.58 mmol, 2.0 equiv) of N,N-diethyltrimethylsilylamine and allowed to stir for 1.5 hours. The solvent was evaporated and the residue was evaporated from benzene and dried at high vacuum for 0.5 hour.

The residue was dissolved in 7 mL of dry CH$_2$Cl$_2$ at 0° C. under nitrogen and treated with one drop of dimethyl formamide and 1.30 mL (2.58 mmol, 2.0 equiv) of a 2.0M solution of oxalyl chloride in CH$_2$Cl$_2$. The reaction was stirred for two hours at room temperature and the solvent was evaporated. The residue was evaporated from benzene and dried at high vacuum for 0.5 hour.

The anion solution was prepared by treating dropwise over five minutes a solution of 310 μL (2.84 mmol, 2.2 equiv) of dimethyl methylphosphonate in 7 mL of tetrahydrofuran at −78° C. under argon with 1.73 mL (2.77 mmol, 2.15 equiv) of a 1.6M solution of n-butyllithium in hexanes. After 0.5 hour, the phosphonic acid chloride prepared above was added dropwise in a solution of 3 mL of tetrahydrofuran. The reaction was stirred two hours at −78° C., quenched with saturated NH$_4$Cl, diluted with 5 mL of CH$_2$Cl$_2$ and allowed to warm to room temperature. Additonal 50 mL of $CH_2Cl_2$, 5 mL of water and 5 mL of 1M HCl was added and the layers were separated. The aqueous phase was re-extracted with 50 mL of $CH_2Cl_2$. The combined organic layers were washed with brine, dried over $MgSO_4$, and evaporated to give 662 mg of crude material as an orange oil. Purification by flash chromatography on 65 g of silica gel, eluted with 2:98 $CH_3OH:CH_2Cl_2$ provided 488 mg (73%) of desired title triester.

TLC Silica gel (5:95 $CH_3OH:CH_2Cl_2$) $R_f=0.27$

IR ($CCl_4$) 2968, 2930, 2876, 2854, 1451, 1375, 1257, 1230, 1105, 1089, 1063, 992, 841 $cm^{-1}$.

$^1$H-NMR ($CDCl_3$, 270 MHz) δ 5.27 (t, 1H, J=7.04 Hz), 5.09 (m, 2H), 4.80 (m, 1H), 4.13 (d, 2H, J=7.04 Hz), 3.82 (d, 2H, J=5.35 Hz), 3.82 (d, 3H, J=11.4 Hz), 3.80 (d, 3H, J=11.4 Hz), 2.50 (m, 2H), 1.9–2.1 (m, 10H), 1.68 (s, 3H), 1.60 (s, 6H), 1.36 (t, 6H, J=7.3 Hz), 0.98 (t, 3H, J=7.65 Hz) ppm.

Mass Spec (CI-$NH_4$, +ions) m/e 496 (M+$NH_4$), 479 (M+H)

EXAMPLE 30

(E,E)-[[[[(3-Ethyl-7,11-dimethyl-2,6,10-dodecatrienyl)oxy]methyl]hydroxyphosphinyl]methyl]phosphonic acid, trisodium salt A solution of 473 mg (0.99 mmol) of Example 29, triester in 5 mL of dry $CH_2Cl_2$ at room temperature under argon was treated with 390 μL (2.97 mmol, 3 equiv) of 2,4,6-collidine and 785 μL (5.94 mmol, 6 equiv) of bromotrimethylsilane and stirred for 28 hours. The solvent was evaporated and the residue was treated with 3.0 mL of 1M NaOH to pH 14 and lyophilized. Purification was effected by chromatography on a 2.5 cm diameter×20 cm height column of CHP20P resin packed in water and eluted with 100 mL of water followed by a gradient created by the gradual addition of 400 mL of $CH_3CN$ into 400 mL of water. Approximately 10 mL fractions were collected every 1.5 minutes. Fractions 29–35 were combined, evaporated, lyophilized and dried at high vacuum overnight to obtain 140 mg (30%) of pure title compound as a white lyophilate. (Additional 108 mg (23%) of product containing a trace impurity were obtained from fractions 36–38).

TLC Silica gel (4:4:1 n-$C_3H_7OH$:con $NH_3$:$H_2O$) $R_f=0.40$.

IR (KBr) 3435, 2966, 2926, 2858, 1652, 1191, 1150, 1138, 1130, 1107, 1078, 1052 $cm^{-1}$.

$^1$H NMR ($D_2O$, 400 MHz) δ 5.33 (t, 1H, J=7 Hz), 5.15 (m, 2H), 4.11 (d, 2H, J=7 Hz), 3.64 (d, 2H, J=6.2 Hz), 2.07 (m, 8H), 1.93 (m, 2H), 1.82 (t, 2H, J=18 Hz), 1.63 (s, 3H), 1.56 (s, 6H), 0.92 (t, 3H, J=7.5 Hz) ppm Mass Spec (FAB, +ions) m/e 497 (M+Na), 475 (M+H)

Anal Calcd for $C_{18}H_{32}P_2O_6Na_3 \times 2.29$ mol $H_2O$: C, 41.99; H, 6.95; P, 12.03 Found: C, 41.59; H, 6.54; P, 11.85

EXAMPLE 31

(2Z,6E)-[[[[(3-Ethyl-7,10-dimethyl-2,6,10-dodecatrienyl)oxy]methyl](1-methylethoxy)phosphinyl]methyl]phosphonic acid, dimethyl ester A. (2Z,6E)-[[(3-Ethyl-7,11-dimethyl-2,6,10-dodecatrienyl)oxy]methyl]phosphonic aicd, bis(1-methylethyl) ester A solution of 336 mg (1.42 mmol) of Example 29, Part D alcohol (approximately 95:5 2Z:2E) in 5 mL of tetrahydrofuran at −78° C. under argon was treated dropwise over three minutes with 0.90 mL (1.44 mmol, 1.0 equiv) of a 1.6M solution of n-butyllithium in hexanes and allowed to stir for 0.5 hour. A solution of 519 mg (1.58 mmol, 1.1 equiv) of Example 1, Part B triflate in 3 mL of tetrahydrofuran was added rapidly by cannula. The reaction was stirred one hour at −78° C. and four hours at 0° C., quenched with $NH_4Cl$ and diluted with 100 mL of diethyl ether. The organic phase was washed with two 20 mL portions of water and 20 mL of brine, dried over $MgSO_4$ and evaporated. Purification by flash chromatography on 70 g of silica gel, eluted with 2:8 ethyl acetate:hexane failed to separate unreacted triflate. A second chromatography on 35 g silica gel, eluted with 1:9 ethyl acetate:$CH_2Cl_2$ provided 321 mg (53%, 65% based on recovered starting alcohol) of desired title product.

TLC Silica gel (1:1 ethyl acetate:hexane) $R_f=0.25$

IR ($CCl_4$) 2979, 2933, 2877, 1452, 1429, 1386, 1375, 1258, 1246, 1220, 1145, 1107 $cm^{-1}$.

$^1$H NMR ($CDCl_3$, 270 MHz) δ 5.30 (t, 1H, J=7.0 Hz), 5.09 (br, 2H), 4.75 (m, 2H), 4.14 (d, 2H, J=7.0 Hz) 3.69 (d, 2H, J=8.80 Hz , 1.9–2.1 (m, 10H), 1.68 (s, 3H), 1.60 (s, 6H), 1.34 (d, 12H, J=6.45 Hz), 1.02 (t, 3H, J=7.6 Hz) ppm Mass Spec (CI-$CH_4/N_2O$, +ions) m/e 455 (M+$C_3H_5$), 443 (M+$C_2H_5$), 415 (M+H), 197, 144

B. (2Z,6E)-[[(3-Ethyl-7,11-dimethyl-2,6,10-dodecatrienyl)oxy]methyl]phosphonic acid, mono(1-methylethyl) ester A mixture of 311 mg (0.75 mmol) of Part A phosphonate, 3.75 mL (3.75 mmol, 5 equiv) of 1M KOH, and 3.75 mL of isopropanol was stirred at 85°–90° C. for 24 hours. The isopropanol was evaporated, and the residue was diluted with 50 mL of diethyl ether, acidified with 10% HCl, and separated. The aqueous phase was re-extracted with 50 mL of diethyl ether. The combined organic layers were washed with 20 mL of brine, dried over $MgSO_4$, and evaporated to provide 262 mg (94%) of crude title phosphonic acid.

TLC Silica gel (8:1:1 n-$C_3H_7OH$:con $NH_3$:$H_2O$) $R_f=0.56$.

$^1$H NMR ($CDCl_3$, 270 MHz) δ 5.31 (t, 1H, J=6.2 Hz), 5.09 (m, 2H), 4.76 (m, 1H), 4.15 (d, 2H, J=6.2 Hz), 3.71 (d, 2H, J=7.62 Hz), 1.9–2.1 (m, 10H), 1.68 (s, 3H), 1.60 (s, 3H), 1.59 (s, 3H), 1.35 (d, 6H, J=5.87 Hz), 1.02 (t, 3H, J=7.3 Hz) ppm.

C. (2Z,6E)-[[[[(3-Ethyl-7,10-dimethyl-2,6,10-dodecatrienyl)oxy]methyl](1-methylethoxy)phosphinyl]methyl]phosphonic acid, dimethyl ester A solution of 250 mg (0.67 mmol) of Part B triester in 3.5 mL of dry $CH_2Cl_2$ at room temperature under argon was treated with 255 μL (1.34 mmol, 2.0 equiv) of N,N-diethyltrimethylsilylamine and stirred for 1.5 hours. The solvent was evaporated, the residue re-evaporated from benzene and dried at high vacuum for 0.5 hour. The residue was dissolved in 3.5 mL of dry $CH_2Cl_2$ and treated at 0° C. under nitrogen with one drop of dimethylformamide and dropwise with a solution of 650 μL (1.34 mmol, 2.0 equiv) of 2M oxalyl chloride in $CH_2Cl_2$. The reaction was stirred at room temperature for two hours, the solvent was evaporated, and the residue was evaporated from benzene and dried at high vacuum for 0.5 hour.

The anion solution was prepared by treating a solution of 160 μL (1.47 mmol, 2.2 equiv) of dimethyl methylphosphonate in 3 mL of tetrahydrofuran at −78° C. under argon dropwise with a solution of 0.90 mL (1.44 mmol, 2.15 equiv) of 1.6M n-butyllithium in hexane and stirring for 0.5 hour. A solution of the phosphonic acid chloride prepared above in 2 mL of tetrahydrofuran was added dropwise. The reaction was stirred for two hours at −78° C., quenched with NH$_4$Cl, diluted with 5 mL of CH$_2$Cl$_2$ and warmed to room temperature. Additional 50 mL of CH$_2$Cl$_2$, 5 mL of H$_2$O and 5 mL of 1M HCl were added and the layers separated. The aqueous phase was extracted with 50 mL CH$_2$Cl$_2$. The combined organic layers were washed with brine, dried over MgSO$_4$, and evaporated to give 331 mg of crude product as a yellow oil. Purification by flash chromatography on 35 g silica gel, eluted with 1.5:98.5 CH$_3$OH:CH$_2$Cl$_2$, provided 170 mg (53%) of pure title product as a light yellow oil.

TLC Silica gel (5:95 CH$_3$OH:CH$_2$Cl$_2$) R$_f$=0.33

IR (CCl$_4$) 2967, 2929, 2877, 1451, 1257, 1230, 1180, 1165, 1105, 1090, 1063, 1036, 992, 841, 824, 815, cm$^{-1}$.

$^1$H NMR (CDCl$_3$, 270 MHZ) δ 5.22 (t, 1H, J=7.04 Hz) 5.02 (m, 2H), 4.73 (m, 1H), 4.06 (d, 2H, J=7.04 Hz), 3.75 (d, 3H, J=11.1 Hz), 3.73 (d, 3H, J=11.1 Hz), 3.6–3.9 (m, 2H , 2.2–2.6 (m, 2H), 1.8–2.1 (m, 10H), 1.60 (s, 3H), 1.52 (s, 6H), 1.28 (t, 6H, J=6.8 Hz), 0.95 (t, 3H, J=7.3 Hz) ppm.

Mass Spec (CI-CH$_4$/N$_2$O, −ions) m/e 477 (M-H)

EXAMPLE 32

(2Z,6E)-[[[[(3-Ethyl-7,10-dimethyl-2,6,10-dodecatrienyl)oxy]methyl]hydroxyphosphinyl]methyl]phosphonic acid, trisodium salt A solution of 165 mg (0.34 mmol) of Example 31 triester in 2 mL of dry CH$_2$Cl$_2$ was treated with 135 μL (1.02 mmol, 3 equiv) of 2,4,6-collidine and 270 μL (2.04 mmol, 6 equiv) of bromotrimethylsilane and stirred for 24 hours. The solvent was evaporated and the residue was treated with 1.05 mL (1.05 mmol, 3 equiv) of 1M NaOH to pH 14, and lyophilized. Purification was by chromatography on a 2.5 cm diameter×18 cm height column of CHP20P resin packed in water and eluted with 100 mL of water followed by a gradient created by the gradual addition of 300 mL of CH$_3$CN into 300 mL of water. Approximately 8 mL fractions were collected every 1.3 minutes. Fractions 41–50 were combined, evaporated, lyophilized and dried at high vacuum overnight to obtain 90 mg (56%) of title product as a white lyophilate.

TLC Silica gel (4:4:1 n-C$_3$H$_7$OH:con NH$_3$:H$_2$O) R$_f$=0.63

IR (KBr) 3437, 3053, 2924, 2876, 1652, 1192, 1133, 1106, 1047, 899, 864, 766 cm$^{-1}$.

$^1$H NMR (D$_2$O, 400 MHz) δ 5.36 (t, 1H, J=7 Hz), 5.13 (m, 2H), 4.11 (d, 2H, J=7 Hz), 3.62 (d, 2H, J=6.2 Hz), 1.9–2.2 (m, 12H), 1.63 (s, 3H), 1.55, 1.56 (two s 6H), 0.96 (t, 3H, J=7 Hz) ppm Mass Spec (FAB, +ions) m/e 497 (M+Na), 475 (M+H)

Anal Calcd for C$_{18}$H$_{32}$P$_2$O$_6$Na$_3$×0.30 mol H$_2$O: C, 45.07; H, 6.64; P, 12.91 Found: C, 45.12; H, 6.81; P, 12.77

EXAMPLE 33

(E)-[[[[(8,12-Dimethyl-7,11-tridecadien-3-ynyl)oxy]methyl](1-methylethoxy)phosphinyl]methyl]phosphonic acid, dimethyl ester A. (E)-8,12-Dimethyl-7,11-tridecadien-3-yn-1-ol A solution of 602.3 mg (3.40 mmol) of Example 16, Part A acetylene in 15 mL of tetrahydrofuran at −78° C. under argon was treated dropwise over 5 minutes with 2.35 mL (3.75 mmol, 1.1 equiv) of a 1.6M solution of n-butyllithium in hexanes and stirred for 0.5 hour. To this yellow solution was rapidly added 530 μL (6.8 mmol, 2.0 equiv) of a 12.8M solution of ethylene oxide in tetrahydrofuran which had been cooled to −78° C., followed by 460 μL (3.75 mmol, 1.1 equiv) of boron trifluoride etherate. The reaction was stirred for three hours at −78° C., quenched with saturated NH$_4$Cl and diluted with 800 mL of diethyl ether. The organic phase was washed with water and brine, dried over MgSO$_4$ and evaporated to give 753.4 mg of crude product. Purification by flash chromatography on 75 g of silica gel, eluted with 1:9 ethyl acetate: hexane gave 476.6 mg (64%) of the desired title product as a clear, colorless oil. In addition, 204.4 mg (34%) of Example 1, Part A acetylene was recovered.

TLC Silica gel (2:8 ethyl acetate: hexane) R$_f$=0.36

IR (CCl$_4$) 3634, 3590, 2966, 2915, 2883, 2855, 1444, 1434, 1383, 1378, 1329, 1184, 1108, 1053, 850, 830, 810, 790, 780, 760, 740 cm$^{-1}$.

$^1$H NMR (CDCl$_3$, 270 MHz) δ 5.16 (m, 1H), 5.10 (dt, 1H, J=1.17), 3.66 (t, 2H, J=6.45 ppm), 2.42 (t, 2H, J=6.45 ppm), 2.18 (br, 4H), 2.0–2.1 (m, 5H), 1.68 (s, 3H), 1.62 (s, 3H), 1.60 (s, 3H) ppm.

Mass Spec (CI-NH$_3$, +ions) m/e 238 (M+NH$_4$), 221 (M+H)

B. (E)-[[(8,12-Dimethyl-7,11 tridecadien-3-ynyl)oxy]methyl]phosphonic acid, bis(1-methylethyl) ester A solution of 450.7 mg (2.04 mmol) of Part A alcohol in 5 mL of tetrahydrofuran at −78° C. under argon was treated over five minutes with 1.35 mL (2.14 mmol, 1.05 equiv) of 1.6M n-butyllithium in hexanes and stirred for 0.5 hour. A solution of 702 mg (2.14 mmol, 1.05 equiv) of Example 1, Part B triflate in 2 mL of tetrahydrofuran was added via cannula. After 45 minutes at −78° C., the reaction was allowed to warm to 0° C. gradually over one hour, then stirred at 0° C. for four hours. The reaction was quenched with NH$_4$Cl and diluted with diethyl ether. The organic phase was washed with water and brine, dried over MgSO$_4$, and evaporated to yield 793.7 mg of crude product. Purification by flash chromatography on 70 g of silica gel, eluted with 3:7 ethyl acetate: hexane, provided 643.1 mg (79%) of title diester as a clear, colorless oil.

TLC Silica gel (3:7 ethyl acetate: hexane) R$_f$=0.17

IR (CCl$_4$) 2980, 2929, 2885, 1449, 1436, 1385, 1375, 1258, 1242, 1141, 1107, 1007, 991, 906 cm$^{-1}$.

$^1$H NMR (CDCl$_3$, 270 MHz) δ 5.15 (m, 1H), 5.10 (dt, 1H, J=1.17, 7.04 Hz), 4.76 (m, 2H) 3.76 (d, 2H, J=8.80 Hz), 3.65 (t, 2H, J=7.3 Hz), 2.45 (tt, 2H, J=2.3, 7.3 Hz), 1.9–2.2 (m, 8H), 1.68 (s, 3H), 1.60 (s, 6H), 1.34 (d, 12H, J=5.9 Hz) ppm.

Mass Spec (CI-NH$_3$, +ions) m/e 416 (M+NH$_4$), 399 (M+H), 202, 69

C. (E)-[[(8,12-Dimethyl-7,11-tridecadien-3-ynyl)oxy]methyl]phosphonic acid, mono(1-methylethyl) ester A mixture of 621.3 mg (1.56 mmol) of Part B diester, 15.6 mL (15.6 mmol, 10 equiv) of 1M KOH and 16 mL of 2-propanol was stirred under nitrogen at 90° C. for 24 hours. After cooling, the 2-propanol was evaporated and the residue was diluted with 50 mL of CH$_2$Cl$_2$ and acidified to pH 1 with 10% HCl. The aqueous phase was re-extracted with 50 mL of CH$_2$Cl$_2$, and the combined organic layers were washed with brine, dried over MgSO$_4$ and evaporated to afford 559.2 mg (100%) of title phosphonic acid as a clear, colorless oil.

TLC Silica gel (8:1:1 n-C$_3$H$_7$OH: con NH$_3$:H$_2$O) R$_f$=0.52

$^1$H NMR (CDCl$_3$, 270 MHz) δ 11.17 (br s, 1H), 5.12 (m, 2H), 4.75 (m, 1H), 3.79 (d, 2H, J=8.79 Hz), 3.66 (t, 2H, J=7.3 Hz), 2.45 (t, 2H, J=7.3 Hz), 1.9-2.2 (m, 8H), 1.68 (s, 3H), 1.60 (s, 6H), 1.35 (d, 6H) ppm.

D. (E)-[[[[(8,12-Dimethyl-7,11-tridecadien-3-ynyl)oxy]methyl](1-methylethoxy)phosphinyl]methyl]phosphonic acid, dimethyl ester To a solution of 553.8 mg (1.55 mmol) of Part C phosphonic acid in 10 mL of CH$_2$Cl$_2$ at room temperature under argon was added 590 μL (3.10 mmol, 2 equiv) of N,N-diethyl(trimethylsilyl)amine. After stirring for 1.5 hours, the solvent was evaporated and the residue was evaporated from benzene and dried at high-vacuum for 30 minutes. The residue was dissolved in 10 mL of CH$_2$Cl$_2$ and one drop of dimethylformamide at 0° C. under nitrogen. The solution was treated with 1.40 mL (2.8 mmol, 1.8 equiv) of a 2.0M solution of oxalyl chloride in CH$_2$Cl$_2$ over five minutes. After stirring for three hours, the solvent was evaporated, and the residue was evaporated from benzene and dried at high vacuum for 30 minutes.

The anion solution was prepared by treating a solution of 370 μL (3.45 mmol, 2.2 equiv) of dimethyl methylphosphonate in 10 mL of tetrahydrofuran at −78° C. under argon with 2.10 mL (3.35 mmol, 2.15 equiv) of 1.6M n-butyllithium in hexanes over ten minutes. After 30 minutes, a solution of the phosphonic acid chloride prepared above in 5 mL of tetrahydrofuran was added dropwise over ten minutes, and the resulting solution was stirred for 1.5 hours at −78° C. After quenching with saturated NH$_4$Cl and diluting with CH$_2$Cl$_2$, the mixture was allowed to warm to room temperture, then treated with H$_2$O and 1M HCl and separated. The aqueous phase was re-extracted with two portions of CH$_2$Cl$_2$. The combined organic layers were washed with brine, dried over MgSO$_4$ and evaporated to give 802.0 mg of an orange oil. The crude product was purified by chromatography on silica gel, eluted with 2:98 CH$_3$OH:CH$_2$Cl$_2$ to obtain 331.2 mg (46%) of title triester as a yellow oil.

TLC Silica gel (5:95 CH$_3$OH:CH$_2$Cl$_2$) R$_f$=0.46

IR (CCl$_4$) 2977, 2954, 2919, 2875, 2853, 1450, 1436, 1385, 1375, 1256, 1231, 1180, 1166, 1140, 1109, 1064, 1036, 993, 842, 820 cm$^{-1}$.

$^1$H NMR (CDCl$_3$, 270 MHz) δ 5.12 (m, 2H), 4.80 (m, 1H,), 3.90 (m, 2H), 3.83 (d, 3H, J=10.8 Hz), 3.80 (d, 3H, J=10.8 Hz), 3.66 (td, 2H, J=7.0 and 2.0 Hz), 2.3-2.7 (m, 4H), 1.9-2.2 (m, 8H), 1.68 (s, 3H), 1.61 (s, 6H), 1.37 (d, 3H, J=6.45 Hz), 1.35 (d, 3H, J=6.45 Hz) ppm.

Mass Spec (CI-CH$_4$/N$_2$O, +ions) m/e 491 (M+C$_2$H$_5$), 463 (M+H), 421.

EXAMPLE 34

(E)-[[[[(8,12-Dimethyl-7,11-tridecadien-3-ynyl)oxy]methyl]hydroxyphosphinyl]methyl]phosphonic acid, trisodium salt A solution of 363 mg (0.78 mmol) of Example 33 triester in 5 mL of CH$_2$Cl$_2$ at room temperture under argon was treated with 310 μL (2.35 mmol, 3 equiv) of 2,4,6-collidine and 620 μL (4.68 mmol, 6 equiv) of bromotrimethylsilane and stirred overnight. The solvent was evaporated and the residue was basified to pH 14 with 2.35 mL of 1M NaOH. Purification was by chromatography on a 2.5 cm diameter×20 cm height column on CHP20P gel eluted with 100 mL of water, followed by a gradient created by the gradual addition of 400 mL of acetonitrile into 400 mL of water. Approximately 10 mL fractions were collected every 1.5 minutes. Fractions 31-40 were combined, evaporated, lyophilized, and dried at high vacuum to obtain 255 mg (70%) of title salt as a white lyophilate.

TLC Silica gel (4:4:1 n-C$_3$H$_7$OH: con NH$_3$:H$_2$O) R$_f$=0.41

IR (KBr) 3453 (br), 2967, 2917, 1666, 1437, 1179, 1149, 1099, 998 cm$^{-1}$.

$^1$H NMR (D$_2$O, 400 MHz) δ 5.19, 5.15 (two t, 1H each) 3.68 (d, 2H, J=6.2 Hz), 3.62 (t, 2H, J=6.6 Hz), 2.42 (t, 2H, J=6.6 Hz), 2.14 (m, 4H), 2.07 (q, 2H, J=7 Hz), 1.99 (t, 2H, J=7 Hz), 1.92 (t, 2H, J=18 Hz), 1.63 (s, 3H), 1.58, 1.57 (two s, 3H each) ppm.

Mass Spec (FAB, +ions) m/e 481 (M+Na), 459 (M+H), 437 (M+2H-Na).

Anal Calc'd for C$_{17}$H$_{27}$P$_2$O$_6$Na$_3$.1.48 mol H$_2$O: C, 42.10; H, 6.23; P, 12.77 Found: C, 41.91; H, 6.15; P, 12.93

EXAMPLE 35

(E,E)-[[(3,7,11-Trimethyl-2,6,10-dodecatrienyl)oxy]methyl]phosphonic acid, diethyl ester Following the procedure of Example 1, Part C (1) except substituting the Example 5 Part A carbinol for the carbinol employed in Example 1, Part C (1), the title compound is obtained.

EXAMPLE 36

(E,E)-6,10,14-Trimethyl-5,9,13-pentadeca-trien-1-ol

A. (E,E)-1-Chloro-3,7,11-trimethyl-2,6,10-dodecatriene (Note: all temperatures indicated are for the contents of the reaction flask). To a stirred solution of 299 mg (2.24 mmol) of N-chlorosuccinimide in 15 ml of dichloromethane at −30° C. under argon was added 0.18 ml (2.45 mmol) of distilled dimethyl sulfide over 5 minutes. After 10 minutes at −30° C., the reaction was allowed to warm to 0° C. for 10 minutes, followed by cooling to −40° C. A solution of 441.4 mg (1.99 mmol) of (E,E)-3,7,11-trimethyl-2,6,10-tridecatrien-1-ol in 5 ml of dichloromethane was added dropwise over 10 minutes. The reaction was allowed to warm gradually to 0° C. over 1 hour, and then maintained at 0° C. for 1 hour. After quenching with cold water, the mixture was extracted with hexane and the hexane extract was washed with cold water and cold brine, dried (MgSO$_4$) and evaporated to afford 483 mg of a crude product. Rapid flash chromatography on 20 g of silica gel eluted with 3:97 ethyl acetate:pet ether provided 406.5 mg (85%) of a colorless liquid. $^{13}$C NMR indicated that this material contained a trace (3%) impurity.

TLC:Silica gel (2:98 ethyl acetate:hexane) Rf=0.56

$^1$H NMR(CDCl$_3$) (270 MHz) δ 5.44 (t, 1, J=7.9 Hz) 5.09 (t, 2, J=5.8 Hz) 4.07 (d, 2, J=7.9 Hz) 1.9-2.2 (m, 9) 1.72 (s, 3) 1.68 (s, 3) 1.60 (s, 6) ppm.

B. Dichloro[mu-[1-propanolato(2-)-C$^3$:O$^1$]]dimagnesium

A modification of the procedure of G. Cahiez et al. was employed (Tetrahedron Letters, 1978, 3013-4): To a stirred solution of 1.89 g (20 mmol) of 3-chloropropanol in 20 ml of THF under argon at −20° C. was added 10 ml (20 mmol) of 2M phenylmagnesium chloride in THF over 15 minutes. After 10 minutes at −20° C., the reaction was allowed to warm to room temperature, 730 mg (30 mmol) of magnesium turnings were added and the reaction was heated to reflux. Two 40 μl portions of 1,2-dibromoethane were added, the first portion injected at the start of reflux, and the second after 1 hour. After refluxing for a total of 2 hours, the reaction was allowed to cool to room temperature.

C. (E,E)-6,10,14-Trimethyl-5,9,13-pentadecatrien-1-ol

A solution of 37.5 mL (20.3 mmol, 5.1 eq.) of a 0.54M solution of Grignard reagent (Part B) in tetrahydrofuran and 9 mL of hexamethylphosphoramide at room temperature under argon was treated over 10 minutes with a solution of 955.5 mg (3.97 mmol) of (E,E)-farnesyl chloride (Part A) in 5 mL of tetrahydrofuran. After one hour, the reaction mixture was diluted with a mixture of 1:1 diethyl ether : hexane and quenched with 1M HCl. The organic phase was washed with three 25 mL portions of saturated $NaHCO_3$, three 25 mL portions of $H_2O$, and 25 mL of brine, dried over $MgSO_4$ and evaporated to obtain 995.0 mg of crude product. Purification required two chromatographies. The first was run on 70 g of silica gel, eluting with 1:99 ethyl acetate:$CH_2Cl_2$ to provide 484.3 mg of impure material and 307.7 mg of pure title compound. The second chromatography, of the impure fractions, on 50 g of silica gel eluted with 0.75:99.25 ethyl acetate:$CH_2Cl_2$ gave 117.2 mg of slightly impure material and 302.8 mg of pure title compound. Combination of pure material from both columns gave a yield a yield of 610.5 mg (58%) of pure desired title isomer.

TLC:Silia gel (10:90 ethyl ether:$CH_2Cl_2$) Rf=0.38

IR ($CCl_4$) 3639, 3450, 2964, 2930, 2858, 1449, 1382, 1058, 1028, 776, 750 $cm^{-1}$.

$^1H$ NMR ($CDCl_3$) (270 MHz) δ 5.10 (m, 3H) 3.62 (t, 2H, J=6.5 Hz) 2.00 (m, 10H) 1.69 (s, 3H) 1.61 (s, 9H) 1.2–1.7 (m, 5H, OH) ppm.

Mass Spec (CI-$CH_4$/$N_2O$, +ions) m/e 282 (M+$NH_4$), 265 (M+H), 263 (m+H-$H_2$).

EXAMPLES 37 to 110

Following procedures of Examples 1 to 36, the following additional compounds may be prepared in accordance with the present invention. It will be appreciated that the compounds listed include all stereoisomers thereof.

$$CH_3-\overset{H}{\underset{CH_3}{C}}=\overset{H}{C}-\overset{H}{\underset{H}{C}}\overset{H}{\underset{H}{C}}-C=CH-CH_2-Q^4-(CH_2)_n-X-(CH_2)_m-\overset{O}{\underset{OR^2}{P}}-\overset{Y^1}{\underset{Y^2}{C}}-\overset{O}{\underset{OR^4}{P}}-OR^3$$

| Ex. No. | $Q^4$ | X | n | m | $Y^1$ | $Y^2$ | $R^3$ | $R^2$ | $R^4$ |
|---|---|---|---|---|---|---|---|---|---|
| 37. | $-CH_2-C(CH_3)=CH-CH_2-$ | O | 2 | 3 | H | H | K | K | K |
| 38. | bond | O | 0 | 1 | F | F | Na | Na | Na |
| 39. | $-CH_2-C(CH_3)=CH-CH_2-$ | O | 1 | 1 | Cl | Cl | Na | Na | Na |
| 40. | $-CH_2-C(CH_3)=CH-CH_2-$ | O | 0 | 1 | H | Cl | Na | Na | Na |
| 41. | $\{-CH_2-C(CH_3)=CH-CH_2\}_2$ | O | 0 | 1 | H | H | K | K | K |
| 42. | $-CH_2-C(CH_3)=CH-CH_2-$ | —NH— | 0 | 1 | H | F | $CH_3$ | K | K |
| 43. | $-CH_2-C(CH_3)=CH-CH_2-$ | —$NCH_3$— | 0 | 1 | H | H | Na | Na | Na |
| 44. | $-CH_2-C(CH_3)=CH-CH_2-$ | O | 0 | 1 | H | F | K | K | K |

-continued

| Ex. | | X | n | m | Y¹ | Y² | R² | R³ | R⁴ |
|---|---|---|---|---|---|---|---|---|---|
| 45. | [—CH₂—C(CH₃)=CH—CH₂—]₂ | S | 3 | 3 | F | H | H | | —Mg— |
| 46. | —CH₂—C(CH₃)=CH—CH₂— | O | 0 | 1 | Cl | Cl | K | K | K |
| 47. | —CH₂—C(CH₃)=CH—CH₂— | —NH— | 1 | 1 | H | H | K | K | K |
| 48. | —CH₂—C(CH₃)=CH—CH₂— | O | 2 | 1 | F | F | Na | Na | Na |
| 49. | [—CH₂—C(CH₃)=CH—CH₂—]₂ | O | 0 | 1 | H | F | K | K | K |
| 50. | —CH₂—C(CH₃)=CH—CH₂— | S | 1 | 1 | F | F | K | K | K |
| 51. | bond | O | 0 | 2 | H | H | Na | Na | Na |
| 52. | —CH₂—C(CH₃)=CH—CH₂— | NH | 1 | 1 | F | F | K | K | K |
| 53. | bond | NH | 1 | 1 | H | H | Na | Na | Na |

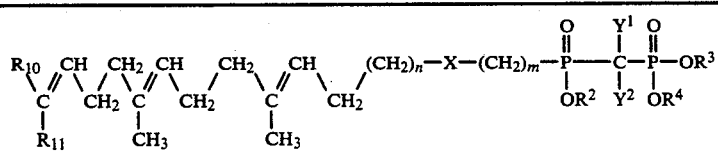

| Ex. No. | R⁷ | R⁶ | R⁸ | n | X | m | Y¹ | Y² | R² | R³ | R⁴ |
|---|---|---|---|---|---|---|---|---|---|---|---|
| 54 | H | I | H | 0 | O | 1 | F | F | K | K | K |
| 55 | H | H | I | 1 | O | 1 | H | H | Na | Na | Na |
| 56 | H | CH₃ | CH₃ | 0 | O | 1 | F | H | | Mg | CH₃ |
| 57 | CH₃S | CH₃ | H | 1 | O | 1 | H | H | K | K | K |
| 58 | F | CH₃ | H | 0 | S | 1 | H | H | Na | Na | Na |
| 59 | CH₃ | CH₃ | H | 1 | O | 1 | H | H | K | K | K |
| 60 | H | CH₃ | CH₃ | 1 | O | 1 | H | H | Na | Na | Na |
| 61 | H | CH₃ | Cl | 0 | O | 1 | H | H | K | K | K |
| 62 | H | CF₃ | H | 0 | O | 1 | H | H | K | K | K |
| 63 | H | Cl | H | 1 | O | 1 | H | H | K | K | K |
| 64 | H | CH₃ | (CH₃)₃Si | 0 | O | 1 | H | H | Na | Na | Na |
| 65 | H | CH₃ | F | 1 | O | 1 | F | H | K | K | K |

$$R_{10}\text{—C(R}_{11}\text{)=CH—CH}_2\text{—C(CH}_3\text{)=CH—CH}_2\text{—C(CH}_3\text{)=CH—CH}_2\text{—(CH}_2)_n\text{—X—(CH}_2)_m\text{—P(=O)(OR}^2\text{)—C(Y}^1\text{)(Y}^2\text{)—P(=O)(OR}^3\text{)(OR}^4\text{)}$$

| Ex. No. | R¹⁰ | R¹¹ | n | X | m | Y¹ | Y² | R² | R³ | R⁴ |
|---|---|---|---|---|---|---|---|---|---|---|
| 66 | C₂H₅ | CH₃ | 0 | O | 1 | H | H | CH₃ | K | K |

-continued

| Ex. No. | | | | | | | | | | |
|---|---|---|---|---|---|---|---|---|---|---|
| 67 | $CH_3$ | $C_2H_5$ | 1 | O | 1 | Cl | Cl | Na | Na | Na |
| 68 | $N-C_3H_7$ | $CH_3$ | 1 | O | 1 | H | H | | Mg | H |
| 69 | $CH_3$ | $n-C_3H_7$ | 0 | O | 1 | Cl | H | K | K | K |
| 70 | $CH_3$ | $n-C_4H_9$ | 0 | O | 1 | H | H | K | $CH_3$ | K |
| 71 | $t-C_4H_9$ | $CH_3$ | 0 | O | 1 | F | H | K | K | $CH_3$ |
| 72 | $-(CH_2)_5-$ | | 0 | O | 1 | H | H | K | K | K |
| 73 | H | H | 0 | O | 1 | H | H | Na | Na | Na |
| 74 | F | F | 0 | O | 1 | H | H | | Mg | H |
| 75 | Cl | Cl | 1 | O | 1 | H | H | K | K | K |
| 76 | $CH_2F$ | $CH_3$ | 0 | O | 1 | H | H | Na | Na | Na |
| 77 | $-CH=CH_2$ | H | 1 | O | 1 | H | H | K | K | K |

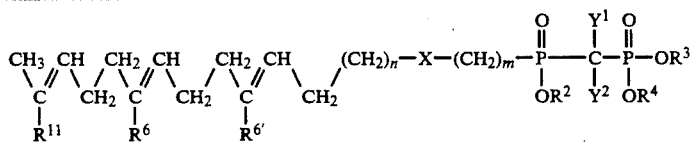

| Ex. No. | $R^{11}$ | $R^6$ | $R^{6'}$ | n | X | m | $Y^1$ | $Y^2$ | $R^2$ | $R^3$ | $R^4$ |
|---|---|---|---|---|---|---|---|---|---|---|---|
| 78 | $C_2H_5$ | $C_2H_5$ | $CH_3$ | 0 | O | 1 | H | H | K | K | K |
| 79 | $CH_3$ | $CH_3$ | $C_2H_5$ | 1 | O | 1 | H | H | Na | Na | Na |
| 80 | $CH_3$ | $C_2H_5$ | $C_2H_5$ | 0 | O | 1 | H | H | | Mg | H |
| 81 | $C_2H_5$ | $C_2H_5$ | $C_2H_5$ | 0 | O | 1 | H | H | $CH_3$ | K | K |
| 82 | $CH_3$ | $C_2H_5$ | $CH_3$ | 0 | O | 1 | H | H | K | K | K |
| 83 | $CH_3$ | H | $CH_3$ | 1 | O | 1 | H | H | Na | Na | Na |
| 84 | $CH_3$ | $CH_3$ | H | 0 | O | 1 | H | H | K | K | K |
| 85 | H | H | H | 0 | O | 1 | H | H | K | K | K |

Ex. No.

86
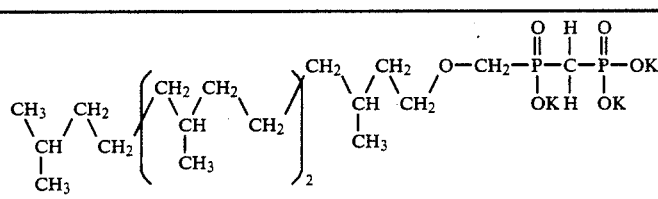

87
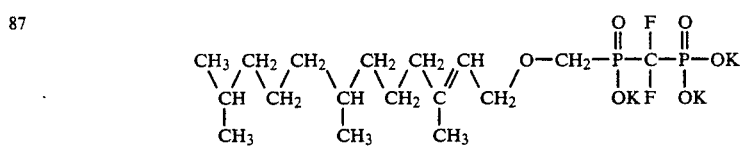

88
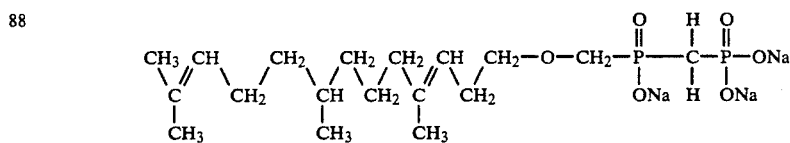

89
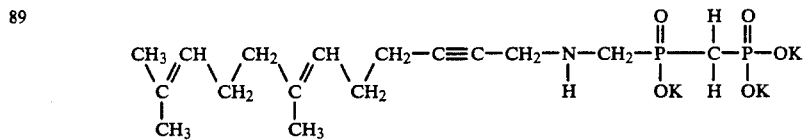

90
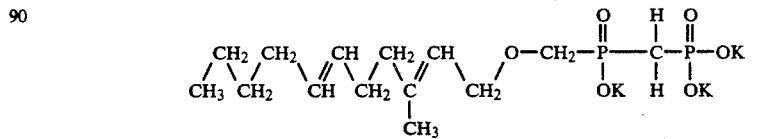

91
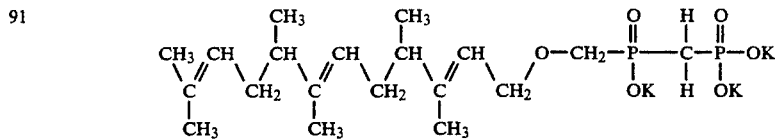

-continued
92 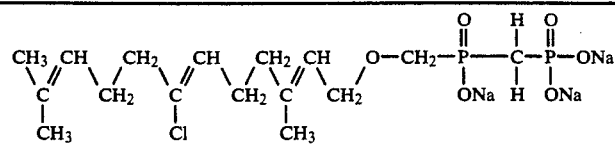
93 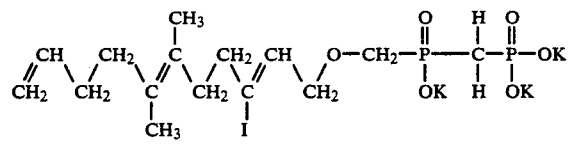
94 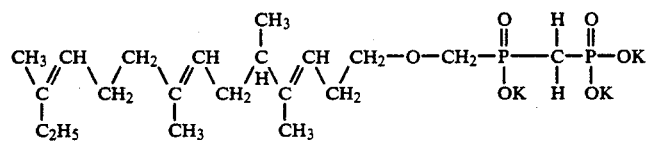
95 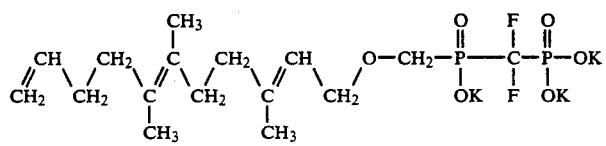
96 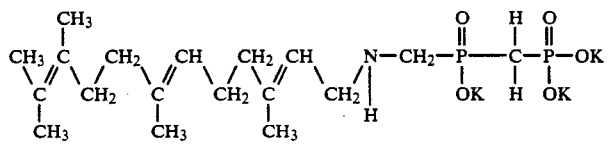
97 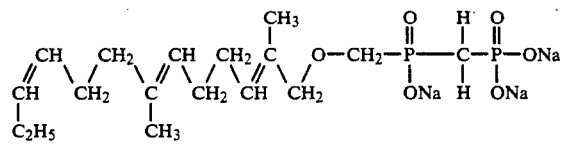
98 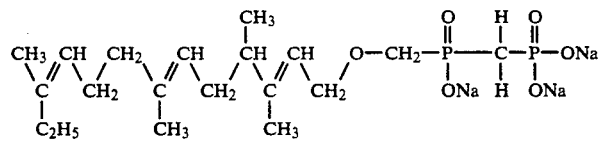
99 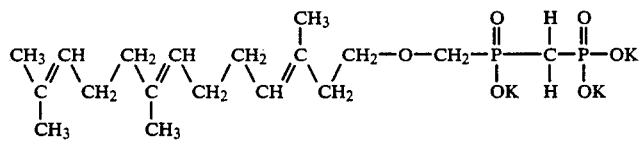
100 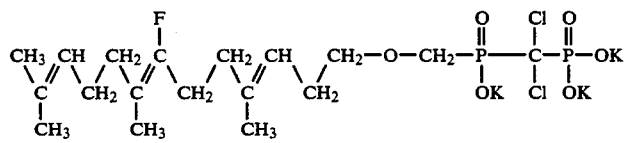
101 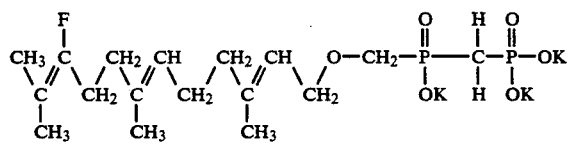
102 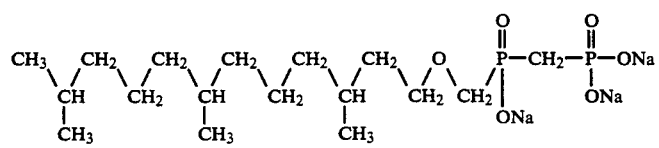

| | |
|---|---|
| 103 | 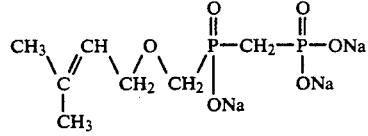 |
| 104 | 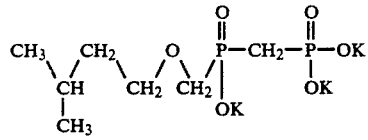 |
| 105 | 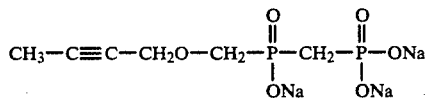 |
| 106 | 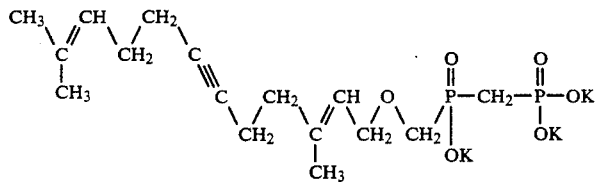 |
| 107 | 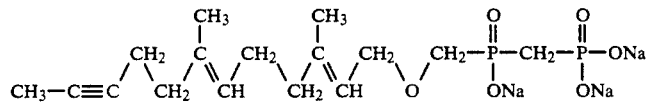 |
| 108 | 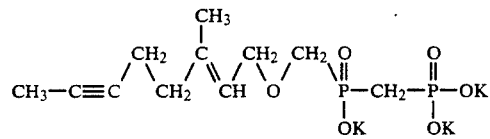 |
| 109 | 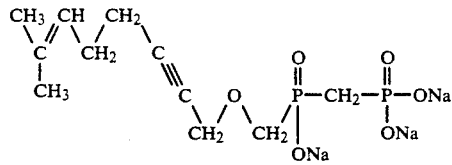 |
| 110 | 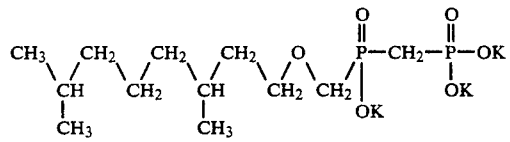 |

EXAMPLE 111

[[Methoxy[(3,7,11-trimethyl-2,6,10-dodecatrienyl-)amino]phosphinyl]methyl]phosphonic acid, dimethyl ester A. Trimethyl methylenediphosphonate Tetramethylmethylene diphosphonate (Lancaster Synthesis #5847) (2.50 g, 10.8 mmol) in a mixture of 8.65 ml of methanol and 8.65 ml (8.65 mmol, 0.8 eq.) of 1M NaOH was stirred at room temperature under argon for 24 hours. After removing the solvent under reduced pressure, the remaining starting material was removed by extraction with five 15 ml portions of $CH_2Cl_2$. The aqueous phase was loaded onto a 90 ml (10 eq.) AG-50W-X4 ion-exchange column in the acid form and eluted with water. Fractions containing the desired product were combined, and water was removed under reduced pressure. The residue was dissolved in 75 ml of $CH_2Cl_2$, dried over $Na_2SO_4$ overnight and evaporated to provide 1.63 g (69%) of title compound as a clear, viscous oil.

TLC: Silica gel (6:3:1 n-$C_3H_7$OH:con.$NH_3$:$H_2O$) Rf=0.48.

$^1$H NMR (CDCl$_3$) (270 MHz) δ 11.55 (br s, 1H) 3.82 (d, 6H, J=11.5 Hz) 3.80 (d, 3H, J=11.5 Hz) 2.56 (t, 2H, J=21 Hz) ppm.

Mass Spec (CI-NH$_3$, +ions) m/e 236 (M+H+NH$_3$), 219 (M+H).

B. [[Methoxy[(3,7,11-trimethyl-2,6,10-dodecatrienyl-)amino]phosphinyl]methyl]phosphonic acid, dimethyl ester To a solution of 620 mg (2.84 mmol, 1.1 eq.) of Part A compound and 495 μL (2.84 mmol, 1.1 eq.) of diisopropylethylamine in 5 ml of dry $CH_2Cl_2$ at room temperature under argon was added 590 μL (2.84 mmol, 1.1 eq.) of diphenylchlorophosphate. The resulting solution was stirred for 2 hours, then cooled to 0° C. A mixture of 525 mg (2.37 mmol) of Example 13, Part A(2) farnesyl amine and 515 μL (2.96 mmol, 1.25 eq.) of diisopropylethylamine in 5 ml of dry $CH_2Cl_2$ was added dropwise and the resulting solution was stirred for 4 hours. The reaction mixture was diluted with 50 ml of ethyl ether and washed with 10 ml of $NaHCO_3$ and 10 ml of brine, dried over $MgSO_4$ and evaporated to yield 1.13 g of crude product. Purification by flash chromatography on 120 g of Merck 9385 silica, eluted with 4:96 $CH_3OH:CH_2Cl_2$ provided 479.6 mg (48%) of pure title product and 89.7 mg (9%) of slightly impure title product.

TLC:Silica gel (5:95 $CH_3OH:CH_2Cl_2$) Rf=0.21.

IR($CCl_4$) 2953, 2926, 2853, 1254, 1184, 1038, 849, 819 $cm^{-1}$.

$^1$H NMR($CDCl_3$) (270 MHz) δ 5.25 (t, 1H, J=7 Hz) 5.09 (m, 2H) 3.79 (d, 3H, J=11 Hz) 3.77 (d, 3H, J=11 Hz) 3.70 (d, 3H, J=11 Hz) 3.62 (m, 2H) 3.25 (m, 1H) 2.45 (dt, 1H, J=15.5, 20.5 Hz) 2.38 (dt, 1H, J=15.5, 20.5 Hz) 1.9–2.1 (m, 8H) 1.67 (s, 6H) 1.60 (s, 6H) ppm.

Mass Spec (CI-$CH_4/N_2O$, +ions) m/e 843 (2M+H), 462 (m+$C_3H_5$), 450 (M+$C_2H_5$), 422 (m+H), 218.

Also isolated as a by-product was 291.2 mg (27%) of the following compound

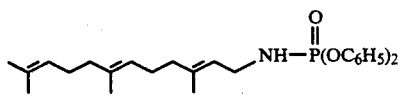

TLC:Silica gel (5:95 $CH_3OH:CH_2Cl_2$) Rf=0.84.

EXAMPLE 112

[[Hydroxy[(3,7,11-trimethyl-2,6,10-dodecatrienyl)-amino]phosphinyl]methyl]phosphonic acid, methyl ester, disodium salt A mixture of 450.2 mg (1.07 mmol) of Example 111 compound in 5.35 ml (5.35 mmol, 5 eq.) of 1M NaOH was heated at 60°–65° C. under nitrogen for 16 hours. The aqueous solution (pH 13) was loaded onto a 2.5 cm diameter×18 cm height column of CHP20P packed with water. The column was eluted with a gradient created by the gradual addition of 350 ml of acetonitrile to 350 ml of 2:98 acetonitrile:water. Approximately 10 ml fractions were collected every two minutes. Fraction 25 contained pure title product and was evaporated, lyophilized and pump-dried overnight to obtain 104.1 mg (22%) of pure title product. (Fractions 26–27 provided 230.4 mg (49%) of title product, containing a minor impurity cospotting on TLC with Example 1 Part B farnesyl amine). A 1.0% solution of title product gave pH 8.55.

TLC:Silica gel (7:2:1 n-$C_3H_7OH$:con.$NH_3$:$H_2O$) Rf=0.43

IR(KBr) 3378, 2967, 2924, 2853, 1444, 1419, 1405, 1380, 1217, 1153, 1109, 1061, 789, 753, 510, 497, 483, 468 $cm^{-1}$.

$^1$H NMR ($D_2O$) (400 MHz) δ 5.26 (t, 1H, J=6.5 Hz) 5.15 (t, 1H, J=6.5 Hz) 5.12 (t, 1H, J=6.0 Hz) 3.50 (d, 3H, J=10.6 Hz) 3.38 (t, 2H, J=6.5 Hz) 1.9–2.1 (m, 10H) 1.63 (s, 3H) 1.61 (s, 3H) 1.56 (s, 6H) ppm.

$^{31}$P-NMR ($D_2O$) (36 MHz) δ 20.0 19.2 ppm.

Mass Spec (FAB, +ions) m/e 460 (M+Na), 438 (M+H), 411, 217.

Anal Calcd for $C_{17}H_{31}NO_5P_2 \cdot Na_2$ (MW 437.370)*: C, 46.69; H, 7.14; N, 3.20; P, 14.16 Found: C, 46.42; H, 7.51; N, 3.13; P, 14.26 *Sample was dried to constant weight at 50° C.

EXAMPLE 113

(E,E)-[[Hydroxy[(4,8,12-trimethyl-3,7,11-tridecatrienyl)oxy]phosphinyl]methyl]phosphonic acid, tripotassium salt A. 4,8,12-Trimethyl-3,7,11-tridecatrien-1-ol, (4-methylphenyl)sulfonate A solution of Example 7, Part A(3) homofarnesol (0.307 g, 1.3 mmole) in 15 ml of dry $CH_2Cl_2$ was stirred at room temperature and under argon atmosphere with pyridine (0.52 g, 6.5 mmol) and dimethyl amino pyridine (DMAP) (0.032 g, 0.26 mmol). At room temperature, p-toluenesulfonyl chloride (TsCl) (0.55 g, 2.8 mmol) was added to the reaction mixture. After stirring for 20 hours, an additional 0.2 g of TsCl was added. After stirring for 20 hours, an additional 0.2 g of TsCl was added. After stirring for 32 hours at room temperature, the reaction was quenched with saturated aqueous $NaHCO_3$ solution and stirred vigorously for 45 minutes. The reaction mixture was then diluted with $H_2O$, and the aqueous layer was extracted several times with $CH_2Cl_2$. The combined $CH_2Cl_2$ extracts were washed once with 5% aqueous $CuSO_4$ solution and once with $H_2O$. The resulting organic extract was dried over $MgSO_4$. Filtration and solvent removal gave 0.50 g of a yellow oil. Purification by flash chromatography (silica gel; 15% ethyl acetate/hexane) provided 0.45 g (89%) of title tosylate as a clear oil.

TLC:Silica gel (20% ethyl acetate/hexane) Rf=0.39

IR (film) 2965, 2920, 2860, 1600, 1445, 1360, 1190, 1175, 1100, 960, 910, 815 $cm^{-1}$.

$^1$H-NMR ($CDCl_3$) (270 MHz) δ 7.78 (d, 2H, J=7.0 Hz, Ar-H) 7.33 (d, 2H, J=7.0 Hz, Ar-H) 5.07 (m, 2H, $CCHCH_2$) 4.98 (m, 1H, $CCHCH_2CH_2OTs$) 3.98 (t, 2H, J=7 Hz, $C_2CH_2OTs$) 2.45 (s, 3H, Ar-$CH_3$) 2.35 (m, 2H, $CHCH_2CH_2OTs$) 2.00 (m, 8H, $CHCH_2CH_2C$) 1.70 (s, 3H, $CH_3$) 1.60 (s, 3H, $CH_3$) 1.58 (s, 3H, $CH_3$) 1.55 (s, 3H, $CH_3$)

$^{13}$C-NMR ($CDCl_3$):(67.8 MHz) δ 144.5, 139.3, 135.2, 133.3, 131.2, 129.7, 127.8, 124.3, 123.8, 117.4, 69.9, 39.6, 39.5, 27.8, 26.7, 26.4, 25.6, 21.5, 17.6, 16.1, 15.9

B. (E,E)-[[Hydroxy(4,8,12-trimethyl-3,7,11-tridecatrienyl)oxy]phosphinyl]methyl]phosphonic acid, tripotassium salt Tris (tetra-n-butyl)ammonium hydrogen methanediphosphate (1.94 g, 2.16 mmol) (prepared by titrating to pH 10.0 a 20 ml deionized $H_2O$ solution of methanediphosphonic acid (1.0 g, 5.68 mmol, Fluka) with 40% w/w aqueous (n-$C_4H_9)_4$NOH and lyophilization of the resulting aqueous solution) was dissolved in 2.0 ml of dry $CH_3CN$ followed by $CH_3CN$ removal via rotary evaporation. Additional $CH_3CN$ was added and removed via rotary evaporation to facilitate water removal. To the resulting residue under argon atmosphere was added 2.0 ml of dry $CH_3CN$ followed by the addition of a 2.0 ml $CH_3CN$ solution of Part A tosylate (0.243 g, 0.63 mmol). After stirring for 2 hours at room temperature, the $CH_3CN$ was removed to give a clear residue which was dissolved in a 1:49 i-$C_3H_7OH$/0.025M $K_2CO_3$ buffer solution and eluted through an ion exchange column (AG50W-8x, K+-form 100–200 mesh, 50 ml of resin in a 20 mm diameter column) with the buffer solution. A milky white eluent eluted from the column. After lyophilization of the eluent, the lyophilate was resubjected to the ion exchange chromatography as above (eluted with 1:49 i-C$_3$H$_7$OH/H$_2$O). The resulting milky white eluent was lyophilized, and the lyophilate was purified by CHP20P chromatography (2.5 cm×20 column of resin). Elution with a H$_2$O-acetonitrile gradient provided 0.14 g (44%) of title product, after lyophilization.

TLC:Silica gel Rf=0.43 (6:3:1 n-C$_3$H$_7$OH:Con NH$_3$:H$_2$O)

IR(KBr) 2966, 2923, 2857, 1666, 1447, 1382, 1211, 1087, 890, 800, 733 cm$^{-1}$.

$^1$H-NMR (D$_2$O) (400 MHz) δ 5.19 (m, 3H, CCHCH2) 3.82 (m, 2H, CH$_2$CH$_2$OPP) 2.34 (m, 2H, CHCH$_2$CH$_2$OPP) 2.05 (m, 10H, CHCH$_2$CH$_2$C) 1.67 (s, 3H, CCH$_3$) 1.65 (s, 3H, CCH$_3$) 1.61 (s, 6H, 2CCH$_3$)

Mass Spec (FAB +ions) m/e 547 (M+K)$^+$ 509 (M$^+$+H)

Anal Calcd for C$_{17}$H$_{29}$O$_6$P$_2$K$_3$ (M.W.=508): C, 40.16; H, 5.71; P, 12.20 Found: C, 41.62; H, 6.60; P, 12.81 (Sample was dried to constant weight at 50° C.).

EXAMPLE 114

(E,E)-[[Hydroxy-[(5,9,13-trimethyl-4,8,12-pentadecatrienyl)oxy]phosphinyl]methyl]phosphonic acid, tripotassium salt A. 5,9,13-Trimethyl-4,8,12-tetradecatrien-1-ol, 4-(methylphenyl)sulfonate A solution of Example 11, Part A(3) bishomofarnesol (1.16 mmol, 0.290 g) in 3.0 ml of dry CH$_2$Cl$_2$ was stirred under argon at room temperature. The following were added in one portion: pyridine (5.79 mmol, 0.458 g, 0.468 ml), p-toluenesulfonyl chloride (2.55 mmol, 0.486 g), and finally dimethylaminopyridine (DMAP) (0.232 mmol, 0.028 g). This reaction mixture was stirred at room temperature for 6.5 hours. The reaction mixture was quenched with 4 ml of saturated aqueous NaHCO$_3$ and stirred vigorously for 40 minutes. The reaction mixture was then diluted with H$_2$O and the aqueous layer extracted with CH$_2$Cl$_2$. The organic extracts were combined and washed twice with 5% CuSO$_4$ (aqueous) followed by an H$_2$O wash. The resulting organic extract was dried over MgSO$_4$, filtered and evaporated to provide a green oil which was purified via flash chromatography (40 mm diameter column, 6" Merck silica gel, 7% ethyl acetate/hexane eluent, 2"/min flow rate) to afford 0.375 g (0.928 mmol) 80% yield of the title tosylate as a pale yellow oil.

TLC:Silica gel Rf=0.53 (20% ethyl acetate/hexane)

IR (film) 2970, 2920, 2860, 1600, 1445, 1365, 1190, 1180, 1100, 970, 935, 840, 815 cm$^{-1}$.

Mass Spec (CI) m/e 405 (M+H)$^+$ $^1$H NMR (270 MHz, CDCl$_3$) δ 7.80 (d, 2H, J=6.0 Hz) 7.35 (d, 2H, J=6.0 Hz) 5.08 (m, 2H) 4.98 (m, 1H) 4.03 (t, 2H, J=5.8 Hz) 2.47 (s, 3H) 2.11-1.97 (m, 10H) 1.73-1.68 (m, 2H) 1.70 (s, 3H) 1.61 (s, 6H) 1.58 (s, 3H)

$^{13}$C NMR (67.8 MHz, CDCl$_3$) δ 144.55, 136.79, 135.03, 133.33, 131.21, 129.73, 127.86, 124.32, 124.01, 122.20, 70.05, 39.67, 39.61, 28.96, 26.75, 26.53, 25.66, 23.63, 21.56, 17.66, 15.96.

B.   (E,E)-[[Hydroxy-[(5,9,13-trimethyl-4,8,12-pentadecatrienyl)oxy]phosphinyl]-methyl]phosphonic acid, tripotassium salt Tris (tetra-n-butylammonium)methylene bisphosphonate (prepared as described in Example 113) (1.76 mmol, 1.58 g) was stirred under argon at room temperature in 1.76 ml of dry CH$_3$CN and treated dropwise (quickly) with a solution of the Part D tosylate (0.838 mmol, 0.339 g) in 1.67 ml of dry CH$_3$CN. The reaction mixture was stirred at room temperature for 4 hours.

The CH$_3$CN was removed in vacuo and the dark golden residue was dissolved in 3 ml of distilled H$_2$O and eluted through an ion exchange column (AG 50W-X8, 100–200 mesh, 45 ml/76.5 meq of resin in a 20 mm diameter column). The column was eluted with 1:49 i-C$_3$H$_7$OH/H$_2$O, and product fractions combined and lyophilized to provide 0.910 g of a yellow powdery solid. The lyophilate was again eluted through an ion exchange column as above (60 ml, 102 meq of resin). Lyophilization of product fractions afforded 0.812 g of a yellow solid (no change in TLC). The desired pure product was obtained by dissolving the lyophilate in 3 ml of distilled H$_2$O and eluting through an CHP20P chromatography column (2.5 cm×15 cm of resin). Elution with 250 ml of H$_2$O, followed by an acetonitrile/H$_2$O gradient, collecting 10 ml fractions every 1.4 minutes afforded (after lyophilization and drying under high vacuum over P$_2$O$_5$), 0.274 g (0.524 mmol), 63% yield of title product in the form of a white lyophilate.

TLC:Silica gel Rf=0.46 (6:3:1/n-C$_3$H$_7$OH:con NH$_3$:H$_2$O)

IR(KBr) 3030, 2966, 2925, 2857, 1636, 1206, 1088, 1048, 971, 801, 519 cm$^{-1}$.

Mass Spec (FAB) m/e 523 (M+H)$^+$ 561 (M+K)$^+$.

$^1$H-NMR (400 MHz, D$_2$O) δ 5.24 (m, 1H) 5.18 (m, 2H) 3.89–3.84 (m, 2H) 2.16–2.00 (m, 12H) 1.68 (s, 3H) 1.68–1.66 (m, 2H) 1.63 (s, 3H) 1.61 (s, 3H)

$^{13}$C NMR (67.8 MHz, D$_2$O, dioxane reference) δ 137.60, 136.82, 133.56, 125.46, 124.99, 65.56, 65.48, 40.17, 40.09, 31.64, 31.55, 30.47, 28.68, 27.12, 26.84, 26.06, 24.80, 18.14, 16.46

Anal Calcd for C$_{18}$H$_{32}$O$_6$P$_2$K$_2$ M.W.=484.574: C, 44.61; H, 6.66; P, 12.78 Found: C, 45.27; H, 6.81; P, 13.52

Sample was dried at 50° C. for 6 hours.

EXAMPLE 115

(E,E)-[[Hydroxy[(6,10,14-trimethyl-5,9,13-pentadecatrienyl)oxy]phosphinyl]methyl]phosphonic acid, tripotassium salt A. (E,E)-1-Chloro-3,7,11-trimethyl-2,6,10-dodecatriene (Note: all temperatures indicated are for the contents of the reaction flask). To a stirred solution of 299 mg (2.24 mmol) of N-chlorosuccinimide in 15 ml of dichloromethane at −30° C. under argon was added 0.18 ml (2.45 mmol) of distilled dimethyl sulfide over 5 minutes. After 10 minutes at −30° C., the reaction was allowed to warm to 0° C. for 10 minutes, followed by cooling to −40° C. A solution of 441.4 mg (1.99 mmol) of (E,E)-3,7,11-trimethyl-2,6,10-tridecatrien-1-ol in 5 ml of dichloromethane was added dropwise over 10 minutes. The reaction was allowed to warm gradually to 0° C. over 1 hour, and then maintained at 0° C. for 1 hour. After quenching with cold water, the mixture was extracted with hexane and the hexane extract was washed with cold water and cold brine, dried (MgSO$_4$) and evaporated to afford 483 mg of a crude product. Rapid flash chromatography on 20 g of Merck 9385 silica gel eluted with 3:97 ethyl acetate:pet ether provided 406.5 mg 85%) of a colorless liquid. $^{13}$C NMR indicated that this material contained a trace (3%) impurity.

TLC:Silica gel (2:98 ethyl acetate:hexane) Rf=0.56

$^1$H NMR(CDCl$_3$) (270 MHz) δ 5.44 (t, 1, J=7.9 Hz) 5.09 (t, 2, J=5.8 Hz) 4.07 (d, 2, J=7.9 Hz) 1.9–2.2 (m, 9) 1.72 (s, 3) 1.68 (s, 3) 1.60 (s, 6) ppm.

B.   Dichloro[mu-[1-propanolato(2-)-C$^3$:O$^1$]]-dimagnesium

A modification of the procedure of G. Cahiez et al. was employed (Tetrahedron Letters, 1978, 3013–4): To a stirred solution of 1.89 g (20 mmol) of 3-chloropropanol in 20 ml of THF under argon at −20° C. was added 10 ml (20 mmol) of 2M phenylmagnesium chloride in THF over 15 minutes. After 10 minutes at −20° C., the reaction was allowed to warm to room temperature, 730 mg (30 mmol) of magnesium turnings were added and the reaction was heated to reflux. Two 40 μl portions of 1,2-dibromoethane were added, the first portion injected at the start of reflux, and the second after 1 hour. After refluxing for a total of 2 hours, the reaction was allowed to cool to room temperature and was diluted with 37 ml of THF for a theoretical concentration of 0.3M.

C. (E,E)-6,10,14-Trimethyl-5,9,13-pentadecatrien-1-ol

A solution of 37.5 mL (20.3 mmol, 5.1 eq.) of a 0.54M solution of Grignard reagent (Part B) in tetrahydrofuran and 9 mL of hexamethylphosphoramide at room temperature under argon was treated over 10 minutes with a solution of 955.5 mg (3.97 mmol) of farnesyl chloride (Part A) in 5 mL of tetrahydrofuran. After one hour, the reaction mixture was diluted with a mixture of 1:1 diethyl ether : hexane and quenched with 1M HCl. The organic phase was washed with three 25 mL portions of saturated $NaHCO_3$, three 25 mL portions of $H_2O$, and 25 mL of brine, dried over $MgSO_4$ and evaporated to obtain 995.0 mg of crude product. Purification required two chromatographies. The first was run on 70 g of silica gel, eluting with 1:99 ethyl acetate:$CH_2Cl_2$ to provide 484.3 mg of impure material and 307.7 mg of pure title compound. The second chromatography, of the impure fractions, on 50 g of silica gel eluted with 0.75:99.25 ethyl acetate:$CH_2Cl_2$ gave 117.2 mg of slightly impure material and 302.8 mg of pure title compound. Combination of pure material from both columns gave a yield a yield of 610.5 mg (58%) of pure desired title isomer.

TLC:Silia gel (10:90 ethyl ether:$CH_2Cl_2$) Rf=0.38

IR ($CCl_4$) 3639, 3450, 2964, 2930, 2858, 1449, 1382, 1058, 1028, 776, 750 cm$^{-1}$.

$^1$H NMR ($CDCl_3$) (270 MHz) δ 5.10 (m, 3H) 3.62 (t, 2H, J=6.5 Hz) 2.00 (m, 10H) 1.69 (s, 3H) 1.61 (s, 9H) 1.2–1.7 (m, 5H, OH) ppm.

Mass Spec (CI-$CH_4$/$N_2O$, +ions) m/e 282 (M+$NH_4$), 265 (M+H), 263 (m+H-$H_2$).

D. 6,10,14-Trimethyl-5,9,13-pentadecatrien-1-ol, 4-methylbenzenesulfonate

Following the procedure of Example 114 Part A, except substituting the above Part C alcohol for the Example 11 Part A(3) alcohol, the title tosylate is obtained.

E. (E,E)-[[Hydroxy[(6,10,14-trimethyl-5,9,13-pentadecatrienyl)oxy]phosphinyl]methyl]phosphonic acid, tripotassium salt Following the procedure of Example 114 Part B except substituting the above Part D tosylate for the Example 114 Part A tosylate, the title compound is obtained.

EXAMPLES 116 to 133

Following the procedures of Examples 111 to 115, the following additional compounds may be prepared in accordance with the present invention.

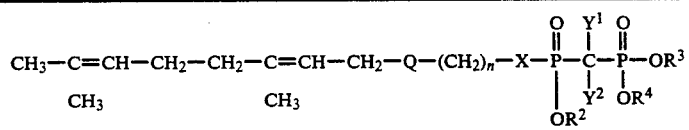

| Ex. No. | Q | X | n | $Y^1$ | $Y^2$ | $R^3$ | $R^2$ | $R^4$ |
|---|---|---|---|---|---|---|---|---|
| 116. | —CH₂—C(=CH—CH₂—)CH₃ | O | 2 | H | H | K | K | K |
| 117. | bond | O | 1 | F | F | Na | Na | Na |
| 118. | —CH₂—C(=CH—CH₂—)CH₃ | —NH— | 1 | Cl | Cl | Na | Na | Na |
| 119. | —CH₂—C(=CH—CH₂—)CH₃ | —N(CH₃)— | 2 | H | Cl | Na | Na | Na |
| 120. | —CH₂—C(=CH—CH₂—)CH₃ | O | 1 | F | H | K | K | K |
| 121. | —CH₂—C(=CH—CH₂—)CH₃ | —NH— | 4 | H | H | $CH_3$ | K | K |

-continued $$CH_3-C=CH-CH_2-CH_2-C=CH-CH_2-Q-(CH_2)_n-X-\overset{\overset{O}{\|}}{\underset{\underset{OR^2}{|}}{P}}-\overset{\overset{Y^1}{|}}{\underset{\underset{Y^2}{|}}{C}}-\overset{\overset{O}{\|}}{\underset{\underset{OR^4}{|}}{P}}-OR^3$$
$$\phantom{CH_3-C=CH-CH_2-CH_2}\underset{CH_3}{|}\phantom{xxxxxxxx}\underset{CH_3}{|}$$

| Ex. No. | Q | X | n | $Y^1$ | $Y^2$ | $R^3$ | $R^2$ | $R^4$ |
|---|---|---|---|---|---|---|---|---|
| 122. | 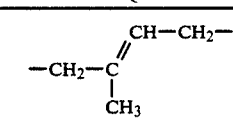 | —NC$_2$H$_5$— | 3 | H | F | Na | Na | Na |
| 123. | bond | O | 4 | H | H | K | K | K |
| 124. | 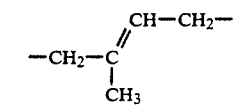 | O | 3 | F | H | H | Mg | Mg |
| 125. | 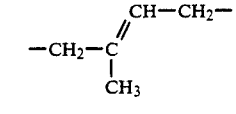 | —NH— | 2 | Cl | Cl | K | K | K |
| 126. | 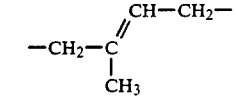 | —NH— | 1 | H | H | K | K | K |
| 127. | 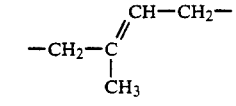 | O | 1 | F | F | K | K | K |
| 128. | 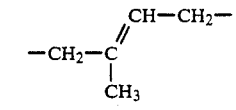 | O | 3 | F | F | K | K | K |
| 129. | 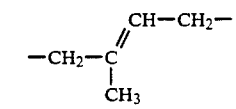 | O | 4 | F | F | K | K | K |
| 130. | bond | O | 4 | F | F | K | K | K |
| 131. | 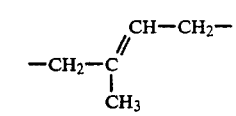 | NH | 1 | F | F | K | K | K |
| 132. | bond | NH | 1 | H | H | K | K | K |
| 133. | —CH$_2$—C—CH$_2$—CH$_2$—<br>$\phantom{xxxx}\|\|$<br>$\phantom{xxxx}$CH$_2$ | O | 1 | H | H | Na | Na | Na |

The following additional compounds may be prepared employing procedures as set out hereinbefore.

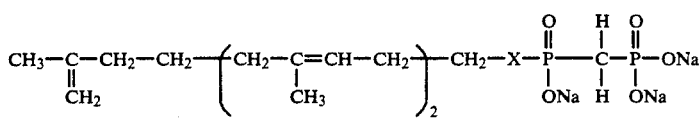

-continued

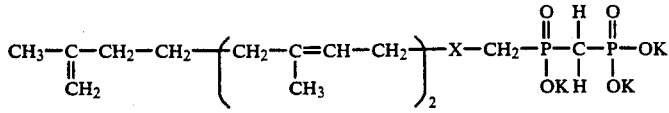

wherein X may be O, NH, Nalkyl or S.

EXAMPLE 134

(E)-[[[[(7,11-Dimethyl-3-methylene-6,10-dodecadienyl-)oxy]methyl]hydroxyphosphinyl]methyl]phosphonic acid, trisodium salt A. (E)-[[(7,11-Dimethyl-3-methylene-6,10-dodecadienyl)oxy]methyl]phosphonic acid, bis(1-methylethyl) ester To a stirred solution of 1.0 g (4.49 mmol) of (E)-7,11-dimethyl-3-methylene-6,10-dodecadien-1-ol (prepared using the procedure of L. Poppe et al, Syn. Commun. 1987, 17, 173-179) in 25 mL of THF under argon at −78° C. was added 2.95 mL (4.72 mmol) of 1.6M n-butyllithium in hexanes over 10 minutes. The pale yellow solution was allowed to stir at −78° for 40 minutes when 1.46 g (4.45 mmol) of the Example 1B triflate in 7 mL of THF was added via cannula. After 0.5 hours at −78° C., the reaction was allowed to warm to 0° C. for 2 hours. The reaction was quenched with saturated ammonium chloride and partitioned between diethyl ether and water. The ether layer was washed with brine, dried over MgSO$_4$ and evaporated to provide 1.9 g of crude product. Flash chromatography was performed on 200 g of silica gel packed and loaded with 15:1 dichloromethane/EtOAc and eluted with 11:1 dichloromethane/EtOAc collecting 30 mL fractions. Fractions 46 to 92 were combined and evaporated to provide 1.27 g (70%) of title compound in the form of a clear colorless oil.

TLC Silica gel (3:1 hexane/ethyl acetate) R$_f$=0.20.

IR (CCL$_4$) 2979, 2930, 2859, 1466, 1451, 1385, 1375, 1257, 1242, 1178, 1142, 1107, 991, 891 cm$^{-1}$.

$^1$H-NMR (CDCL$_3$, 270 MHz) δ 5.10 (m, 2H), 4.75 (m, 4H), 3.72 (d, 2H, J=8.2 Hz), 3.68 (t, 2H, J=7 Hz), 2.32 (t, 2H, J=7 Hz), 2.04 (m, 8H), 1.67 (s, 3H), 1.59 (s, 6H), 1.34 (d, 6H, J=5.9 Hz), 1.32 (d, 6H, J=6.5 Hz) ppm.

MS (CI-NH$_3$, +ions) m/e 418 (M+NH$_4$), 401 (M+H), 321, 214, 197.

B. (E)-[[(7,11-Dimethyl-3-methylene-6,10-dodecadienyl)oxy]methyl]phosphonic acid, mono(1-methylethyl) ester To a stirred solution of 1.25 g (3.12 mmol) of Part A compound in 20 mL of 2-propanol under argon was added 17 mL (17 mmol) of 1N KOH and the reaction was heated to 100° C. for 42 hours. The 2-propanol solvent was evaporated and the aqueous residue was stirred in dichloromethane and acidified with 10% HCl solution. The organic layer was washed with water, brine, dried over MgSO$_4$ and evaporated to provide 986 mg (88%) of title compound in the form of a pale yellow oil.

TLC Silica gel (8:1:1 1-propanol/con. NH$_3$/H$_2$O) R$_f$=0.51.

C. (E)-[[[[(7,11-Dimethyl-3-methylene-6,10-dodecadienyl)oxy]methyl](1-methylethoxy)phosphinyl]methyl]phosphonic acid, dimethyl ester To a stirred solution of 986 mg (2.75 mmol) of Part B compound in 8 mL of dichloromethane under argon at room temperature was added 1.15 mL (6.02 mmol) of N,N-diethyltrimethylsilylamine. The reaction was allowed to stir at room temperature for 1.5 hours, the solvent was evaporated and the residue was dissolved in benzene, evaporated and then pumped at high vacuum. The remainder was dissolved in 10 mL of dichloromethane containing 3 drops of DMF under nitrogen at 0° C. and 3.0 mL (6.0 mmol) of 2M oxalyl chloride in dichloromethane was added dropwise over 10 minutes with much gas evolution. After 45 minutes at 0° C., the reaction was allowed to warm to room temperature for 45 minutes. The solution was evaporated, dissolved in benzene, evaporated, and then pumped at high vacuum for 1 hour.

To a solution of 0.72 mL (6.62 mmol) of dimethyl methylphosphonate in 10 mL of THF under argon at −78° C. was added 3.95 mL (6.32 mmol) of 1.6M n-butyllithium in hexanes over 10 minutes to give a white suspension. After 40 minutes at −78° C., the acid chloride prepared above was added in 10 mL of THF over 10 minutes. The mixture was allowed to stir at −78° C. for 1 hour when it was quenched with saturated ammonium chloride and diluted with ether. The aqueous layer was made acidic with 10% HCl solution and the organic layer was separated and washed with brine. The aqueous layer was re-extracted with dichloromethane and the dichloromethane layer was washed with brine. The combined organic layers were dried over MgSO$_4$ and evaporated to provide 1.18 g of crude product. Flash chromatography was performed on 120 g of silica gel packed and loaded and eluted with 2:98 methanol/dichloromethane collecting 30 mL fractions. Fractions 50 to 85 were combined and evaporated to provide 864 mg (67%) of title compound in the form of a clear colorless oil.

TLC Silica gel (5:95 methanol/dichloromethane) R$_f$=0.27.

IR (CCl$_4$) 2979, 2955, 2927, 2856, 1450, 1385, 1375, 1256, 1231, 1180, 1166, 1107, 1064, 1036, 993, 896, 842 cm$^{-1}$.

$^1$H-NMR (CDCl$_3$, 270 MHz) δ 5.10 (m, 2H), 4.79 (m, 3H), 3.84 (m, 8H, H$_{10}$) 3.69 (m, 2H), 2.49 (m, 2H), 2.33 (t, 3H, J=7 Hz), 2.06 (m, 8H), 1.68 (s, 3H), 1.60 (s, 6H), 1.35 (m, 6H) ppm.

MS (CI-NH$_3$, +ions) m/e 482 (M+NH$_4$), 465 (M+H), 261, 236, 219.

D. (E)-[[[[(7,11-Dimethyl-3-methylene-6,10-dodecadienyl)oxy]methyl]hydroxyphosphinyl]methyl]phosphonic acid, trisodium salt To a stirred solution of 860 mg (1.98 mmol) of Part C compound in 10 mL of dichloromethane under argon at room temperature was added 0.85 mL (6.41 mmol) of 2,4,6-collidine followed by 1.70 mL (12.8 mmol) of bromotrimethylsilane and the reaction was allowed to stir at room temperature for 21 hours. The solvent was evaporated and pumped at high vacuum for 1 hour. The remainder was dissolved in 12.8 mL (12.8 mmol) of 1M sodium hydroxide solution, stirred for 1 hour, diluted with water and lyophilized. The crude material was purified by MPLC on a column of CHP20P gel (2.5 cm diameter×20 cm height) eluted with water (fractions 1 to 12) followed by a gradient created by the gradual addition of 500 mL of acetonitrile to a reservoir of 450 mL of water. Approximately 12 mL fractions were collected. Fractions 26 to 37 were combined, the acetonitrile was evaporated at reduced pressure and the aqueous solution was lyophilized to provide 788 mg (94%) of title compound in the form of an amorphous white lyophilate.

TLC Silica gel (5:4:1 n-propanol/con. $NH_3/H_2O$) $R_f = 0.40$.

IR (KBr) 3440, 3435, 3426, 3418, 3094, 3081, 3029, 2966, 2923, 2859, 1644, 1176, 1152, 1094, 975, 798 cm$^{-1}$.

$^1$H-NMR ($D_2O$, 500 MHz): δ 5.13 (m, 2H), 4.81 (s, 1H), 4.80 (s, 1H), 3.68 (t, 2H, J=7 Hz), 3.66 (d, 2H, J=6 Hz), 2.29 (t, 2H, J=6.8 Hz), 2.10 (m, 6H), 1.96 (t, 2H, J=7.2 Hz), 1.90 (t, 2H, J=18 Hz), 1.62 (s, 3H), 1.56 (s, 3H), 1.55 (s, 3H) ppm.

MS (FAB, +ions) m/e 483 (M+Na), 461 (M+H), 439 (M+2H-Na).

Anal. calc'd for $C_{17}H_{29}Na_3O_6P_2 \cdot H_2O$ (MW=478.32): C, 42.68; H, 6.53; P, 12.95 Found: C, 42.51; H, 6.47; P, 13.13.

EXAMPLE 135

(E)-[[Hydroxy[[(3,7,11-trimethyl-6,10-dodecadienyl)oxy]methyl]phosphinyl]methyl]phosphonic acid, trisodium salt A. (6E)-3,7,11-Trimethyl-1-[(triethylsilyl)oxy]-1,6,10-dodecatriene To a suspension of 13 mg (0.01% mmol) of tris(triphenylphosphine)rhodium(I) chloride in 0.65 mL (4.07 mmol) of triethylsilane under argon at 50° C. was added 600 mg (2.72 mmol) of neat Example 7, Part A(1) aldehyde via cannula. After 1 hour at 50° C., the very dark reaction mixture was allowed to cool to room temperature. The mixture was diluted with 10 mL of hexane and filtered through a plug of celite washing copiously with hexane. The solvent was evaporated to provide 896 mg (98%) of crude product. Flash chromatography was performed on 90 g of silica gel packed and loaded with 15:1 hexane/toluene and eluted with 9:1 hexane/toluene collecting 20 mL fractions. Fractions 12 to 25 were combined and evaporated to provide 543 mg (60%) of the desired title silyl enol ether, a colorless liquid as a 4:1 mixture of 1Z and 1E isomers.

TLC Silica gel (9:1 hexane/toluene) $R_f = 0.64$ (1Z), $R_f = 0.43$ (1E).

$^1$H-NMR (CDCl$_3$, 270 MHz) δ 6.20 (d, J=12.9 Hz, E isomer), 6.16 (d, J=5.9 Hz, Z isomer), 5.12 (m, 2H), 4.85 (dd, J=8.8 and 12 Hz, E isomer), 4.23 (dd, J=5.9 and 9.4 Hz, Z isomer) 2.69 (m, 1H) 2.02 (m, 6H), 1.67 (s, 3H), 1.59 (s, 6H), 1.27 (m, 2H), 0.96 (m, 12H), 0.67 (m, 6H) ppm.

B. (E)-3,7,11-Trimethyl-6,10-dodecadienal

To a stirred solution of 543 mg (1.61 mmol) of Part A silyl enol ether in 10 mL of THF at 0° C. was added 0.14 mL (2.39 mmol) of glacial acetic acid followed by 1.8 mL (1.80 mmol) of 1M tetrabutylammonium fluoride in THF. After 1.5 hours at 0° C., the reaction was diluted with 100 mL of diethyl ether and washed with 25 mL portions each of water, saturated sodium bicarbonate, brine and then dried over MgSO$_4$. The solvent was evaporated to provide 307 mg (87%) of crude title aldehyde as a colorless oil.

TLC Silica gel (9:1 hexane/toluene) $R_f = 0.16$.

$^1$H-NMR (CDCl$_3$, 270 MHz) δ 9.75 (t, 1H, J=2.3 Hz), 5.09 (m, 2H), 2.40 (ddd, 1H, J=2.5,6 and 16 Hz), 2.25 (ddd, 1H, J=2.5,8 and 16 Hz) 2.04 (m, 6H), 1.67 (s, 3H), 1.60 (s, 6H), 1.33 (m, 3H), 0.961 (d, 3H, J=7 Hz) ppm.

C. (E)-3,7,11-Trimethyl-6,10-dodecadien-1-ol

To a stirred solution of 983 mg (4.44 mmol) of Part B aldehyde in 20 mL of diethyl ether at −78° C. under argon was added 4.4 mL (6.66 mmol) of 1.5M diisobutylaluminum hydride in toluene dropwise over 5 minutes. After 1.5 hours at −78° C., the cold bath was removed and the reaction was allowed to warm to 0° C. After 15 minutes at 0° C. the reaction was quenched by the addition of 1.4 mL (34.6 mmol) of methanol. The reaction was diluted with 300 mL of diethyl ether and washed with 10% HCl solution followed by water, saturated sodium bicarbonate, brine, and dried over MgSO$_4$. The solvent was evaporated to provide 1.03 g of crude product. Flash chromatography was performed on 105 g of silica gel packed and loaded with 10:1 hexane/EtOAc and eluted with 5:1 hexane/EtOAc collecting 30 mL fractions. Fractions 28 to 45 were combined and evaporated to provide 950 mg (96%) of title compound in the form of a colorless oil.

TLC silica gel (4:1 hexane/EtOAc) $R_f = 0.17$.

IR (CCl$_4$) 3333, 3326, 2962, 2924, 2873, 2857, 1451, 1377, 1057, 1011 cm$^{-1}$.

$^1$H-NMR (CDCL$_3$, 270 MHz) δ 5.10 (m, 2H), 3.68 (m, 2H), 2.01 (m, 6H), 1.68 (s, 3H), 1.60 (s+m, 8H), 1.38 (m, 2H), 1.19 (m, 2H), 0.91 (d, 3H, J=6.4 Hz) ppm.

Mass Spec (CI-NH$_3$, +ions) m/e 242 (M+NH$_4$), 225 (M+H).

D. (E)-[[(3,7,11-Trimethyl-6,10-dodecadienyl)oxy]methyl]phosphonic acid, bis(1-methylethyl) ester To a stirred solution of 906 mg (4.05 mmol) of Part C alcohol in 20 mL of THF at −78° C. under argon was added 2.7 mL (4.25 mmol) of 1.6M n-butyllithium in hexanes over 10 minutes. The reaction was allowed to stir for 40 minutes at −78° C., when 1.33 g (4.05 mmol) of the Example 1, Part B triflate in 5 mL THF was added via cannula. After 0.5 hours at −78° C., the reaction was allowed to warm to 0° C. After 2 hours at 0° C., the reaction was quenched by the addition of saturated ammonium chloride and partitioned between diethyl ether and water. The ether layer was washed with brine, dried over MgSO$_4$, and evaporated to provide 1.52 g of crude oil. Flash chromatography was performed on 150 g of silica gel packed and loaded with 15:1 dichloromethane/EtOAc and eluted with 10:1 dichloromethane/EtOAc collecting 50 mL fractions. Fractions 48 to 74 were combined and evaporated to provide 1.16 g (71%) of title compound in the form of a colorless oil.

TLC Silica gel (3:1 hexane/EtOAc) $R_f = 0.093$.

$^1$H-NMR (CDCl$_3$, 270 MHz) δ 5.09 (m, 2H), 4.75 (m, 2H), 3.70 (d, 2H, J=8.2 Hz), 3.59 (t, 2H, J=7 Hz), 2.01 (m, 6H), 1.68 (s, 3H), 1.59 (s+m, 8H), 1.1–2.5 (m, 15H), 0.89 (d, 3H, J=6.4 Hz) ppm.

E. (E)-[[(3,7,11-Trimethyl-6,10-dodecadienyl)oxy]methyl]phosphonic acid, mono(1-methylethyl) ester To a solution of 1.16 g (2.88 mmol) of Part D compound in 14 mL of 2-propanol under argon was added 14.7 mL (14.7 mmol) of 1N potassium hydroxide and the reaction was heated to 100° C. for 48 hours. The 2-propanol was evaporated and the aqueous residue was stirred with dichloromethane and acidified with 10% HCl solution. The organic layer was washed with water and brine, dried over MgSO$_4$, and evaporated to provide 975 mg (94%) of title compound in the form of a colorless oil.

TLC Silica gel (8:1:1 n-C$_3$H$_7$OH/con. NH$_3$/H$_2$O) R$_f$=0.48.

$^1$H-NMR (CDCl$_3$, 270 MHz) δ 5.08 (m, 2H), 4.75 (m, 1H), 3.74 (d, 2H), 3.60 (t, 2H, J=7 Hz), 2.01 (m, 6H), 1.68 (s, 3H), 1.60 (s+m, 8H), 1.30 (m, 9H), 0.89 (d, 3H, J=6.4 Hz) ppm.

F. (E)-[[(1-Methylethoxy)[[(3,7,11-trimethyl-6,10-dodecadienyl)oxy]methyl]phosphinyl]methyl]phosphonic acid, dimethyl ester To a stirred solution of 975 mg (2.70 mmol) of Part E compound in 6 mL of dichloromethane under argon was added 1.0 mL (5.41 mmol) of N,N-diethyltrimethylsilylamine. The reaction was allowed to stir for 1.5 hours at room temperature, the solvent was evaporated and the residue was dissolved in benzene, evaporated and then pumped at high vacuum. The remainder was dissolved in 8 mL of dichloromethane containing 3 drops of DMF under nitrogen at 0° C. and 27 mL (5.41 mmol) of 2.0M oxalyl chloride in dichloromethane was added dropwise over 10 minutes with much gas evolution. After 45 minutes at 0° C., the reaction was allowed to warm to room temperature for 45 minutes. The solution was evaporated and the residue was dissolved in benzene, evaporated, and then pumped at high vacuum.

To a solution of 0.65 mL (5.95 mmol) of dimethyl methylphosphonate in 15 mL THF at −78° C. under argon was added 3.5 mL (5.68 mmol) of 1.6M n-butyllithium in hexanes over 5 minutes to give a white suspension. After 40 minutes, the acid chloride prepared above was added in 8 mL of THF over 10 minutes. The reaction was allowed to stir for 1 hour at −78° C. when it was quenched with saturated ammonium chloride and diluted with diethyl ether. The aqueous layer was made acidic with 10% HCl and the organic layer was separated and washed with brine. The aqueous layer was re-extracted with dichloromethane and the dichloromethane layer was washed with brine. The combined organic layers were dried over MgSO$_4$ and evaporated to provide 1.2 g of a crude yellow oil. Flash chromatography was performed on 120 g of silica gel packed, loaded and eluted with 2:98 methanol/dichloromethane collecting 50 mL fractions. Fractions 59 to 91 were combined and evaporated to provide 1.01 g (80%) of title compound in the form of a colorless oil.

TLC Silica gel (5:95 methanol/dichloromethane) R$_f$=0.27.

IR (CCl$_4$) 2957, 2927, 2873, 2856, 1452, 1385, 1376, 1257, 1231, 1179, 1165, 1106, 1064, 1037, 993, 842, 816 cm$^{-1}$.

$^1$H-NMR (CDCl$_3$, 270 MHz) δ 5.09 (m, 2H), 4.80 (m, 1H), 3.83, 3.79 (two d, 6H, J=11 Hz), 3.7-3.9 (m, 2H), 3.58 (m, 2H), 2.48 (m, 2H), 2.01 (m, 6H), 1.68 (s, 3H), 1.60 (s+m, 8H), 1.1-1.5 (m, 9H), 0.89 (d, 3H, J=6.4 Hz) ppm.

Mass Spec (CI, NH$_3$, +ions) m/e 484 (M+MH4), 467 (M+H).

G. (E)-[[Hydroxy[[(3,7,11-trimethyl-6,10-dodecadienyl)oxy]methyl]phosphinyl]methyl]phosphonic acid, trisodium salt To a stirred solution of 700 mg (1.50 mmol) of Part F compound in 8 mL of dichloromethane at room temperature was added 0.60 mL (4.50 mmol) of 2,4,6-collidine followed by 1.2 mL (9.00 mmol) of bromotrimethylsilane. The reaction was allowed to stir for 21 hours at room temperature. The solution was evaporated and pumped at high vacuum for 1 hour. The remainder was dissolved in 9 mL (9.00 mmol) of 1N sodium hydroxide, stirred for 1 hour, diluted with water and lyophilized. The crude material was purified by MPLC on a column of CHP20P gel (2.5 cm diameter×19 cm height) packed with water and eluted with water (fractions 1 to 12) followed by a gradient created by the gradual addition of acetonitrile (500 mL) to a reservoir of 450 mL of water. Approximately 12 mL fractions were collected. Fractions 26 to 35 were combined, the acetonitrile was evaporated at reduced pressure, and the aqueous solutin was lyophilized to provide 646 mg (93%) of title compound as an amorphous, white lyophilate.

TLC Silica gel (5:4:1 n-C$_3$H$_7$OH/con. NH$_3$/H$_2$O) R$_f$=0.36.

IR (KBr) 3400 (br), 2964, 2923, 2875, 1667, 1650, 1452, 1442, 1380, 1177, 1150, 1101, 977, 875, 797, 710 cm$^{-1}$.

$^1$H-NMR (D$_2$O, 400 MHz) (CH$_3$OH reference) δ 5.18, 5.15 (two triplets, J=7 Hz, 2H), 3.64 (d, 2H, J=5.9 Hz), 3.58 (m, 2H), 1.8-2.2 (m, 8H), 1.63 (s, 3H), 1.56 (s, 6H), 1.1-1.7 (m, 5H), 0.83 (d, 3H, J=6.6 Hz) ppm.

$^{31}$P-NMR (D$_2$O, 36.2 MHz) (85% H$_3$PO$_4$ external reference) δ 30.3 (d, J=11.7 Hz, CPC), 11.2 (d, J=11.7 Hz, CPO$_3$) ppm.

The $^{31}$P-NMR spectrum was accumulated in the $^1$H decoupled mode.

Mass Spec (FAB, +ions) m/e 463 (M+H), 441 (M+2H-Na), 419 (M+3H-2Na).

Anal. Calc'd for C$_{17}$H$_{31}$Na$_3$P$_2$O$_6$+0.90 mol H$_2$O: C, 42.66; H, 6.91; P, 12.94 Found: C, 42.33; H, 7.01; P, 13.32.

EXAMPLE 136

(2Z,6E)-[[Hydroxy[[(3,7,11-trimethyl-2,6,10-dodecatrienyl)oxy]methyl]phosphinyl]methyl]phosphonic acid, trisodium salt A. (6E)-3,7,11-Trimethyl-2,6,10-dodecatrienoic acid, ethyl ester To a suspension of 2.47 g (62.0 mmol) of 60% NaH in mineral oil (twice washed with pentane) in 80 mL of dry THF at 0° C. under argon was added dropwise 12.3 mL (62.0 mmol) of triethyl phosphonoacetate. After hydrogen evolution had ceased, the pale yellow solution was allowed to warm to room temperature, treated dropwise with 11.5 mL (50.0 mmol) of geranyl acetone and allowed to stir at room temperature for 3 days. The very viscous reaction mixture was transferred to a larger flask with the aid of diethyl ether and the solvent evaporated. The residue was partitioned between water and hexane, and the water layer was back-extracted with hexane. The organic layers were combined, washed with brine, dried over MgSO$_4$ and evaporated to provide 13.68 g of crude product. Flash chromatography was performed on 300 g of silica gel packed and loaded with a 2:98 ether/petroleum ether and eluted with 4:96 ether/petroleum ether collecting 50 mL fractions. Fractions 19 to 34 were combined and evaporated to provide 13.03 g (98.5%) of title compound in the form of a crude mixture of isomers - approximately 1:3 of 2Z, 6E and 2E, 6E.

TLC Silica gel (5:95 Ethyl acetate:hexane) R$_f$=0.38 2Z, 6E; R$_f$=0.31 2E, 6E.

B. (Z,E)-3,7,11-Trimethyl-2,6,10-dodecatrien-1-ol

Samples of Part A compound enriched in the 2Z isomer were obtained by flash chromatography. A stirred solution of 896 mg (3.39 mmol) of Part A compound, enriched in the Z isomer, in 15 mL of toluene at 0° C. under argon was treated dropwise with 6.8 mL (10.2 mmol) of 1.5M diisobutylaluminum hydride in toluene over 5 minutes. After 0.5 hours, the reaction mixture was quenched with 0.41 mL water, 0.41 mL 15% sodium hydroxide solution and then 1.2 mL water. A volume of 25 mL diethyl ether and 20 mL 1N HCl was then added with stirring at room temperature. The phases were separated and the aqueous layer washed twice with diethyl ether. The organic phases were combined, washed with brine, dried over MgSO4, and evaporated to give 915 mg of the crude mixture of isomers. Flash chromatography was performed on 125 g of silica gel packed and loaded with 10:1 hexane/ethyl acetate collecting 30 mL fractions. Fractions 36 to 58 were combined and evaporated to provide 560 mg (74%) of title compound in the form of the desired 2Z, 6E isomer.

TLC Silica gel (7:1 hexane/ethyl acetate) $R_f=0.22$.

$^1$H-NMR (CDCl$_3$, 270 MHz) δ 5.43 (td, 1H, J=7 and 1.2 Hz), 5.10 (m, 2H), 4.09 (d, 2H, J=7 Hz), 2.04 (m, 9H), 1.75 (d, 3H, J=1.75 Hz), 1.67 (d, 3H, J=1.18 Hz), 1.59 (s, 6H) ppm.

C. (Z,E)-[[(3,7,11-Trimethyl-2,6,10-dodecatrienyl)oxy]methyl]phosphonic acid, bis(1-methylethyl) ester To a stirred solution of 841 mg (3.76 mmole) of Part B compound in 12 mL of THF under argon at −78° C. was added 2.3 mL (3.76 mmole) of 1.6M n-butyllithium in hexanes over 10 minutes. The reaction mixture was allowed to stir for 40 minutes at −78° C., when 1.15 g (3.50 mmole) of the Example 1, Part B triflate in 4 mL THF was added via cannula. After 30 minutes at −78° C., the reaction was allowed to warm to 0° C. After 2 hours at 0° C., the reaction was quenched with saturated ammonium chloride and partitioned between diethyl ether and water. The ether layer was washed with brine, dried over MgSO4 and evaporated to provide 1.6 g of crude product. Flash chromatography was performed on 170 g silica gel packed and loaded with 15:1 dichloromethane/ethyl acetate and eluted with 10:1 dichloromethane/ethyl acetate collecting 20 mL fractions. Fractions 59 to 97 were combined and evaporated to provide 1.13 g (76%) of title compound in the form of a pale yellow oil.

TLC Silica gel (2:1 hexane:ethyl acetate) $R_f=0.21$.

IR (CCl$_4$) 2978, 2931, 2875, 2858, 1670, 1450, 1385, 1375, 1257, 1240, 1107, 1007, 990 cm$^{-1}$.

$^1$H-NMR (CDCl$_3$, 270 MHz) δ 5.32 (t, 1H, J=7 Hz), 5.09 (m, 2H), 4.76 (m, 2H), 4.10 (d, 2H, J=7 Hz), 3.68 (d, 2H, J=8.2 Hz), 2.03 (m, 8H), 1.76 (d, 3H, J=1.2 Hz), 1.68 (s, 3H), 1.60 (s, 6H), 1.34 (dd, 12H, J=6.4 Hz, 1.7 Hz) ppm.

Mass Spec (Cl-CH$_4$/N$_2$O, +ions) m/e 441 (M+C$_3$H$_5$), 429 (M+C$_2$H$_5$), 401 (M+H), 197:

D. (Z,E)-[[(3,7,11-Trimethyl-2,6,10-dodecatrienyl)oxy]methyl]phosphonic acid, mono(1-methylethyl) ester To a stirred solution of 1.12 g (2.79 mmol) of Part C compound in 14 mL of 2-propanol under argon was added 14 mL of 1N KOH and heated to 100° C. for 45 hours. The 2-propanol was evaporated and the aqueous residue was stirred with dichloromethane and acidified with 10% HCl solution. The organic layer was washed with water and brine, dried over MgSO4, and evaporated to provide 981 mg (98%) of a pale yellow oil.

TLC Silica gel (8:1:1 1-propanol:con. NH$_3$:H$_2$O) $R_f=0.57$.

$^1$H-NMR (CDCl$_3$, 270 MHz) δ 11.92 (s, 1H), 5.31 (t, 1H, J=7 Hz), 5.08 (m, 2H), 4.74 (m, 1H), 4.09 (d, 2H, J=7 Hz), 3.70 (d, 2H, J=8.8 Hz), 2.12 (m, 8H), 1.74 (s, 3H), 1.66 (s, 3H), 1.58 (s, 6H), 1.33 (d, 6H) ppm.

E. (Z,E)-[[(1-Methylethoxy)[[(3,7,11-trimethyl-2,6,10-dodecatrienyl)oxy]methyl]phosphinyl]methyl]phosphonic acid, dimethyl ester To a stirred solution of 981 mg (2.74 mmole) of Part D compound in 6 mL of dichloromethane under argon was added 1.1 mL (5.76 mmol) of N,N-diethyltrimethylsilylamine. The reaction was allowed to stir for 1.5 hours at room temperature, the solvent was evaporated and the residue was dissolved in benzene, evaporated and then pumped at high vacuum. The remainder was dissolved in 8 mL of dichloromethane containing 3 drops of DMF under nitrogen at 0° C. and 2.7 mL (5.47 mmol) of 2M oxalyl chloride in dichloromethane was added dropwise over 10 minutes with much gas evolution. After 45 minutes at 0° C., the reaction was allowed to warm to room temperature for 45 minutes. The solution was evaporated and the residue was dissolved in benzene and evaporated, followed by pumping at high vacuum. A solution of 0.64 mL (5.90 mmol) of dimethyl methylphosphonate in 15 mL of THF at −78° C. under argon was added 3.5 mL (5.67 mmol) of 1.6M n-butyllithium in hexanes over 5 minutes to give a white suspension. After 40 minutes, the acid chloride prepared above was added in 8 mL of THF over 10 minutes. The reaction was allowed to stir for 1 hour at −78° C., when it was quenched with saturated ammonium chloride and diluted with ether. The aqueous layer was made acidic with 10% HCl and the organic layer was separated and washed with brine. The aqueous layer was re-extracted with dichloromethane and the dichloromethane layer was washed with brine. The combined organic layers were dried over MgSO4 and evaporated to provide 1.3 g of crude product. Flash chromatography was performed on 130 g of silica gel eluted with 2:98 methanol/dichloromethane collecting 20 mL fractions. Fractions 70 to 155 were combined and evaporated to provide 626 mg (50%) of title compound in the form of oil.

TLC Silica gel (5:95 methanol/dichloromethane) $R_f=0.27$.

IR (CCl$_4$) 2976, 2953, 2916, 2853, 1675, 1449, 1385, 1375, 1256, 1229, 1179, 1165, 1104, 1089, 1063, 1036, 992, 896 cm$^{-1}$.

$^1$H-NMR (CDCl$_3$, 270 MHz) δ 5.32 (t 1H J=7 Hz) 5.09 (m, 2H), 4.80 (m, 1H), 4.09 (d, 2H, J=7 Hz), 3.80, 3.82 (two d, 6H, J=11 Hz), 3.7-3.9 (m, 2H), 2.49 (m, 2H), 2.02 (m, 8H), 1.76 s, 3H), 1.68 s, 3H), 1.60 (s, 6H), 1.36, 1.34 (two d, 6H, J=7.02 Hz, 6.45 Hz) ppm.

Mass Spec (Cl-NH$_3$, +ions) m/e 482 (M+NH$_4$).

F. (2Z,6E)-[[Hydroxy[[(3,7,11-trimethyl-2,6,10-dodecatrienyl)oxy]methyl]phosphinyl]methyl]phosphonic acid, trisodium salt To a stirred solution of 623 mg (1.34 mmol) of Part E compound in 7 mL of dichloromethane at room temperature under argon was added 0.53 mL (4.01 mmol) of 2,4,6-collidine followed by 1.0 mL (7.80 mmol) of bromotrimethylsilane. The reaction was allowed to stir for 22 hours at room temperature. The solution was evaporated and pumped at high vacuum for 1 hour. The remainder was dissolved in 7.8 mL (7.80 mmol) of 1N NaOH, stirred for 1 hour, diluted with water and lyophilized. The crude material was purified by MPLC on a column of CHP20P gel (2.5 cm diameter×20 cm height) eluted with water (fractions 1 to 13), followed by a gradient created by the gradual addition of acetonitrile (500 mL) to a reservoir of 450 mL of water. Approximately 12 mL fractions were collected. Fractions 26 to 33 were combined, the acetonitrile was evaporated at reduced pressure and the aqueous solution was lyophilized to provide 579 mg (97%) of title compound in the form of an amorphous white lyophilate.

TLC Silica gel (5:4:1 n-$C_3H_7OH$/con. $NH_3$/$H_2O$) $R_f$=0.35.

IR (KBr) 3425, 3275, 3067, 3053, 3029, 3025, 2967, 2924, 2858, 1192, 1132, 1106, 1082, 1054, 975 $cm^{-1}$.

$^1$H-NMR ($D_2O$, 400 MHz) δ 5.38 (t, 1H), 5.12 (m, 2H), 4.07 (d, 2H, J=7 Hz), 3.62 (d, 2H, J=7.0 Hz), 1.9-2.2 (m, 8H), 1.93 (t, 2H, J=18 Hz), 1.72 (s, 3H), 1.63 (s, 3H), 1.56 (s, 6H) ppm.

$^{31}$P-NMR ($D_2O$, 36.2 MHz) δ 32.4 (d, J=10.2 Hz, $CPO$), 12.6 (d, J=10.3 Hz, $CPO_3$) ppm.

The -P-NMR spectra was accumulated in the $^1$H decoupled mode, referenced to external 8% $H_3PO_4$.

Mass Spec (FAB, +ions) m/e 483 (M+Na), 461 (M+H), 439 (M+2H-Na).

Anal. Calc'd for $C_{17}H_{29}Na_3P_2O_6$+1.13 mole $H_2O$ Effective MW=480.72 C, 42.48; H, 6.56; P, 12.89 Found: C, 42.48; H, 6.80; P, 12.75.

EXAMPLE 137

(E)-[[[[(7,11-Dimethyl-6,10-dodecadienyl)oxy]methyl]-hydroxyphosphinyl]methyl]phosphonic acid, trisodium salt A. (E)-7,11-Dimethyl-6,10-dodecadien-2-ynoic acid, methyl ester A solution of 1.15 g (6.54 mmol) of Example 16, Part A acetylene in 15 mL of THF at −78° C. under argon was treated with 4.5 mL (7.19 mmol) of 1.6M n-butyllithium in hexanes over 10 minutes to give a purple solution. The reaction was allowed to stir at −78° C. for 1 hour when 1 mL (13.1 mmol) of methyl chloroformate was added to give a yellow solution. The reaction was allowed to stir at −78° C. for 1 hour when it was quenched with saturated $NH_4Cl$ and diluted with diethyl ether. The ether extract was washed with water, saturated $NaHCO_3$, brine, dried over $MgSO_4$ and evaporated to provide 1.73 g of a crude yellow oil. Flash chromatography was performed on 180 g of silica gel packed and loaded with 25:1 hexane/EtOAc and eluted with 20:1 hexane/EtOAc collecting 20 mL fractions. Fractions 59 to 83 were combined and evaporated to provide 1.34 g (87%) of title compound in the form of a pale yellow oil.

TLC Silica gel (12:1 hexane/EtOAc) $R_f$=0.35.

$^1$H-NMR ($CDCl_3$, 270 MHz) δ 5.08, 5.15 (two m, 1H each), 3.75 (s, 3H), 2.32 (m, 4H), 2.04 (m, 4H), 1.68 (s, 3H), 1.62 (s, 3H), 1.60 (s, 3H) ppm.

B. (E)-7,11-Dimethyl-6,10-dodecadienoic acid, methyl ester

To a stirred solution of 1.03 g (4.37 mmol) of Part C compound in 35 mL of dry methanol at room temperature under argon was added 531 mg (21.8 mmol) of magnesium turnings. After 1.5 hours at room temperature, the reaction was diluted with ether and water, acidified with 10% HCl, and stirred for 0.5 hour. The phases were separated and the organic layer was washed with water, saturated sodium bicarbonate, brine, dried over $MgSO_4$ and evaporated to provide 1.17 g of crude product. Flash chromatography was performed on 120 g of silica gel packed and loaded with hexane and eluted with 4:1 hexane:EtOAc collecting 30 mL fractions. Fractions 43 to 79 were combined and evaporated to provide 702 mg (67%) of impure title ester as a colorless oil.

TLC Silica gel (1:1 hexane/toluene) $R_f$=0.17.

$^1$H-NMR ($CDCl_3$, 270 MHz) δ 5.10 (m, 2H), 3.66 (s, 3H), 2.30 (t, 2H, J=7.6 Hz), 2.00 (m, 6H), 1.67 (s, 3H), 1.59 (s, 6H), 1.7-1.5 (m, 2H), 1.36 (q, 2H, J=7 Hz) ppm.

C. (E)-7,11-Dimethyl-6,10-dodecadien-1-ol

To a suspension of 112 mg (2.93 mmol) of lithium aluminum hydride (LAH) in 15 mL of THF under argon at 0° C. was added 702 mg (2.93 mmol) of Part B ester in 15 mL of THF dropwise over 10 minutes. After 0.5 hour, the reaction was diluted with 20 mL THF and quenched with 0.12 mL of water, 0.12 mL of 15% sodium hydroxide solution and then with 0.35 mL of water. After 0.5 hour, sodium sulfate was added and the slurry was stirred for 1 hour before filtering through a pad of celite, washing copiously with diethyl ether. The solvent was evaporated to provide 632 mg of crude product. Flash chromatography was performed on 70 g of silica gel packed and loaded with 10:1 hexane/EtOAc and eluted with 8:1 hexane/EtOAc collecting 25 mL fractions. Fractions 58 to 83 were combined and evaporated to provide 347 mg (56%) of title compound in the form of a clear colorless oil.

TLC Silica gel (7:1 hexane/EtOAc) $R_f$=0.16.

$^1$H-NMR ($CDCL_3$, 270 MHz) δ 5.11 (m, 2H), 3.63 (t, 2H, J=7 Hz), 2.03 (m, 6H), 1.68 (s, 3H), 1.59 (s, 6H), 1.6-1.5 (m, 2H), 1.36 (m, 4H) ppm.

D. (E)-[[(7,11-Dimethyl-6,10-dodecadienyl)oxy]methyl]phosphonic acid, bis(1-methylethyl) ester To a stirred solution of 486 mg (2.31 mmole) of Part C compound in 15 mL of THF at −78° C. under argon was added 1.4 mL (2.31 mmol) of 1.6M n-butyllithium in hexanes over 10 minutes. The reaction was allowed to stir for 40 minutes at −78° C. when 751 mg (2.29 mmol) of the Example 1, Part B triflate in 5 mL of THF was added via cannula. After 0.5 hour at −78° C., the reaction was allowed to warm to 0° C. After 2.5 hours at 0° C., the reaction was quenched by the addition of saturated $NH_4Cl$ and partitioned between diethyl ether and water. The ether layer was washed with brine, dried over $MgSO_4$, and evaporated to provide 912 mg of crude product. Flash chromatography was performed on 92 g of silica gel packed and loaded with 15:1 dichloromethane/EtOAc and eluted with 10:1 dichloromethane/EtOAc collecting 30 mL fractions. Fractions 38 to 78 were combined to provide 550 mg of product. The 550 mg of material was further purified by flash chromatography on 55 g of silica gel packed and loaded with 10:1 hexane/EtOAc and eluted with 5:1 hexane/EtOAc collecting 7 mL fractions. Fractions 85 to 157 were combined to provide 497 mg (55%) of title compound in the form of an oil.

TLC Silica gel (2:1 hexane/EtOAc) $R_f$=0.13.

IR ($CCl_4$) 2979, 2933, 2858, 1465, 1452, 1385, 1375, 1258, 1240, 1178, 1142, 1108, 1009, 990, 903, 889, 808, 797 $cm^{-1}$.

$^1$H-NMR ($CDCl_3$, 270 MHz) δ 5.09 (m, 2H), 4.74 (m, 2H), 3.70 (d, 2H, J=8.2 Hz), 3.55 (t, 2H, J=6.4 Hz), 2.02 (m, 6H), 1.67 (s, 3H), 1.60 (s, 3H), 1.58 (s, 3H), 1.34 (m, 16H) ppm.

Mass Spec (CI, $CH_4$/$H_2O$, +ions) m/e 777 (2M+H), 389 (M+H).

E. (E)-[[(7,11-Dimethyl-6,10-dodecadienyl)oxy]methyl]phosphonic acid, mono(1-methylethyl) ester To a solution of 495 mg (1.27 mmol) of Part D compound in 7 mL of 2-propanol under argon was added 6.5 mL (6.5 mmol) of 1N KOH and the reaction was heated to 100° C. for 38 hours. The 2-propanol was evaporated and the aqueous residue was stirred in dichloromethane and acidified with 10% HCl solution. The organic layer was washed with water, brine, dried over MgSO$_4$ and evaporated to provide 429 mg (97%) of title compound in the form of a pale yellow oil.

TLC Silica gel (8:1:1 n-C$_3$H$_7$OH/con. NH$_3$/H$_2$O) R$_f$=0.60.

F. (E)-[[(1-Methylethoxy)][[(7,11-dimethyl-6,10-dodecadienyl)oxy]methyl]phosphinyl]methyl]phosphonic acid, dimethyl ester To a stirred solution of 429 mg (1.24 mmol) of Part E compound in 3 mL of dichloromethane under argon at room temperature was added 0.47 mL (2.48 mmol) of N,N-diethyltrimethylsilylamine. The reaction was allowed to stir at room temperature for 1.5 hours, the solvent was evaporated and the residue was dissolved in benzene, evaporated and then pumped at high vacuum. The remainder was dissolved in 4 mL of dichloromethane containing 3 drops of DMF under nitrogen at 0° C. and 1.3 mL (2.48 mmol) of 2M oxalyl chloride in dichloromethane was added dropwise over 10 minutes with much gas evolution. After 45 minutes at 0° C., the reaction was allowed to warm to room temperature for 45 minutes. The solution was evaporated and the residue was dissolved in benzene, evaporated and then pumped at high vacuum.

To a solution of 0.30 mL (2.73 mmol) of dimethyl methylphosphonate in 7 mL of THF at −78° C. under argon was added 1.6 mL (2.60 mmol) of 1.6M n-butyllithium in hexanes over 5 minutes to give a white suspension. After 40 minutes, the acid chloride prepared above was added in 8 mL of THF over 10 minutes. The reaction was allowed to stir for 1 hour at −78° C. when it was quenched with saturated NH$_4$Cl and diluted with diethyl ether. The aqueous layer was made acidic with 10% HCl and the organic layer was separated and washed with brine. The aqueous layer was re-extracted with dichloromethane and the dichloromethane layer was washed with brine. The combined organic layers were dried over MgSO$_4$ and evaporated to provide 527 mg of crude product. Flash chromatography was performed on 53 g of silica gel eluted with 2:98 methanol/dichloromethane collecting 25 mL fractions. Fractions 26 to 39 were combined and evaporated to provide 329 mg (59%) of title compound in the form of an oil.

TLC Silica gel (2:98 methanol/dichloromethane) R$_f$=0.093.

$^1$H-NMR (CDCl$_3$, 270 MHz) δ 5.09 (m, 2H), 4.79 (m, 1H), 3.9–3.7 (m, 8H), 3.56 (m, 2H), 2.51 (m, 2H), 2.00 (m, 6H), 1.67 (s, 3H), 1.59 (s, 6H) 1.6–1.5 (m, 2H), 1.35 (m, 10H, H$_3$, H$_4$) ppm.

G. (E)-[[[[(7,11-Dimethyl-6,10-dodecadienyl)oxy]methyl]hydroxyphosphinyl]methyl]phosphonic acid, trisodium salt To a stirred solution of 327 mg (0.723 mmol) of Part F compound in 4 mL of dichloromethane at room temperature was added 0.30 mL (2.17 mmol) of 2,4,6-collidine followed by 0.60 mL (4.34 mmol) of bromotrimethylsilane. The reaction was allowed to stir for 23 hours at room temperature when the solvent was evaporated and pumped at high vacuum for 1 hour. The remainder was dissolved in 4.5 mL (4.50 mmol) of 1M sodium hydroxide, diluted with water and lyophilized. The crude material was purified by MPLC on a column of CHP20P gel (2.5 cm diameter×20 cm height) eluted with water fractions (1 to 12) followed by gradient created by the gradual addition of 450 mL of 2:1 acetonitrile/water to a reservoir of 450 mL of water. Approximately 5 mL fractions were collected. Fractions were analyzed by HPLC and the pure fractions (46–58) were combined. The acetonitrile was evaporated at reduced pressure and the aqueous solution was lyophilized to provide 162 mg (50%) of title compound as an amorphous white lyophilate which was >99% pure by HPLC.

TLC Silica gel (5:4:1 n-C$_3$H$_7$OH/Con. NH$_3$/H$_2$O) R$_f$=0.37.

IR (KBr) 3430 (br), 3011, 2966, 2928, 2856, 1652, 1644, 1636, 1382, 1192, 1153, 1135, 1102, 1058, 971 cm$^{-1}$.

$^1$H-NMR (D$_2$O, 400 MHz) δ 5.13, 5.18 (two t, 2H total, J=7 Hz), 3.64 (d, 2H, J=5.9 Hz), 3.55 (t, 2H, J=7 Hz), 2.05 (m, 2H), 1.98 (m, 6H), 1.62 (s, 3H), 1.6–1.5 (m, 2H), 1.56 (s, 6H), 1.28 (m, 4H) ppm.

Mass Spec (FAB) m/e 471 (M+Na), 449 (M+H), 427 (M-Na+2H), 405 M-2Na+3H).

Anal. Calc'd for C$_{15}$H$_{29}$Na$_3$P$_2$O$_6$+1.40 mole H$_2$O: C, 40.59; H, 6.77; P, 13.08 Found: C, 40.75; H, 7.02; P, 13.04.

EXAMPLE 138

(E)-[[[[(6,10-Dimethyl-5,9-undecadienyl)oxy]methyl]hydroxyphosphinyl]methyl]phosphonic acid, trisodium salt A. (E)-3,7-Dimethyl-2,6-octadien-1-yl chloride (Geranyl chloride)

To a stirred solution of 4.75 g (35.6 mmol) of N-chlorosuccinimide in 180 mL of dichloromethane at −35° C. (internal thermometer) under argon was added 3.3 mL (45.4 mmol) of dimethyl sulfide over 10 minutes. The mixture was allowed to warm to 0° C. for 15 minutes then cooled again to −35° C. A solution of 5.0 g (32.4 mmol) of (E)-3,7-dimethyl-2,6-octadien-1-ol (geraniol) in 25 mL of dichloromethane was added dropwise over 10 minutes. After addition, the reaction was allowed to warm gradually to 0° C. over 2 hours. After 1 hour at 0° C., the reaction was quenched with ice-cold water, diluted with 500 mL of hexane, and the organic layer was separated. The hexane extract was washed with water, brine, dried over MgSO$_4$ and evaporated to provide 5.21 g (93%) of title compound in the form of a yellow liquid.

TLC Silica gel (8:1 hexane/EtOAc) R$_f$=0.68.

$^1$H-NMR (CDCl$_3$, 270 MHz) δ 5.44 (m, 1H), 5.08 (m, 1H), 4.09 (d, 2H, J=8.2 Hz), 2.08 (m, 4H), 1.73 (s, 3H), 1.68 (s, 3H), 1.60 (s, 3H) ppm.

B (E)-6,10-Dimethyl-5,9-undecadien-1-ol

A solution of 198 mL (58.0 mmol) of 0.29M Example 36 part B Grignard reagent in THF and 48 mL (275.9 mmol) of hexamethyl phosphoric anhydride (HMPA) at 0° C. under argon was treated dropwise with 2.0 g (11.6 mmol) of Part A geranyl chloride in 20 mL of THF. After addition, the reaction was allowed to warm to room temperature for 2 hours, at which point the reaction was diluted with 1:1 hexane/ether and quenched with 1N HCl solution. The organic layer was washed with 1N HCl followed by water, saturated sodium bicarbonate, brine, dried over MgSO$_4$ and evaporated to provide 3.59 g of crude oil. Flash chromatography was performed on 360 g of silica gel packed and loaded with 10:1 hexane/EtOAc and eluted with 7:1 hexane/EtOAc collecting 30 mL fractions. Fractions 32 to 49 were combined and evaporated to provide 1.68 g (74%) of title compound in the form of an oil.

TLC Silica gel (7:1 hexane/EtOAc) R$_f$=0.19.

¹H-NMR (CDCl₃, 270 MHz) δ 5.11 (m 2H) 3.61 (t, 2H, J=6.45 Hz), 2.03 (m, 6H), 1.68 (s, 3H), 1.59 (s, 6H), 1.5–1.6 (m, 2H), 1.41 (m, 2H) ppm.

C. (E)-[[(6,10-Dimethyl-5,9-undecadienyl)oxy]methyl]phosphonic acid, bis(1-methylethyl) ester To a stirred solution of 800 mg (4.07 mmol) of Part B compound in 20 mL of THF at −78° C. under argon was added 2.7 mL (4.27 mmol) of 1.6M n-butyllithium in hexanes over 10 minutes. The reaction was allowed to stir for 40 minutes, at −78° C. when 1.32 g (4.03 mmol) of the Example 1, Part B triflate in 4 mL of THF was added via cannula. After 0.5 hours at −78° C., the reaction was allowed to warm to 0° C. for 2 hours. The reaction was quenched by the addition of saturated ammonium chloride and partitioned between diethyl ether and water. The ether layer was washed with brine, dried over MgSO₄ and evaporated to provide 1.64 g of crude product. Flash chromatography was performed on 164 g of silica gel packed and loaded with 9:1 hexane/EtOAc and eluted with 3:1 hexane/EtOAc collecting 75 mL fractions. Fractions 62 to 89 were combined and evaporated to provide 902 mg (59%) of oil. The material was further purified by flash chromatography using a 6:1 hexane:acetone solvent system. The second purification provided 750 mg (49%) of title compound in the form of an oil.

TLC Silica gel (3:1 hexane/EtOAc) R$_f$=0.097.

¹H-NMR (CDCl₃, 270 MHz) δ 5.10 (m, 2H), 4.75 (m, 2H), 3.70 (d, 2H, J=8.2 Hz), 3.55 (t, 2H, J=6.45), 2.01 (m, 6H), 1.67 (s, 3H), 1.59 (s+m, 8H), 1.2–1.5 (m, 14H) ppm.

D. (E)-[[(6,10-Dimethyl-5,9-undecadienyl)oxy]methyl]phosphonic acid, mono(1-methylethyl) ester To a solution of 750 mg (2.00 mmol) of Part C compound in 12 mL of 2-propanol under argon was added 10 mL (10.0 mmol) of 1N KOH and the reaction was heated to 100° C. for 29 hours. The 2-propanol was evaporated and the aqueous residue was stirred in dichloromethane and acidified with 10% HCl solution. The organic layer was washed with water, brine, dried over MgSO₄ and evaporated to provide 638 mg (96%) of title compound in the form of an oil.

TLC Silica gel (8:1:1 1-propanol/con. NH₃/H₂O) R$_f$=0.57.

E. (E)-[[[[(6,10-Dimethyl-5,9-undecadienyl)oxy]methyl](1-methylethoxy)phosphinyl]methyl]phosphonic acid, dimethyl ester To a stirred solution of 638 mg (1.92 mmol) of Part D compound in 5 mL of dichloromethane was added 0.73 mL (3.84 mmol) of N,N-diethyltrimethylsilylamine under argon at room temperature and the reaction was allowed to stir for 1.5 hours. The solvent was evaporated and the residue was dissolved in benzene, evaporated and pumped at high vacuum. The remainder was dissolved in 6 mL of dichloromethane containing 3 drops of DMF under nitrogen at 0° C. and 1.92 mL (3.84 mmol) of 2M oxalyl chloride in dichloromethane was added dropwise over 10 minutes with much gas evolution. After 45 minutes at 0° C., the reaction was allowed to warm to room temperature for 45 minutes. The solution was evaporated, dissolved in benzene and evaporated, and then pumped at high vacuum.

To a solution of 0.50 mL (4.22 mmol) of dimethyl methylphosphonate in 12 mL of THF at −78° C. under argon was added 2.5 mL (4.03 mmol) of 1.6M n-butyllithium in hexanes over 5 minutes to give a white suspension. After 40 minutes, the acid chloride prepared above was added in 10 mL of THF over 10 minutes. The reaction was allowed to stir for 1 hour at −78° C. when it was quenched with saturated ammonium chloride and diluted with diethyl ether. The aqueous layer was made acidic with 10% HCl and the organic layer was separated and washed with brine. The aqueous layer was re-extracted with dichloromethane and the dichloromethane layer was washed with brine. The combined organic layers were dried over MgSO₄ and evaporated to provide 870 mg of crude product. Flash chromatography was performed on 90 g of silica gel eluted with 2:98 methanol/dichloromethane collecting 30 mL fractions. Fractions 50 to 86 were combined and evaporated to provide 587 mg (70%) of a clear oil.

TLC Silica gel (5:95 methanol/dichloromethane) R$_f$=0.31.

IR (CCl₄) 2978, 2952, 2932, 2857, 1451, 1385, 1375, 1257, 1231, 1179, 1165, 1107, 1064, 1036, 993, 842, 823 cm⁻¹.

¹H-NMR (CDCl₃, 270 MHz) δ 5.08 (m, 2H), 4.80 (m, 1H), 3.82, 3.78 (two d, 6H total, J=6.45 Hz), 3.6–4.0 (m, 2H), 3.55 (m, 2H), 2.47 (m, 2H), 2.03 (m, 6H), 1.67 (s, 3H), 1.59 (s+m, 8H), 1.3–1.5 (m, 8H) ppm.

Mass Spec (CI-NH₃, +ions) m/e 456 (M+NH₄), 439 (M+H).

F. (E)-[[[[(6,10-Dimethyl-5,9-undecadienyl)oxy]methyl]hydroxyphosphinyl]methyl]phosphonic acid, trisodium salt To a stirred solution of 584 mg (1.33 mmol) of Part E compound in 6 mL of dichloromethane under argon at room temperature was added 0.53 mL (3.99 mmol) of 2,4,6-collidine followed by 1.1 mL (7.98 mmol) of bromotrimethylsilane and the reaction was allowed to stir at room temperature for 24 hours. The solvent was evaporated and pumped at high vacuum for 1 hour. The remainder was dissolved in 8 mL (8.00 mmol) of 1M NaOH, diluted with water and lyophilized. The crude material was purified by MPLC on a column of CHP20P gel (2.5 cm diameter×19 cm height) eluted with water (fractions 1 to 12) followed by a gradient created by the gradual addition of 500 mL of acetonitrile to a reservoir of 450 mL of water. Approximately 12 mL fractions were collected. Fractions 26 to 32 were combined, the acetonitrile was evaporated at reduced pressure and the aqueous solution was lyophilized to provide 479 mg (83%) of title compound in the form of an amorphous white lyophilate.

TLC Silica gel (5:4:1 n-C₃H₇OH/con. NH₃/H₂O) R$_f$=0.40.

IR (KBr) 3438 (broad), 3083, 3055, 2928, 2858, 1638, 1449, 1441, 1177, 1150, 1096, 974, 874, 794 cm⁻¹.

¹H-NMR (D₂O, 400 MHz): δ 5.13, 5.19 (two t, 1H each, J=7 Hz), 3.64 (d, 2H, J=5.9 Hz), 3.56 (t, 2H, J=7 Hz), 2.06 (q, 2H, J=7 Hz), 1.97 (m, 4H), 1.91 (t, 2H, J=18 Hz), 1.62 (s, 3H), 1.56 (s, 6H), 1.54 (m, 2H), 1.32 (quint, 2H, J=7.5 Hz) ppm.

Mass Spec (FAB, +ions) m/e 457 (M+Na), 435 (M+H), 413 (M+2H-Na), 391 (M+3H-2Na).

Anal. Cald'd for C₁₅H₂₇Na₃O₆P₂.H₂O (MW=452.33): C, 39.83; H, 6.46; P, 13.69 Found: C, 39.50; H, 6.40; P, 13.61.

EXAMPLE 139

(E,E)-Fluoro[[(3,7,11-trimethyl-2,6,10-dodecatrienyl)oxy]methyl]phosphinic acid, 1-methylethyl ester To a suspension of 500 mg (1.39 mmol) of Example 1 Part D acid and 473 mg (1.67 mmol) of 2-fluoro-1-methylpyridinium toluene-4-sulfonate in 5 mL of dry $CH_2Cl_2$ under argon at 0° C. was added 1.35 mL (3.34 mmol) of diisopropylethylamine dropwise over 5 minutes. The reaction was allowed to warm to room temperature and stir for 18 hours. The orange yellow solution was diluted with ethyl acetate and washed successively with 1M HCl, water, and brine, dried ($MgSO_4$) and evaporated to provide 491 mg (98%) of the Example 139 acid fluoride as a pale yellow oil.

TLC silica gel (1:1 hexane/ethyl acetate) $R_f = 0.21$.

$^1H$ NMR ($CDCl_3$, 270 MHz) δ 5.32 (5,1H,J=7Hz), 5.09 (m,2H), 4.95 (m,1H), 4.15 (d,2H,J=7Hz), 3.85 (dd,2H,J=4 and 8Hz), 2.04 (m,8H), 1.69 (s,3H), 1.68 (s,3H), 1.60 (s,6H), 1.39, 1.41 (two d,6H,J=6Hz) ppm.

$^{13}C$ NMR ($CDCl_3$, 67.8 MHz) δ 142.6, 135.4, 131.2, 124.2, 123.5, 119.1, 73.8 (d,J=7.8Hz), 69.2 (d,J=11.7Hz), 61.9 (dd,J=171 and 30Hz), 39.5, 26.6, 26.2, 25.6, 23.7 (d,J=6Hz), 17.6, 16.4, 15.9 ppm.

Mass Spec (CI, +ions) m/e 378 ($M+NH_4$), 360 (M).

Example 139 acid fluoride was utilized in place of the corresponding acid chloride in Example 1 Part E, to provide Example 1 Part E triester in 67% yield.

What is claimed is:

1. A compound having the structure

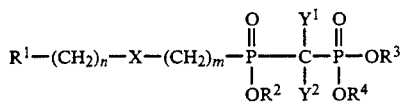

wherein m is 0, 1, 2 or 3; n is 0, 1, 2, 3 or 4;

$Y^1$ and $Y^2$ are H;

$R^2$, $R^3$ and $R^4$ may be the same or different and are independently H, metal ion, $C_1$ to $C_8$ alkyl or $C_3$ to $C_{12}$ alkenyl;

X is O or S; and $R^1$ is $R^5-Q^1-Q^2-Q^3-$ wherein $Q^1$, $Q^2$ and $Q^3$ are the same or different and are independently

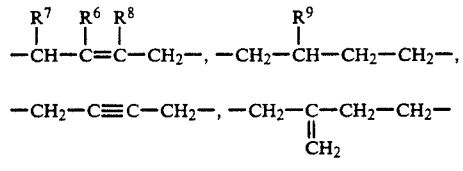

or a single bond, with the proviso that if $Q^1$ is a bond, then $Q^2$ and $Q^3$ are bonds, and if $Q^2$ is a bond then $Q^3$ is a bond, and wherein $R^6$ is H, lower alkyl, halo or haloalkyl; $R^7$ is H, halogen, lower alkyl or lower alkylthio; $R^8$ is H, halogen, trimethylsilyl or lower alkyl; and $R^9$ is H or lower alkyl;

$R^5$ is

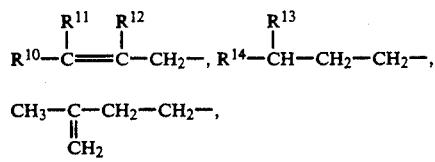

$CH_3(CH_2)_p$ where p is an integer from 2 to 7, or $R^{16}-C\equiv C-CH_2-$ where $R^{16}$ is H or lower alkyl; $R^{10}$, and $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl; with the proviso that if all of $Q^1$, $Q^2$ and $Q^3$ are bonds, then $R^{10}$ and $R^{11}$ cannot both be H, and $R^5$ cannot be $CH_3(CH_2)_p$- with p less than or equal to 4; and when m is O, X is O, and n is 1, 2, 3 or 4; and including all stereoisomers thereof.

2. A compound having the structure

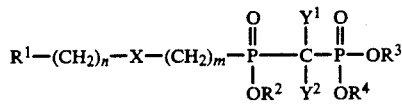

wherein m is 1, 2 or 3; n is 0, 1, 2, 3 or 4;

$Y^1$ and $Y^2$ are H;

$R^2$, $R^3$ and $R^4$ may be the same or different and are independently H, metal ion, $C_1$ to $C_8$ alkyl or $C_3$ to $C_{12}$ alkenyl;

X is O or S; and $R^1$ is $R^5-Q^1-Q^2-Q^3-$ wherein $Q^1$, $Q^2$ and $Q^3$ are the same or different and are independently

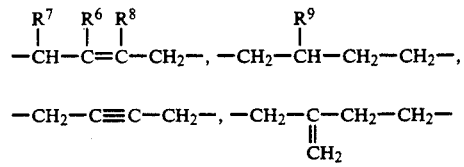

or a single bond, with the proviso that if $Q^1$ is a bond, then $Q^2$ and $Q^3$ are bonds, and if $Q^2$ is a bond then $Q^3$ is a bond, and wherein $R^6$ is H, lower alkyl, halo or haloalkyl; $R^7$ is H, halogen, lower alkyl or lower alkylthio; $R^8$ is H, halogen, trimethylsilyl or lower alkyl; and $R^9$ is H or lower alkyl;

$R^5$ is

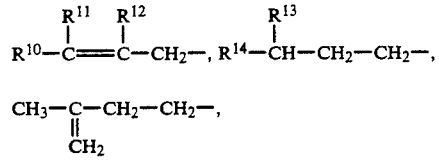

$CH_3(CH_2)_p$ where p is an integer from 2 to 7, or $R^{16}-C\equiv C-CH_2-$ where $R^{16}$ is H or lower alkyl; $R^{10}$, and $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl; with the proviso that if all of $Q^1$, $Q^2$ and $Q^3$ are bonds, then both $R^{10}$ and $R^{11}$ cannot be H, and $R^5$ cannot be $CH_3(CH_2)_p-$ with a p less than or equal to 4, and including all stereoisomers thereof.

3. The compound as defined in claim 2 wherein X is O.

4. The compound as defined in claim 2 wherein m is 1 or 2 and n is 0 or 1.

5. The compound as defined in claim 2 wherein $R^1$ is $R^5$—$Q^1$—$Q^2$ wherein $Q^1$ and $Q^2$ are other than a single bond.

6. The compound as defined claim 4 wherein $R^5$ is

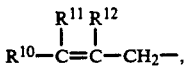

$Q^1$ is

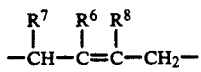

and $Q^2$ is the same as or different from $Q^1$ and is

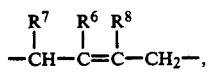

and $Q_3$ is a bond.

7. The compound as defined in claim 5 wherein X is O.

8. The compound as defined in claim 5 wherein X is O, n is 0, m is 1, $Y^1$ and $Y^2$ are H.

9. The compound as defined in claim 1 wherein $R^5$ is

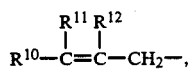

$Q^1$ is

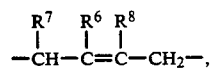

$Q^2$ is —$CH_2$—$C\equiv C$—$CH_2$—, and $Q_3$ is a bond.

10. The compound as defined in claim 2 wherein $R^5$ is $CH_3(CH_2)_p$—, $Q^1$ is

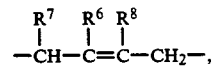

and $Q^2$ is the same as or different from $Q^1$ and is

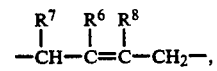

$Q^3$ is a bond.

11. The compound as defined in claim 2 wherein $R^5$ is

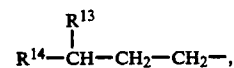

$Q^1$ is

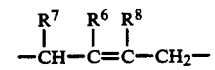

and $Q^2$ is the same as or different from $Q^1$ and is

and $Q^3$ is a bond.

12. The compound as defined in claim 2 wherein one or more of $R^2$, $R^3$ and $R^4$ are an alkali metal salt or alkaline earth metal salt.

13. The compound as defined in claim 2 wherein $R^2$, $R^3$ and $R^4$ are each H.

14. The compound as defined in claim 2 where one or more of $R^2$, $R^3$ and $R^4$ are lower alkyl or lower alkenyl.

15. The compound as defined in claim 2 having the name (E,E)-[[1-methylethoxy[[(3,7,11-trimethyl-2,6,10-dodecatrienyl)oxy]methyl]phosphinyl]methyl]phosphonic acid, dimethyl ester.

16. The compound as defined in claim 2 having the name (E,E)-[[hydroxy[[(3,7,11-trimethyl-2,6,10-dodecatrienyl)oxy]methyl]phosphinyl]methyl]phosphonic acid, or its tripotassium salt or trisodium salt.

17. The compound as defined in claim 2 having the name (E)-[[[[(7,11-dimethyl-6,10-dodecadien-2-ynyl)oxy]methyl](1-methylethoxy)phosphinyl]methyl]phosphonic acid, dimethyl ester.

18. The compound as defined in claim 2 having the name (E)-[[[[(7,11-dimethyl-6,10-dodecadien-2-ynyl)oxy]methyl]hydroxyphosphinyl]methyl]phosphonic acid, or its tripotassium salt.

19. The compound as defined in claim 2 having the name (E,E)-[[[[(7,11-dimethyl-2,6,10-dodecatrienyl)oxy]methyl](1-methylethoxy)phosphinyl]methyl]phosphonic acid, dimethyl ester.

20. The compound as defined in claim 2 having the name (E,E)-[[[[(7,11-dimethyl-2,6,10-dodecatrienyl)oxy]methyl]hydroxyphosphinyl]methyl]phosphonic acid, or its trisodium salt.

21. The compound as defined in claim 2 having the name (E,E)-[[methoxy[[(3,7,11-trimethyl-2,6,10-dodecatrienyl)oxy]methyl]phosphinyl]methyl]-phosphonic acid, dimethyl ester;

(E)-[[[[(3,7-dimethyl-2,6-octadienyl)oxy]methyl]ethoxyphosphinyl]-methyl]phosphonic acid, dimethyl ester, (E) -[[[[(3,7-dimethyl-2,6-octadienyl)oxy]methyl]hydroxyphosphinyl]methyl]phosphonic acid, or its trisodium salt;

(E,E)-[[ethoxy[[[4,8,12-trimethyl-3,7,11-tridecatrienyl]oxy]methyl]phosphinyl]methyl]phosphonic acid, dimethyl ester;

(E,E)-[[hydroxy[[[4,8,12-trimethyl-3,7,11-tridecatrienyl]oxy]methyl]phosphinyl]methyl]phosphonic acid, or its trisodium salt;

(E,E)-[[hydroxy[[(3,7,11-trimethyl-2,6,10-dodecatrienyl)oxy]methyl]phosphinyl]methyl]phosphonic acid, monomethyl ester, dipotassium salt;

(E,E)-[[ethoxy[[(5,9,13-trimethyl-4,8,12-tetradecatrienyl)oxy]methyl]phosphinyl]methyl]phosphonic acid, dimethyl ester;

(E,E)-[[hydroxy[[(5,9,13-trimethyl-4,8,12-tetradecatrienyl)oxy]methyl]phosphinyl]methyl]phosphonic acid, or its trisodium salt, (E,E)-[[ethoxy[2-[(3,7,11-trimethyl-2,6,10-dodecatrienyl)oxy]ethyl]phosphinyl]methyl]phosphonic acid, dimethyl ester;

(E,E)-[[hydroxy[2-[(3,7,11-trimethyl-2,6,10-dodecatrienyl)oxy]ethyl]phosphinyl]methyl]phosphonic acid, or its trisodium salt;

(E,E)-[[[[(3,7-dimethyl-2,6-dodecadienyl)oxy]methyl](1-methylethoxy)phosphinyl]methyl]phosphonic acid, dimethyl ester;

(E,E)-[[[[(3,7-dimethyl-2,6-dodecadienyl)oxy]methyl]hydroxyphosphinyl]methyl]phosphonic acid, or its trisodium salt;

(E,E)-[[(1-methylethoxy)[[(3,7,11-trimethyl-2,6-dodecadienyl)oxy]methyl]phosphinyl]methyl]phosphonic acid, dimethyl ester;

(E,E)-[[hydroxy[[(3,7,11-trimethyl-2,6-dodecadienyl)oxy]methyl]phosphinyl]methyl]phosphonic acid, or its trisodium salt;

(E,E)-[[methoxy[[(3,7,11-trimethyl-2,6,10-dodecatrienyl)oxy]methyl]phosphinyl]difluoromethyl]phosphonic acid, diethyl ester;

(E,E)-[[hydroxy[[(3,7,11-trimethyl-2,6,10-dodecatrienyl)oxy]methyl]phosphinyl]difluoromethyl]phosphonic acid, monoethyl ester, disodium salt;

(E,E)-[[hydroxy[[(3,7,11-trimethyl-2,6,10-dodecatrienyl)oxy]methyl]phosphinyl]difluoromethyl]phosphonic acid, or its trisodium salt;

(E,E)-[[[[(3-chloro-7,11-dimethyl-2,6,10-dodecatrienyl)oxy]methyl]ethoxyphosphinyl]methyl]phosphonic acid, dimethyl ester;

(E,E)-[[[[(3-chloro-7,11-dimethyl-2,6,10-dodecatrienyl)oxy]methyl]hydroxyphosphinyl]methyl]phosphonic acid, or its trisodium salt;

(E,E)-[[ethoxy[[(3,7,11-trimethyl-2,6,10-dodecatrienyl)thio]methyl]phosphinyl]methyl]phosphonic acid, dimethyl ester;

(E,E)-[[hydroxy[[(3,7,11-trimethyl-2,6,10-dodecatrienyl)thio]methyl]phosphinyl]methyl]phosphonic acid, or its trisodium salt;

(E,E)-[[[[(3-ethyl-7,11-dimethyl-2,6,10-dodecatrienyl)oxy]methyl](1-methylethoxy)phosphinyl]methyl]phosphonic acid, dimethyl ester;

(E,E)-[[[[(3-ethyl-7,11-dimethyl-2,6,10-dodecatrienyl)oxy]methyl]hydroxyphosphinyl]methyl]phosphonic acid, or its trisodium salt;

(2E,6E)-[[[[(3-ethyl-7,10-dimethyl-2,6,10-dodecatrienyl)oxy]methyl](1-methylethoxy)phosphinyl]methyl]phosphonic acid, dimethyl ester;

(2E,6E)-[[[[(3-ethyl-7,10-dimethyl]-2,6,10-dodecatrienyl)oxy]methyl]hydroxyphosphinyl]methyl]phosphonic acid, or its trisodium salt;

(E)-[[[[(8,12-dimethyl-7,11-tridecadien-3-ynyl)oxy]methyl](1-methylethoxy)phosphinyl]methyl]phosphonic acid, dimethyl ester;

(E)-[[[[(8,12-dimethyl-7,11-tridecadien-3-ynyl)oxy]methyl]hydroxyphosphinyl]methyl]phosphonic acid, or its trisodium salt;

(E)-[[[[(7,11-dimethyl-3-methylene-6,10-dodecadienyl)oxy]methyl]hydroxyphosphinyl]methyl]phosphonic acid, or its trisodium salt;

(E)-[[hydroxy[[(3,7,11-trimethyl-6,10-dodecadienyl)oxy]methyl]phosphinyl]methyl]phosphonic acid, or its trisodium salt;

(2Z,6E)-[[hydroxy[[(3,7,11-trimethyl-2,6,10-dodecatrienyl)oxy]methyl]phosphinyl]methyl]phosphonic acid, or its trisodium salt;

(E)-[[[[(7,11-dimethyl-6,10-dodecadienyl)oxy]methyl]hydroxyphosphinyl]methyl]phosphonic acid, or its trisodium salt; or (E)-[[[[(6,10-dimethyl-5,9-undecadienyl)oxy]methyl]hydroxyphosphinyl]methyl]phosphonic acid, or its trisodium salt.

22. A method of inhibiting or treating hypercholesterolemia, which comprises administering to a patient in need of such treatment an effective amount of a compound as defined in claim 1.

23. A method of inhibiting or treating atherosclerosis which comprises administering to a patient in need of such treatment an effective amount of a compound as defined in claim 1.

24. A hypocholesterolemic or hypolipemic composition comprising a compound as defined in claim 1 and a pharmaceutically acceptable carrier therefor.

25. A method of inhibiting cholesterol biosynthesis, which comprises administering to a patient in need of such treatment an effective cholesterol biosynthesis inhibiting amount of a compound as defined in claim 1.

26. A compound having the structure

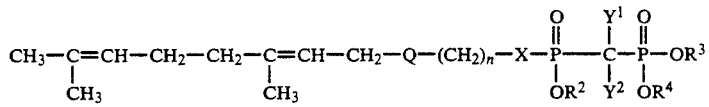

wherein Q is

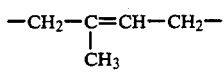

or a bond;

n is 1 to 4;

X is O;

$R^2$, $R^3$ and $R^4$ are the same or different and are H, lower alkyl, lower alkenyl, or a metal ion;

$Y^1$ and $Y^2$ is H.

27. The compound as defined in claim 26 having the structure

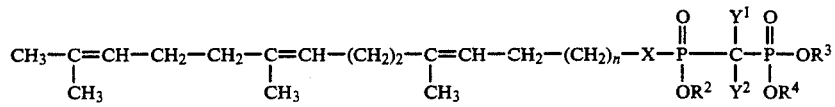

28. The compound as defined in claim 26 having the structure

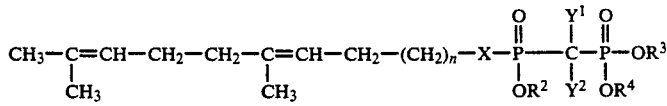

29. The compound as defined in claim 26 having the structure

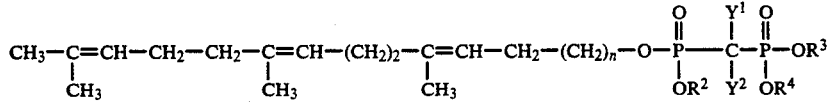

wherein n is 1, 2, 3, or 4.

30. The compound as defined in claim 26 having the name (E,E)-[[hydroxy[(4,8,12-trimethyl-3,7,11-tridecatrienyl)oxy]phosphinyl]methyl]phosphonic acid, or its tri-potassium salt; (E,E)-[[hydroxy[(5,9,11-trimethyl-4,8,12-tetradecatrienyl)oxy]phosphinyl]methyl]phosphonic acid, or its tripotassium salt; (E,E)-[[hydroxy(6,10,14-trimethyl-5,9,13-pentadecatrienyl)oxy]phosphinyl]methyl]phosphonic acid, or its tripotassium salt.

31. A compound having the structure

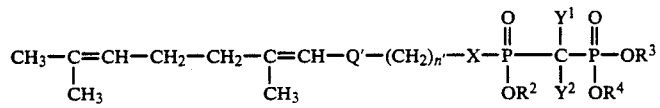

wherein Q' is

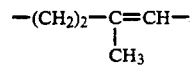

or a bond;
n' is 1, 2, 3 or 4;
X is O;
$R^2$, $R^3$ and $R^4$ are the same or different and are H, lower alkyl, lower alkenyl, or a metal ion;
$Y^1$ and $Y^2$ H;
$R^{15}$ is H or lower alkyl;
with the proviso that when X is O, n' is 2, 3, or 4.

32. A compound having the structure

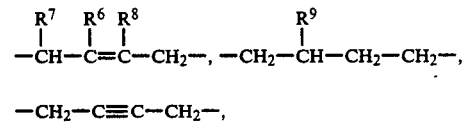

$-CH_2-C\equiv C-CH_2-$, wherein m' is 1, 2 or 3; n" is 0, 1, 2 or 3;
$Y^1$ and $Y^2$ are H;

$R^2$, $R^3$ and $R^4$ may be the same or different and are independently H, metal ion, $C_1$ to $C_8$ alkyl or $C_3$ to $C_{12}$ alkenyl;
X is O or S; and
$R^1$ is $R^5$—$Q^1$—$Q^2$—$Q^3$— wherein $Q^1$, $Q^2$ and $Q^3$ are the same or different and are independently

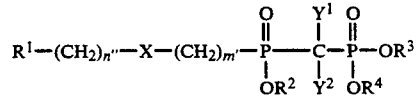

or a single bond, with the proviso that if $Q^1$ is a bond, then $Q^2$ and $Q^3$ are bonds, and if $Q^2$ is a bond then $Q^3$ is a bond, and wherein $R^6$ is H, lower alkyl, halo or haloalkyl; $R^7$ is H, halogen, lower alkyl or lower alkylthio; $R^8$ is H, halogen, trimethylsilyl or lower alkyl; and $R^9$ is H or lower alkyl;

$R^5$ is $R^{10}$—C=C—$CH_2$—, $R^{14}$—CH—$CH_2$—$CH_2$—, (with $R^{11}$, $R^{12}$ on the first group and $R^{13}$ on the second)

$CH_3(CH_2)_p$ where p is an integer from 2 to 7, or $R^{16}$—C≡C—$CH_2$— where $R^{16}$ is H or lower alkyl; $R^{10}$, and $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl; with the proviso that is all of $Q^1$, $Q^2$ and $Q^3$ are bonds, then both $R^{10}$ and $R^{11}$ cannot be H, and $R^5$ cannot be $CH_3(CH_2)_p$— with a p less than or equal to 4, and including all stereoisomers thereof.

* * * * *

UNITED STATES PATENT AND TRADEMARK OFFICE
CERTIFICATE OF CORRECTION

PATENT NO. : 5,212,164
DATED : May 18, 1993
INVENTOR(S) : Scott A. Biller et al

It is certified that error appears in the above-identified patent and that said Letters Patent is hereby corrected as shown below:

Col. 113, claim 6, after "defined" and before "claim 4" please insert --in--.

Col. 115, line 51, please change "(2E,6E)" to --(2Z,6E)--.
Col. 115, line 54, please change "(2E,6E)" to --(2Z,6E)--.

Please switch structures from column 117, between lines 48-53, to column 118, line 20.
Please switch structure from column 118, line 20, to column 117, between lines 48-53.
Col. 118, line 51, after "proviso that" please change "is" to --if--.

Signed and Sealed this

Twenty-fifth Day of October, 1994

Attest:

BRUCE LEHMAN

Attesting Officer

Commissioner of Patents and Trademarks